(12) United States Patent
Kularatne et al.

(10) Patent No.: US 10,676,487 B2
(45) Date of Patent: Jun. 9, 2020

(54) SYNTHESIS AND COMPOSITION OF PHOTODYNAMIC THERAPEUTIC AGENTS FOR THE TARGETED TREATMENT OF CANCER

(71) Applicant: On Target Laboratories, LLC, West Lafayette, IN (US)

(72) Inventors: Sumith A. Kularatne, West Lafayette, IN (US); Pravin Gagare, West Lafayette, IN (US); Carrie H. Myers, Chesterfield, MO (US)

(73) Assignee: On Target Laboratories, LLC, West Lafayette, IN (US)

( * ) Notice: Subject to any disclaimer, the term of this patent is extended or adjusted under 35 U.S.C. 154(b) by 305 days.

(21) Appl. No.: 15/257,566

(22) Filed: Sep. 6, 2016

(65) Prior Publication Data
US 2017/0145035 A1   May 25, 2017

Related U.S. Application Data

(60) Provisional application No. 62/216,148, filed on Sep. 9, 2015.

(51) Int. Cl.
*A61K 9/00* (2006.01)
*C07D 519/00* (2006.01)
(Continued)

(52) U.S. Cl.
CPC ........ *C07D 519/00* (2013.01); *A61K 41/0071* (2013.01); *A61K 47/551* (2017.08);
(Continued)

(58) Field of Classification Search
CPC .................................................. C07D 519/00
See application file for complete search history.

(56) References Cited

U.S. PATENT DOCUMENTS

| 6,093,382 A | 7/2000 | Wedeking et al. |
| 2008/0269112 A1 | 10/2008 | Zheng et al. |

(Continued)

FOREIGN PATENT DOCUMENTS

| EP | 2431366 A1 | 3/2012 | |
| WO | 01/27625 A1 | 4/2001 | |
| WO | WO-2013051778 A1 * | 4/2013 | ......... A61K 41/0033 |

OTHER PUBLICATIONS

Zhao, Cholesterol as a Bilayer Anchor for PEGylation and Targeting Ligand in Folate-Receptor-Targeted Liposomes, 2006, 96(9), 2007.*

(Continued)

*Primary Examiner* — Paul W Dickinson
(74) *Attorney, Agent, or Firm* — McAndrews, Held & Malloy, Ltd.

(57) ABSTRACT

The present invention describes new compounds that are useful for image-guided surgery and photodynamic therapy. In particular the compounds may be targeted to the nucleus or the mitochondria after compounds were delivered to diseased tissues such as cancer using a ligand that target receptor that express on the diseased tissue and followed by receptor mediated endocytosis and provide effective activity against cancer cells as well as other disorders. Methods and compositions for use of the same are described.

67 Claims, 52 Drawing Sheets

M = 2H: (1)
M = Pd: (2)

(51) Int. Cl.
| | |
|---|---|
| C07D 493/04 | (2006.01) |
| C07D 487/22 | (2006.01) |
| C07H 13/04 | (2006.01) |
| A61K 47/55 | (2017.01) |
| A61K 41/00 | (2020.01) |
| A61K 49/00 | (2006.01) |
| C07F 15/00 | (2006.01) |

(52) U.S. Cl.
CPC ........ *A61K 49/0052* (2013.01); *C07D 487/22* (2013.01); *C07D 493/04* (2013.01); *C07F 15/0066* (2013.01); *C07H 13/04* (2013.01)

(56) References Cited

U.S. PATENT DOCUMENTS

| | | | |
|---|---|---|---|
| 2010/0075899 | A1 | 3/2010 | Zheng et al. |
| 2010/0323973 | A1 | 12/2010 | Leamon et al. |
| 2012/0059018 | A1* | 3/2012 | Park ............... A61K 41/0071 514/262.1 |
| 2012/0294801 | A1 | 12/2012 | Scherz et al. |
| 2013/0079259 | A1 | 3/2013 | Perry et al. |

OTHER PUBLICATIONS

Stefflova (Peptide-Based Pharmacomodulation of a Cancer-Targeted Optical Imaging and Photodynamic Therapy Agent, Bioconjugate Chem. 2007, 18, 379-388.*

Stallivieri (The Interest of Folic Acid in Targeted Photodynamic Therapy, Current Medicinal Chemistry, 2015, 22, 1-23.*

Machine translation of WO 2013051778, Apr. 2019.*

Supplemental Search Report regarding Application No. PCT/US2016/050482, European Patent Office, dated Mar. 8, 2019, 8 pages.

PCT, International Search Report and Written Opinion, Application Nos. PCT/US2016/050478 and PCT/US2016/050482, dated Mar. 22, 2018.

PCT, International Search Report, Application No. PCT/US2016/050478, dated Nov. 7, 2016.

Hofer, T. el al., Molecularly defined antibody conjugation through a selenocysteine Interface Biochemistry, vol. 48, No. 50, Dec. 22, 2009, pp. 12047-12057; abstract; p. 3.

Manjappa, AS et al., Antibody derivatization and conjugation strategies; Application in preparation of stealth immunollposome to target chemotherapeutics to tumor. Journal of Controlled Release, vol. 150, 2011, pp. 2-22; p. 3, col. 1, paragraph 2; p. 3, col. 2, paragraph 1; p. 15, figure 23.

Siegel, BA et al. Evaluation of 111 In-DTPA-Folate as a Receptor-Targeted Diagnostic Agent for Ovarian Cancer: Initial Clinical Results. The Journal of Nuclear Medicine, vol. 44, No. 5, May 2003, pp. 700-707; abstract; p. 701, col. 1, paragraph 3.

Puig-Kroger, A. et al., Folate Receptor B Is Expressed by Tumor-Associated Macrophages and Constitutes a Marker or M2 Anti-Inflammatory/Regulatory Macrophages, Cancer Research, vol. 69, No. 24, Dec. 15, 2009, pp. 9395-9403; abstract.

Castillo, JJ et al. Detection of cancer cells using a peplide nanotube-folic acid modified graphene electrode. Analyst, vol. 138, 2013, pp. 1026-1031; p. 1027, col. 1, paragraph 2.

De Jesus, E. et al., Comparison of Folate Receptor Targeted Optical Contrast Agents for Intraoperative Molecular Imaging. International Journal of Molecular Imaging, vol. 2015, Article ID 469047, 10 pages.

Rossin, R. et al., Cu-Labeled Folate-Conjugated Shell Cross-Linked Nanoparticles for Tumor Imaging and Radiotherapy: Synthesis, Radiolabeling, and Biologic Evaluation, The Journal of Nuclear Medicine, 2005.

First Examination Report regarding Application No. 201817008643, Indian Patent Office, dated Mar. 16, 2020, 6 pages.

Stallivieri, A., et al., The Interest of Folic Acid in Tarageted Photodynamic Therapy, Curr. Med. Chem. dated Jan. 7, 2015, vol. 22, No. 1, 22(27):3185-207, 24 pages.

Kim, J., et al., Smart dual-functional warhead for folate receptor-specific activate imaging and photodynamic therapy, Chem. Commun. (Camb), Sep. 21, 2014, 50(73):10600-3, 4 pages.

Azais, H., et al., Assessment of the specificity of a new folate-targeted photosensitizer for peritoneal metastasis of epithelial ovarian cancer to enable intraperitoneal photodynamic therapy: a preclinical study, Photodiagnosis and Photodynamic Therapy Elsevier, Amsterdam, Jan. 8, 2015, vol. 13, 130-138, 9 pages.

\* cited by examiner

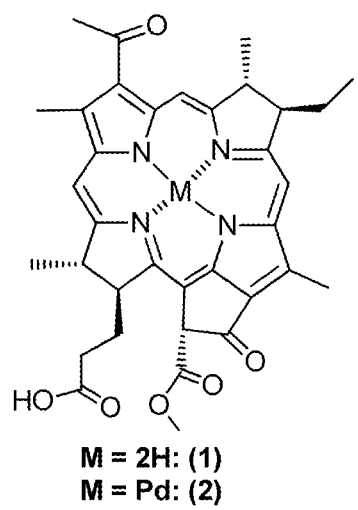
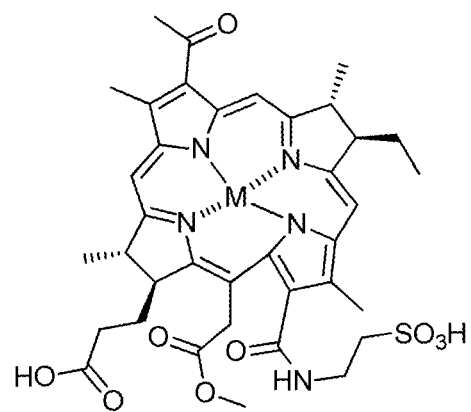
M = 2H: (1)
M = Pd: (2)
M = 2H: (3)
M = Pd: (4)
Fig. 1A
Fig. 1B
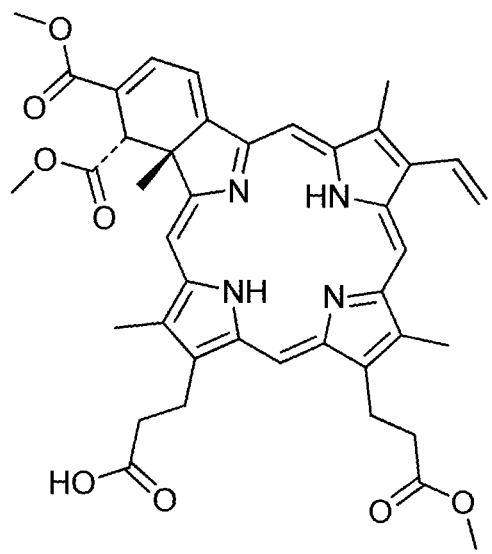
+
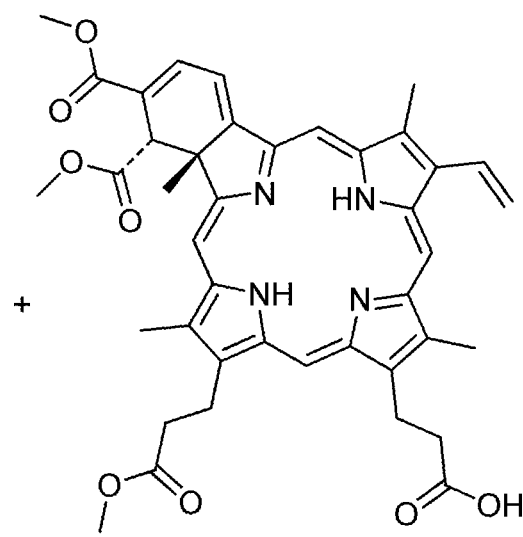
Visudyne (1:1 mixture)
(5)
Fig. 1C

Foscan
(6)

Photofrin
n = 0 - 6, R = CH$_3$CH(OH)- and/ or CH$_2$=CH-
(7)

n = 0: (20a)
n = 1: (20b)

R = Br: (21a)
R = OH: (21b)

(22)

R = COOH: (23a)
R = NH2: (23b)

M = 2H: (24)
M = Pd: (25)

M = 2H: (26)
M = Pd: (27)

M = 2H: (28)
M = Pd: (29)

M = 2H: (30)
M = Pd: (31)

(39)

(40)

(41)

(42)

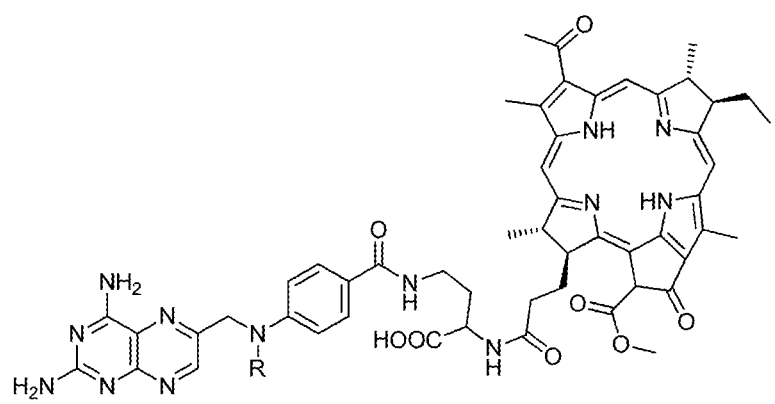
R = H: (43)
R = Me: (44)
Fig. 9E
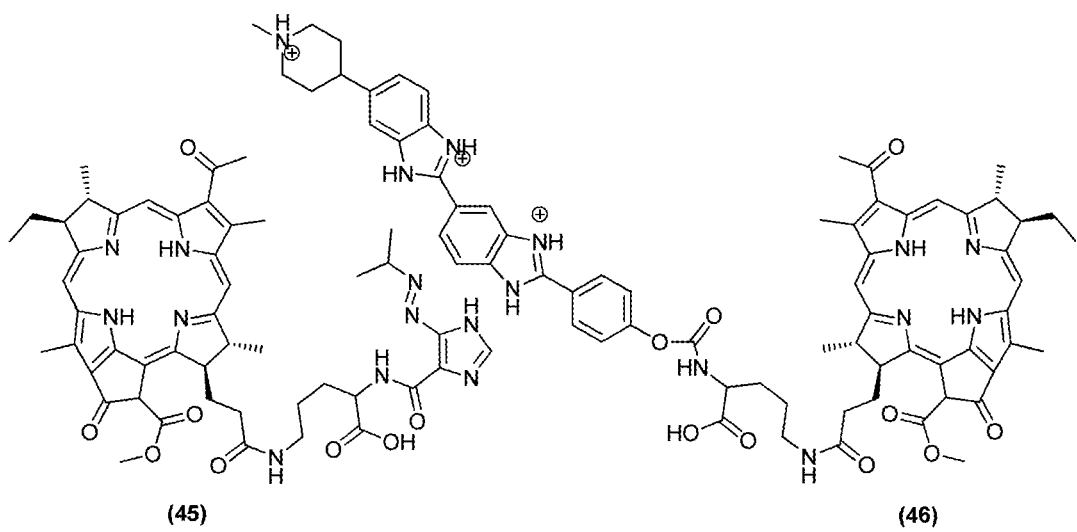
(45)　　　　　　　　　　　　　　　　(46)
Fig. 9F　　　　　　　　　　Fig. 9G

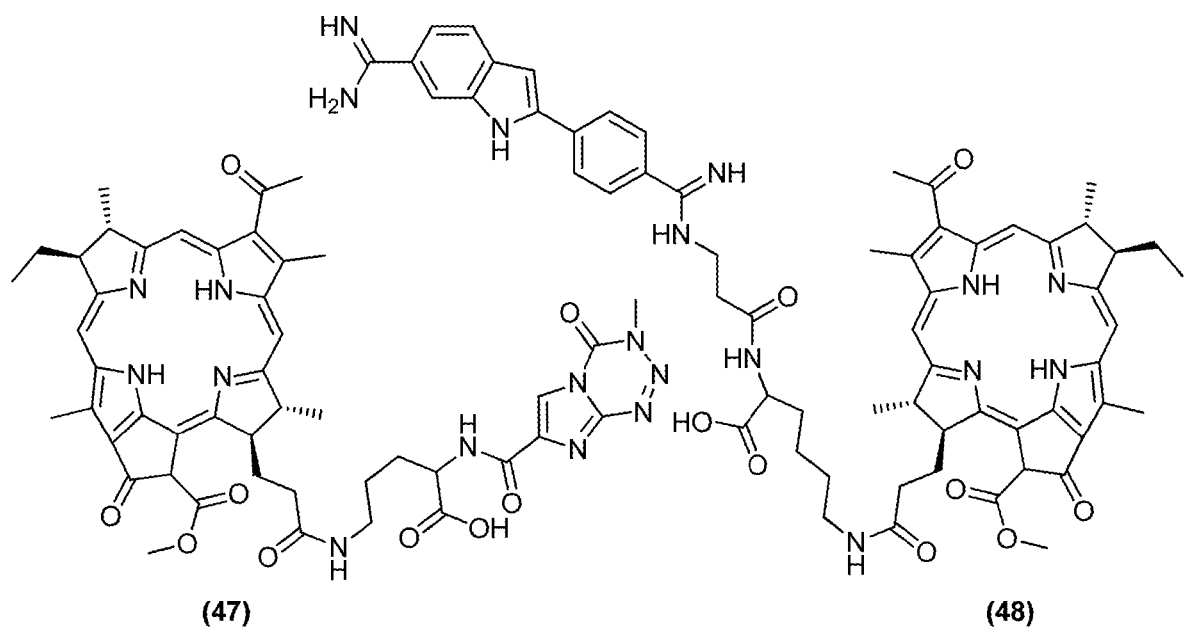
(47)  
Fig. 9H
(48)  
Fig. 9I
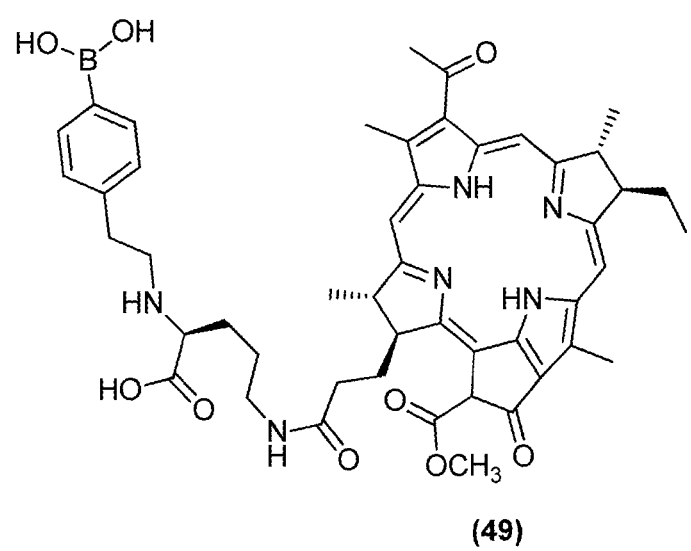
(49)  
Fig. 9J

SYNTHESIS AND COMPOSITION OF PHOTODYNAMIC THERAPEUTIC AGENTS FOR THE TARGETED TREATMENT OF CANCER

RELATED APPLICATIONS

The present patent application is related to and claims the priority benefit of U.S. Provisional Patent Application Ser. No. 62/216,148, filed Sep. 9, 2015, the content of which is hereby incorporated by reference in its entirety into this disclosure.

FIELD OF DISCLOSURE

The present disclosure relates to methods of treating folate receptor expressing diseased cells such as cancer cells, tumor associated macrophages and compositions and compounds for use therein. This disclosure provides methods of utilizing targeted photodynamic therapeutic (PDT) agents for the treatment of tumors. The PDT agents may be modified to target either the mitochondria or the nucleus and then conjugated to ligand, such as folic acid or folate, that targets a receptor overexpress in a pathogenic/diseased cell, such as folate receptor, to increase specificity and detection of the compound via a suitable linker to improve water solubility, pharmacokinetic properties, and bioavailability, etc., to release the PDT agent inside the diseased cell thereby guiding to the mitochondria or the nucleus in the cell, to prevent developing drug resistant by efflux pumps [e.g. ATP Binding Cassette family (ABC transporters)], etc. Methods of treatment using the conjugated compounds involving use thereof are contemplated.

BACKGROUND OF THE DISCLOSURE

Treatment for cancer most commonly involves surgery, radiation therapy, hormone administration, and/or chemotherapy. Unfortunately, none of these therapies is highly effective against metastatic disease. Moreover, each has sufficient disadvantages such that patients often decline these therapies.

Surgical removal of malignant disease constitutes one of the most common and effective therapeutic interventions for primary treatment for cancer. Resection of all detectable malignant lesions results in no detectable return of the disease in approximately 50% of all cancer patients and may extend life expectancy or reduce morbidity for patients in whom recurrence of the cancer is seen. Not surprisingly, surgical methods for achieving more quantitative cytoreduction are now receiving greater scrutiny.

For optimal surgical resection of the cancer, it is important for the surgeon to locate the entire cancer tissue and lymph nodes, and be able to remove both the cancer and the nodes without significantly compromising adjacent structures and residual function of the organ. It is estimated that in over 40% cancer patients surgical resection still leaves the patient with some cancer cells even after resection either because the cancerous tissue could not be identified, or if identified, it was not amenable to resection. These "escaped" malignant cells lead to a significant risk of disease recurrence or even death unless they are identified and removed. In prostate cancer, the primary tumor can be treated by removal of prostate gland. However, radical prostatectomy (complete removal of the prostate) has significant drawbacks and may result in loss of urinary control and impotence.

Another therapeutic intervention involves radiation therapy either alone, or as part of a combined therapeutic regimen. However, radiation therapy can increase the risk of appearance of a second type of cancer. For example, treatment of prostate cancer using radiation therapy can increase risk of colon and bladder cancer. Treatment of invasive or metastatic cancer is often limited to palliative hormonal therapy and/or chemotherapy. While hormonal treatment induces remission of hormonally responsive cancer, the longevity of tumor remission is limited and it is not without significant toxicity, including liver damage associated with the drugs being administered, cardiovascular disease, weight gain, and osteoporosis.

Although chemotherapy may also extend lifespan, side effects of such antimitotic drugs often outweigh their benefits. Most cancer therapies today involve treatment with cytotoxic drugs that, upon administration, distribute indiscriminately to virtually all cells of the body and cause damage to both malignant and healthy cells alike. Because such conventional chemotherapies are primarily designed to kill rapidly dividing cells, they also destroy proliferating healthy cells, leading to off-target toxicities that can include myelosuppression, mucositis, alopecia, nausea/vomiting, anemia, peripheral neuropathy, and fatigue, etc. Clearly, cytotoxic therapies that can be targeted selectively to pathologic cells, avoiding collateral damage to healthy cells, would constitute a significant advance in the treatment of cancer. Therefore, there is a significant need for safer and more potent methods of treating cancer Image-guided surgery is an emerging technique that aids surgeons to more accurately identify and remove malignant tissue without compromising the surrounding healthy tissue. One of the inherent challenges in the field of image-guided surgery is the development of imaging agents (probes) that are specific and sensitive for the cancer tissue and that selectively accumulate in the tumor to help identify the tumor. This is particularly true for occult lesions that cannot readily be identified by usual techniques. While FDA has approved indocyanine green (ICG), a non-targeted near infrared (NIR)-dye for use in image-guided surgery for certain cancers, it has been found to have significant limitations with respect to sensitivity and specificity in the identification of tumor tissue.

Motivated by a need for improved tumor identification, certain of the present inventors have previously developed a novel high affinity folate receptor (FR)-targeted NIR probe (OTL38) for use in image-guided tumor surgery for folate receptor positive cancer. OTL38 is highly stable during synthesis and storage, demonstrates ease of synthesis in small scale to GMP manufacturing, and is highly specific for FR-positive cancer cells in culture and in animal models for both primary and metastatic cancer cells, with no toxicity in rats and dogs. Based on these successful preclinical data, OTL38 entered into a Phase 1a clinical trial in Leiden, the Netherlands in January 2014 and Phase II at six different sites in USA for ovarian and lung cancer. In this study, approximately 5× more malignant lesions were removed with the aid of the OTL38 than without it. Furthermore, all the resected fluorescent lesions were confirmed by pathology to be malignant. The use of OTL38-guided resection is able to remove approximately 95% of the tumor cells. Thus, there is a need to find or improve therapies in such a way as to eliminate as much of the remaining 5% of such cancers as possible.

Part of the present invention is to identify a novel approach using a cocktail of OTL38 (folate-targeted NIR dye) and folate-targeted therapeutic agent that can be used after or during the image-guided surgery. However, one disadvantage of this approach is that both OTL38 and folate-targeted therapeutic agent will compete for same folate receptor and compound with higher affinity for the receptor will dominate the function. For example, if OTL38 has less affinity compared to folate-targeted therapeutic agent, there will be less fluorescence in the tumor and surgeon may not able to resect 5× more tumor when compared to naked eye. If on the other hand, the imaging agent is presented has a greater affinity for the receptor, then the therapeutic agent will likely be ineffective at producing the desired therapeutic outcome. Therefore, it is necessary to find the correct ratio between two compounds or adjust the pharmacokinetic properties of folate-targeted therapeutic agent to match OTL38. Alternatively, instead of adjusting pharmacokinetic properties of folate-targeted therapeutic agent to differentiate it from OTL38, the time between administration of OTL38 for image-guided surgery and administration of folate-targeted therapeutic agent for treatment can be varied. In a further alternative, a therapeutic modality that could serve the both purposes of image-guided surgery as well as a therapeutic agent would be an ideal situation.

Photodynamic therapy (PDT) is a new innovative technology that could be used both in image-guided surgery as well as in therapy. It is a treatment modality that uses a photosensitizer (PS) in combination with a particular type of light source. When the appropriate dose of PS is irradiated a photodynamic reaction occurs and generates reactive oxygen species (ROSs). These ROSs induce cell death and necrosis of diseased cells such as malignant cells, inflammatory cells, and microbial cells. PDT has been using to treat diseases ranging from cancer to age-related macular degeneration and antibiotic-resistant infections When the photosensitizer is exposed to a specific wavelength of light, it becomes activated from a ground state (singlet state) to an excited state (triplet state) by absorbing photon (energy) from light. Then it relaxes to its ground state in three ways: through non-radiative decay, by emitting photon, and/or by transferring the energy. The detectable outcome of emitting a photon results is fluorescence. Transformation of energy causes the production of ROS that eventually lead to phototoxicity. However, the ratio between these two processes (fluorescence and phototoxicity) depends on the type of PS used. Therefore, finding the right PS with right balance is important for its use in PDT as a perfect candidate for both image-guided surgery as well as for therapy during or after surgery.

Based on the type of ROS generated, there are two types of photodynamic reaction that can occur. Type I PDT: First, the activated sensitizer can react directly with the substrate, such as the cell membrane or a molecule, and generate free radicals by abstracting an electron to form a superoxide anion radical ($O_2^-$) or transferring an electron or hydrogen atom to form a hydroxyl radical (OH*) and/or peroxide radical (OOH*). These radicals then interact with oxygen to produce oxygenated products ($^1O_2$).

In Type II PDT: the activated sensitizer can transfer its energy directly to oxygen to form singlet oxygen ($^1O_2$), which is a highly reactive oxygen species. These species oxidize various substrates.

After the PS is activated, both type I and type II PDT reactions can occur, however, the ratio between these processes depends on the type of PS used, the concentrations of substrate, amount of oxygen present within tissue, and number of PS molecules localized in the substrate or tissue.

Therefore, there is an unmet medical demand to develop innovative technologies that can selectively target PS not only to diseased cell but also to appropriate compartment within the diseased cell and to eliminate of the disease. Moreover, a PS should overcome the drawbacks that conventional non-targeted PDT agents present. For example, such a molecule should have high potency, high specificity, higher water solubility, low toxicity for healthy cells with no or minimal side effects (especially skin toxicity).

Based on the limited distribution of folate receptor (FR) in normal tissues and the higher receptor expression levels in various disease cells, folic acid (FA) remains an attractive and high affinity ligand for the selective delivery of therapeutic and imaging agents to FR+ cancer cells, activated macrophages, and tumor associate macrophages. To date, four isoforms of FR have been identified (FR-α, FR-β, FR-γ, and FR-δ), however, only FR-α and FR-β are expressed in adequate number for use in diagnostic and therapeutic applications. Over-expressed in epithelial-derived cancers, FR-α, is found in high levels in cancers such as lung, ovarian, kidney, breast, myelogenous, and brain. In contrast, FR-β is expressed on activated macrophages associated with inflammatory disease states and tumor associated macrophages, but not on quiescent or resting macrophages. Importantly, most cells accumulate their required FA (vitamin B9) via a reduced folate carrier or proton coupled folate transporter, which is unable to transport folate conjugates. Due to this selective over-expression of FR receptor on specific type cells, folate-targeted $^{99m}$Tc and $^{111}$In SPECT imaging agents, $^{19}$F PET imaging agents and NIR optical imaging agents (OTL38) have been developed for the detection of FR+ cancers and inflammatory conditions in the clinic. Moreover, folate-targeted chemotherapeutic agents are also being evaluated.

BRIEF SUMMARY OF THE DISCLOSURE

This disclosure provides a method for synthesizing a photodynamic therapeutic agent that is conjugated through a suitable linker to a ligand that targets a receptor overexpressed on diseased cells. The therapeutic agent can be used for photodynamic therapy for the treatment of tumors and other malignant lesions. In certain embodiments, this disclosure relates to a compound or a salt derivative thereof that comprises a folate or pteroyl ligand, an amino acid, a linker an organelle targeting moiety to guide the PDT agent once PDT agent is inside the diseased cell, and a photodynamic therapeutic agent. The agents of the invention have high water solubility with better PK properties, and high PDT efficacy. The releasable linker releases organelle targeted PDT agent inside the diseased cells, thereby organelle targeted PDT agent can move to the specific organelle. In certain embodiments, the amino acid can be naturally occurring amino acid. In certain embodiments, the linking group can be a polyether compound, sulfonic acid, a glycan, an amino acid, an isomer, a derivative, or a racemic mixture thereof. In certain embodiments, releasable linker contains a disulfide bond, avid sensitive group, enzyme sensitive group, and the like. In other aspects, the organelle targeting agent is a mitochondrial or nucleus targeting agent. In yet another aspect the photodynamic therapeutic agent can be selected from the group consisting of Bpheid-a conjugates and Visudyne conjugates.

In some aspects, this disclosure provides a method of modifying the photodynamic therapeutic agent with the targeting agent, wherein the targeting agent can target the nucleus or mitochondria. It is noted that the Compounds of the present invention may be particularly useful in the treatment of cancer. Particularly preferred compounds of the present invention include but are not limited to Compound 9, Compound 11a, Compound 11b, Compound 12b, Compound 13, Compound 14, Compound 15, Compound 26, Compound 27, Compound 41, Compound 58a, Compound 59a, Compound 60a, Compound 64, Compound 65a, Compound 65c, Compound 76a, Compound 76c, Compound 88a, Compound 89, Compound 92a, Compound 99, Compound 100, Compound 104, Compound 112a, Compound 112b, Compound 116, and Compound 117. Such compounds may be used alone or in combination with other therapies. Indeed, any compound described herein that has a better EC50 value than BPheid-a may prove useful as a therapeutic, diagnostic or research compound for the present invention. Methods and compositions for making the aforementioned compounds are detailed in the examples herein below.

In some aspect of this disclosure the linking group is an amino acid. In other aspects the linking group is a polyether, a sulfonic acid and derivatives thereof, glycans and derivatives thereof, or amino acids and derivatives thereof.

In additional aspects, this disclosure provides a method of conjugating the linking group with a folate ligand, wherein the linking group is polyethylene glycol (PEG), polyethylene oxide (PEO), or polyoxyethylene (POE).

This disclosure provides a method for conjugating the linking group to a pteroyl ligand, wherein the linking group is polyethylene glycol (PEG) polyethylene oxide (PEO), or polyoxyethylene (POE).

In additional aspects, this disclosure provides a method of conjugating the linking group with a folate ligand, wherein the linking group is sulfonic acid or a disulfide compound.

This disclosure provides a method for conjugating the linking group to a pteroyl ligand, wherein the linking group is sulfonic acid or a disulfide compound.

In some aspects, this disclosure provides a method for conjugating the amino acid to a photodynamic therapeutic agent, wherein the amino acid is tyrosine, serine, threonine, lysine, arginine, asparagine, aspartic acid, glutamine, cysteine, selenocysteine, isomers or the derivatives thereof, and is to the conjugation to the photodynamic therapeutic agent is through a disulfide bond.

This disclosure provides a method for conjugating the amino acid to a targeting agent, wherein the amino acid is tyrosine, serine, threonine, lysine, arginine, asparagine, aspartic acid, glutamine, cysteine, selenocysteine, isomers or the derivatives thereof, and is to the conjugation to the targeting agent is through an amine bond.

In some aspects, this disclosure provides a method for conjugating the amino acid to a targeting agent, wherein the amino acid is tyrosine, serine, threonine, lysine, arginine, asparagine, aspartic acid, glutamine, cysteine, selenocysteine, isomers or the derivatives thereof, and is to the conjugation to the targeting agent is through a disulfide bond.

In additional aspects, the compound is highly selective for targeting to tumor cells expressing the target receptor.

In some aspects, this disclosure relates to the conjugation of the amino acid linking group to a PDT agent that has an absorption and emission maxima between about 500 nm and about 900 nm. In other aspects, the amino acid linking group is conjugated to a PDT agent that has an absorption and emission maxima between about 600 nm and about 800 nm.

In specific embodiments, this disclosure relates to the use of folate-targeted organelle targeted releasable disulfide linked BPheid-a conjugates for photodynamic therapy, photochemotherapy, photoradiation therapy, phototherapy for cancer, forensic applications, mineral applications, dental, gel staining, DNA sequencing, nerve staining, or plastic surgery.

In certain aspects, this disclosure relates to a compound used for the targeted tumors therapy, wherein the compound could be used for research, diagnostic, or therapeutic purposes. In other embodiments, this disclosure provides a composition comprising a photodynamic therapy compound and a pharmaceutically acceptable carrier, excipient, diluents, or salts.

In other aspects, this disclosure relates to a compound which has a formula selected from the group consisting of:

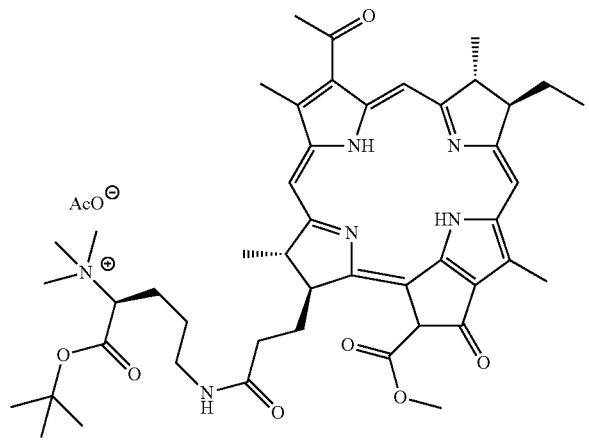

(9)

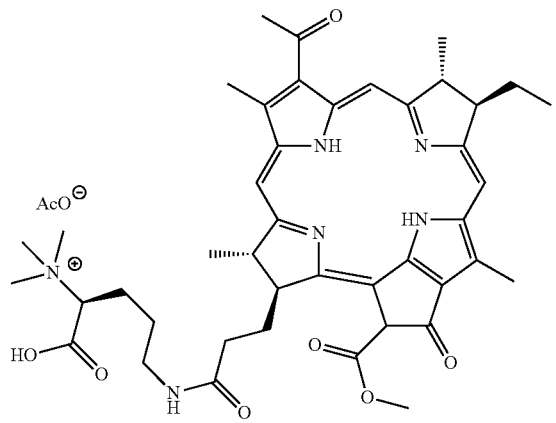

(11a)

-continued
(11b)
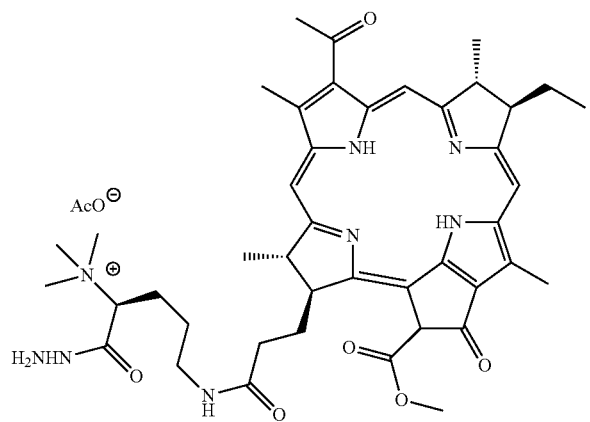
(12b)
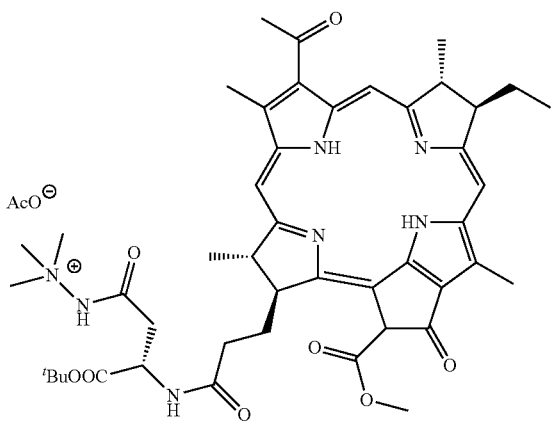
(13)
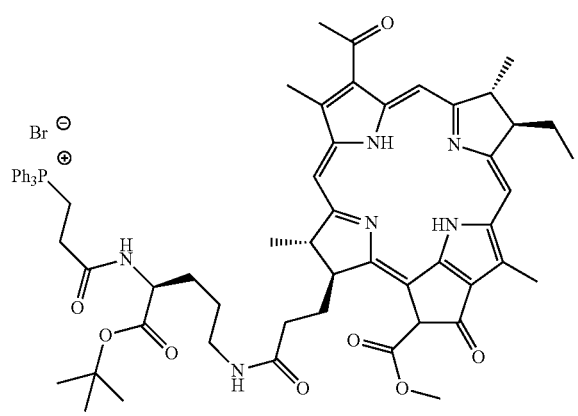
(14)
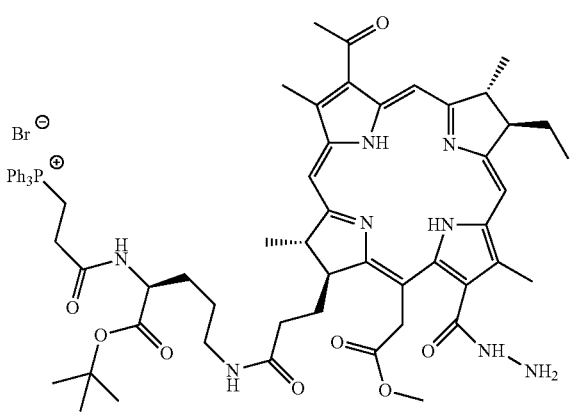
(15)
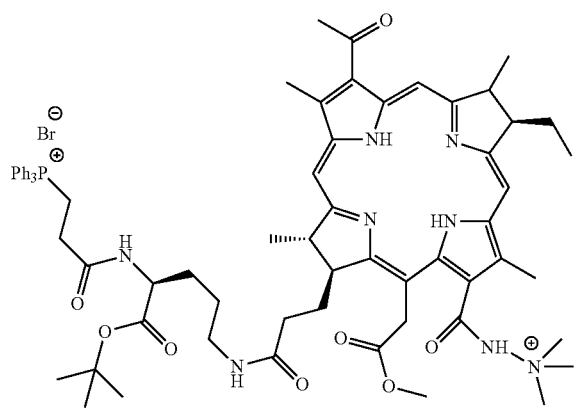
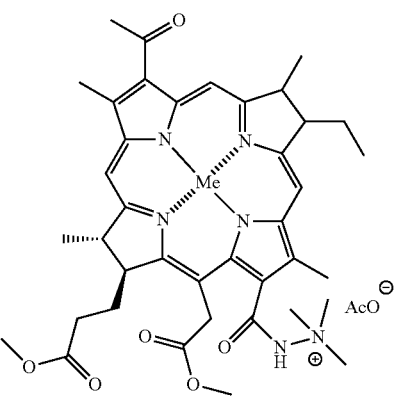
M = 2H: (26)
M = Pd: (27)

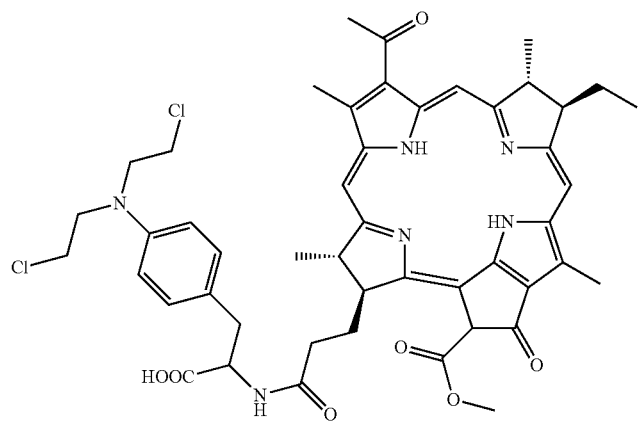
(41)
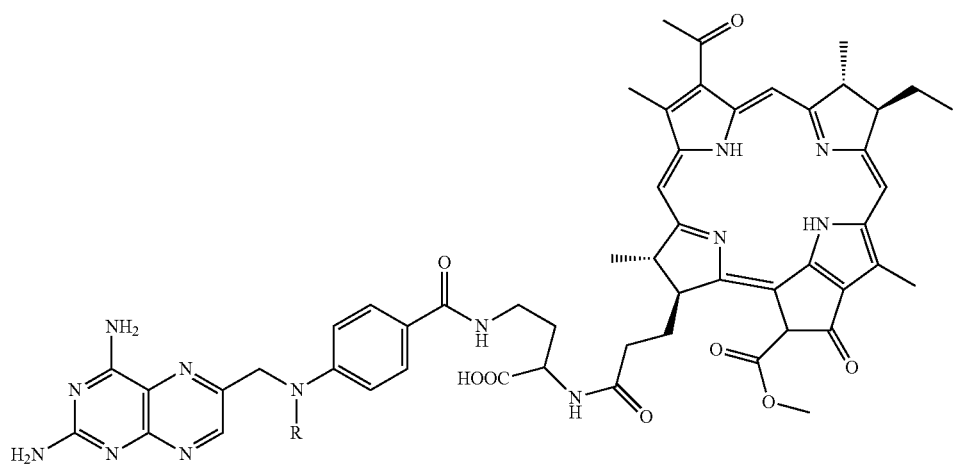
R = H: (43)
R = Me: (44)
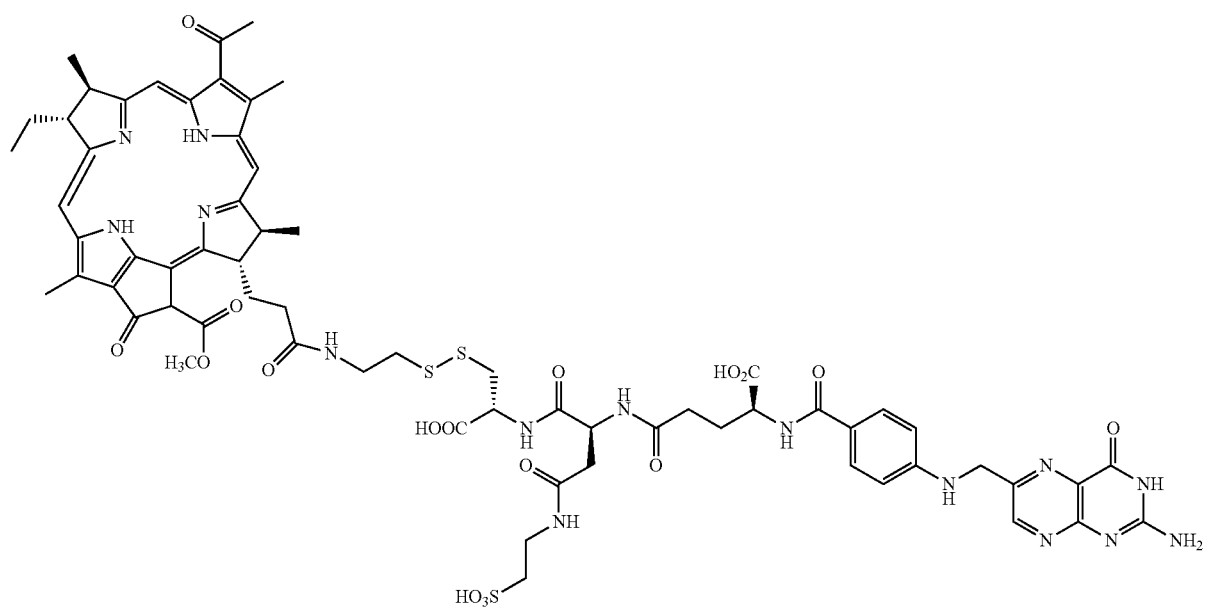
(64)

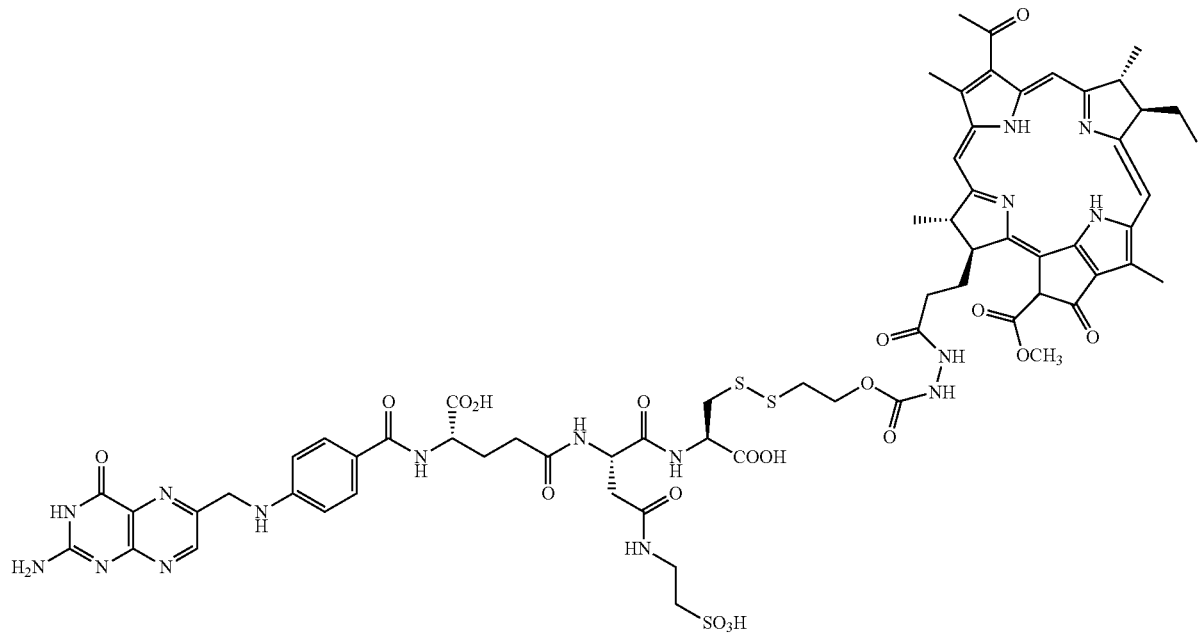
(65a)
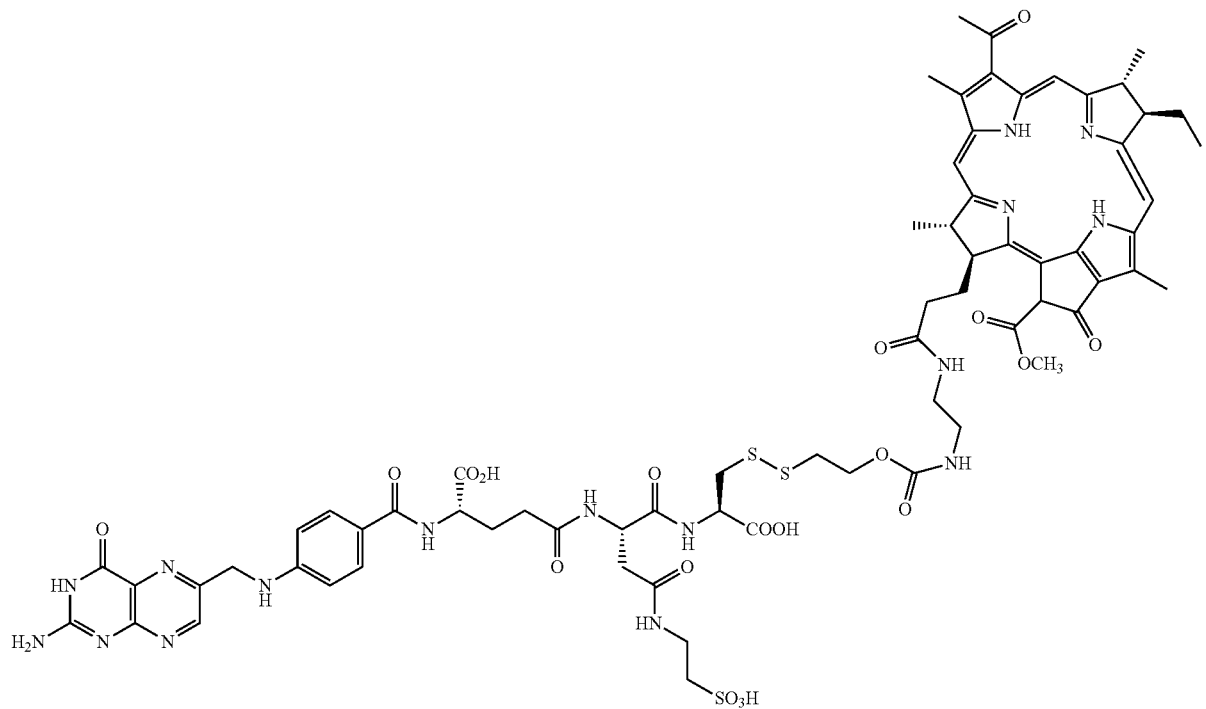
(65c)

-continued
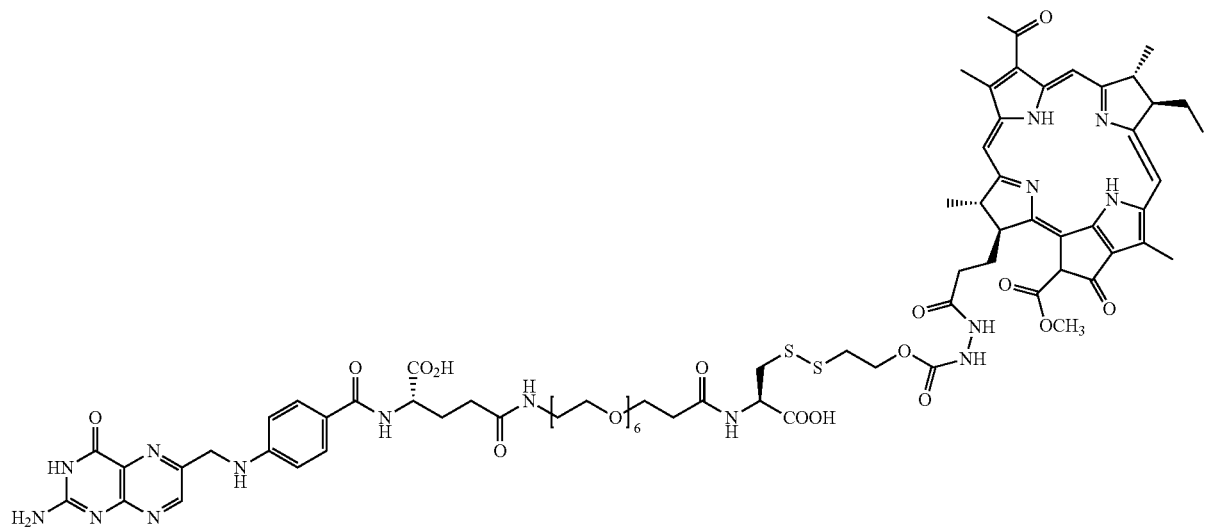
(76a)
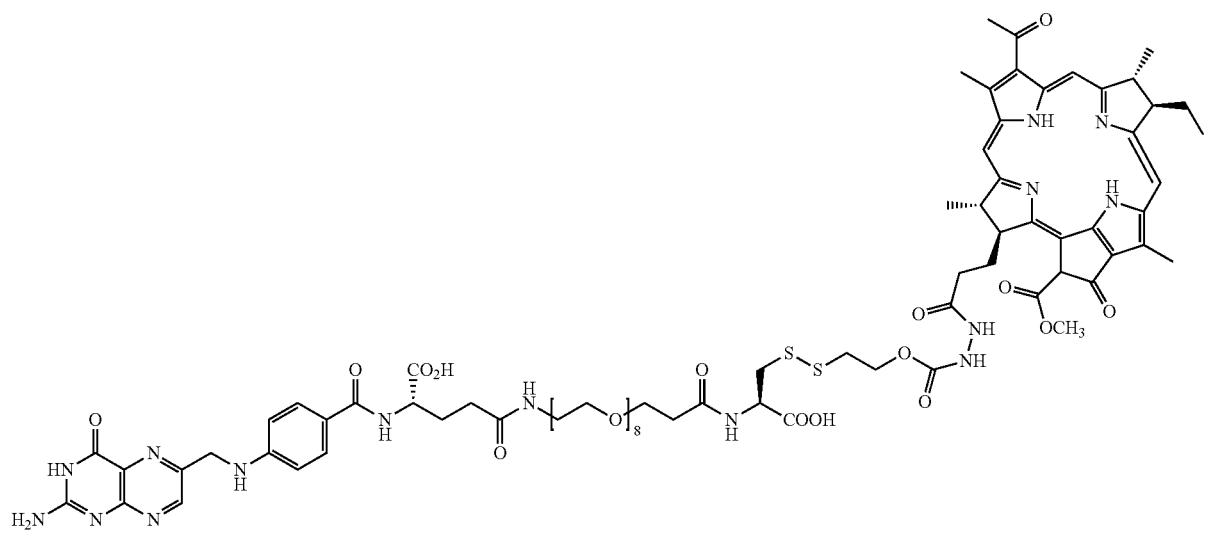
(76c)
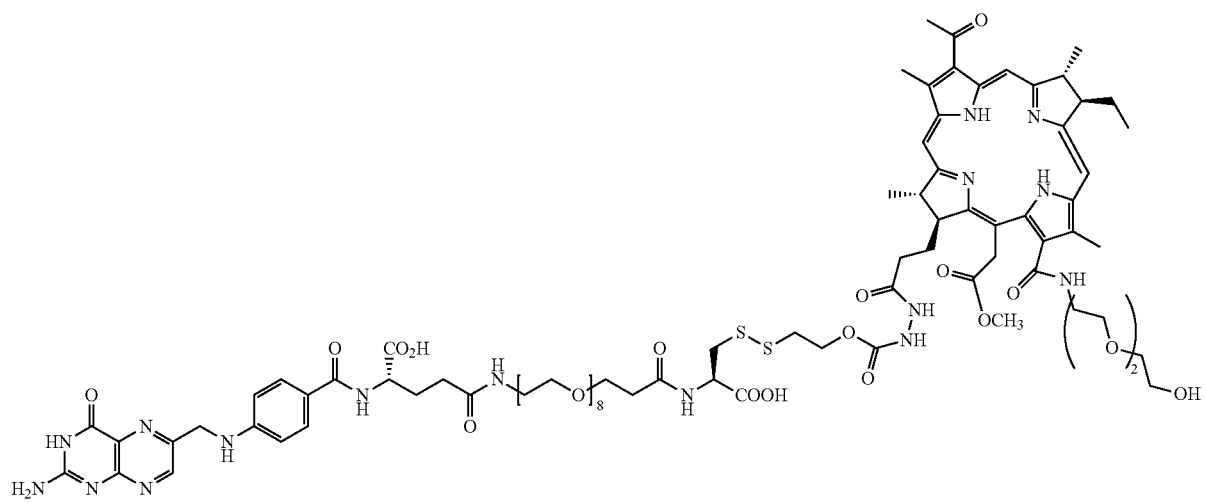
(88a)

(89a)
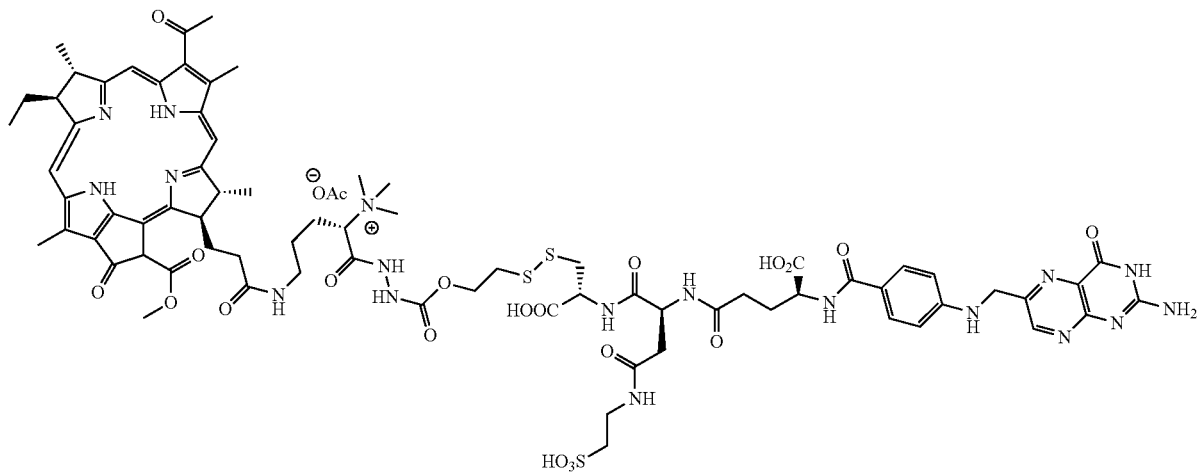
(89b)
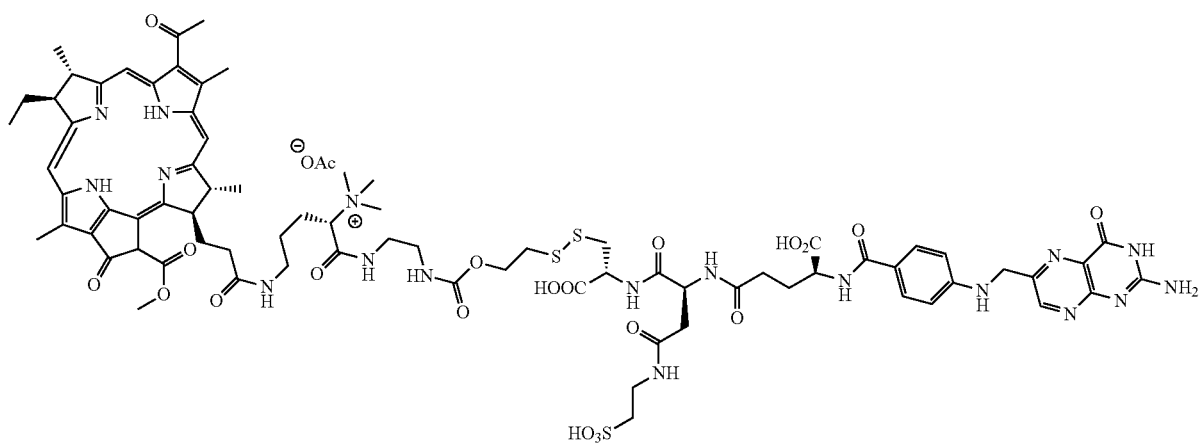
(92a)
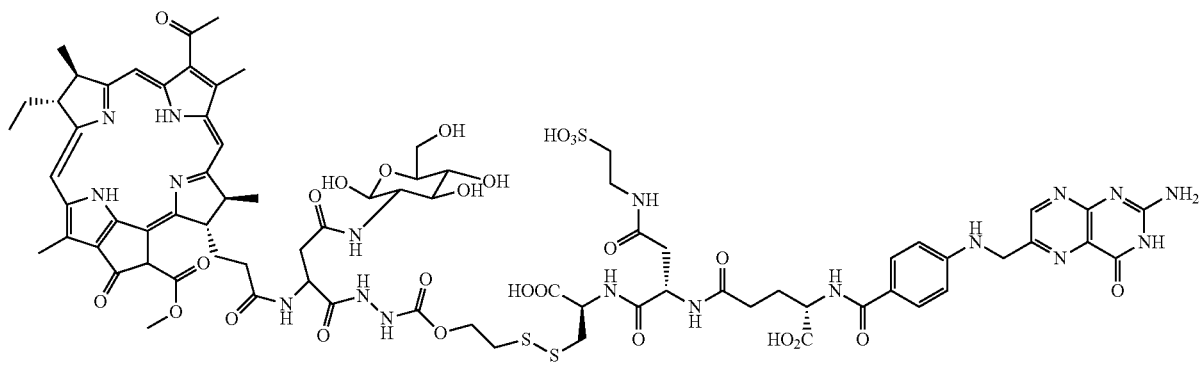

-continued
(99)
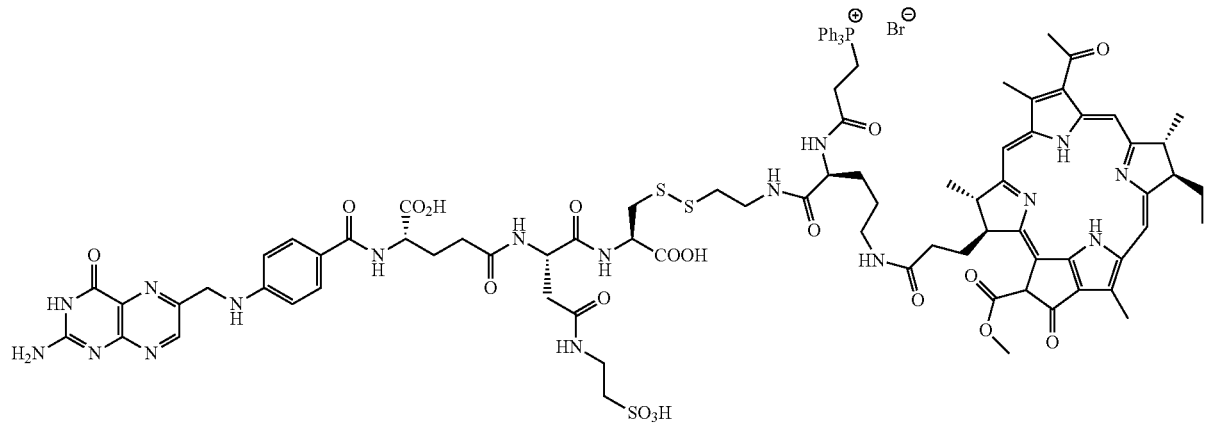
(100)
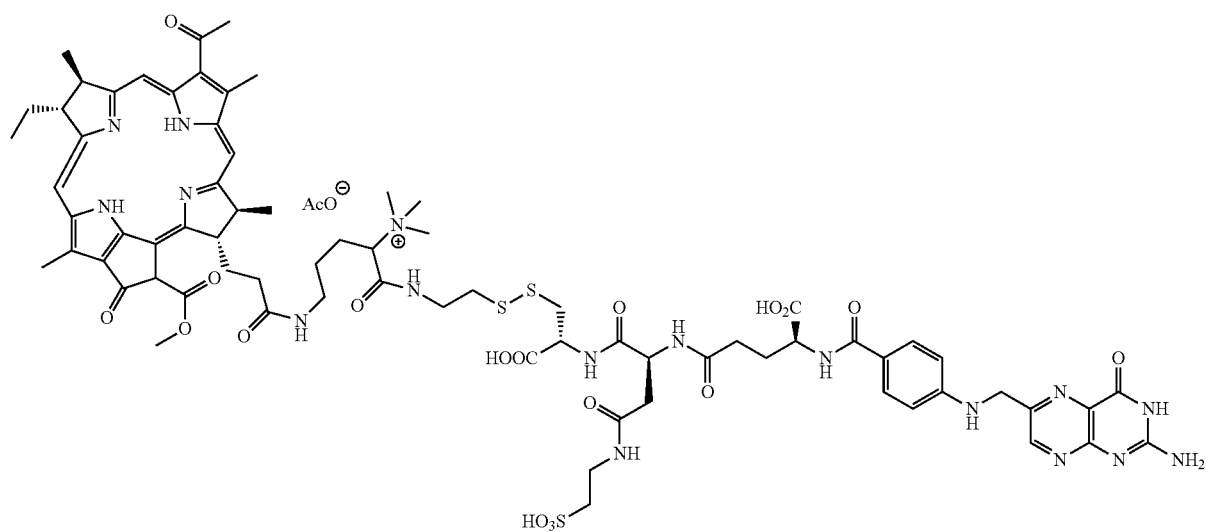
(104)
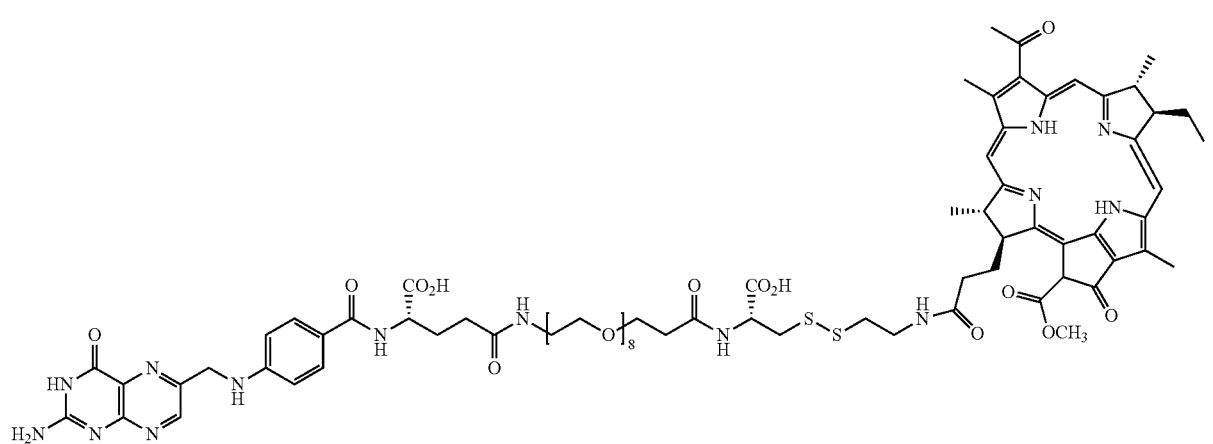

-continued
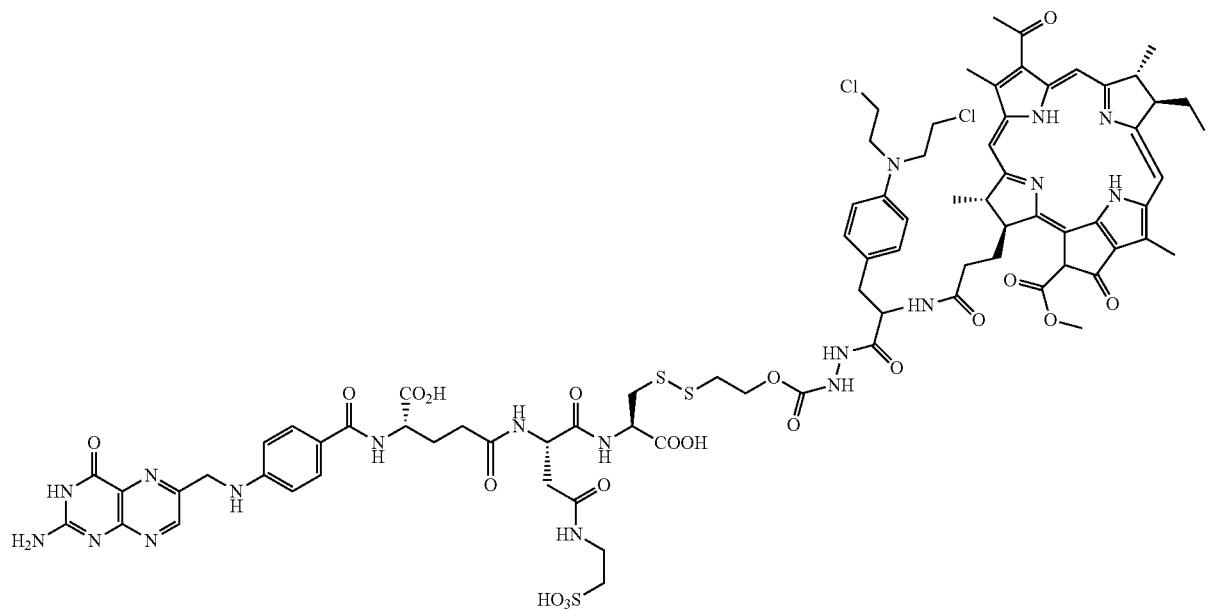
(112a)
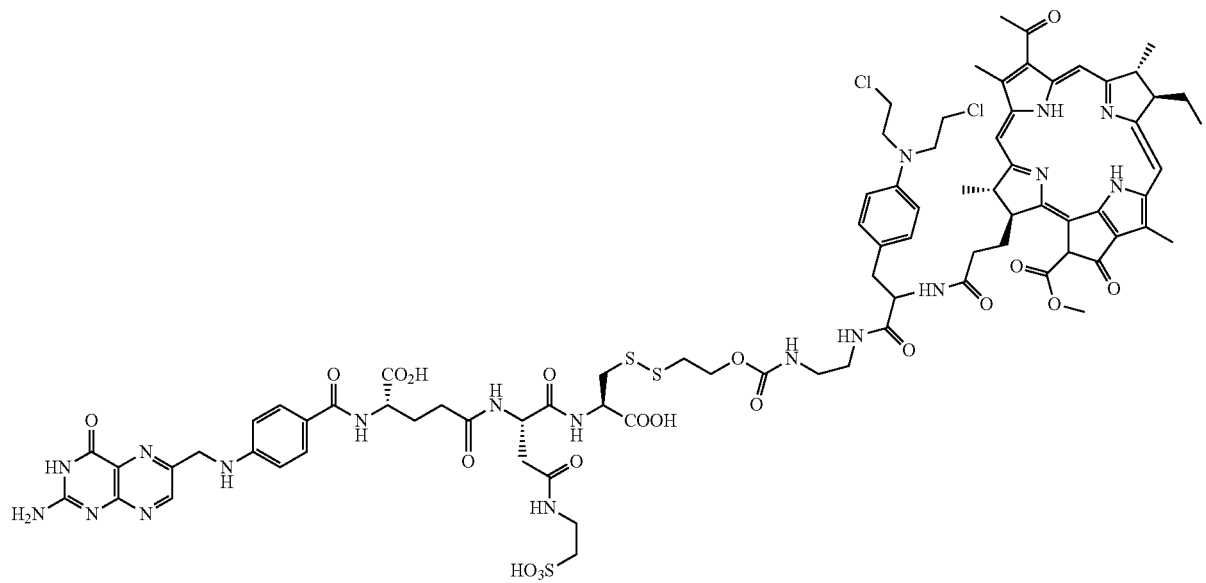
(112b)

-continued

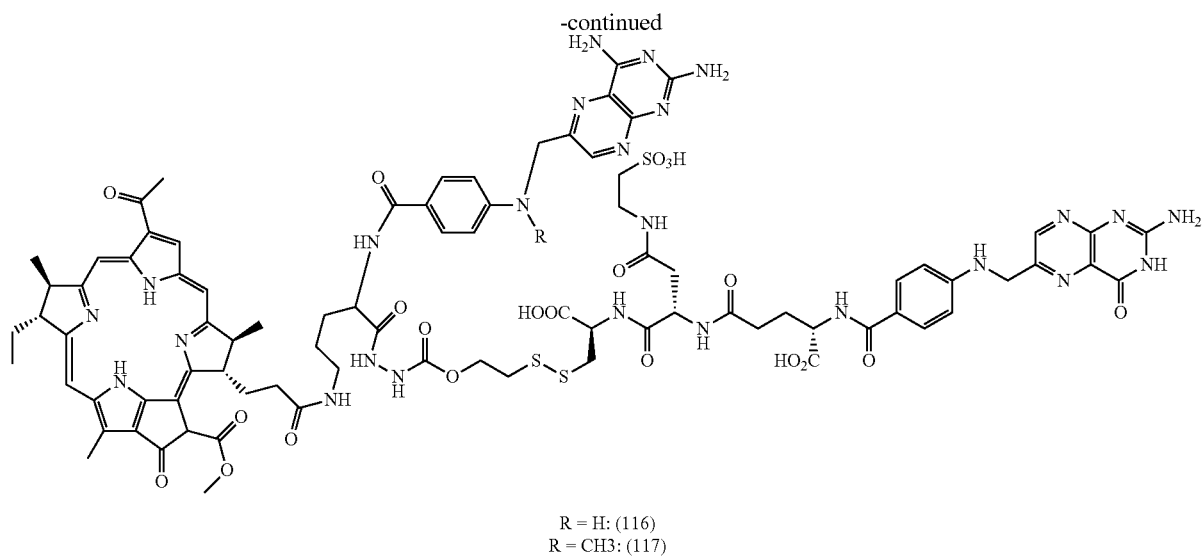

R = H: (116)
R = CH3: (117)

BRIEF DESCRIPTION OF SEVERAL VIEWS OF THE DRAWINGS

FIG. 1A-1E depict structures of non-targeted PDT agents (5, 6, 7 already approved and 2 & 4 are in clinical trials).

FIGS. 9A-9J depict structures of nucleus-targeted PDT agents.

FIG. 42 depicts an overlay of whole body fluorescence image over white light images after adjusting the threshold. KB tumor bearing mice injected with 10 nmol of 112a and image with IVIS imager (ex=745 nm, em=ICG, exposure time=1 s) 2 h after administering 112a.

DETAILED DESCRIPTION OF THE DISCLOSURE

Figure 1D:
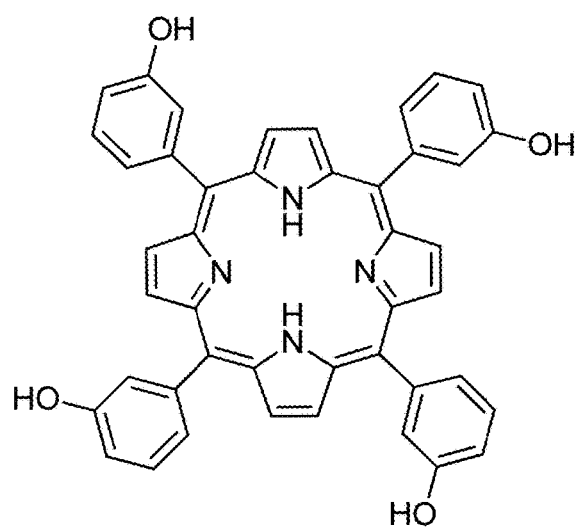
Figure 1E:
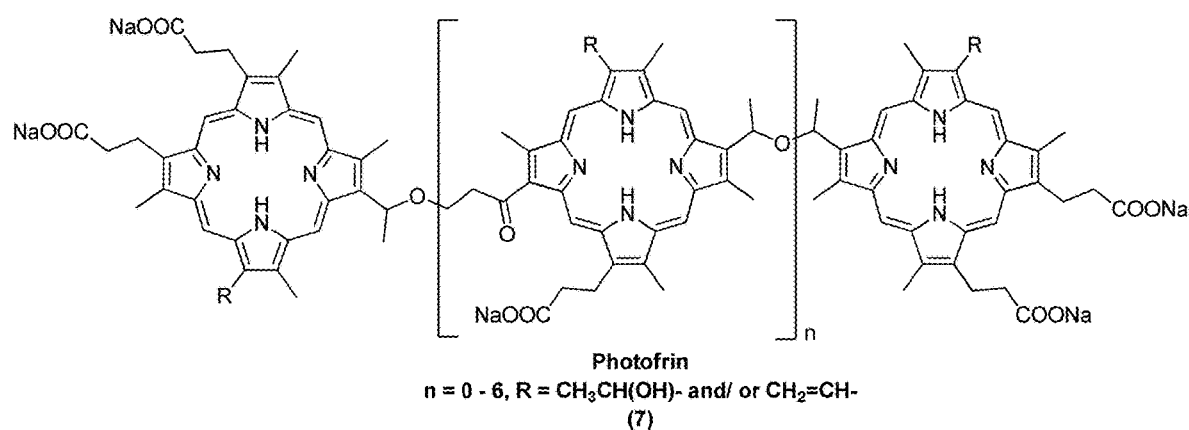

The present invention is directed to specific folate-targeted-organelle (mitochondrial or nucleus)-targeted-PDT agents that have high water solubility with better PK properties, and high PDT efficacy in both in cell culture and in animal models for folate receptor (FR)-positive cancers, tumor associated macrophages, and myeloid-derived suppressor cells. These compounds are non- or minimally toxic to healthy tissues, and with no detectable side effects. Moreover, these molecules have high fluorescence and are localized within the tumor within one hour of administration. No fluorescence was observed in other tissues leading to very high tumor-to-background (signal-to-noise) ratio. Therefore, these molecules can be used in imaging FR positive diseases, image-guided surgery, and in photodynamic therapy Surgery is one of the best therapies for all the solid tumors, such as prostate, ovarian, lung, breast, colon, and pancreatic cancer. While surgery is effective in 50% of patients with solid tumors in the US, chemo- and radiotherapy alone are effective in less than 5% of all cancer patients. Over 700,000 patients undergo cancer surgery every year in the US and 40% of surgical patients have a recurrence of locoregional disease within 5 years. Despite major advances in the oncology field over the last decade, there remain significant hurdles to overcome in the field. For example, it remains difficult to achieve complete resection of the primary tumor with negative margins, removal of the lymph nodes harboring metastatic cancer cells and identification of satellite disease. Achieving improvements in these three cases not only improves disease clearance but also guides decisions regarding postoperative chemotherapy and radiation.

In addition to image guided surgery, the present invention provides specific PS molecules that are effective for PDT. For use in oncology, there are three major mechanisms by which PDT contributes to destruction of a tumor. Firstly, the ROS generated by PDT can destroy malignant cells directly. Secondly, PDT can also damage the tumor-associated vasculature thereby inhibiting blood flow to the tumor and leading to tumor infarction. Lastly, PDT can redirect immune cells towards tumor cells and activate an immune response to tumor cells. A combination of all three mechanisms may be in play to produce a long-term cure of the disease.

Therefore, design and/or development of a useful PS that has precise PDT properties to make it amenable for use in intracellular localization is important. The PS should have an a good ratio between fluorescence and phototoxicity, a good ratio between type I and type II ROS production, high selectivity and specificity for diseased cells, and correct intracellular localization such as mitochondria or nucleus within the diseased cell. Moreover, ease synthesis in both small and large scale, stability during the synthesis and storage, availability of starting materials for low cost, water solubility, effectively diminish the diseased cell but nontoxic other tissues, long term safety are also important factors and features to consider before designing a PS.

Blue light penetrates least efficiently through tissue, whereas red and infrared radiation yields a deeper penetration (1-1.5 cm). The wavelength of light between 600 and 1200 nm is often called the optical window of tissue. However, only light up to approximately 800 nm has the sufficient energy to generate singlet oxygen ($^1O_2$), because longer wavelengths have insufficient energy to initiate a photodynamic reaction. Therefore, a PS excitation wavelength between 700-800 nm is preferred as it fits the optical window for tissue as well as having the appropriate wavelength for initiating a photodynamic reaction.

The choice of light source has to be based on absorption of PS (fluorescence excitation and action spectra), disease (location, size of lesions, accessibility, and tissue characteristics), cost, and size. The clinical efficacy of PDT will depend on complex dosimetry: total light dose, light exposure time, light delivery mode (single vs fractionated or even metronomic) and fluence rate.

Both lasers and incandescent light sources have been used in PDT and have shown similar efficacies. When compared to large and inefficient pumped dye lasers, diode lasers are smaller, more cost-effective, and are simple to install. They also have automated dosimetry and calibration features with a longer operational life. Light-emitting diodes (LEDs) are alternative light sources with relatively narrow spectral bandwidths and high fluence rates. Lasers can be coupled into fibers with diffusing tips to treat tumors in minimally invasive methods. Inflatable balloons covered on the inside with a strongly light scattering material and formed to fit an organ, are also commercially available. Hence, it is quite feasible to implant a light source in solid organs deep in the body under image guided approach.

The choice of optimal combinations of PSs, light sources, and treatment parameters is crucial for successful PDT. The extent of photodamage and cytotoxicity produced is also multifactorial and depends on the type of PS, its extracellular (biodistribution) and intracellular localization (organelle), the total dose administered, the total light exposure (amount of energy and time), light fluence rate, oxygen availability, and the time between the administration of the drug and light exposure.

In oncology, an ideal PS should have several characteristics including: being available in pure form with known chemical composition, high singlet oxygen quantum yield ($\phi\Delta$), strong absorption in the NIR region of the visible spectrum (700-800 nm) with a high extinction coefficient ($\varepsilon_{max}$=50,000-100,000 M$^{-1}$ cm$^{-1}$), low photo bleaching, effective accumulation in tumor tissue and possession of low dark toxicity for both photosensitizer and its metabolites, stability and solubility in circulation and in tissue fluids, easy delivery to a disease tissue site via injection or other methods, and it must be easily excreted from the body upon completion of treatment, and it must have an easily scalable synthesis for production for large quantities required for human use.

A wide array of photosensitizers has been reported in the literature, most belong to class of porphyrins, chlorophylls, and dyes (mostly near Infra-red dyes). Porphyrins and chlorophylls have higher absorption at longer wavelength (750-850 nm), high single oxygen quantum yield, low photo bleaching, and natural fluorescence making the porphyrin-based PS a perfect candidate for image-guided therapy.

Several photosensitizers such as Photofrin, Visudyne, Foscan, Allumera, Levulan, Metvix, Hexvix, Cysview, and Laserphyrin are commercially available for clinical use. Few photosensitizers such as Tookad, Antrin, Photochlor, Photosens, Photrex, Lumacan, Cevira, Visonac, BF-200, ALA, Amphinex, and Azadipyrromethenes are found at various stages in clinical trials or preclinical developments.

Despite the effectiveness of PDT, the traditional non-targeted photosensitizers have many drawbacks. These non-targeted photosensitizes are highly hydrophobic and have very poor water solubility. Therefore, formulating agents, such as cremophor, tween 20 and the like, have been used prior to administer into patients. However, these formulating agents are well known to be toxic to human. Furthermore, even after formulation into an administrable formulation, PS will take over 24 hours to localize into the tumor or diseased site with a longer lead time. Moreover, due to the poor water solubility, bio-availability of the drug in the tumor or diseased tissue is very low making the drug less effective. Due to the non-targeted nature of previously available PS, they are highly non-specific and accumulate into healthy tissues. Furthermore, while it is possible to avoid dark toxicity for internal organs such as liver (because medical practitioner will shine the light to disease tissues), phototoxicity in skin uptake is well established (prolonged sun sensitivity). Therefore, patients undergoing traditional PDT must avoid light exposure even from sunlight and remain in darkened environments for prolonged periods of time. On the other hand, accumulation of PS into healthy tissues leads to non-PDT related toxicities as well as causing severe side effects due to activation of immune response toward the healthy cells. Therefore, there is a need for new PS agents that are specific and targeted to a diseased cell.

The inventors evaluated 5 commercially available PS and found that they are water insoluble, less effective in cancer cells, had very high skin uptake in nude mice, took over 24 h to accumulate in the tumor of mice bearing tumor xenograft, had very low fluorescence (likely due to lack of accumulation of the PS molecule in the tumor), and were not able to be eliminated from the tumor xenograft on mice. Thus, there is a need for improved tumor-targeting approaches by targeting to tumor tissues and/or to organelle within the tumor cells.

Location of the PS localization within the cell (intracellular compartments such as mitochondria or nucleus) or organelle-targeted PS also is an important characteristic for the PS in PDT. The two most important organelles in drug delivery are the mitochondria and the nucleus. Mitochondria are the powerhouses of cells and key regulators of apoptosis and cell death. The nucleus possesses genetic material and controls the major biological activities of the cell.

Targeting mitochondria in a therapeutic approach has been recognized as a key factors in PDT as targeting these organelles can result in the shutdown of cellular metabolic activities. Mitochondria generate most of the cell's supply of adenosine triphosphate (ATP), used as a source of chemical energy. Mitochondria also have a very high content of oxygen. In addition to oxidative phosphorylation and metabolism, mitochondria play a central role in cell death, neoplasia, cell differentiation, innate immune system, oxygen and hypoxia sensing, and calcium metabolism.

There are a number of ways to deliver a PS to mitochondria. The first is to develop a PS that selectively accumulates within mitochondria. The second is to conjugate the PS to a molecule that binds selectively to a target within mitochondria. Thirdly, it is possible to use membrane potential and conjugate PS to a positive charge molecule and in this manner the PS is driven into mitochondria by the large negative potential inside the mitochondria.

Lipophilic cations and mitochondria-targeted peptides have both been developed to target drugs and bioactive molecules to mitochondria. Lipophilic cations such as triphenylphosphonium (TPP) derivatives are rapidly and extensively taken up by mitochondria in vivo driven by the large mitochondrial membrane potential. Use of these strategies can lead to a higher concentration of the targeted compound within mitochondria, thereby increasing potency and enabling a reduction in the dose of compound to be used, minimizing the extramitochondrial metabolism that can lead to inactivation, excretion or toxic side effects. Moreover, this approach also enables molecules that are poorly taken up by mitochondria for various reasons (e.g. hydrophobicity) to be directed to mitochondria in vivo. However, a major limitation of using lipophilic cations and mitochondria-targeted peptides is that they are not organ-specific and the compounds generally accumulate preferentially in tissues with high mitochondrial content leading to off-targeted toxicities.

Based on the above findings, the inventors have designed and developed, a library of mitochondrial-targeted PSs either by conjugating to a molecule that binds selectively to a target within mitochondria or by conjugating to a positively charge molecule (by taking the advantage of negative potential of mitochondria). The inventors found that most of mitochondrial-targeted PSs of the invention are very active when compared to PSs that are currently available in the clinic. The PS molecules identified herein were able to diminish cancer cells in culture (in vitro). However, the PS molecules were not tumor specific and took a long time to clear from healthy tissues. This poor tumor specificity is due to non-targeted nature of the drug to tumor cells. Moreover, the highly hydrophobic nature of the compounds leads to poor water solubility and poor pharmacokinetic properties thereby coursing poor bioavailability of the compound to the tumor cells. Therefore, photosensitizers that are modified with mitochondrial-targeting agents have to target to diseased tissues. Another issue in delivering agents to the mitochondria is their highly impermeable inner membranes.

Unlike the mitochondria, the membrane surrounding the nucleus—the nuclear envelope (NE), allows transport of biomolecules via nuclear pore complexes. Small drug molecules can, therefore, enter the nucleus and potentially cause DNA damage and cell cycle arrest. Therefore, the inventors also designed and developed a library of nuclear-targeted PSs by conjugating to DNA staining agents, DNA alkylating agents, etc. DNA-targeted PSs were active and were able to kill cancer cells in culture but again less active in animal models (mice bearing tumors). Poor solubility and poor tumor targeting may have been reasons for low efficacy in animal models.

In general, organelle-targeted therapy has the potential to improve PDT as targeted therapy, however, there are few more issue to overcome with this technology. The low concentrations of drugs that actually reach the intended target, low specificity for the intended tissue, slow clearance from the healthy tissue, low signal to background ratio, adverse effects due to non-specific uptake in healthy tissues, immune response to the administered material, poor water solubility, and fast degradation during the circulation, are a few of the hurdles to overcome before a PS can be used in PDT. In order for a photodynamic therapy to be useful it is important to overcome these drawbacks.

Thus, several criteria were considered in preparation of photodynamic therapy conjugates. Ease of synthesis and chemical stability were primary chemical attributes. Spectral properties, such as absorption and emission spectra and quantum yield, were considered. Several biological properties were evaluated, such as binding affinity in cell studies, whole body animal imaging using mice with tumors, and biodistribution. Specifically for biodistribution several aspects were considered including dead mice after 2 hours per oral distribution, live mice imaging and dose escalation. Finally, safety considerations were taken including Maximum Tolerance Dose (MTD), ImmunoHistoChemical (IHC) analysis, and general clinical pathology analysis.

The present disclosure provides of photodynamic therapy conjugates that are stable, fluoresce in the infrared range, and penetrate deep within targeted tissue to eradicate tumors in areas of tissue that express folate receptor. More specifically, the pteroyl conjugates are linked to the photodynamic agent which has been modified by a targeting agent through linking group and an amino acid. Even more specifically, it has been found that where the linking group is an amino acid, the linker is releasable.

An amino acid is defined as including an amine functional group linked to a carboxylic acid functional group, and a side-chain specific to each amino acid. An alpha amino acid is any compound of the general formula $R^5CH(NH_2)COOH$ (α-amino acid), wherein $R^5$ is selected from the group consisting of H or any known amino acid side chain.

A beta amino acid is defined as including an amine functional group linked at a beta carbon and a carboxylic acid functional group linked at the alpha carbon. A beta homo amino acid is defined as including an amine functional group linked at a beta carbon, a carboxylic acid functional group linked at the alpha carbon and a side-chain starting at either the alpha carbon or the beta carbon wherein the side-chain is bound to another amino acid.

Naturally occurring amino acids can be divided into the following four groups: (1) acidic amino acids, (2) basic amino acids, (3) neutral polar amino acids, and (4) neutral nonpolar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine.

Conserved substitution for an amino acid within a naturally occurring amino acid sequence can be selected from other members of the group to which the naturally occurring amino acid belongs. For example, the aliphatic side chains group of amino acids is glycine, alanine, valine, leucine, and isoleucine. Conserved substitution of naturally occurring amino acid valine includes use of glycine, alanine, leucine, or isoleucine.

The aliphatic-hydroxyl side chain group of amino acids is serine and threonine. The amide-containing side chain group of amino acids is asparagine and glutamine. The aromatic side chain group of amino acids is phenylalanine, tyrosine, and tryptophan. The basic side chain group of amino acids is lysine, arginine, and histidine. The sulfur-containing side chain group of amino acids having is cysteine and methionine. Examples of naturally conservative amino acids substitutions are: valine for leucine, serine for threonine, phenylalanine for tyrosine, lysine for arginine, cysteine for methionine, and asparagine for glutamine.

In preferred embodiments, it is shown herein that such photodynamic therapy conjugates specifically target to tumor cells within a tissue and result in a therapeutic destruction of the tumor cell. Thus, the compounds of the present disclosure lead to more economical imaging techniques. Moreover, there is an added advantaged that a lower dose of the compounds of the disclosure as compared to conventional imaging compounds minimizes the toxicity and other side effects that are attendant with administration of foreign materials to a body.

Furthermore, the use of such photodynamic therapy conjugates will lead to a more accurate and more effective resection of the primary tumor to produce negative margins, as well as accurate identification and removal of the lymph nodes harboring metastatic cancer cells and identification of satellite disease. Each of these advantages positively correlates with a better clinical outcome for the patient being treated.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can be used for deep tissue three dimensional imaging, targeted surgery, and methods for quantifying the amount of a target cell type in a biological sample.

Compounds

In an aspect the disclosure relates to compounds comprising the formula:

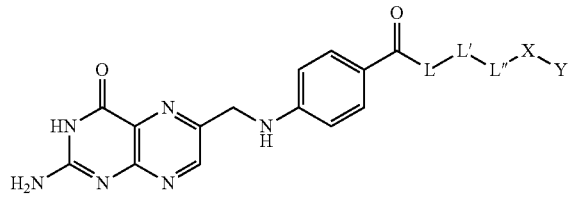

Formula (I)

or a pharmaceutically acceptable salt thereof, or isotopes thereof, wherein

L is an amino acid,

L' is a linker to improve pharmacokinetic (PK) properties,

L'' is a releasable linker to release an organelle-targeted photodynamic therapeutic (PDT) agent X is an organelle-targeting agent, and Y is a photodynamic therapeutic agent.

Non-limiting examples of such amino acids can include cysteine, methionine, threonine, serine, tyrosine, phenylalanine, tryptophan, histidine, lysine, ornithine, arginine, aspartic acid, glutamic acid, asparagine, and glutamine, or derivatives thereof.

In specific preferred embodiments, the compounds disclosed herein include a ligand that is effective to target the compound to a particular cell or tissue type and allow for imaging of that targeted cell or tissue. It is preferable the ligand is either pteroyl moiety or folate moiety and more preferable that ligand is pteroyl moiety. However, it is contemplated that the skilled person may use some other ligand to target the compounds to a particular cell surface protein or receptor protein of interest. In specific and preferred embodiments, the ligand comprises pteroyl:

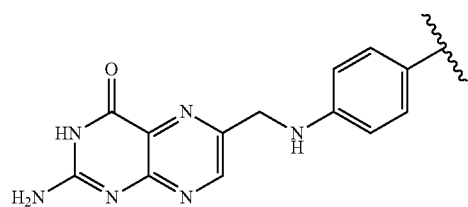 [SMILES: *c1ccc(NCc2cnc3nc(N)[nH]c(=O)c3n2)cc1]

Synthesis of Compounds

The compounds disclosed herein can be made using conventional methods known in the literature. See for example, the photodynamic therapy agents compounds were synthesized as previously reported.

However, in specific preferred embodiments, the present disclosure provides more efficient synthetic methods for generating the compounds described herein (i.e., Compounds of Formula I). For example, the compounds of the invention can be prepared in accordance to the general schemes outlined in each of Schemes 1-12 below.

Synthesis of Base Drugs

Scheme 1

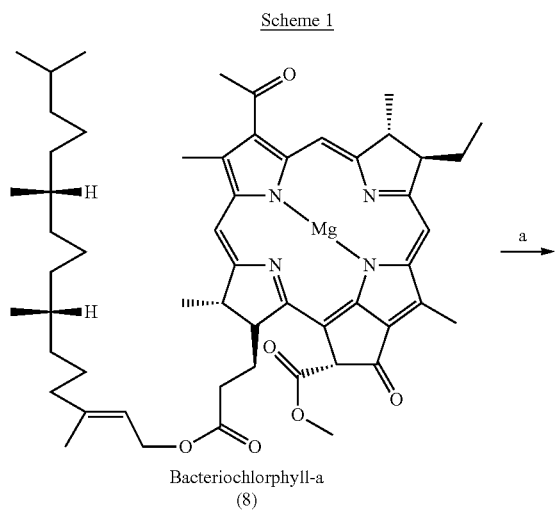

Bacteriochlorphyll-a
(8)

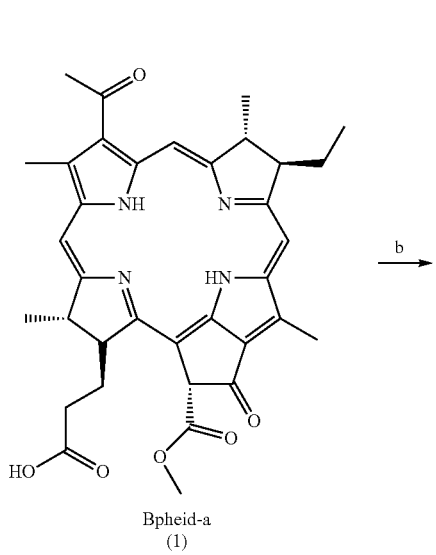

Bpheid-a
(1)

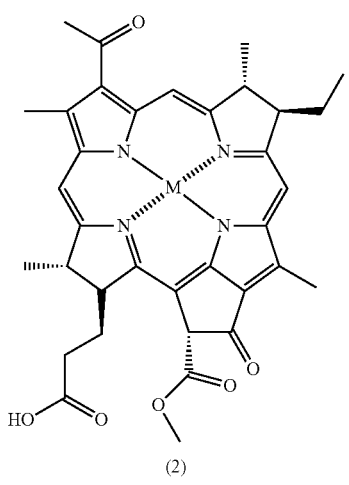

(2)

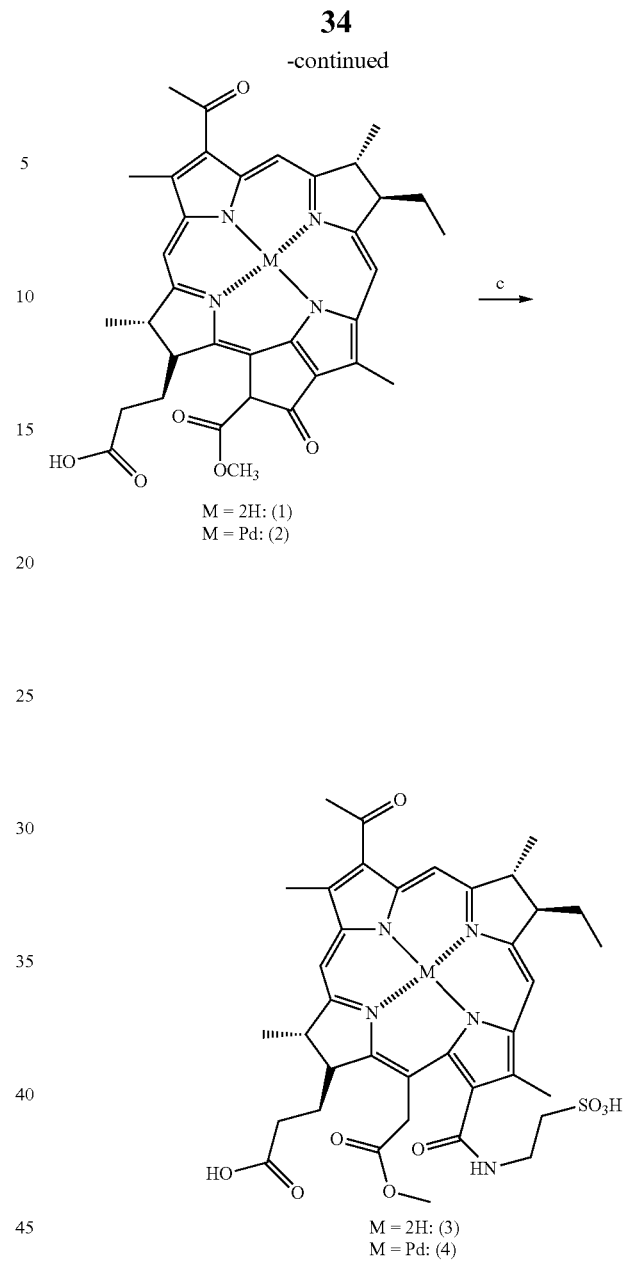

M = 2H: (1)
M = Pd: (2)

M = 2H: (3)
M = Pd: (4)

Reagents and conditions: (a) MeOH, under argon, 14 h, (b) TFA, under argon, 1 h (c) $NH_2CH_2CH_2SO_3H$, DMF, 12 h Scheme 1, illustrates a synthetic scheme previously used to generate non-targeted PDT agents that are currently in clinical trials. In one embodiment, bacteriochlorophyll-a is reacted with methanol under argon for 14 hours to yield Bpheid-a (Product (1)). The Bpheid-a is reacted with trifluoroacetic acid under argon to yield compound (2). Compound (2) is reacted with taurine and Dimethylformamide (DMF) for 12 hours to yield compounds (3) and (4). Compounds (5), (6) and (7) are commercially available.

However, it is notable that these commercially available PDT are general poorly water insoluble, are not effective in cancer cells, have a very high skin uptake in nude mice, and while they take a long time to accumulate in mice tumor models, they exhibit very low fluorescence and poor elimination. Thus the present inventors sought to overcome these drawbacks by preparing modified Bpheid compounds.

Synthesis of Selected Modified Bpheid-a Compounds

Scheme 2:

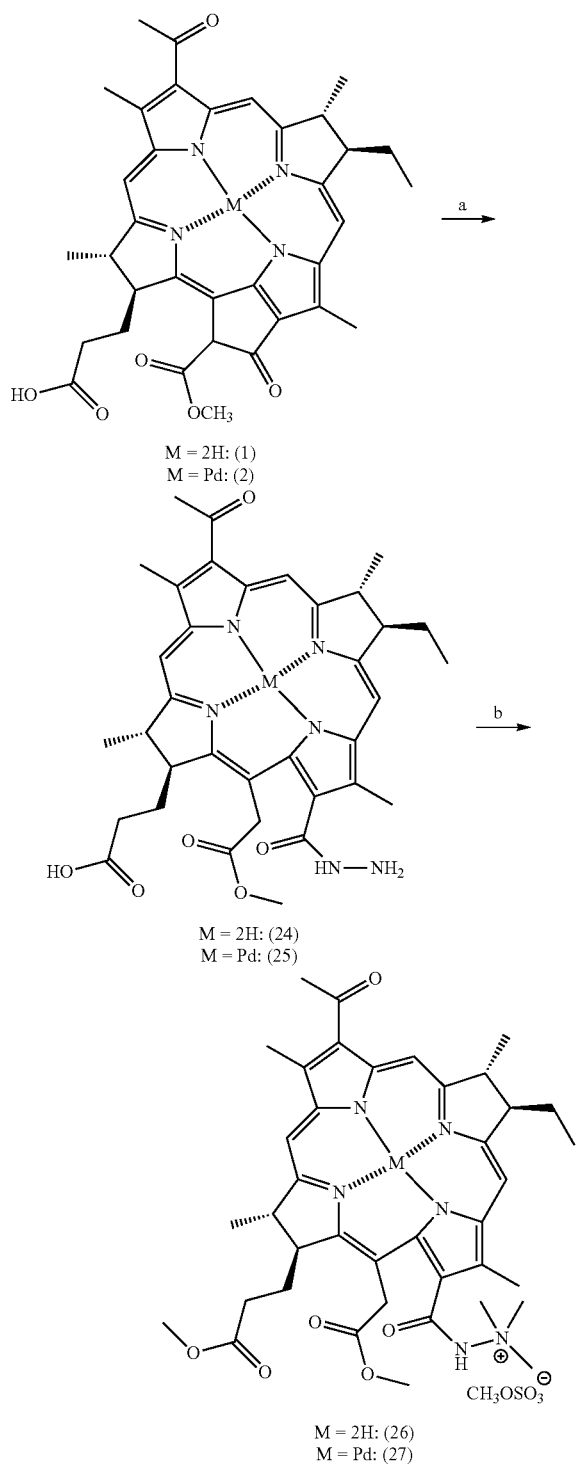

Reagents and conditions: (a) NH₂NH₂, DMF, under argon, 23° C., 3 h; (b) CH₃I, CHCl₃, 23° C., under argon, 4 days Scheme 2, illustrates a synthetic scheme used to generate modified Bpheid-a compounds. In one embodiment, compound (1) is reacted with Hydrazine and Dimethylformamide under argon at 23° C. for 3 hours. Resulting compound (24) is reacted with Methyl iodide and Chloroform at 23° C., under argon for 4 days to yield compound (26). In another embodiment, compound (2) is reacted with Hydrazine and Dimethylformamide under argon at 23° C. for 3 hours. Resulting compound (25) is reacted with Methyl iodide and Chloroform at 23° C., under argon for 4 days to yield compound (27).

Scheme 3:

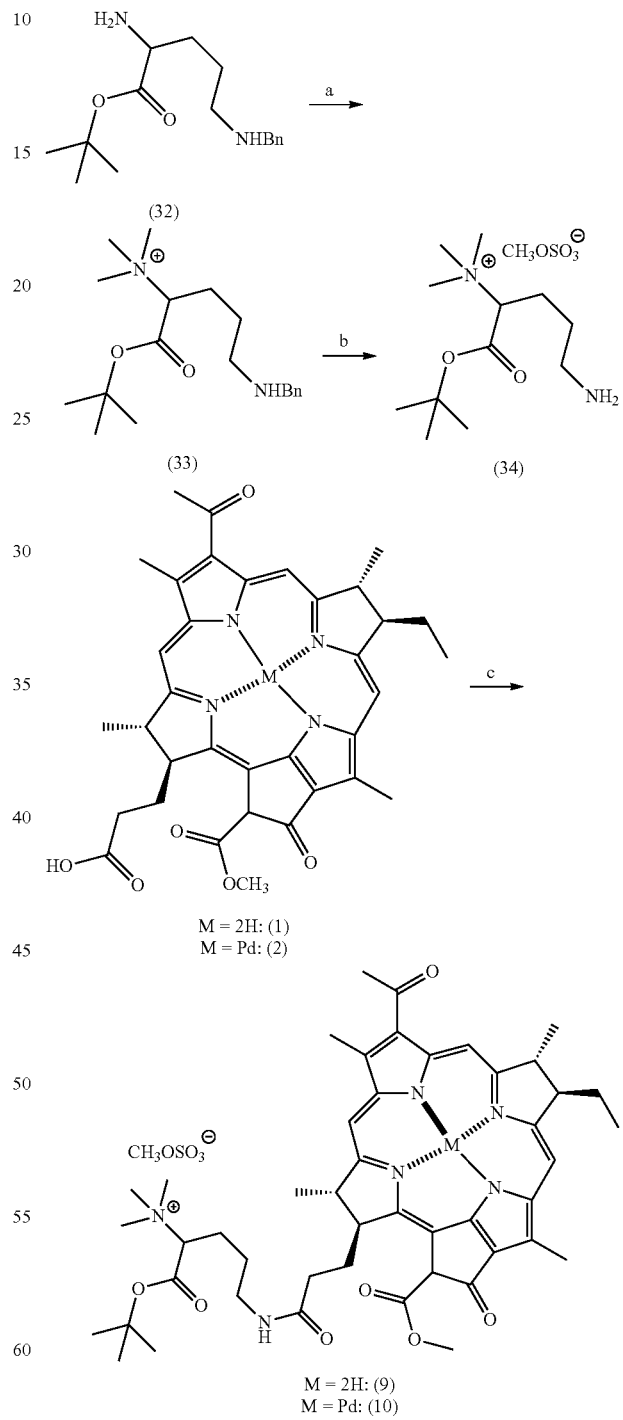

Reagents and conditions: (a) Dimethyl sulfate, MeOH/H₂O, 65° C., 2 h; (b) H₂/Pd, DCM, 23° C., 4 h; (c) (i) HATU, DIPEA, DMF, 23° C., 15 min, (ii) 34, DIPEA, DMF, 23° C., 2 h Scheme 3, illustrates another embodiment of a synthetic scheme used to generate modified Bpheid-a compounds. In one embodiment, compound (32) is reacted with Dimethyl sulfate, MeOH/H$_2$O, 65° C., 2 h. Resulting compound (33) is reacted with H$_2$/Pd, DCM, 23° C., 4 h to yield compound (34). Compound (1) is reacted with HATU, DIPEA, DMF, 23° C., 15 min, and then reacted with compound (34), DIPEA, DMF, 23° C., 2 h to yield compound (9). In another embodiment, compound (2) is reacted with HATU, DIPEA, DMF, 23° C., 15 min, and then reacted with compound (34), DIPEA, DMF, 23° C., 2 h to yield compound (10).

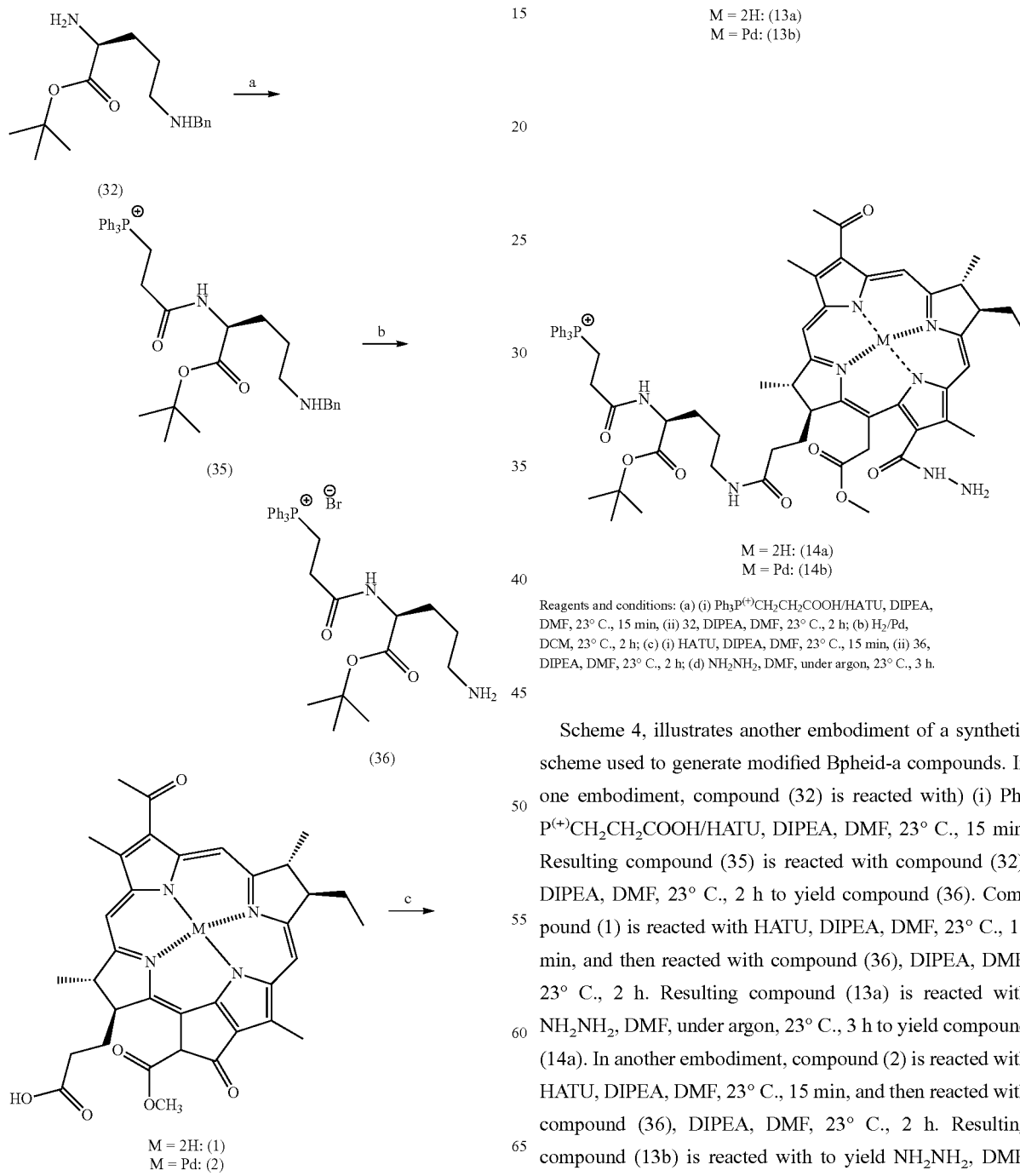

Reagents and conditions: (a) (i) Ph$_3$P$^{(+)}$CH$_2$CH$_2$COOH/HATU, DIPEA, DMF, 23° C., 15 min, (ii) 32, DIPEA, DMF, 23° C., 2 h; (b) H$_2$/Pd, DCM, 23° C., 2 h; (c) (i) HATU, DIPEA, DMF, 23° C., 15 min, (ii) 36, DIPEA, DMF, 23° C., 2 h; (d) NH$_2$NH$_2$, DMF, under argon, 23° C., 3 h.

Scheme 4, illustrates another embodiment of a synthetic scheme used to generate modified Bpheid-a compounds. In one embodiment, compound (32) is reacted with) (i) Ph$_3$P$^{(+)}$CH$_2$CH$_2$COOH/HATU, DIPEA, DMF, 23° C., 15 min. Resulting compound (35) is reacted with compound (32), DIPEA, DMF, 23° C., 2 h to yield compound (36). Compound (1) is reacted with HATU, DIPEA, DMF, 23° C., 15 min, and then reacted with compound (36), DIPEA, DMF, 23° C., 2 h. Resulting compound (13a) is reacted with NH$_2$NH$_2$, DMF, under argon, 23° C., 3 h to yield compound (14a). In another embodiment, compound (2) is reacted with HATU, DIPEA, DMF, 23° C., 15 min, and then reacted with compound (36), DIPEA, DMF, 23° C., 2 h. Resulting compound (13b) is reacted with to yield NH$_2$NH$_2$, DMF, under argon, 23° C., 3 h to yield compound (14b)

Scheme 5:

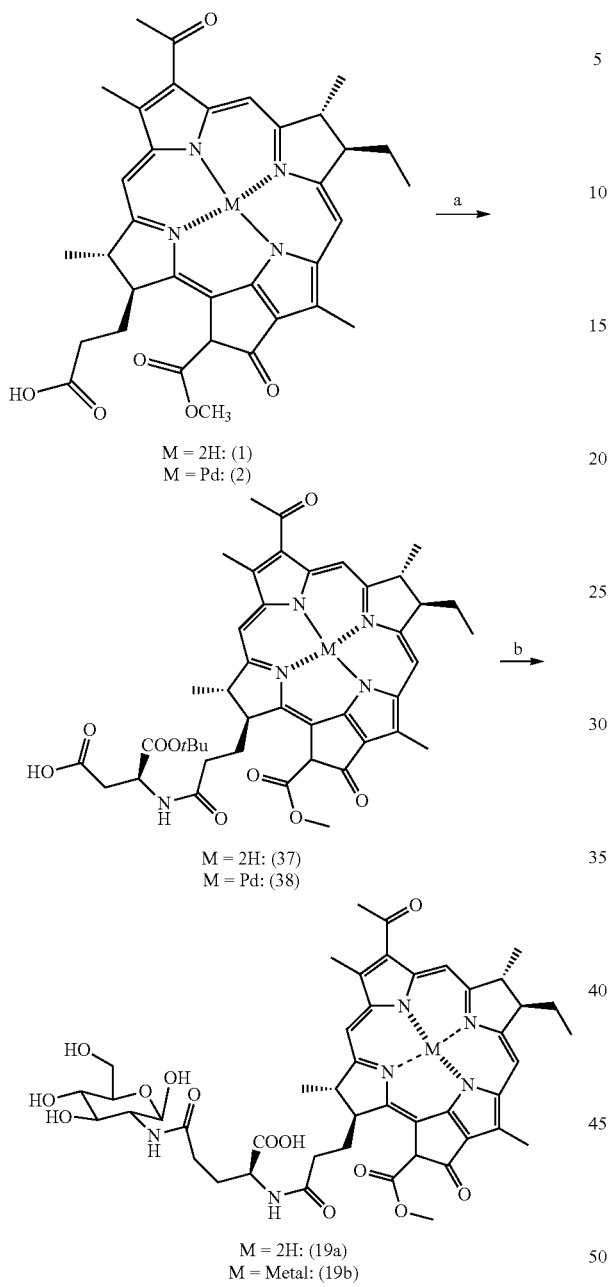

M = 2H: (1)
M = Pd: (2)

M = 2H: (37)
M = Pd: (38)

M = 2H: (19a)
M = Metal: (19b)

Reagents and conditions: (a) (i) HATU, DIPEA, DMF, 23° C., 15 min; (ii) NH$_2$-Glu-(O$^t$Bu)—OH, DIPEA, DMF, 23° C., 2 h; (b) (i) HATU, DIPEA, DMF, 23° C., 15 min; (ii) glucosamine, DIPEA, DMF, 23° C., 2 h; (iii) TFA, 23° C., 1 h Scheme 5, illustrates another embodiment of a synthetic scheme used to generate modified Bpheid-a compounds. In one embodiment, compound (1) is reacted with HATU, DIPEA, DMF, 23° C., 15 min; (ii) NH$_2$-Glu-(O$^t$Bu)-OH, DIPEA, DMF, 23° C., 2 h. Resulting compound (37) is reacted with) (i) HATU, DIPEA, DMF, 23° C., 15 min; (ii) glucosamine, DIPEA, DMF, 23° C., 2 h; (iii) TFA, 23° C., 1 h to yield compound (19a). In another embodiment compound (2) is reacted with HATU, DIPEA, DMF, 23° C., 15 min; (ii) NH$_2$-Glu-(O$^t$Bu)-OH, DIPEA, DMF, 23° C., 2 h. Resulting compound (38) is reacted with (i) HATU, DIPEA, DMF, 23° C., 15 min; (ii) glucosamine, DIPEA, DMF, 23° C., 2 h; (iii) TFA, 23° C., 1 h to yield compound (19b).

The present invention relates to production of PDT agents that specifically target to the nucleus.

(a) Synthesis of Selected Nucleus-Targeted PDT Agents

Scheme 6:

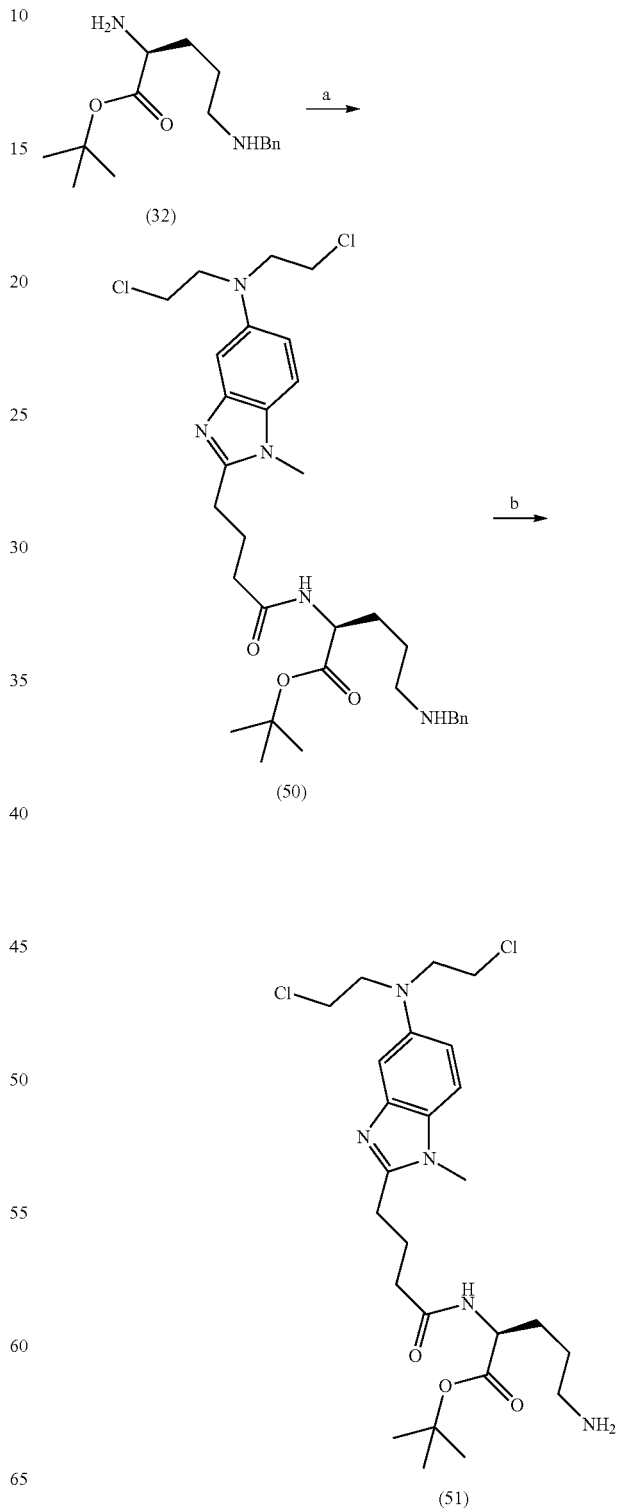

(32)

(50)

(51)

-continued

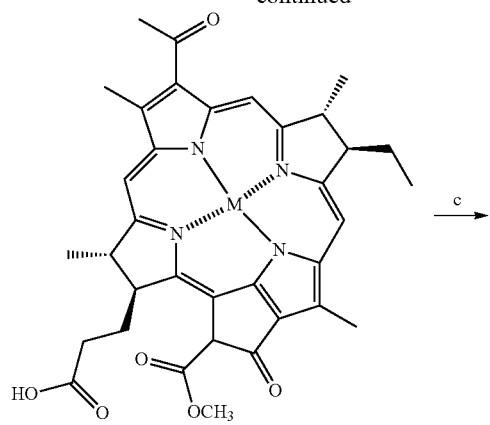

M = 2H: (1)
M = Pd: (2)

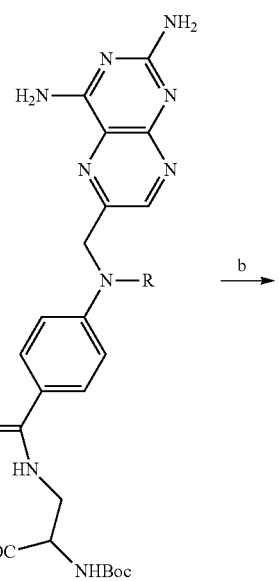

M = 2H: (42a)
M = Metal: (42b)

Reagents and conditions: (a) (i) Bendamustine/HATU, DIPEA, DMF, 23° C., 15 min,
(ii) 32, DIPEA, DMF, 23° C., 2 h; (b) H₂/Pd, DCM, 23° C., 2 h; (c) (i) HATU,
DIPEA, DMF, 23° C., 15 min, (ii) 51, DIPEA, DMF, 23° C., 2 h; (iii) TFA,
23° C., 1 h Scheme 6, illustrates an embodiment of a synthetic scheme used to generate nucleus-targeted PDT agents. In one embodiment, compound (32) is reacted with (i) Bendamustine/HATU, DIPEA, DMF, 23° C., 15 min, (ii) 32, DIPEA, DMF, 23° C., 2 h. Resulting compound (50) is reacted with H₂/Pd, DCM, 23° C., 2 hours to yield compound (51). Compound (1) is reacted with i) HATU, DIPEA, DMF, 23° C., 15 min, (ii) 51, DIPEA, DMF, 23° C., 2 h; (iii) TFA, 23° C., 1 h to yield compound (42a). In another embodiment compound (2) is reacted with i) HATU, DIPEA, DMF, 23° C., 15 min, (ii) 51, DIPEA, DMF, 23° C., 2 h; (iii) TFA, 23° C., 1 h to yield compound (42b).

Scheme 7:

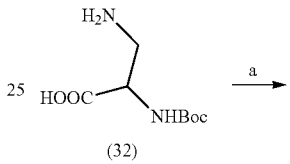

(32)

R = H: (52)
R = Me: (53)

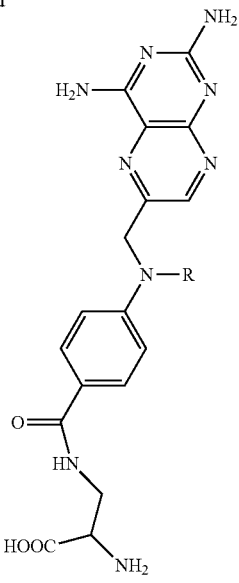

R = H: (54)
R = Me: (55)

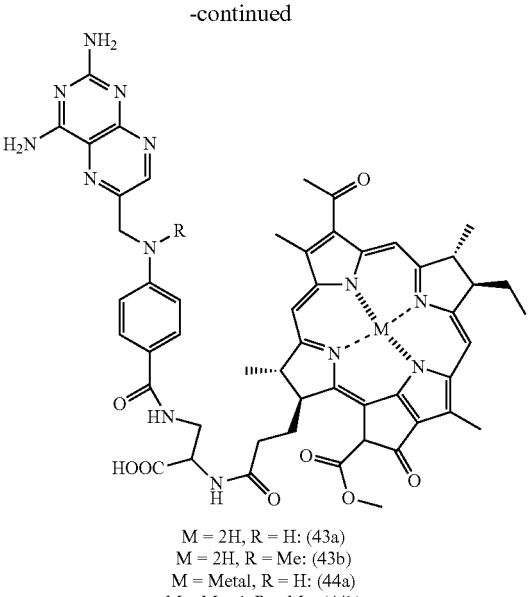

M = 2H, R = H: (43a)
M = 2H, R = Me: (43b)
M = Metal, R = H: (44a)
M = Metal, R = Me: (44b)

Reagents and conditions: (a) (i) $N^{10}$-Methyl-4-amino-4-deoxypteroic acid (R = CH$_3$) or 4-Amino-4-deoxypteroic acid (R = H)/HATU, DIPEA, DMF, 23° C., 15 min, (ii) 32, DIPEA, DMF, 23° C., 2 h; (b) TFA, 23° C., 1 h; (c) (i) HATU, DIPEA, DMF, 23° C., 15 min, (ii) 54 or 55, DIPEA, DMF, 23° C., 2 h Scheme 7, illustrates an embodiment of a synthetic scheme used to generate nucleus-targeted PDT agents. In one embodiment, compound (32) is reacted with 4-Amino-4-deoxypteroic acid (R=H)/HATU, DIPEA, DMF, 23° C., for 15 min. Resulting compound (52) is reacted with TFA at 23° C. for 1 h to yield compound (54).

In another embodiment, compound (32) is reacted with $N^{10}$-Methyl-4-amino-4-deoxypteroic acid (R=CH$_3$), DIPEA, DMF, 23° C., for 15 min. Resulting compound (53) is reacted with TFA at 23° C. for 1 h to yield compound (55).

In one embodiment Compound (1) is reacted with HATU, DIPEA, DMF, 23° C., 15 min and then with compound (54), DIPEA, DMF, 23° C., 2 h to yield compounds (43a). In another embodiment compound (1) is reacted with HATU, DIPEA, DMF, 23° C., 15 min and then with compound (54), DIPEA, DMF, 23° C., 2 h to yield compounds (43b).

In one embodiment Compound (2) is reacted with HATU, DIPEA, DMF, 23° C., 15 min and then with compound (54), DIPEA, DMF, 23° C., 2 h to yield compounds (44a). In another embodiment compound (1) is reacted with HATU, DIPEA, DMF, 23° C., 15 min and then with compound (54), DIPEA, DMF, 23° C., 2 h to yield compounds (44b).

Scheme 8:

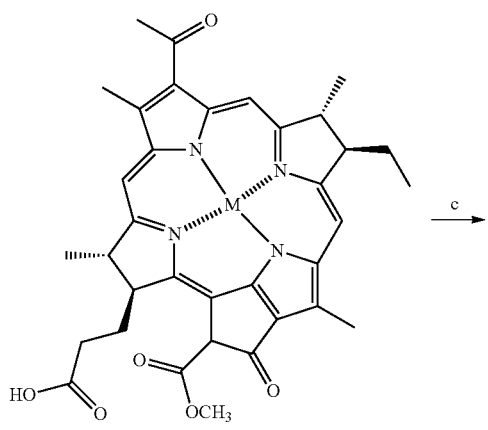

M = 2H: (1)
M = Pd: (2)

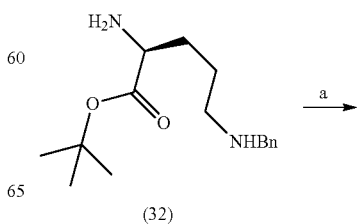

(32)

-continued

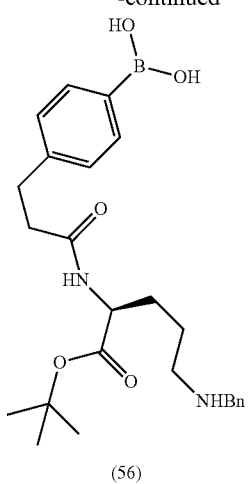

(56)

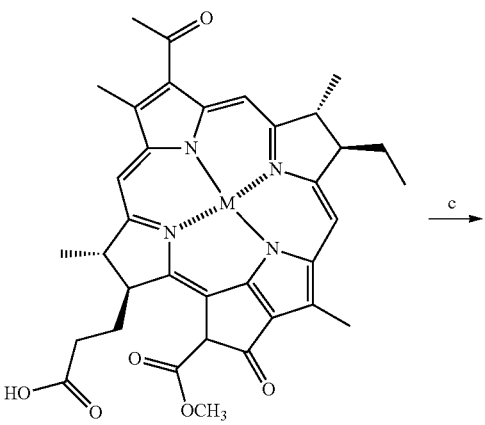

M = 2H: (1)
M = Pd: (2)

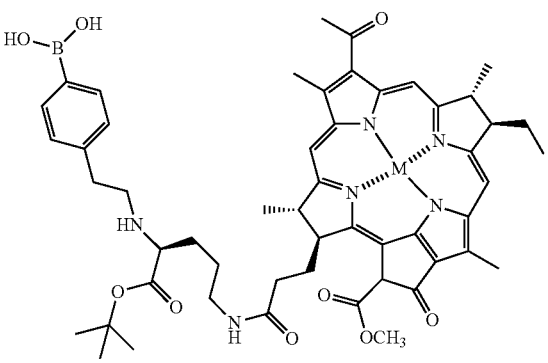

M = 2H: (49a)
M = Metal: (49b)

Reagents and conditions: (a) (i) 3-(4-boronophenyl)-propanoic acid/HATU, DIPEA, DMF, 23° C., 15 min, (ii) 32, DIPEA, DMF, 23° C., 2 h; (b) H$_2$/Pd, DCM, 23° C., 2 h; (c) (i) HATU, DIPEA, DMF, 23° C., 15 min, (ii) 57, DIPEA, DMF, 23° C., 2 h Scheme 8, illustrates an embodiment of a synthetic scheme used to generate nucleus-targeted PDT agents. In one embodiment, compound (32) is reacted with 3-(4-boronophenyl)-propanoic acid/HATU, DIPEA, DMF, 23° C., 15 min and then, DIPEA, DMF, 23° C., 2 h. Resulting compound (56) is reacted with) H$_2$/Pd, DCM, 23° C., 2 h to yield compound (57). Compound (1) is reacted with HATU, DIPEA, DMF, 23° C., 15 min, and then compound (57), DIPEA, DMF, 23° C., 2 h to yield compound (49a).

In another embodiment compound (2) is reacted with HATU, DIPEA, DMF, 23° C., 15 min, and then compound (57), DIPEA, DMF, 23° C., 2 h to yield compound (49b).

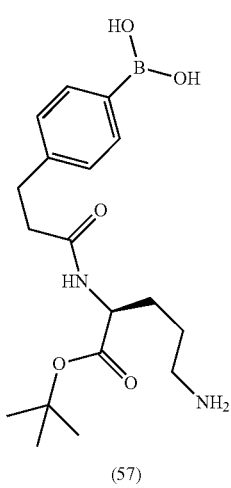

(57)

Scheme 9: Synthesis of folate-Asp(SO₃H)-Cys-SH linker.
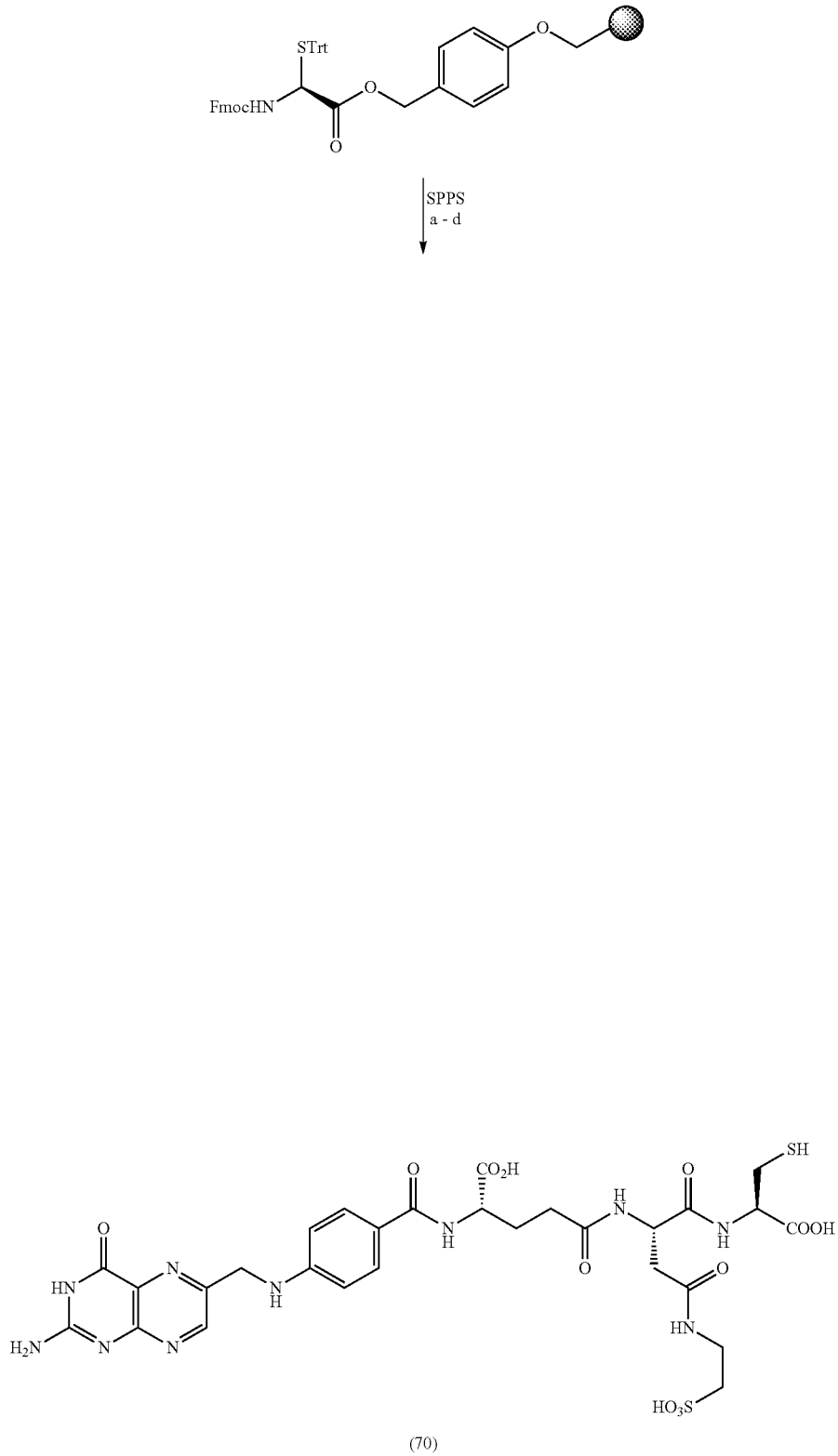
(70)
Reagents and conditions: (a) (i) 20% piperidine/DMF, r.t., 10 min; (ii) Fmoc-Asp(SO₃H)—OH, HATU, DMF/DIPEA, 2 h; b) (i) 20% piperidine/DMF, r.t., 10 min; (ii) Fmoc-Glu(O$^t$Bu)—OH, HATU, DMF/DIPEA, 2 h; c) (i) 20% piperidine/DMF, r.t., 10 min; (ii) N$^{10}$—TFA-Pteroic acid, HATU, DMF/DIPEA, 2 h; d) TFA:H₂O:TIPS:EDTA (92.5:2.5:2.5:2.5), 1 h.

Scheme 10:
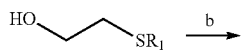
R₁ = SPy: (72)  
R₁ = H: (71)  ⎫a
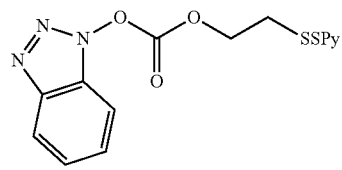
(73)
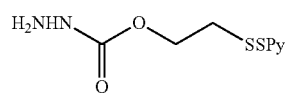
(74)
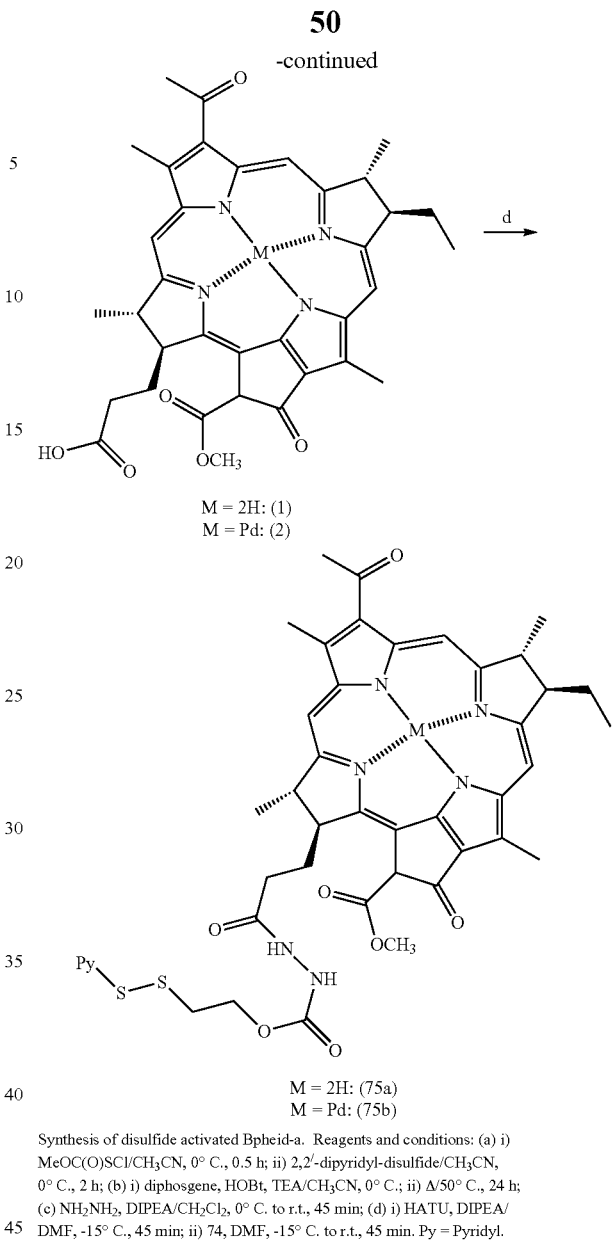
M = 2H: (1)  
M = Pd: (2)
M = 2H: (75a)  
M = Pd: (75b)
Synthesis of disulfide activated Bpheid-a. Reagents and conditions: (a) i) MeOC(O)SCl/CH₃CN, 0° C., 0.5 h; ii) 2,2′-dipyridyl-disulfide/CH₃CN, 0° C., 2 h; (b) i) diphosgene, HOBt, TEA/CH₃CN, 0° C.; ii) Δ/50° C., 24 h; (c) NH₂NH₂, DIPEA/CH₂Cl₂, 0° C. to r.t., 45 min; (d) i) HATU, DIPEA/ DMF, -15° C., 45 min; ii) 74, DMF, -15° C. to r.t., 45 min. Py = Pyridyl.
Scheme 11a:
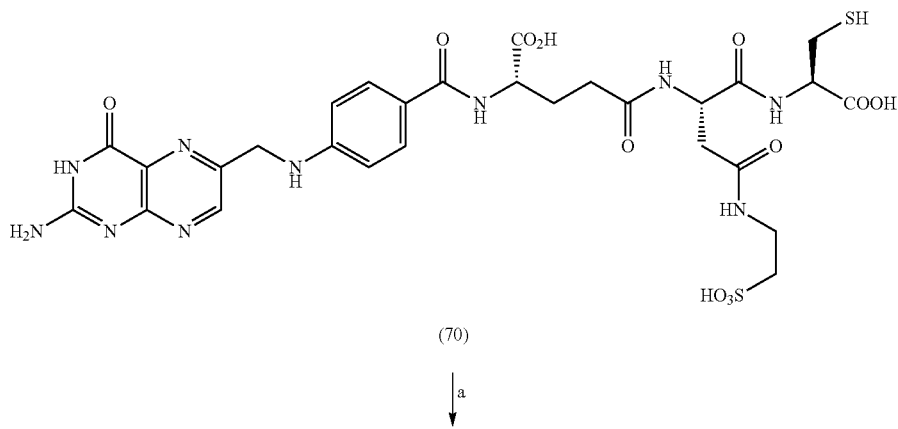
(70)
↓ a -continued

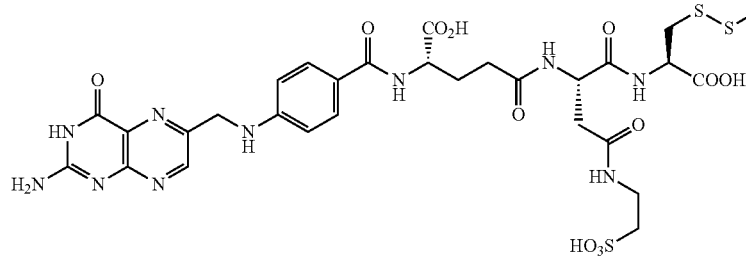

(a) Reagents and conditions: (a) i) H$_2$O/NaHCO$_3$ (pH = 7 ± 0.2), argon, r.t.; ii) 75a or b/DMSO, argon, r.t., 15 min.

Methods of Use

The compounds of the present invention will be used in photodynamic therapy. The term "photodynamic therapy (PDT, photochemotherapy)" used herein refers to a therapy of damaging and destroying a lesion by the existence of a photosensitizer (PDT agent, photodynamic therapeutic agents) and a light ray that can excite the photosensitizer. In a PDT in which a photosensitizer is administered, followed by irradiation with a light ray, cells are damaged by reactive oxygen species (ROS). In a photodynamic therapy, heat is not generated, and localized treatment is enabled. Therefore, since heat denaturation of proteins does not occur, a target site and tissues surrounding the target site are not necrotized, and a target site alone can be reliably damaged. When only a light ray such as a laser beam is used without using a photosensitizer, heat cannot be generated at a site irradiated with a laser beam. Therefore, surrounding tissues cannot be damaged. Therefore, the method using photodynamic therapy of the present invention also have excellent effects as compared with a method or an apparatus for irradiation with a laser alone without using a photosensitizer.

In specific embodiments, the present disclosure relates to methods that incorporate at least one of the compounds disclosed herein (e.g., of Formula I, I(a), I(b), I(c), and/or I(d)) can be used to specifically and sensitively eradicate and/or resect tumors within a tissue using minimally invasive procedures. In this manner, the compounds of the present disclosure may be useful in the treatment of any disorder of a biological tissue that expresses a folate receptor and has a disease that overexpresses the receptor. In some embodiments the disease is selected from the group consisting of cancer, neurodegenerative diseases, respiratory diseases, metabolic diseases, inherited diseases, bone diseases, skin diseases, and environmental diseases. The compounds of the present invention are particularly useful for treating cancer.

The disclosed compounds and methods of the present invention may be used in imaging of target tissue or tumors, to treat any number of cancers or tumors or both. The disclosed compounds are suited for the use in photodynamic treatment of deep tissue tumors, including, but not limited to ovarian cancer, lung cancer, head and neck cancer, pancreatic cancer, mesenteric cancer, prostate cancer, kidney cancer gastric cancer, rectal cancer, stomach cancer, bladder cancer, leukemia (including hairy cell leukemia and chronic myelogenous leukemia), breast cancer, melanoma, malignant melanoma, renal cell carcinoma, colorectal carcinoma, colon cancer, hepatic metastases of advanced colorectal carcinoma, lymphomas (including glandular lymphoma), malignant lymphoma, Kaposi's sarcoma, non-melanoma skin cancer (including squamous cell carcinoma and basal cell carcinoma), hemangioma multiple myeloma, and glioma. The disclosed compounds are suited for the treatment of several types of mammalian tumors, including but not limited to, solid tumors, cutaneous tumors and solid breast tumor growth.

The dose of the disclosed compounds may be optimized by the skilled person depending on factors such as, but not limited to, the photodynamic therapy compound chosen, the nature of the therapeutic protocol, the individual subject, and the judgment of the skilled practitioner.

Accordingly, in disclosure diagnostic methods, the diseased tissue (and bound or taken-up targeting construct) is "exposed" to the excitation light (e.g, by surgically created opening or endoscopic delivery of the light to an interior location. The disclosed method is particularly suited to in vivo detection of diseased tissue located at an interior site in the subject, such as within a natural body cavity or a surgically created opening, where the diseased tissue is "in plain view" (i.e., exposed to the human eye) to facilitate a procedure of biopsy or surgical excision of the area that has been highlighted by uptake of the compounds of the present disclosure. As the precise location and/or surface area of the tumor tissue are readily determined by the uptake of the compounds of the present disclosure, the methods employing the compounds of the present disclosure provide a valuable guide to the surgeon, who needs to "see" in real time exact outlines, size, etc. of the mass to be resected using the photodynamic therapeutic agent and laser source (low energy can be used during the surgery and for imaging).

Following the surgery, residual tumor cells can be diminished by laser source using high energy.

Thus, in specific embodiments, the present disclosure entails that diseased-targeted and organelle-targeted PDT agents with high solubility and better PK properties can be used for image-guided surgery followed by photodynamic treatment.

In like manner, the compounds of the present disclosure are used to identify a target cell type in a biological sample by contacting the biological sample with such compounds for a time and under conditions that allow for binding of the compound to at least one cell of the target cell type. The bound compound is then internalized via receptor mediated endocytosis and releases the organelle-targeted PDT agent in the endosomes of the diseased cell. Then depends on the guided molecule attached to PDT agent, organelle-targeted PDT agent will be carried to either mitochondria or nucleus of the diseased cell. In this case, most preferably, the targeted diseased cell type is a tumor cell or a lymph node to which a tumor cell has spread, or tumor associated macrophages or myeloid-derived suppressor cells.

In practice, the skilled person would administer a compound of the present disclosure either alone or as part of a cocktail of targeting detectable moieties and allow these compounds and targeting moieties to bind to and/or be taken up by any targeting tissue that may be present at the site under investigation and then provide a supply of the light source. Typically, the compounds of the present disclosure and any additional targeting moieties will be administered prior to surgery for a time and in compositions that allow the fluorescent compounds of the present disclosure as well as any additional fluorescent constructs to be taken up by the target tissue.

Those of skill in the art will be able to devise combinations of successively administered fluorescing targeting constructs, each of which specifically binds to the target site. It is preferable that all of the fluorescing targeting constructs used in such cocktails to identify the target tissue comprise fluorophores that fluoresce within the same wavelength band or at the same wave length as does the compound of the present disclosure (e.g. a fluorescing sensitive to near infrared wavelength of light in the compounds of the present disclosure) to minimize the number of different light sources that need to be employed to excite simultaneous fluorescence from all of the different targeting constructs used in practice of the disclosure method. However, it is contemplated that the additional targeting moieties other than the compounds of the present disclosure may fluorescence in response to the irradiating light at a different color (i.e., has a different wavelength) than that from the florescent compounds of the present disclosure. The difference in the colors of the fluorescence emanating from the compounds of the present disclosure and those of the additional targeting compounds may aid the observer in determining the location and size of the diseased tissue. In some examples, it may be desirable to include fluorophores in targeting constructs targeted to target normal tissue and the compounds of the present disclosure to target diseased tissue such that the contrast between the diseased tissue and normal tissue is further enhanced to further aid the observer in determining the location and size of the target tissue. The use of such additional fluorophores and targeting agents in addition to the compounds of the present disclosure provides the advantage that any natural fluorescence emanating from normal tissue is obscured by the fluorescence emanating from fluorophore(s) in supplemental targeting constructs targeted to the normal tissue in the body part. The greater the difference in color between the fluorescence emanating from normal and target tissue, the easier it is for the observer to visualize the outlines and size of the target tissue. For instance, targeting a fluorescing targeting construct comprising a fluorophore producing infrared light from the compounds of the present disclosure to the target tissue (i.e., abnormal tissue) and a fluorophore producing green light to healthy tissue aids the observer in distinguishing the target tissue from the normal tissue. Those of skill in the art can readily select a combination of fluorophores that present a distinct visual color contrast.

A particularly useful combination would be to use the PDT of the present invention in combination with image guided surgery using OTL38. Methods and compositions for use of OTL38 are disclosed in e.g., U.S. Pat. No. 9,061,057, which is incorporated herein by reference.

The spectrum of light used in the practice of the disclosure method is selected to contain at least one wavelength that corresponds to the predominate excitation wavelength of the targeting construct, or of a biologically compatible fluorescing moiety contained within the targeting construct. Generally the excitation light used in practice of the disclosure method comprises at least one excitation wavelength of light in the near infrared wavelength range from about 600 nm to about 850 nm However, when a combination of targeting ligands that fluoresce at different wavelengths is used in practice of the disclosure, the spectrum of the excitation light must be broad enough to provide at least one excitation wavelength for each of the fluorophores used. For example, it is particularly beneficial when fluorophores of different colors are selected to distinguish normal from diseased tissue, that the excitation spectrum of the light(s) include excitation wavelengths for the fluorophores targeted to normal and target tissue.

As noted herein the compounds of the present disclosure are specifically targeted to the folate receptor by way of pteroyl or folate ligand being part of the compounds of the present disclosure. In embodiments where an additional targeting moiety is used, the targeting construct of such an additional targeting moiety is selected to bind to and/or be taken up specifically by the target tissue of interest, for example to an antigen or other surface feature contained on or within a cell that characterizes a disease or abnormal state in the target tissue. As in other diagnostic assays, it is desirable for the targeting construct to bind to or be taken up by the target tissue selectively or to an antigen associated with the disease or abnormal state; however, targeting constructs containing ligand moieties that also bind to or are taken up by healthy tissue or cell structures can be used in the practice of the disclosure method so long as the concentration of the antigen in the target tissue or the affinity of the targeting construct for the target tissue is sufficiently greater than for healthy tissue in the field of vision so that a fluorescent image representing the target tissue can be clearly visualized as distinct from any fluorescence coming from healthy tissue or structures in the field of vision.

For example, colon cancer is often characterized by the presence of carcinoembryonic antigen (CEA), yet this antigen is also associated with certain tissues in healthy individuals. However, the concentration of CEA in cancerous colon tissue is often greater than is found in healthy tissue, so an anti-CEA antibody could be used as a ligand moiety in the practice of the disclosure. In another example, deoxyglucose is taken up and utilized by healthy tissue to varying degrees, yet its metabolism in healthy tissues, except for certain known organs, such as the heart, is substantially lower than in tumor. The known pattern of deoxyglucose consumption in the body can therefore be used to aid in determination of those areas wherein unexpectedly high uptake of deoxyglucose signals the presence of tumor cells.

The disease or abnormal state detected by the disclosure method can be any type characterized by the presence of a known target tissue for which a specific binding ligand is known. For example, various heart conditions are characterized by production of necrotic or ischemic tissue or production of atherosclerotic tissue for which specific binding ligands are known. As another illustrative example, breast cancer is characterized by the production of cancerous tissue identified by monoclonal antibodies to CA15-3, CA19-9, CEA, or HER2/neu. It is contemplated that the target tissue may be characterized by cells that produce either a surface antigen for which a binding ligand is known, or an intracellular marker (i.e. antigen), since many targeting constructs penetrate the cell membrane. Representative disease states that can be identified using the disclosure method include such various conditions as different types of tumors and the like. As used herein "abnormal" tissue includes precancerous conditions, necrotic or ischemic tissue, and tissue associated with connective tissue diseases, and autoimmune disorders, and the like. Further, examples of the types of target tissue suitable for diagnosis or examination using the disclosure method include cardiac, breast, ovarian, uterine, lung, endothelial, vascular, gastrointestinal, colorectal, prostatic tissue, endocrine tissue, and the like, as well as combinations of any two or more thereof.

Simply by way of example, antigens for some common malignancies and the body locations in which they are commonly found are known to those of skill in the art, and targeting ligands, such as antibodies or for these antigens or indeed ligands where the antigens are receptors are known in the art. For example, CEA (carcinoembryonic antigen) is commonly found in tumors from the colon, breast and lung; PSA (prostate specific antigen, or sometimes referred to as prostate specific membrane antigen (PSMA)) is specific for prostate cancer; CA-125 is commonly found in tumors of ovarian cancer origin, CA 15-3, CA19-9, MUC-1, Estrogen receptor, progesterone receptor and HER2/neu are commonly found in breast cancer tumors, alpha-feto protein is found in both testicular cancer and hepatic cancer tumors, beta-human chorionic gonadotropin is found testicular cancer and choriocarcinoma, both estrogen receptor and progesterone receptor also are found in uterine cancer tumors and epidermal growth factor receptor is commonly found in tumors from bladder cancer. Other tumor specific ligands and markers are well known to those of skill in the art. In preferred embodiments, the present disclosure employs folate or pteroyl moieties for targeting the folate receptor and PMSA target moieties for targeting the dyes to prostate cancer cells.

It is contemplated that any of these commonly known markers of tumors can be targeted either using the dyes described herein (by switching out the pteroyl moiety for a moiety that specifically targets these markers) or alternatively, these markers can be targeted in addition and in combination with the folate receptor that is being targeted using the compounds of the present disclosure. As discussed previously, it may be particularly advantageous to have targeting moieties to several different markers on a given tumor to serve as a diagnostic cocktail in which several markers are targeted to more brightly and clearly visualize the tumor.

In addition to chemical compounds, the targeting moieties in such cocktails may include a protein or polypeptide, such as an antibody, or biologically active fragment thereof, preferably a monoclonal antibody. The supplemental fluorescing targeting construct(s) used in practice of the disclosure method may also be or comprise polyclonal or monoclonal antibodies tagged with a fluorophore. The term "antibody" as used in this disclosure includes intact molecules as well as functional fragments thereof, such as Fab, F(ab')2, and Fv that are capable of binding the epitopic determinant. Methods of making these fragments are known in the art. (See for example, Harlow & Lane, Antibodies: A Laboratory Manual, Cold Spring Harbor Laboratory, New York, 1988, incorporated herein by reference). As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

In addition to antibodies, the cocktails may comprise compounds in which the ligand moiety attached to the fluorescent targeting construct is selected from among the many biologically compatible compounds that bind with specificity to receptors and/or are preferentially taken up by tumor cells, and can be used as the ligand moiety in the disclosure targeting constructs. Compounds that are preferentially "taken up" by tumor cells may enter the cells through surface or nuclear receptors (e.g., hormone receptors), pores, hydrophilic "windows" in the cell lipid bilayer, and the like.

Illustrative of this class of compounds to target tumors are somatostatin, somatostatin receptor-binding peptides, deoxyglucose, methionine, and the like. Particularly useful somatostatin receptor-binding peptides are a long-acting, octapeptide analog of somatostatin, known as octreotide (D-phenylalanyl-L-cysteinyl-L-phenylala-nyl-D-tryptophyl-L-lysyl-L-threonyl-N-[2-hydroxy-1-(hydroxymethyl) propyl]-L-cysteinamide cyclic (2→7)-disulfide), lanreotide, an oral formulation of octreotide, P829, P587, and the like. Somatostatin-binding peptides are disclosed in U.S. Pat. No. 5,871,711, and methods for linking such peptides covalently to a radioisotope through their carboxyl terminal amino acid under reducing conditions are disclosed in U.S. Pat. No. 5,843,401, which are both incorporated herein by reference in their entireties. One of skill in the art can readily adapt such teachings for the preparation of fluorescence-sensitive somatostatin receptor-binding peptides by substituting the fluorescing moieties of this disclosure in the place of a radioisotope.

Somatostatin and somatostatin receptor-binding peptides are particularly effective for use as the tumor-targeting ligand moiety in the targeting construct when the disease state is a neuroendocrine or endocrine tumor. Examples of neuroendocrine tumors that can be diagnosed using the disclosure method include adenomas (GH-producing and TSH-producing), islet cell tumors, carcinoids, undifferentiated neuroendocrine carcinomas, small cell and non-small cell lung cancer, neuroendocrine and/or intermediate cell carcinomas, neuroendocrine tumors of ovary, cervix, endometrium, breast, kidney, larynx, paranasal sinuses, and salivary glands, meningiomas, well differentiated glia-derived tumors, pheochromocytomas, neuroblastomas, ganglioneuro(blasto)mas, paragangliomas, papillary, follicular and medullary carcinomas in thyroid cells, Merkel cell carcinomas, and melanomas, as well as granulomas and lymphomas. These tumor cells are known to have somatostatin receptors and can be targeted using somatostatin or somatostatin receptor binding peptides as the tumor-targeting ligand in the disclosure fluorescent targeting construct.

Vasointestinal peptide (VIP), which is used in VIP receptor scintigraphy (I. Virgolini, Eur J. Clin. Invest. 27(10): 793-800, 1997, is also useful in the disclosure method for diagnosis of small primary adenocarcinomas, liver metastases and certain endocrine tumors of the gastrointestinal tract.

Another molecule illustrative of the tumor-targeting ligands that are preferentially taken up by tumors is deoxyglucose, which is known to be preferentially taken up in a variety of different types of tumors. Illustrative of the types of tumors that can be detected using deoxyglucose as the tumor-targeting ligand include melanoma, colorectal and pancreatic tumors, lymphoma (both HD and NHL), head and neck tumors, myeloma, cancers of ovary, cancer, breast, and brain (high grade and pituitary adenomas), sarcomas (grade dependent), hepatoma, testicular cancer, thyroid (grade dependent) small cell lung cancer, bladder and uterine cancer, and the like.

Yet other tumor-targeting compounds that can be used in cocktails of the present disclosure include 1-amino-cyclobutane-1-carboxylic acid and L-methionine. L-methionine is an essential amino acid that is necessary for protein synthesis. It is known that malignant cells have altered methionine metabolism and require an external source of methionine.

Additional examples of biologically compatible tumor-targeting compounds that bind with specificity to tumor receptors and/or are preferentially taken up by tumor cells include mammalian hormones, particularly sex hormones, neurotransmitters, and compounds expressed by tumor cells to communicate with each other that are preferentially taken up by tumor cells, such as novel secreted protein constructs arising from chromosomal aberrations, such as transfers or inversions within the clone.

Hormones, including sex hormones, cell growth hormones, cytokines, endocrine hormones, erythropoietin, and the like also serve well as tumor targeting moieties. As is known in the art, a number of tumor types express receptors for hormones, for example, estrogen, progesterone, androgens, such as testosterone, and the like. Such hormones are preferentially taken up by tumor cells, for example, via specific receptors.

The targeting constructs and supplemental targeting constructs used in practice of the disclosure method can be administered by any route known to those of skill in the art, such as topically, intraarticularly, intracisternally, intraocularly, intraventricularly, intrathecally, intravenously, intramuscularly, intraperitoneally, intradermally, intratracheally, intracavitarily, and the like, as well as by any combination of any two or more thereof.

The most suitable route for administration will vary depending upon the disease state to be treated, or the location of the suspected condition or tumor to be diagnosed. For example, for treatment of inflammatory conditions and various tumors, local administration, including administration by injection directly into the body part to be irradiated by the excitation light (e.g., intracavitarily) provides the advantage that the targeting construct (e.g., fluorescently tagged antibodies) can be administered in a high concentration without risk of the complications that may accompany systemic administration thereof.

The compounds of the present disclosure as well as any additional targeting constructs used in diagnostic cocktails comprising the compounds of the present disclosure are administered in a "effective amount" for diagnosis. An effective amount is the quantity of a targeting construct necessary to aid in direct visualization of any target tissue located in the body part under investigation in a subject. A "subject" as the term is used herein is contemplated to include any mammal, such as a domesticated pet, farm animal, or zoo animal, but preferably is a human. Amounts effective for diagnostic use will, of course, depend on the size and location of the body part to be investigated, the affinity of the targeting construct for the target tissue, the type of target tissue, as well as the route of administration. Local administration of the targeting construct will typically require a smaller dosage than any mode of systemic administration, although the local concentration of the targeting construct may, in some cases, be higher following local administration than can be achieved with safety upon systemic administration.

Since individual subjects may present a wide variation in severity of symptoms and each targeting construct has its unique diagnostic characteristics, including, affinity of the targeting construct for the target, rate of clearance of the targeting construct by bodily processes, the properties of the fluorophore contained therein, and the like, the skilled practitioner will weigh the factors and vary the dosages accordingly.

The compounds of the present disclosure as well as cocktails comprising these compounds can be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1-4, butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

It will be apparent to those skilled in the art that various changes may be made in the disclosure without departing from the spirit and scope thereof, and therefore, the disclosure encompasses embodiments in addition to those specifically disclosed in the specification, but only as indicated in the appended claims.

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

EXAMPLES

In the following examples, synthesis of novel diseased tissue targeted as well as organelle-targeted photosensitizers (PS) for photodynamic therapy (PDT) are explained and the synthesis of those compounds are given.

In the following examples, the in vitro efficacy of the compounds is determined using KB cells. In these assays, KB cells were grown to 70% confluence and pulsed for 2 h with increasing concentrations of PSs. After washing to remove unbound conjugate, cells were exposed to laser beam (6 mW/cm$^2$, 12 J/cm$^2$ and exposure diameter=6 cm for 25 wells) for 32 min and incubated at 37° C. for an additional 24 h in fresh medium. The cell viability was measured by bioluminescent quantitation of released ATP using Cell Titer Glo. The aforementioned 2 h exposure was selected, since the small molecule drugs were found to clear in vivo (from nontargeted tissues) in <2 h, suggesting that longer exposure to the drug might yield nonphysiological results.

The data presented in the following examples show EC50 values. EC50 is half maximal effective concentration, and represents the concentration of a compound where 50% of its maximal effect is observed. The lower the EC50 value higher the activity. We consider that a compound with EC50<50 nM as active and EC50<10 nM as highly active In the following examples, the in vivo efficacy of the compounds is determined using KB tumor cell xenograft in nude mice. In these studies, KB cells were implanted subcutaneously and growth of the tumors was monitored. For time dependent whole body imaging, once tumors become 250-350 mm$^3$, the compounds were injected via tail vein and accumulation of the PS in the tumor was monitored (over 48 hours) using fluorescence imaging using IVIS imager. Moreover, once tumors grow to ~50 mm$^3$, the compounds were injected via tail vein. Three hours (3 h) after injecting with the compound, tumor was treated with laser beam (75 mW/cm$^2$, 137 J/cm$^2$, exposure diameter=7.5-8 mm) for 38 min. In vivo efficacy of BPheid-a was evaluated by monitoring reduction of tumor volume.

Example 1

In the present example, the inventors performed a preclinical evaluation of commercially available non-targeted PDT agents or similar agents that are currently in clinical trials. The objective of the study was two-fold. Firstly, the objective was to evaluate photodynamic therapeutic efficacy of commercially available photosensitizes in cancer cells and secondly to evaluate photodynamic therapeutic efficacy of commercially available photosensitizers in cancer cells in tumor xenograft mouse models.

Synthesis of Tookad and its Analogues

Aqueous paste of *Rhodobacter Sphaeroides* (150 g) was suspended in methanol (2.2 L) and argon was bubbled through the green suspension while stirring in the dark for 14 h. The suspension was filtered through the sintered glass funnel and the residue was washed with methanol until the filtrate was almost colorless. Filtrate was evaporated on rotary evaporator and dried under high vacuum to obtain crude bacteriochlorophyll-a (8) as dark green solid.

The crude Bacteriochlorophyll-a (8) obtained in the previous step was suspended in TFA (120 mL, 80% in water). Argon was bubbled through the reaction mixture for 10 minutes and stirred the content in dark for 1 h. The reaction mixture was poured into water (400 mL) and extracted using chloroform (3×300 mL). The combined organic layers were washed with brine, dried over anhydrous sodium sulfate and concentrated. The residue was dissolved in chloroform (50 mL) and poured on to hexane (800 mL) with vigorous stirring. The precipitated dark brown solid was filtered and dried under high vacuum to obtain Bacteriopheophorbide-a (BPheid-a) (1).

Chloroform (60 mL) which had been bubbled with argon for 10 minutes was added to the mixture of Pd(OAc)$_2$ (784 mg, 3.53 mmol, 6 equiv) and sodium ascorbate (700 mg, 3.53 mmol, 6 equiv) under vigorous stirring followed by the addition of degassed methanol (360 mL). In another flask BPheid-a (360 mg, 0.59 mmol, 1 equiv) was dissolved in degassed chloroform (100 mL) and added to the above solution slowly in 2 minutes. The reaction content was bubbled with argon for 10 minutes and stirred in dark at 23° C. for 15 h. Upon completion, the reaction mixture was filtered through celite and concentrated. The resulting dark brown-purple solid was re-dissolved in methanol/chloroform (20/100 mL) and filtered through the celite and concentrated. The crude solid was purified by column chromatography using sodium (0.4%) ascorbate treated silica and 0-10% methanol in dichloromethane to form compound 2 (Tookad).

Taurine (32 mg, 0.26 mmol) was dissolved in 1M K$_2$HPO$_4$ (1 mL) and pH was adjusted to 8.2 using aq. HCl. Evaporated the water and dried the solid under high vacuum. To this solid was added Pd-Bpheid-a (Compound (3)) (20 mg, 0.032 mmol) and DMSO (3 mL) and argon was bubbled for 2 min through the solution. The reaction mixture was stirred at 60° C. for 6 h. The reaction mixture was filtered and purified by preparative HPLC using C18 column to obtain compound 3 as a dark brown solid.

Pd-Bpheid-a (3) (50 mg, 0.07 mmol) was dissolved in DMSO (7.5 mL) and argon was bubbled for 2 min through the solution. In another flask taurine (70 mg, 0.55 mmol) was dissolved in 1M K$_2$HPO$_4$ (2.17 mL) and pH was adjusted to 8.2 using aq. HCl. This solution was added to the above solution. Argon was bubbled through the reaction mixture for another 5 minutes and stirred the content at 40° C. for 5 h. Water was removed from the reaction mixture using rotary evaporator at 40° C. and stirred the content at 40° C. for 40 h. Filtered the reaction mixture and purified by preparative HPLC using C18 column to obtain tookad soluble (4) as a dark brown solid.

Figure 2:
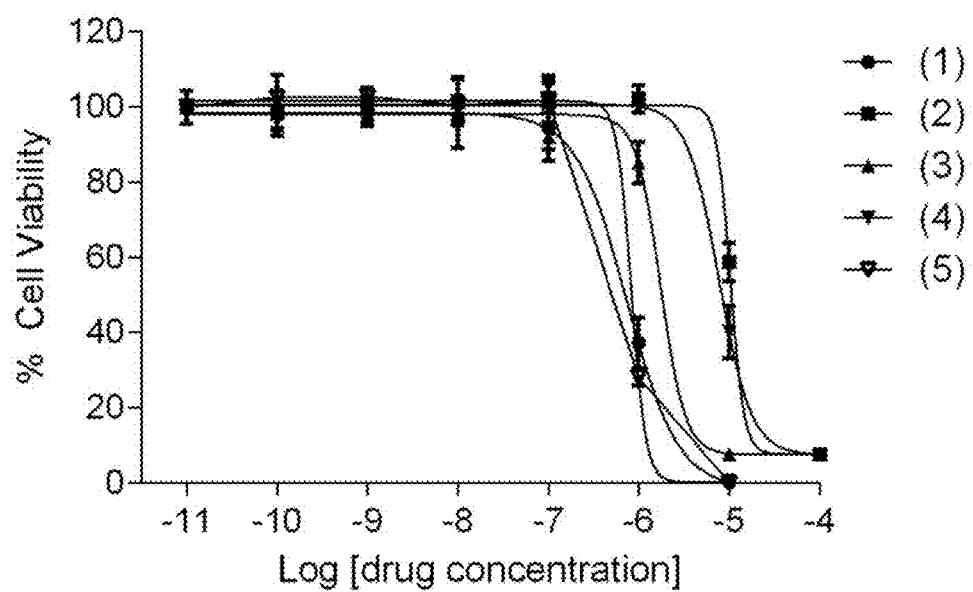
FIG. 2 depicts an effect of the drug concentration on the survival of KB cells [a derivative of HeLa (HeLa has a high number of folate receptors) cell line which are human cervical cancer cell line]. Free drugs dissolved in DMSO were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell viability was measured using CellTiter Glo (Promega). Error bars represent s.d. (n=3).
Figure 3:
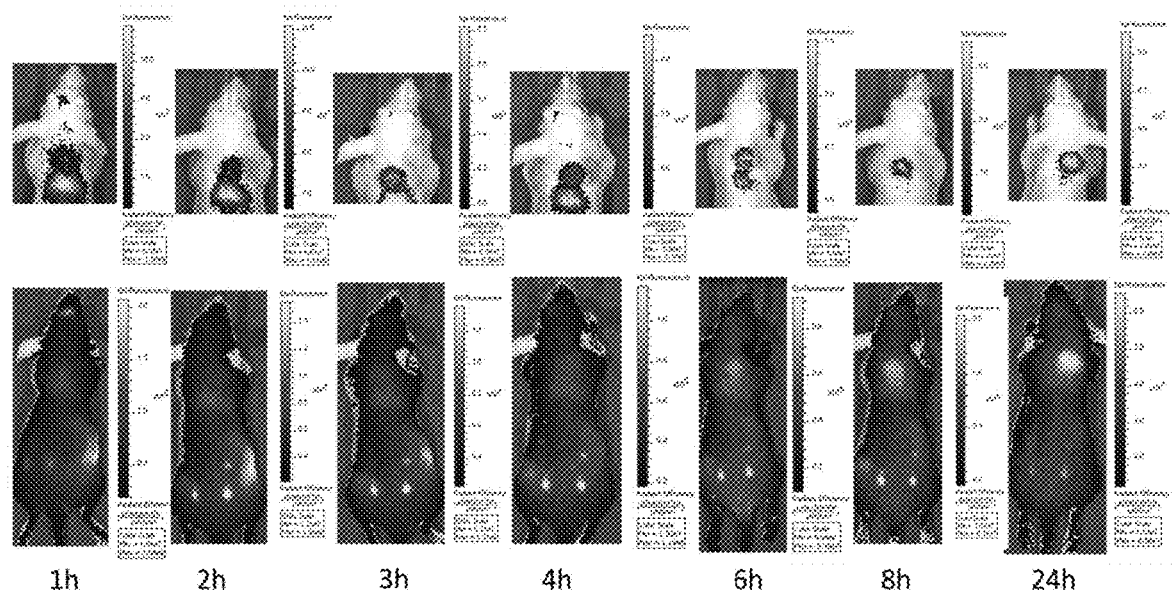
FIG. 3 depicts an overlay of half body (top raw) and whole body (bottom raw) fluorescence image over white light images after adjusting the threshold. KB tumor bearing mice injected with 10 nmol of BPheid-a (1) and image with IVIS imager (ex=745 nm, em=ICG, exposure time=1 s) at different time intervals.
Figure 4A:
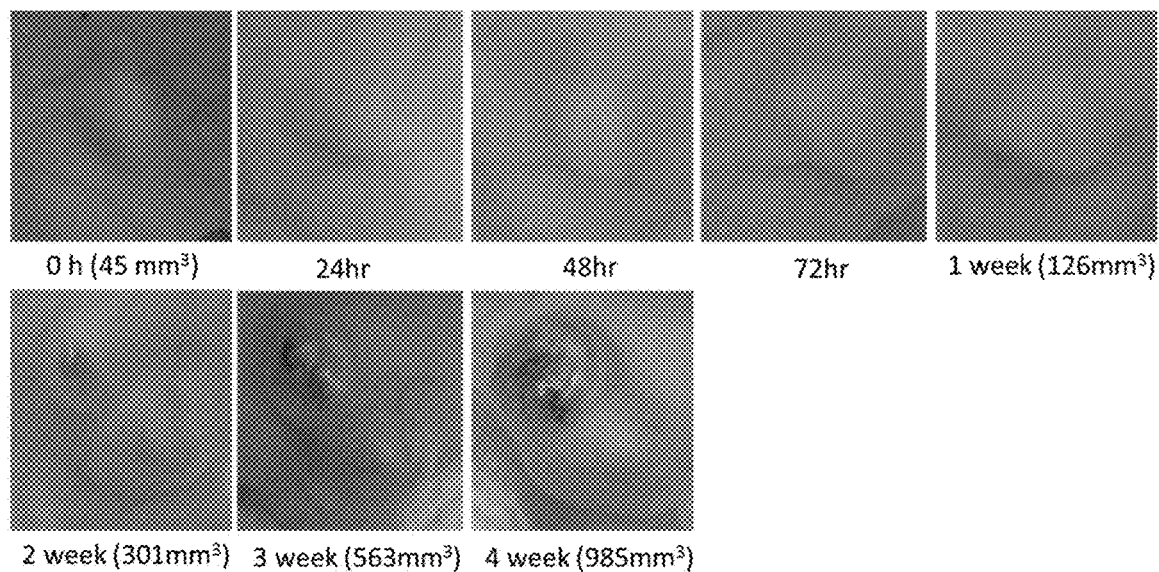
FIG. 4A depicts an effect of 50 nmol dose of BPheid-a (1) on the growth of subcutaneous KB tumor. Three hours (3 h) after injecting with 50 nmol of BPheid-a in phosphate buffered saline, PBS (drug carrier), mouse with 45 mm$^3$ tumor was treated with laser beam (75 mW/cm$^2$, 137 J/cm$^2$, exposure diameter=7.5-8 mm) for 38 min. The growth of the tumor was monitored (images were taken) and tumor volume was measured using caliper.
Figure 4B:
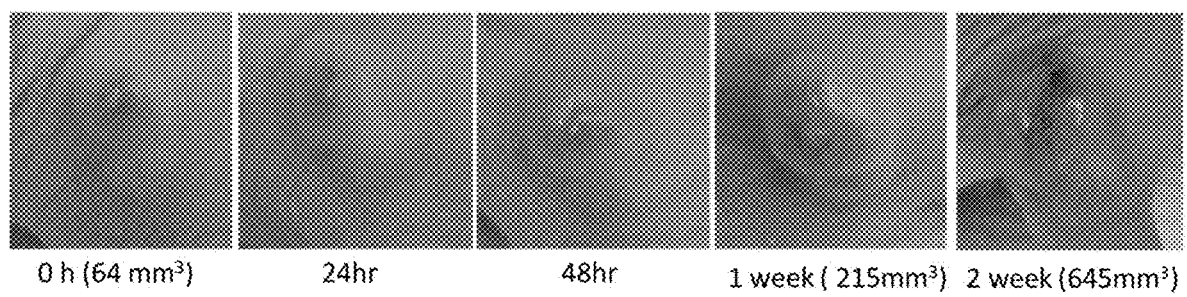
FIG. 4B depicts an effect of PBS (drug carrier or control) on the growth of subcutaneous KB tumor. Three hours (3 h) after injecting with PBS, mouse with 65 mm$^3$ tumor was treated with laser beam (75 mW/cm$^2$, 137 J/cm$^2$, exposure diameter=7.5-8 mm) for 38 min. The growth of the tumor was monitored (images were taken) and tumor volume was measured using caliper.
Figure 5A:
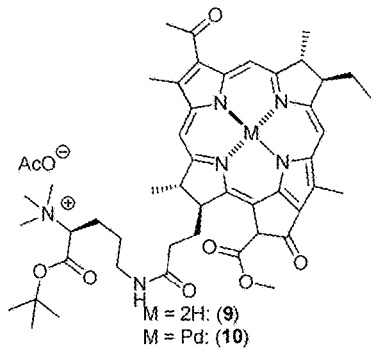
FIGS. 5A-5R depict structures of modified BPheid-a to target mitochondria Positive charged molecules to target the mitochondria.
Figure 5B:
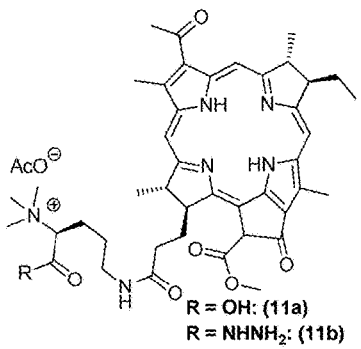
Figure 5C:
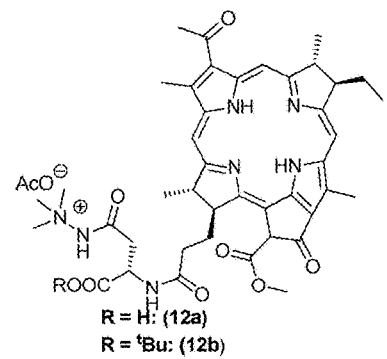
Figure 5D:
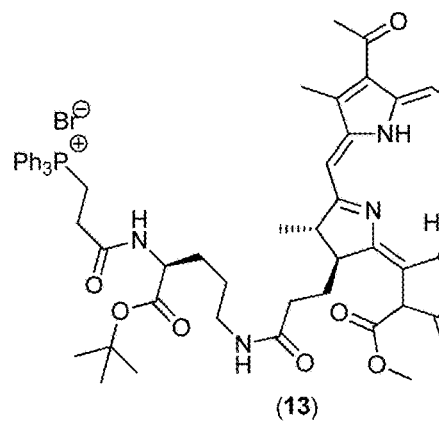
Figure 5E:
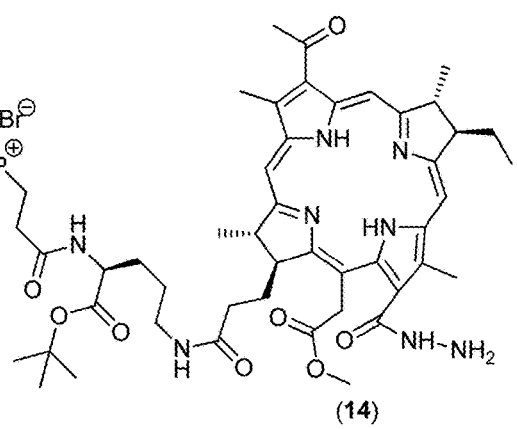
Figure 5F:
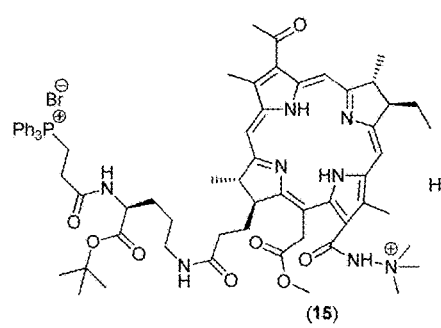
Figure 5G:
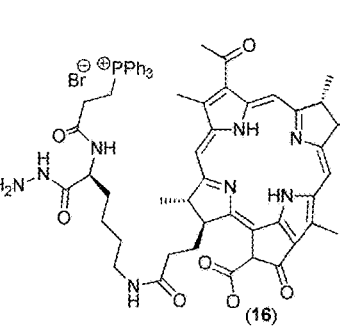
Figure 5H:
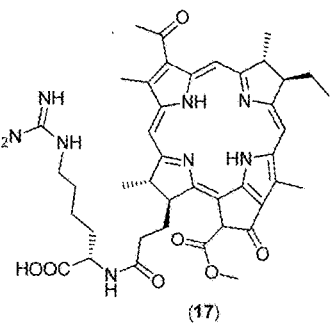
Figure 5I:
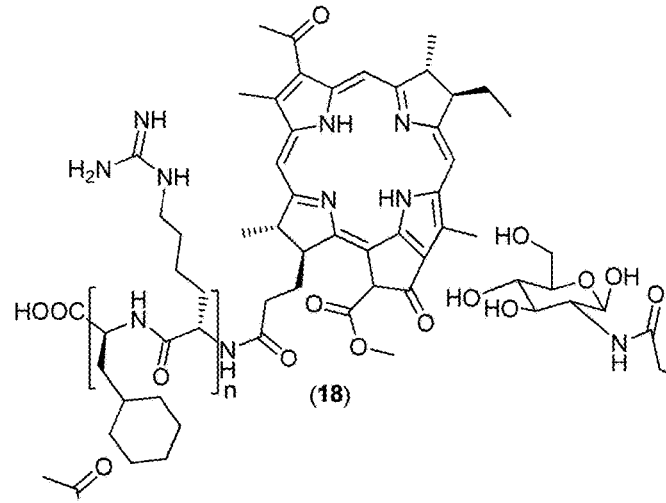
Figure 5J:
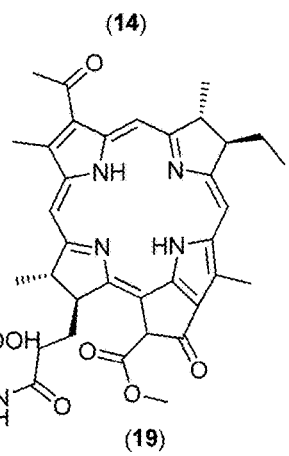
Figure 5K:
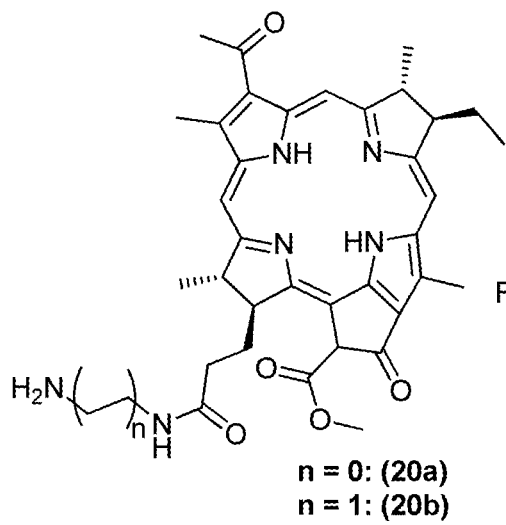
Figure 5L:
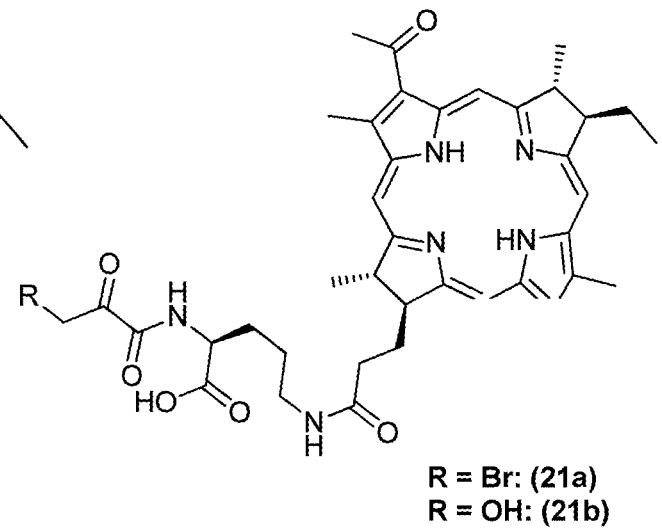
Figure 5M:
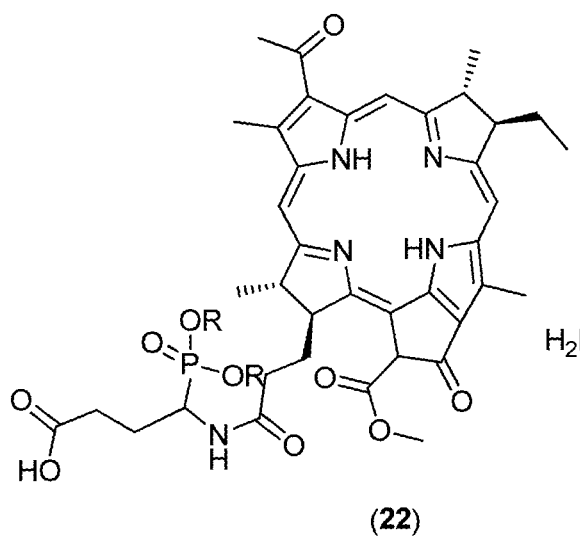
Figure 5N:
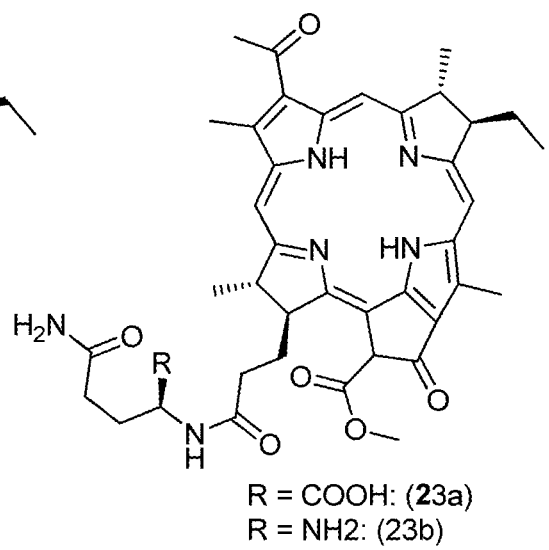
Figure 5O:
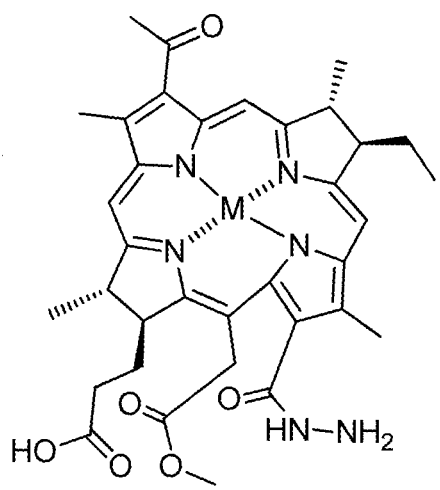
Figure 5P:
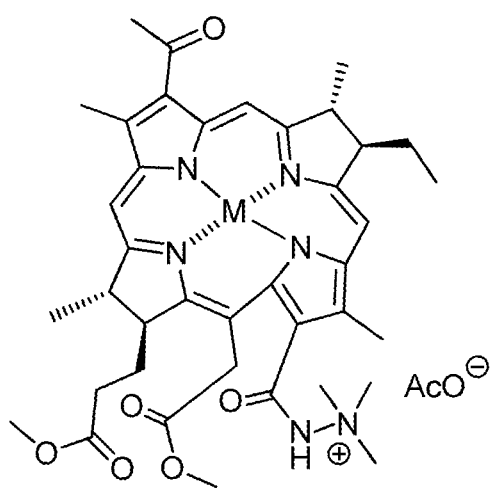
Figure 5Q:
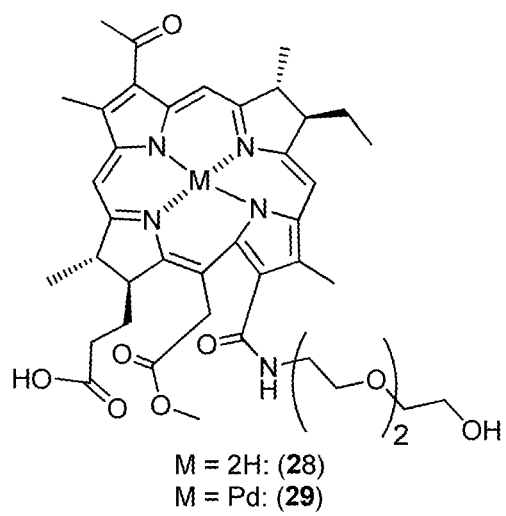
Figure 5R:
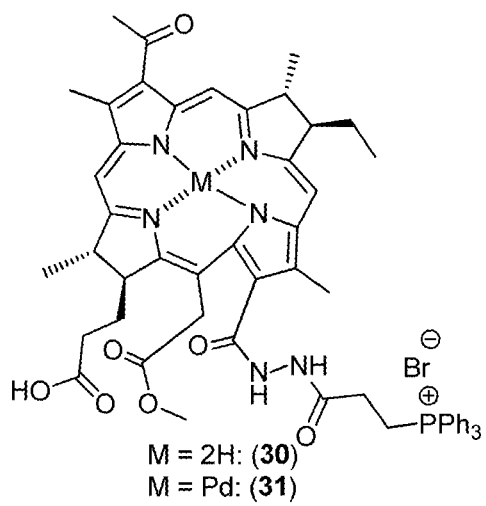
Figure 6A:
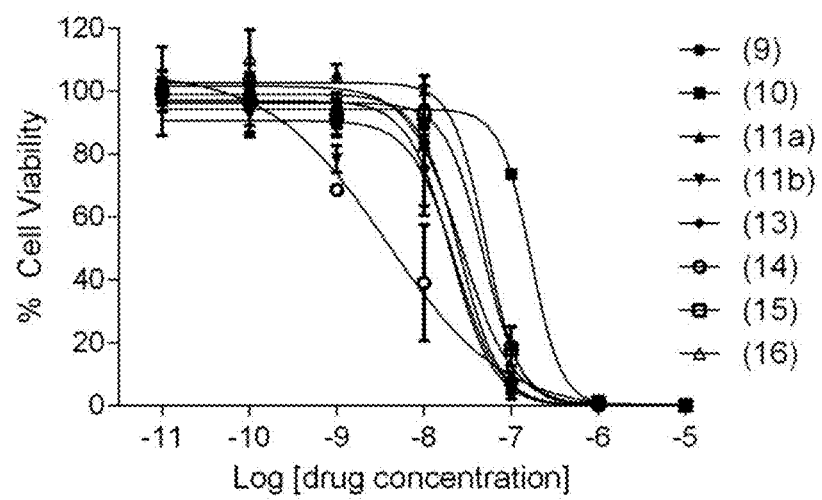
FIGS. 6A and 6B depict an effect of the drug concentration on the survival of KB cells (a derivative of HeLa cell line and HeLa cells are human cervical cancer cell line). Free drugs dissolved in DMSO were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell viability was measured using CellTiter Glo (Promega). Error bars represent s.d. (n=3).
Figure 6B:
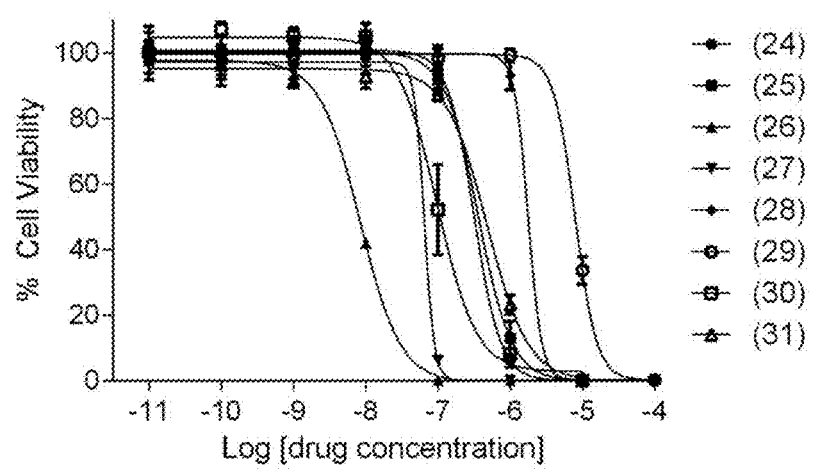
Figure 7:
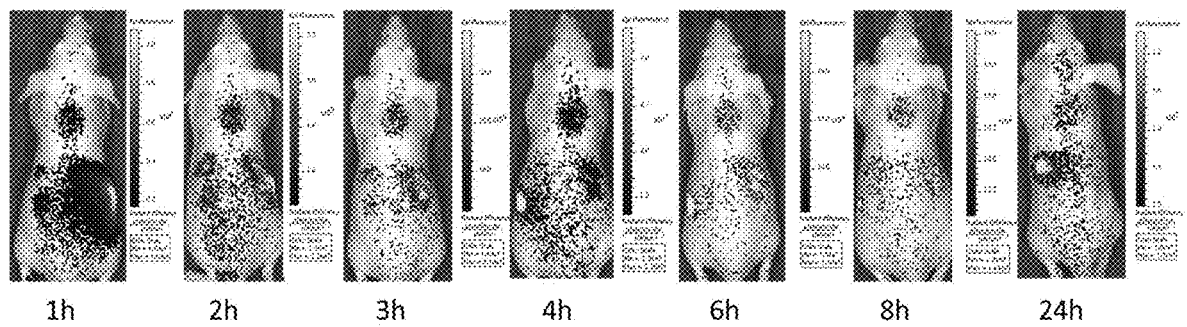
FIG. 7 depicts an overlay of half body (top raw) and whole body (bottom raw) fluorescence image over white light images after adjusting the threshold. KB tumor bearing mice injected with 10 nmol of (14) and image with IVIS imager (ex=745 nm, em=ICG, exposure time=1 s) at different time intervals.
Figure 8:
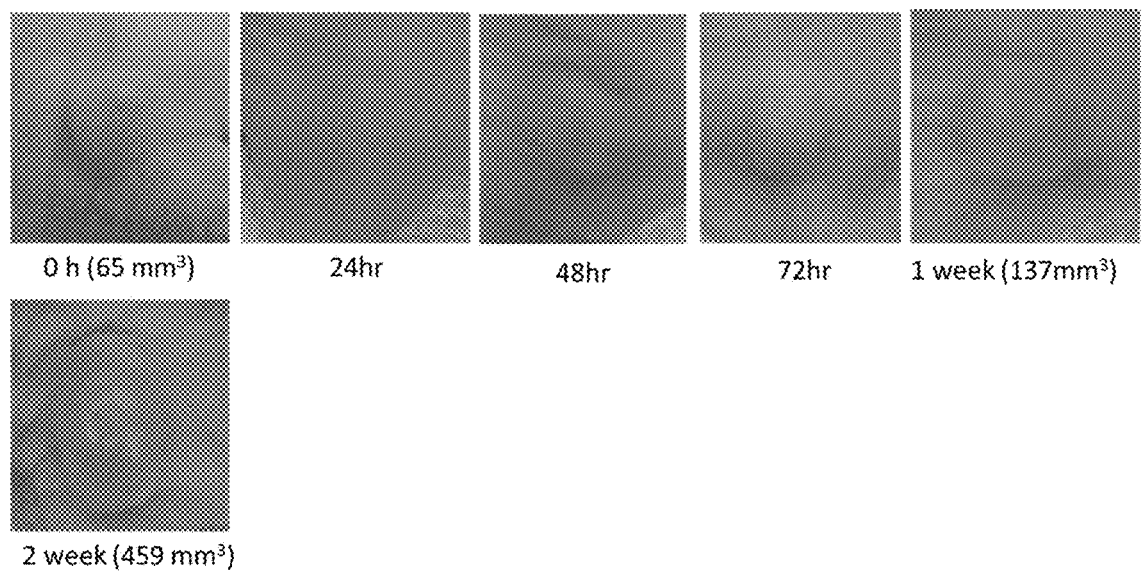
FIG. 8 depicts an effect of 50 nmol dose of (14) on the growth of subcutaneous KB tumor. Three hours (3 h) after injecting with 50 nmol of 14, mouse with 53 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper.
Figure 9A:
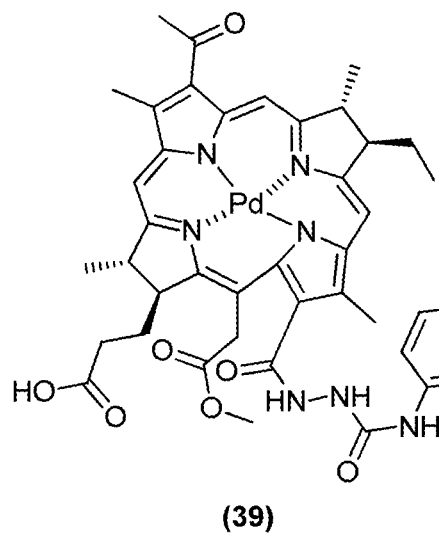
Figure 9B:
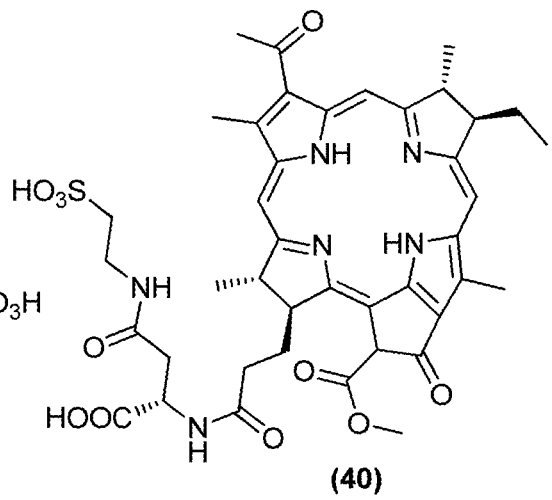
Figure 9C:
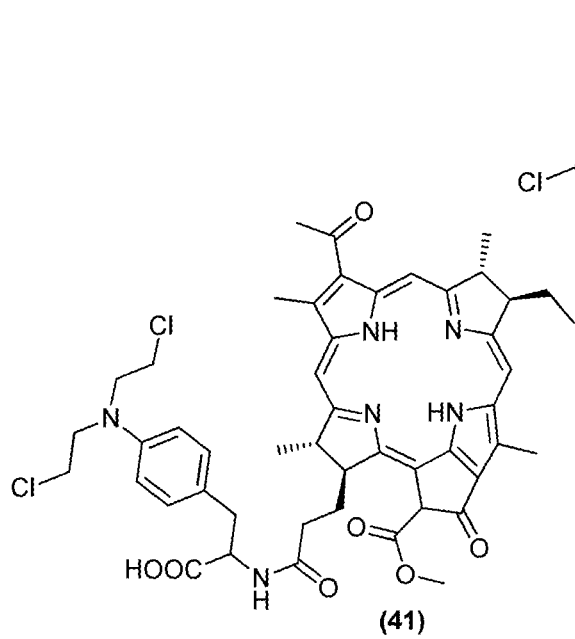
Figure 9D:
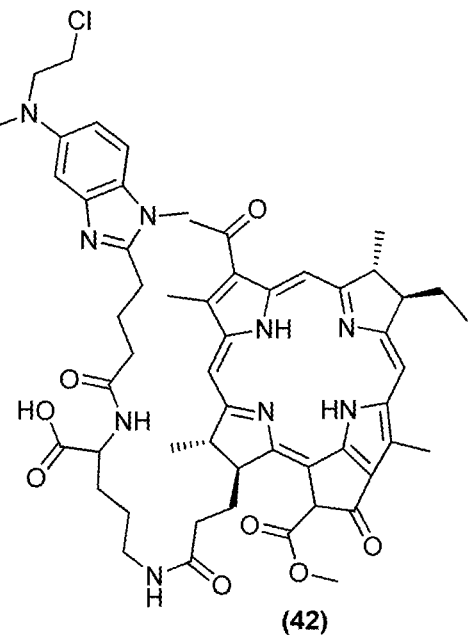
Figure 10:
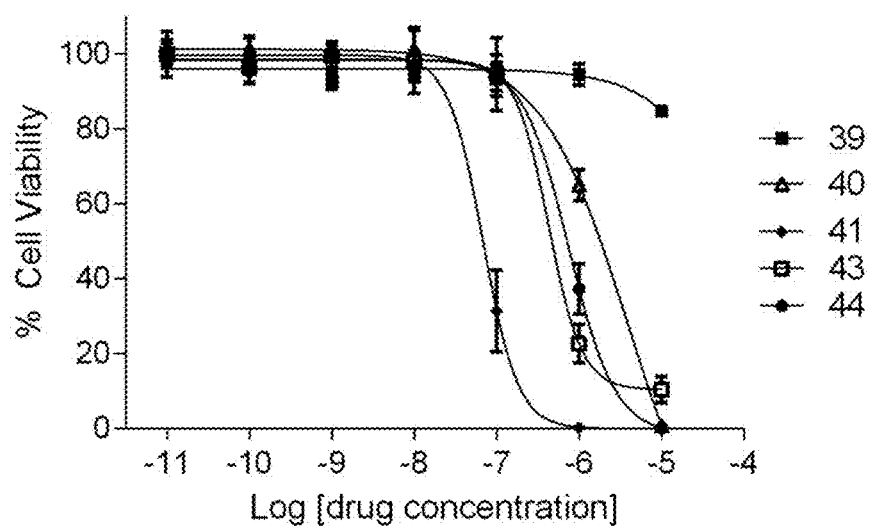
FIG. 10 depicts an effect of the drug concentration on the survival of KB cells (a derivative of HeLa cell line and HeLa cells are human cervical cancer cell line). Free drugs dissolved in DMSO were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell viability was measured using CellTiter Glo (Promega). Error bars represent s.d. (n=3).
Figure 11A:
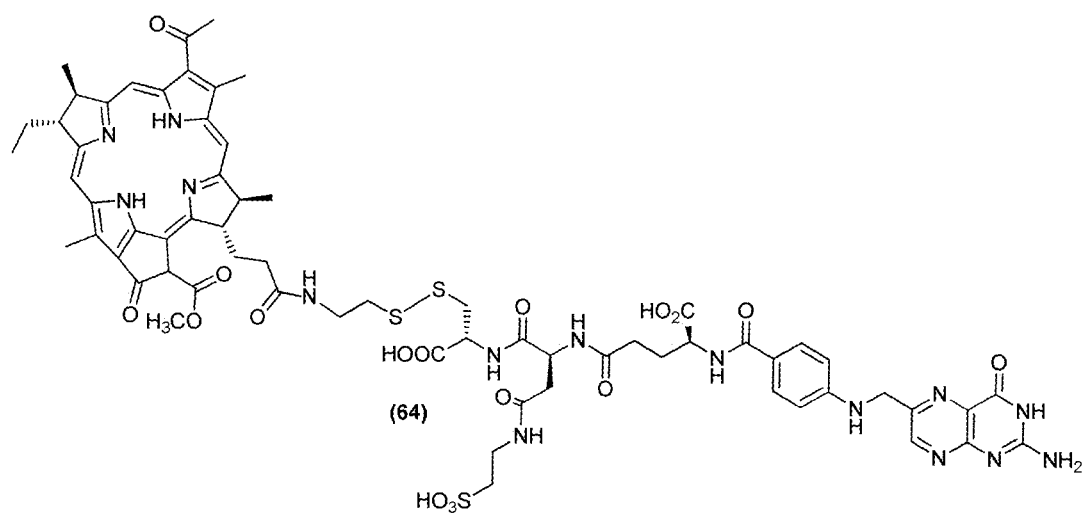
FIGS. 11A-11F depict structures of folate-targeted BPheid-a conjugates with releasable linkers with different mechanism to produce base drug.
Figure 11B:
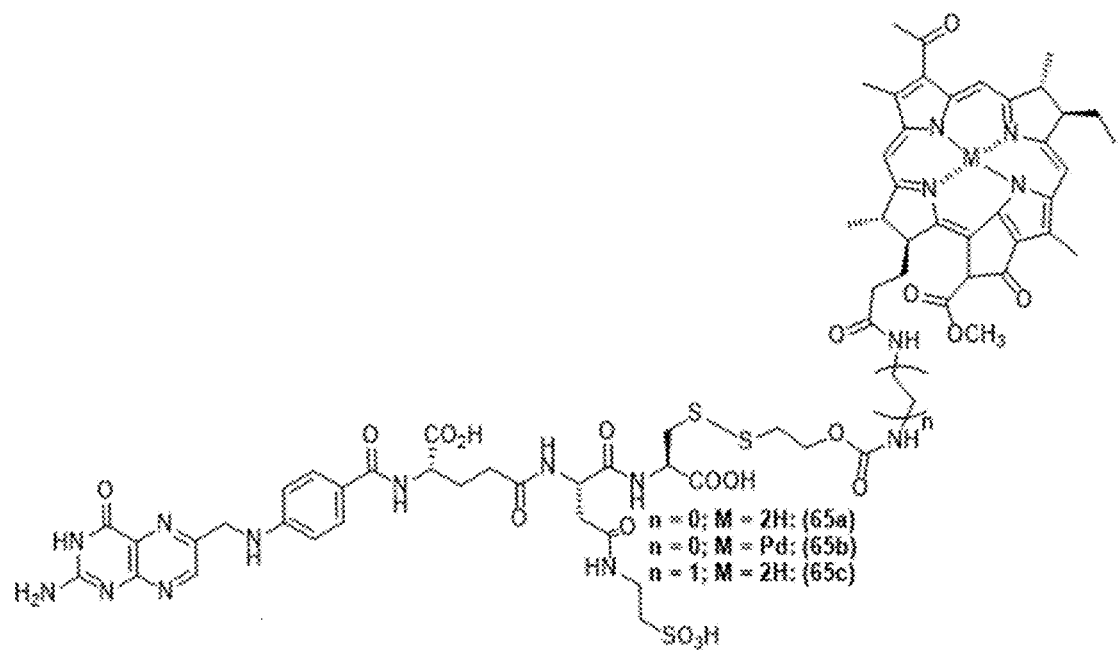
Figure 11C:
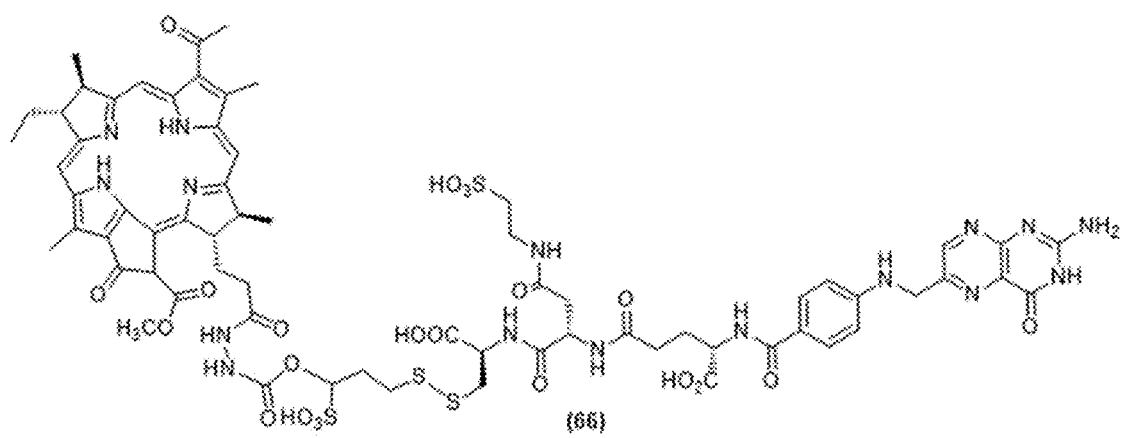
Figure 11D:
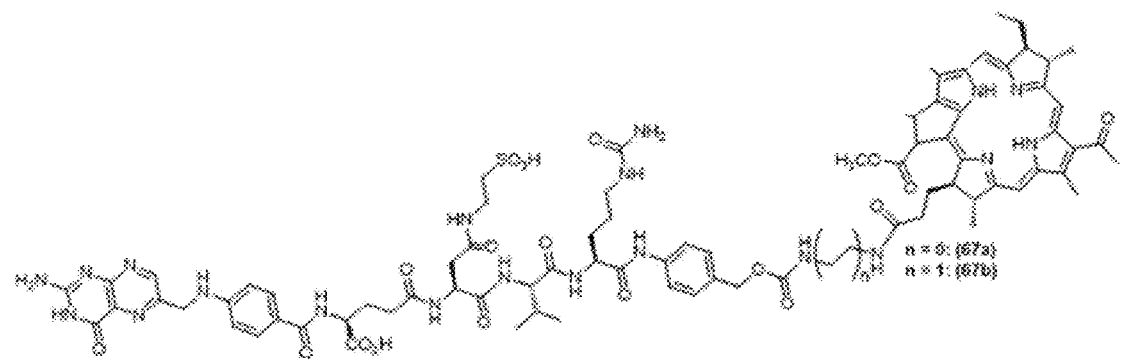
Figure 11E:
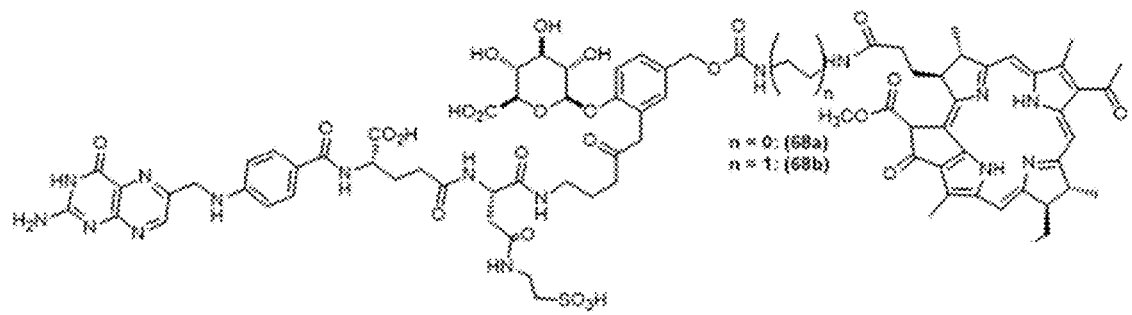
Figure 11F:
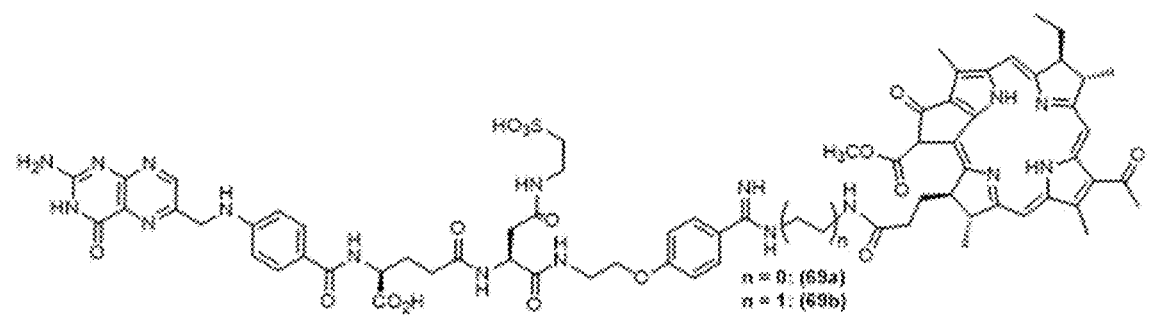
Figure 12:
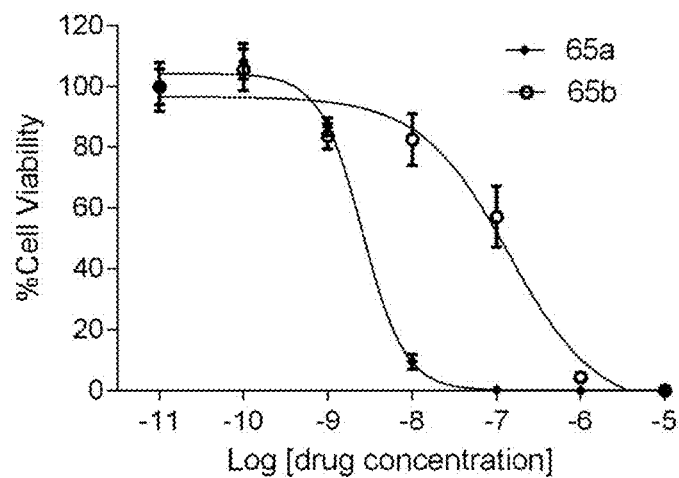
FIG. 12 depicts an effect of the drug concentration on the survival of KB cells (a derivative of HeLa cell line and HeLa cells are human cervical cancer cell line). Folate drug conjugates dissolved in folate free RPMI were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell viability was measured using CellTiter Glo (Promega). Error bars represent s.d. (n=3).
Figure 13:
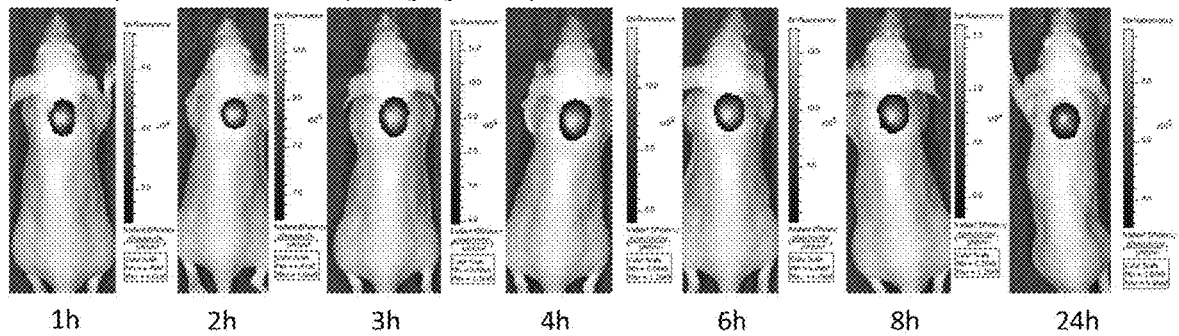
FIG. 13 depicts an overlay of whole body fluorescence image over white light images after adjusting the threshold. KB tumor bearing mice injected with 10 nmol of 65a and image with IVIS imager (ex=745 nm, em=ICG, exposure time=1 s) at different time intervals.
Figure 14:
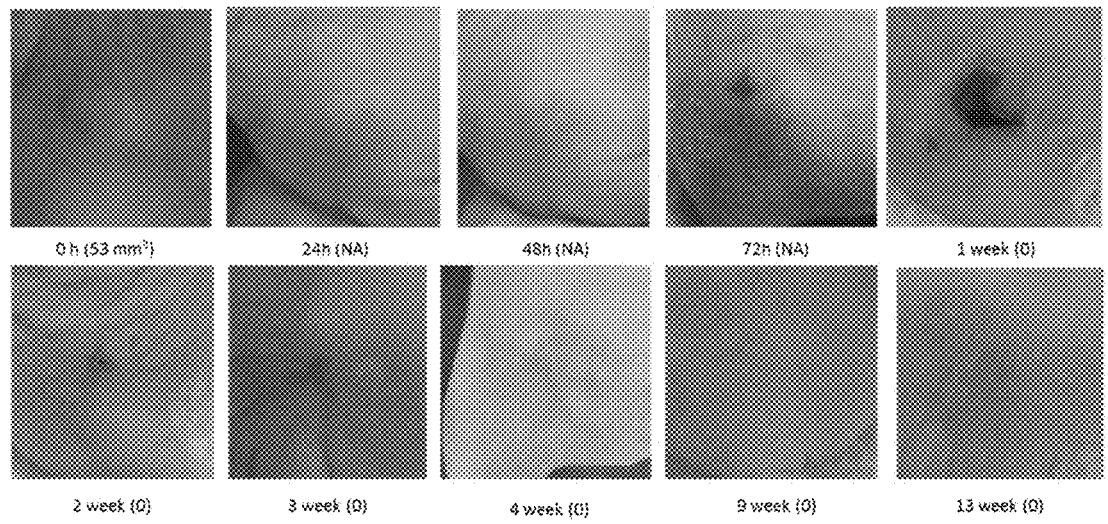
FIG. 14 depicts an effect of 50 nmol dose of 65a on the growth of subcutaneous KB tumor. Three hours (3 h) after injecting with 50 nmol of 65a, mouse with 53 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (13 weeks).
Figure 15A:
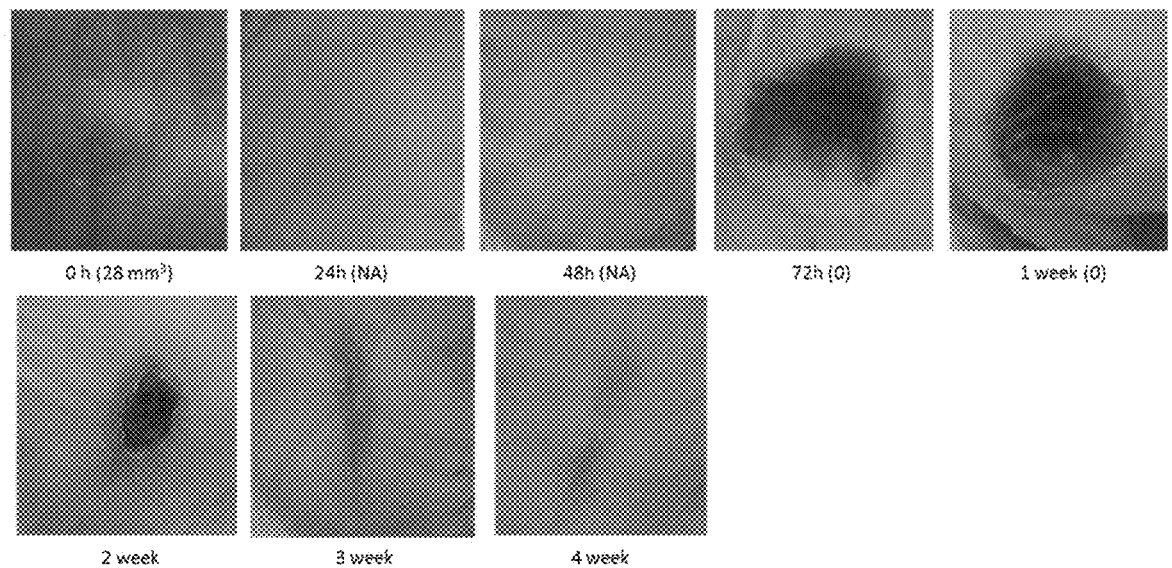
FIG. 15A depicts an effect of 25 nmol dose of 65a on the growth of subcutaneous KB tumor. Three hours (3 h) after injecting with 25 nmol of 65a, mouse with 28 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (4 weeks).
Figure 15B:
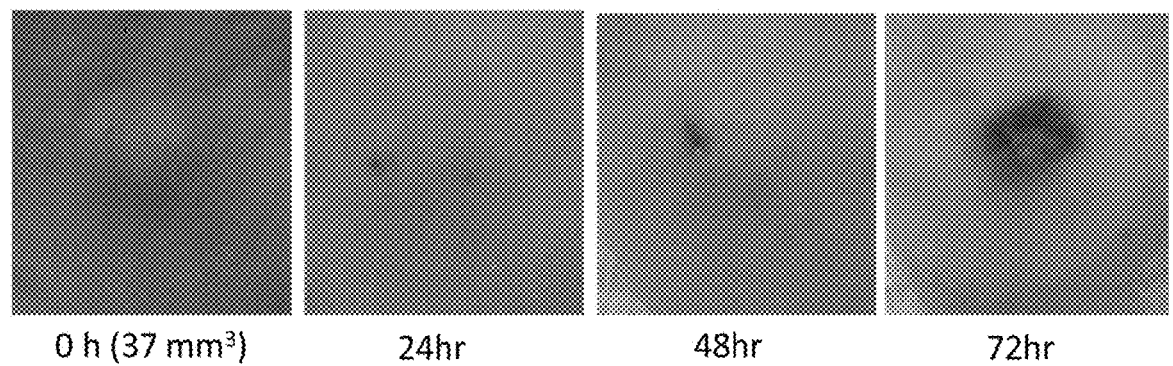
FIG. 15B depicts an effect of 50 nmol dose of 65c on the growth of subcutaneous KB tumor. Three hours (3 h) after injecting with 50 nmol of 65c, mouse with 37 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (3 days).
Figure 16A:
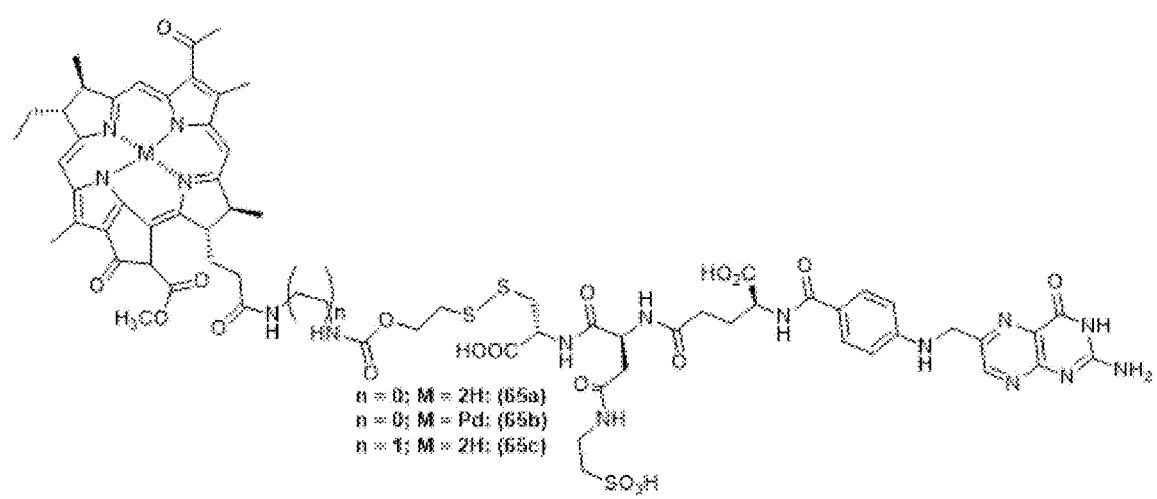
FIGS. 16A-16E depict structures of folate-targeted releasable disulfide linked BPheid-a conjugates with different soluble linkers.
Figure 16B:
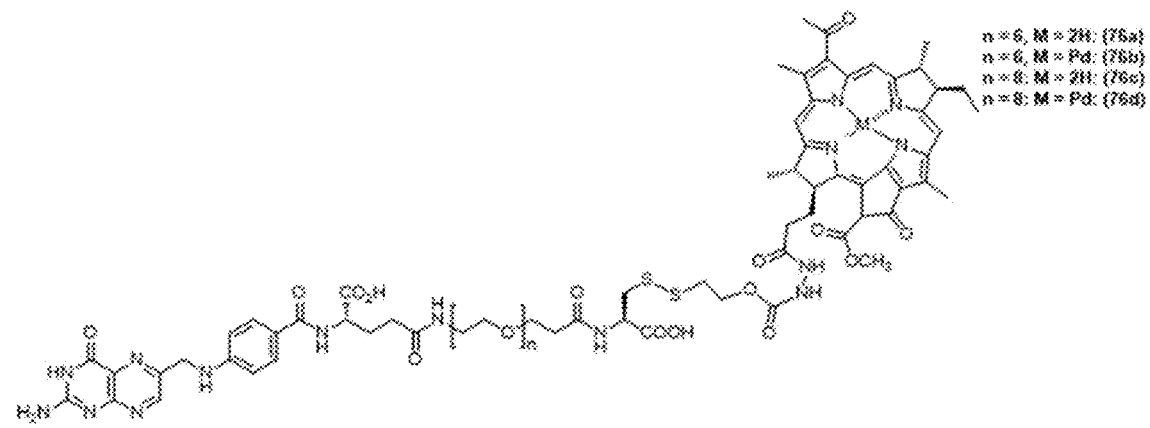
Figure 16C:
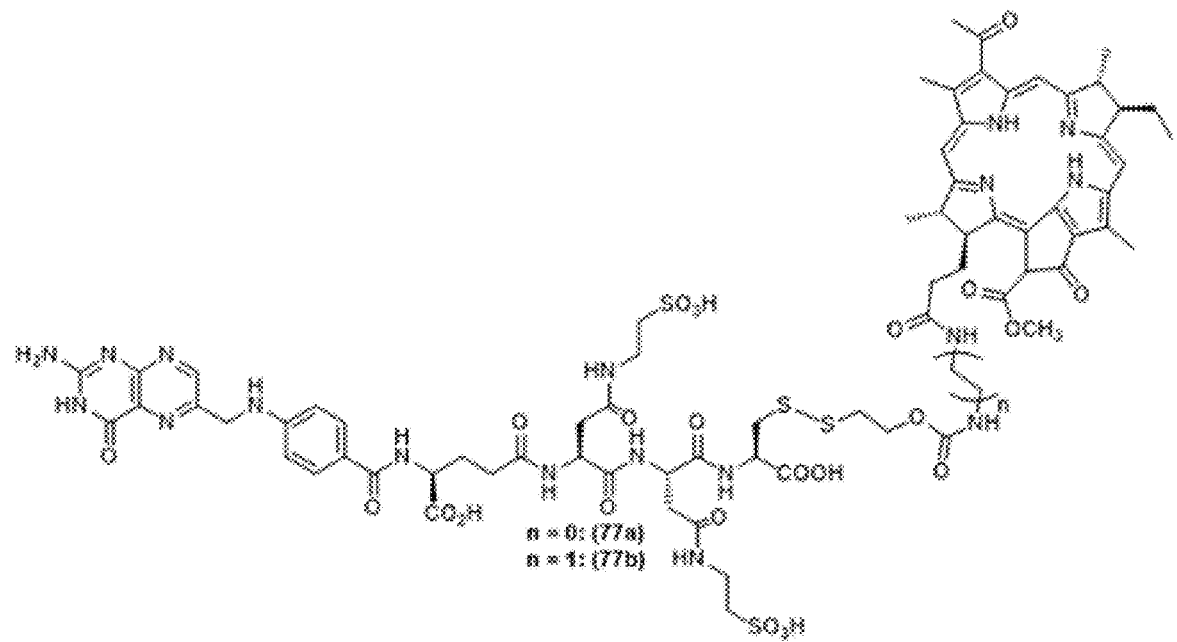
Figure 16D:
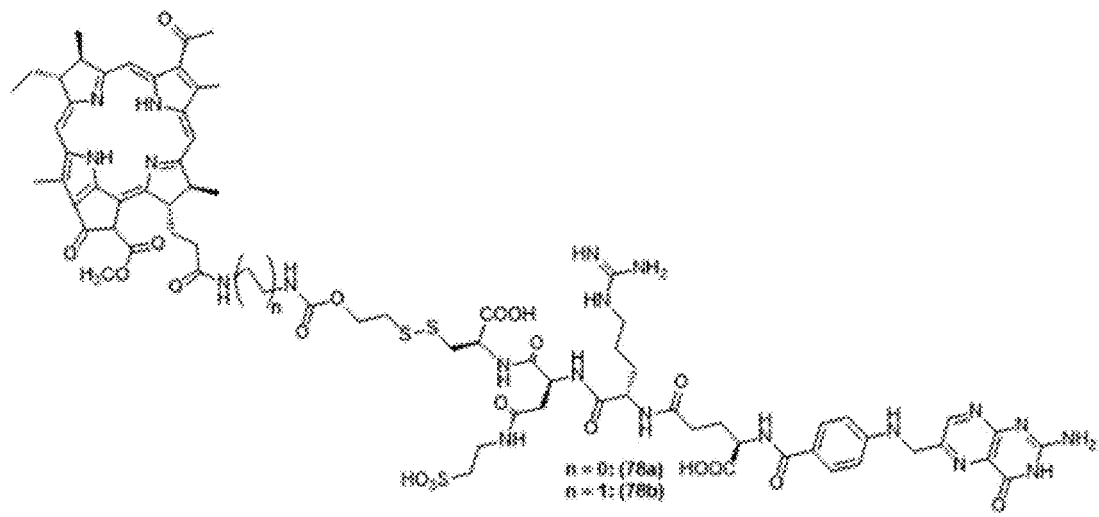
Figure 16E:
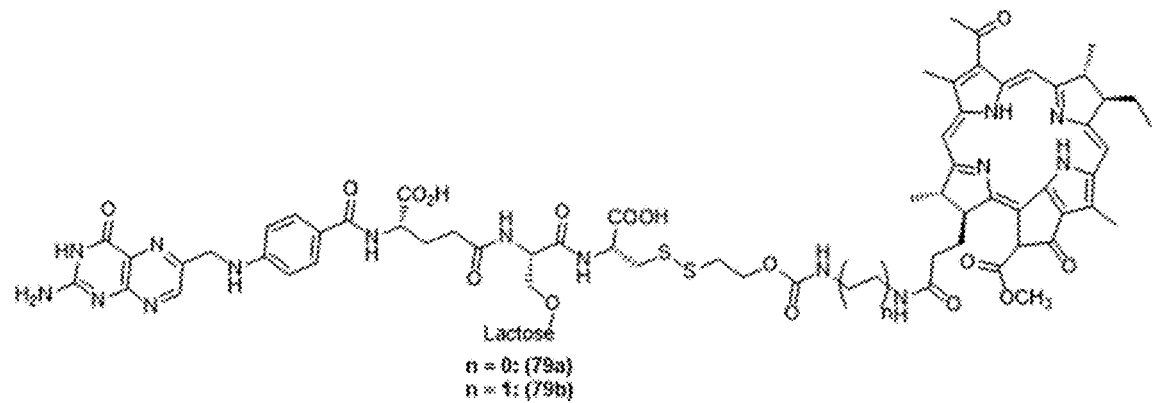
Figure 17:
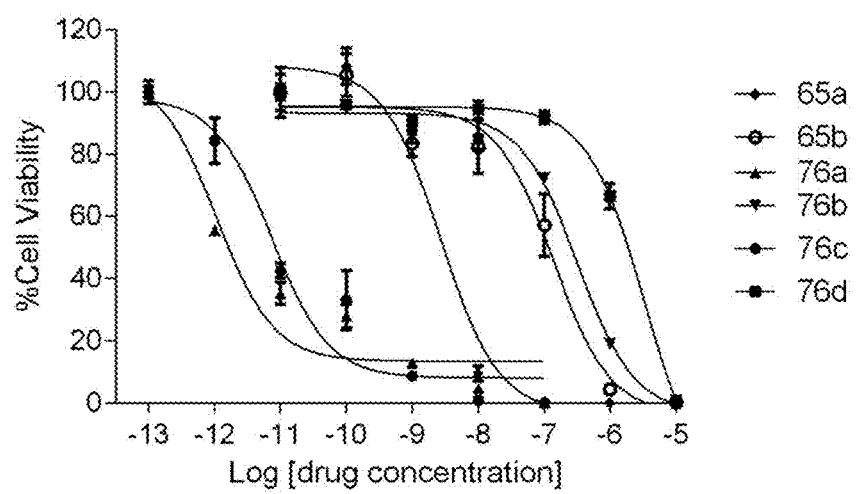
FIG. 17 depicts an effect of the drug concentration on the survival of KB cells (a derivative of HeLa cell line and HeLa cells are human cervical cancer cell line). Folate drug conjugates dissolved in folate free RPMI were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell viability was measured using CellTiter Glo (Promega). Error bars represent s.d. (n=3).
Figure 18A:
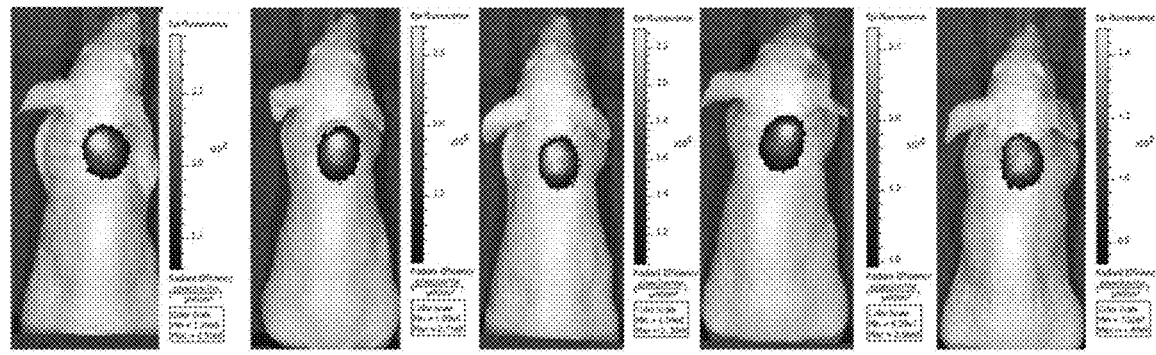
FIGS. 18A and 18B depict an overlay of whole body fluorescence image over white light images after adjusting the threshold. KB tumor bearing mice injected with 10 nmol of 76a and 76c and image with IVIS imager (ex=745 nm, em=ICG, exposure time=1 s) at different time intervals.
Figure 18B:
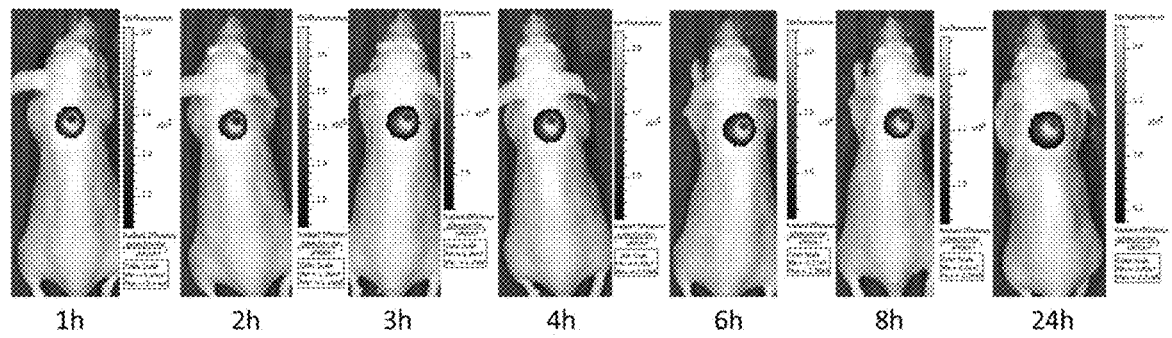
Figure 19:
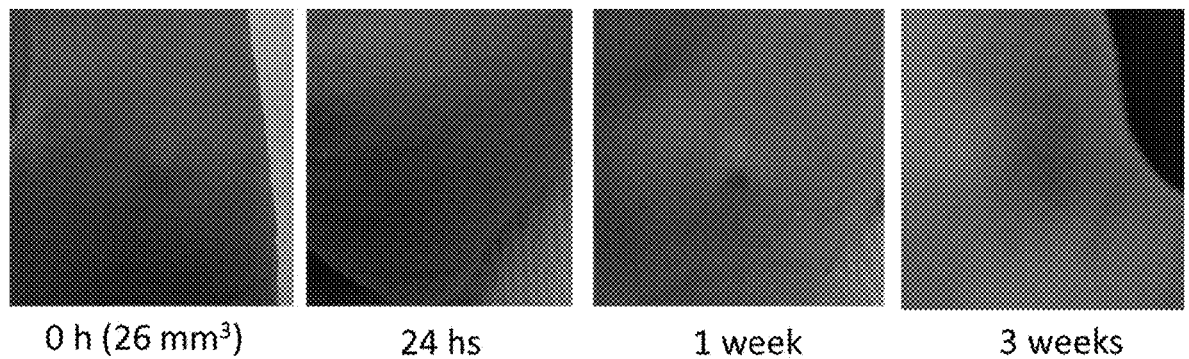
FIG. 19 depicts an effect of 50 nmol dose of 76a on the growth of subcutaneous KB tumor. Three hours (3 h) after injecting with 50 nmol of 76a, mouse with 26 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (3 weeks).
Figure 20:
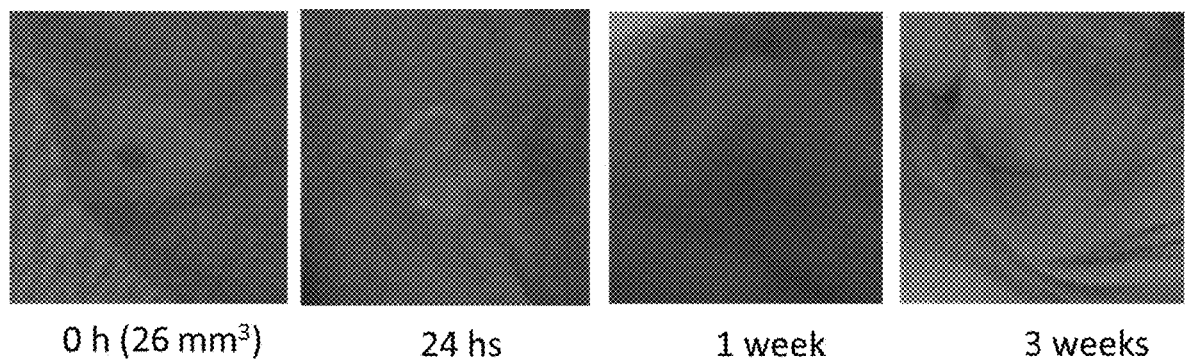
FIG. 20 depicts an effect of 50 nmol dose of 76b on the growth of subcutaneous KB tumor. Three hours (3 h) after injecting with 50 nmol of 76b, mouse with 26 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (3 weeks).
Figure 21:
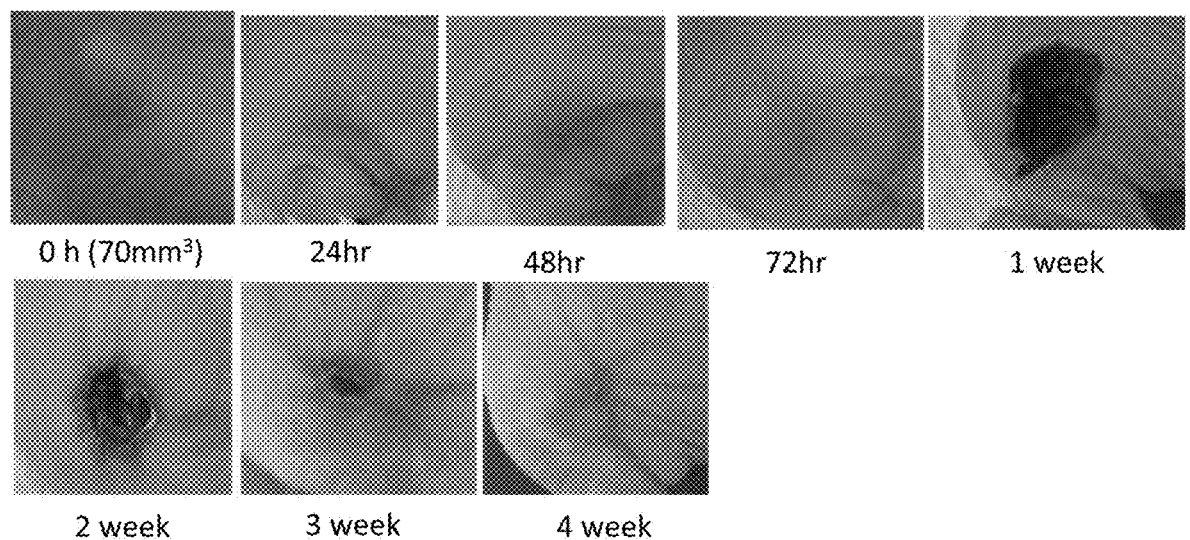
FIG. 21 depicts an effect of 50 nmol dose of 76c on the growth of subcutaneous KB tumor. Three hours (3 h) after injecting with 76c, mouse with 28 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (4 weeks).
Figure 22A:
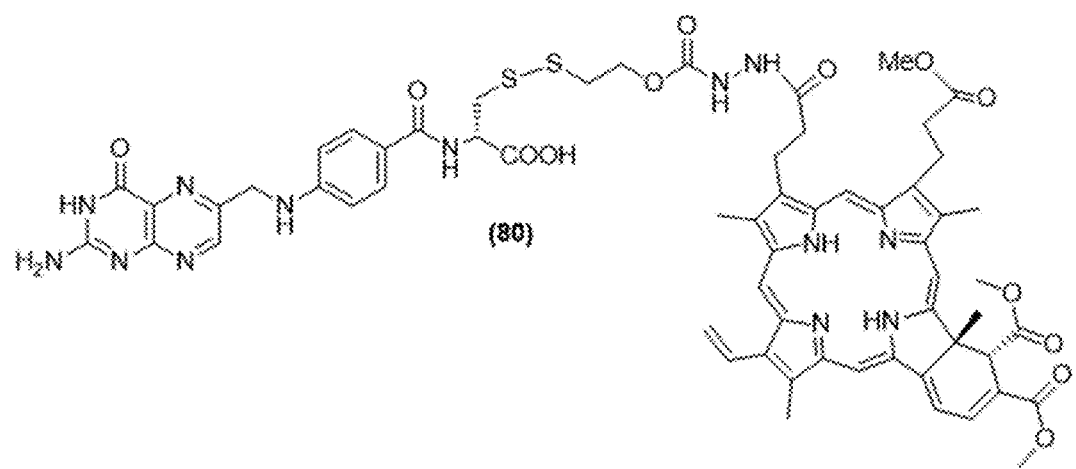
FIGS. 22A-22H depict structures of folate-targeted releasable disulfide linked visudyne conjugates with different soluble linkers.
Figure 22B:
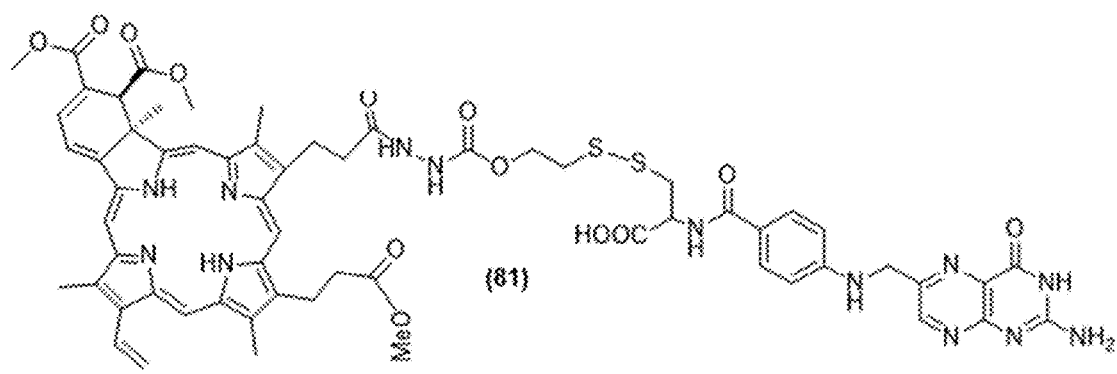
Figure 22C:
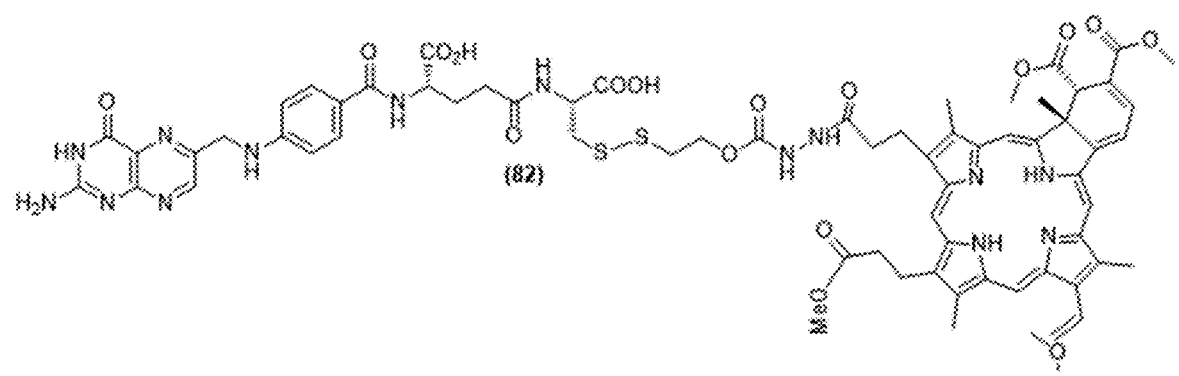
Figure 22D:
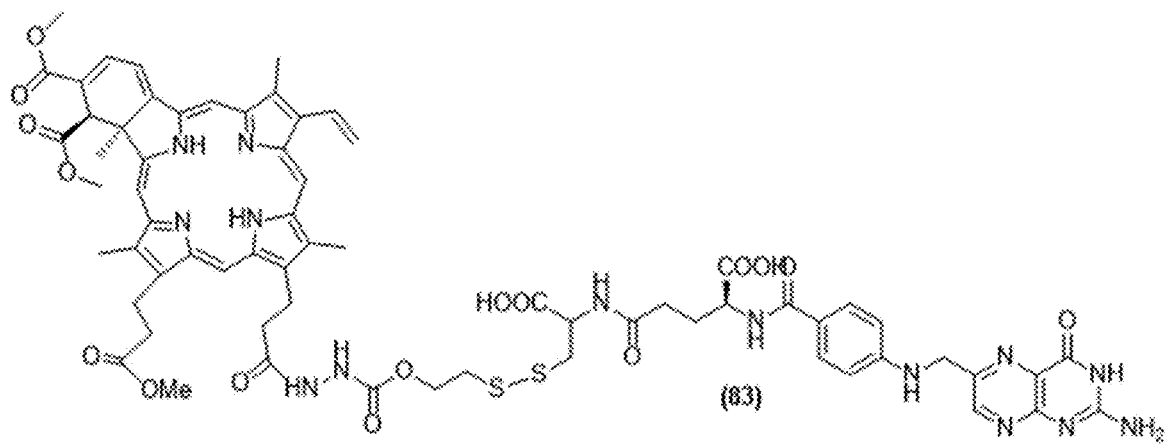
Figure 22E:
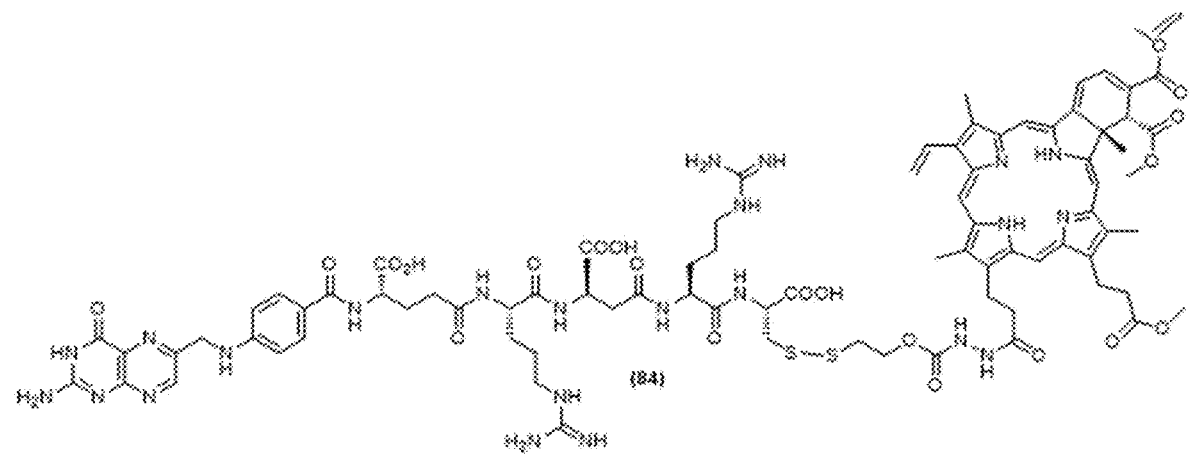
Figure 22F:
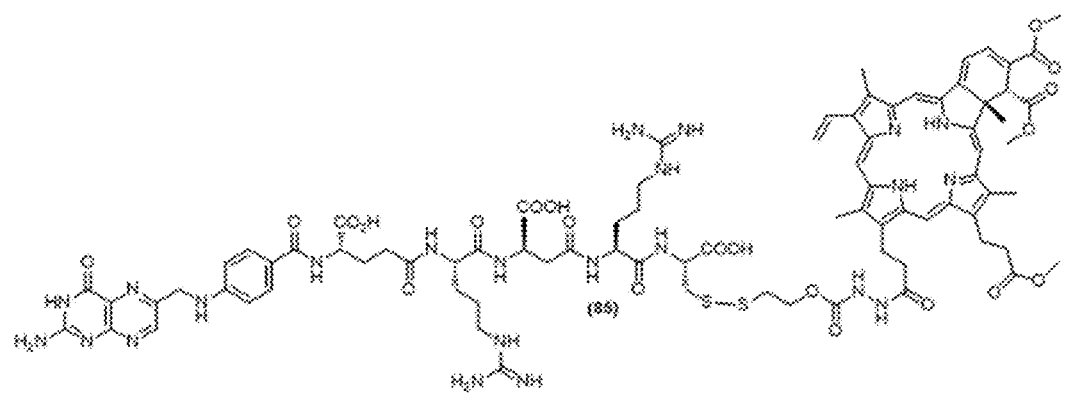
Figure 22G:
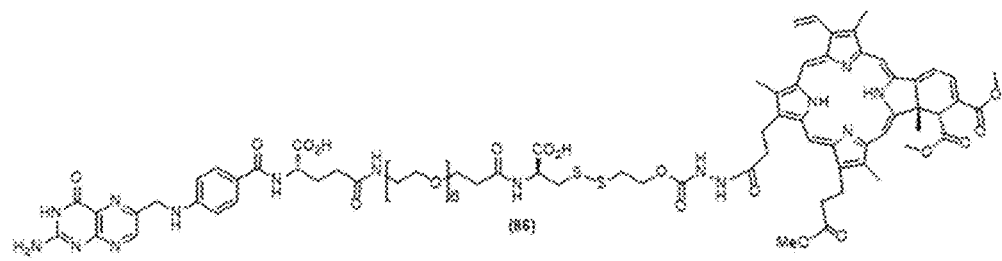
Figure 22H:
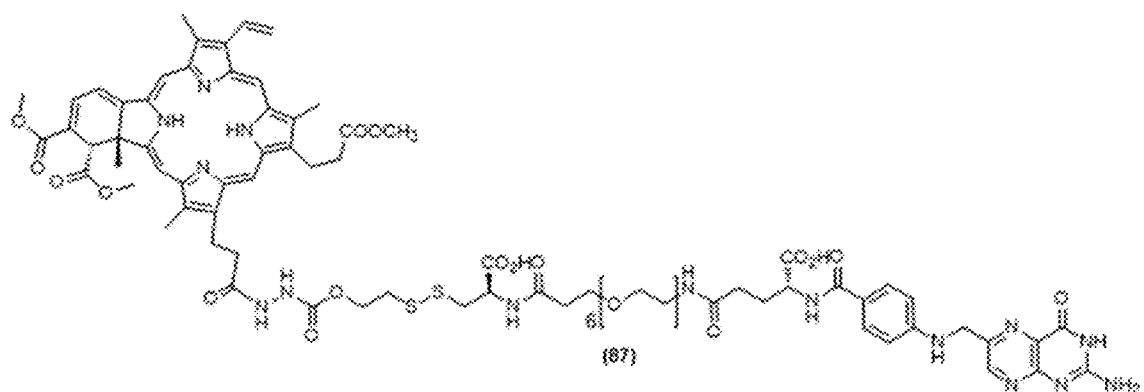
Figure 23:
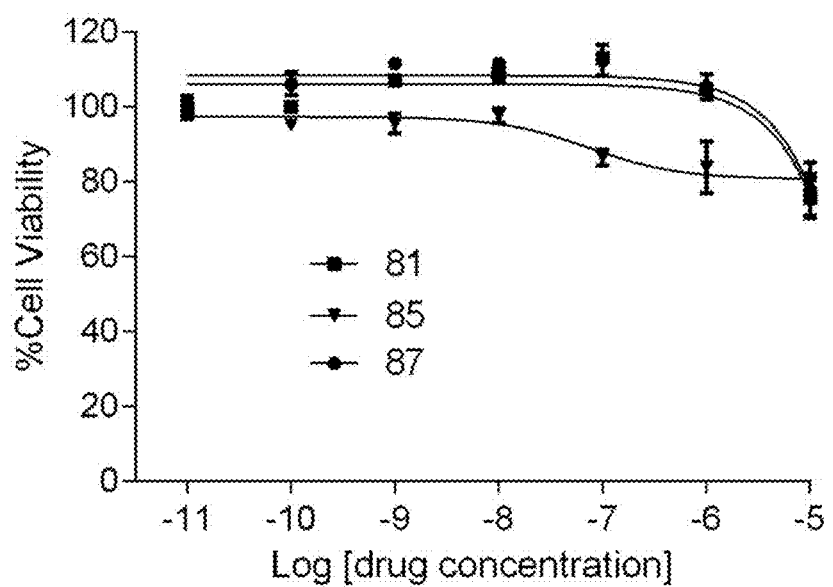
FIG. 23 depicts an effect of the drug concentration on the survival of KB cells (a derivative of HeLa cell line and HeLa cells are human cervical cancer cell line). Folate drug conjugate dissolved in folate free RPMI were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell viability was measured using CellTiter Glo (Promega). Error bars represent s.d. (n=3).
Figure 24A:
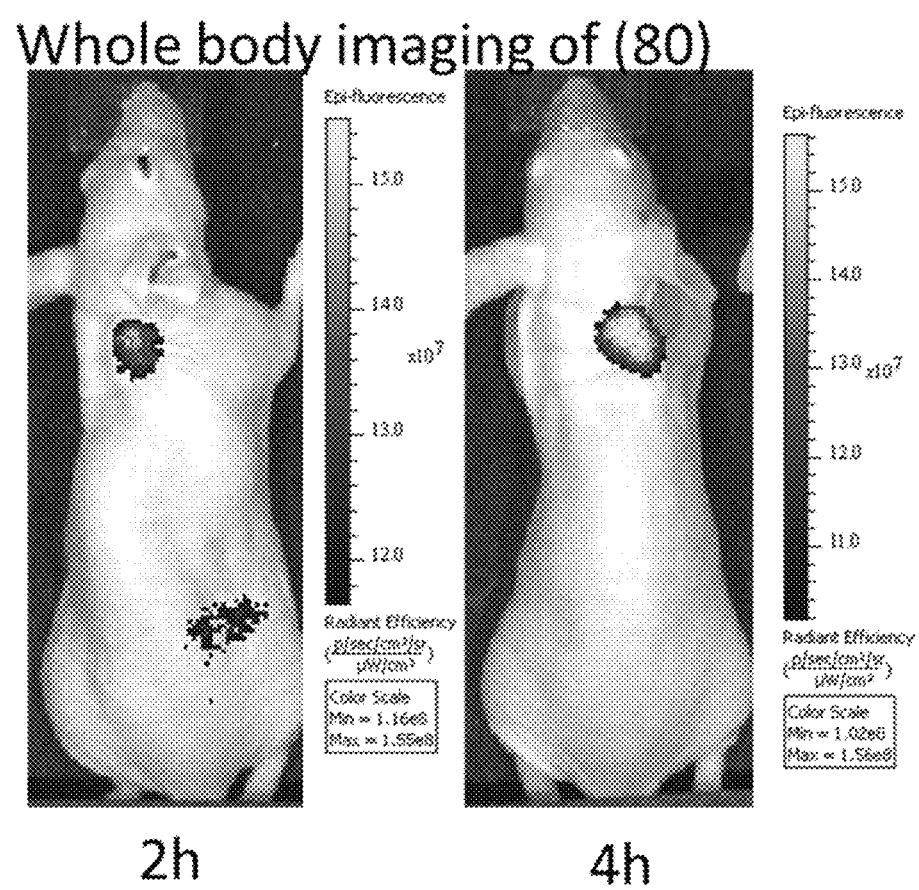
FIGS. 24A-24B depict an overlay of whole body fluorescence image over white light images after adjusting the threshold. KB tumor bearing mice injected with 10 nmol of 80 or 86 and image with IVIS imager (ex=640 nm, em=720 nm, exposure time=1 s) at different time intervals.
Figure 24B:
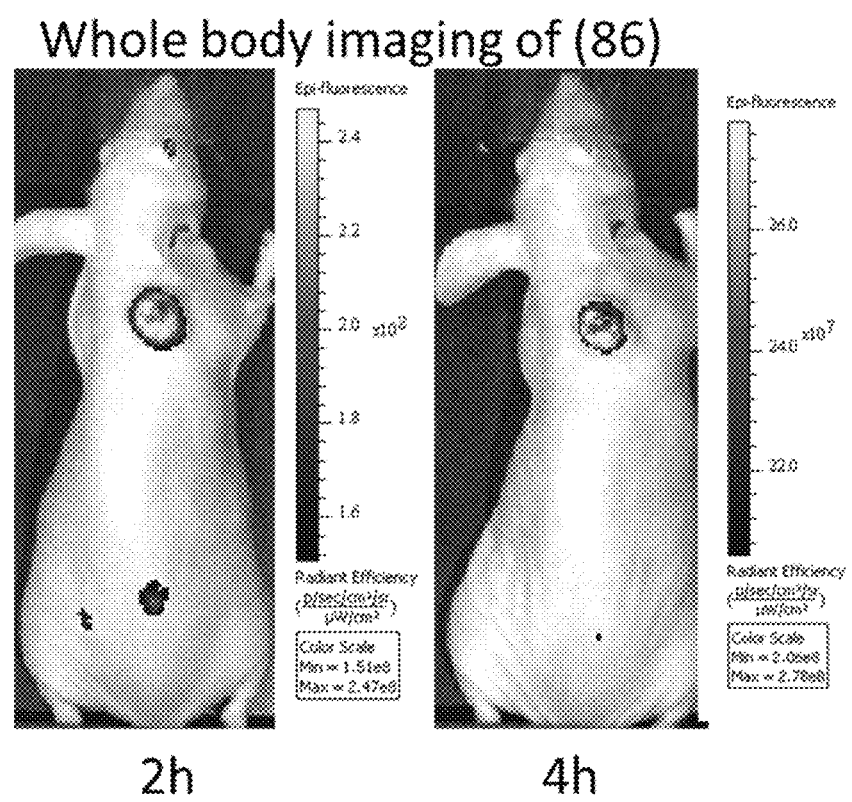
Figure 25A:
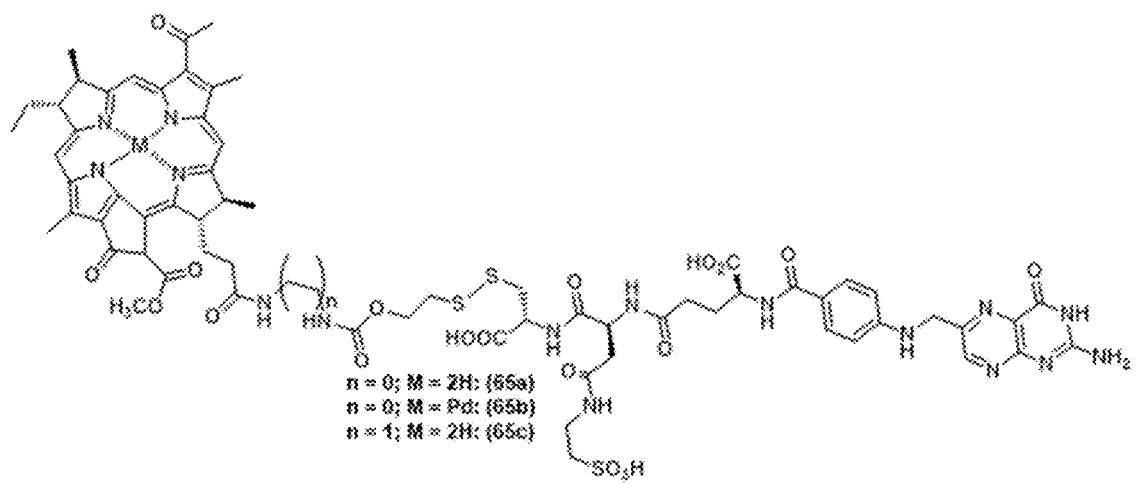
FIGS. 25A-25K depict structures of folate-targeted releasable disulfide linked BPheid-a conjugates to produce positively charged PDT analogues inside the cancer cell.
Figure 25B:
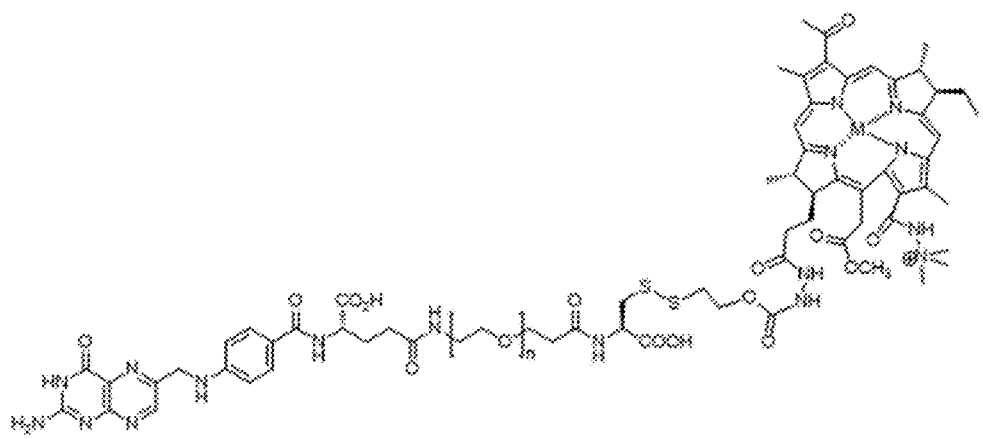
Figure 25C:
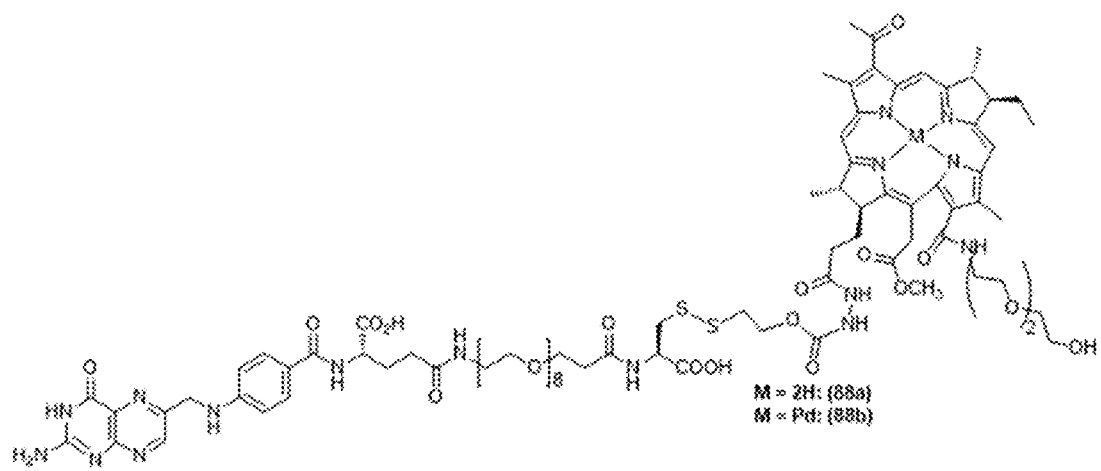
Figure 25D:
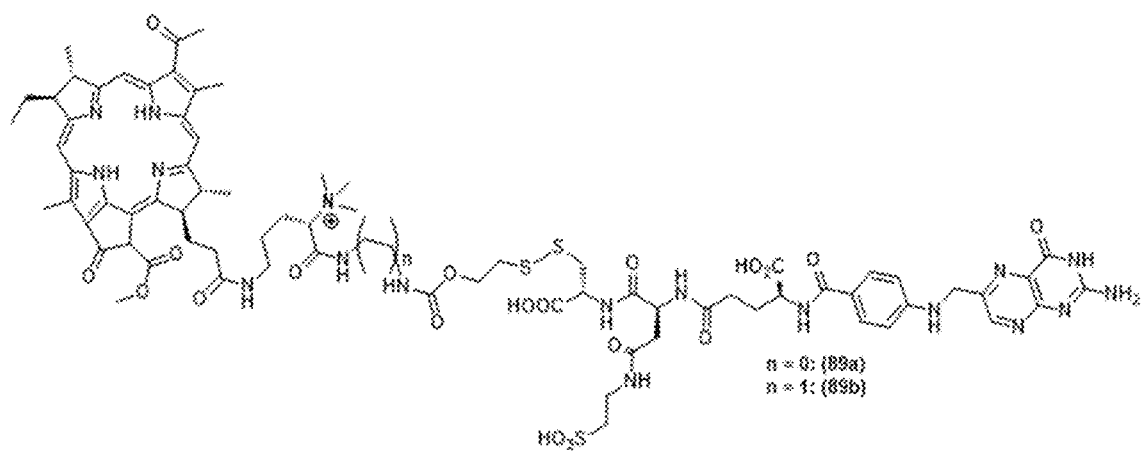
Figure 25E:
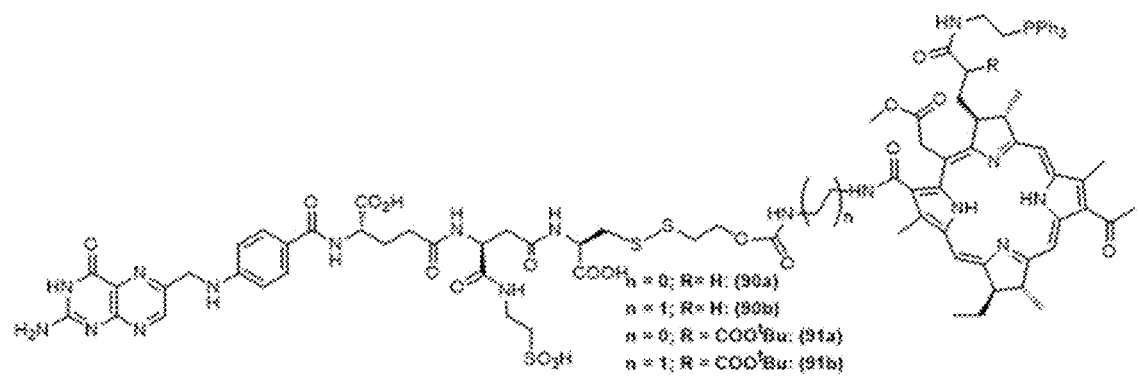
Figure 25F:
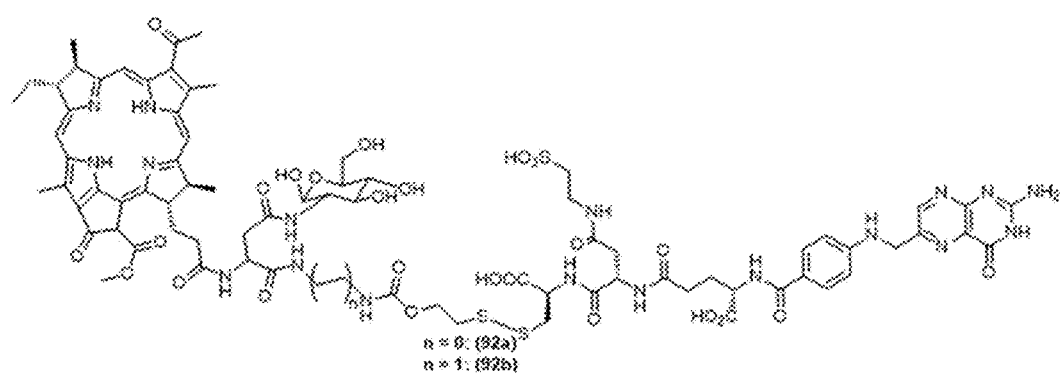
Figure 25G:
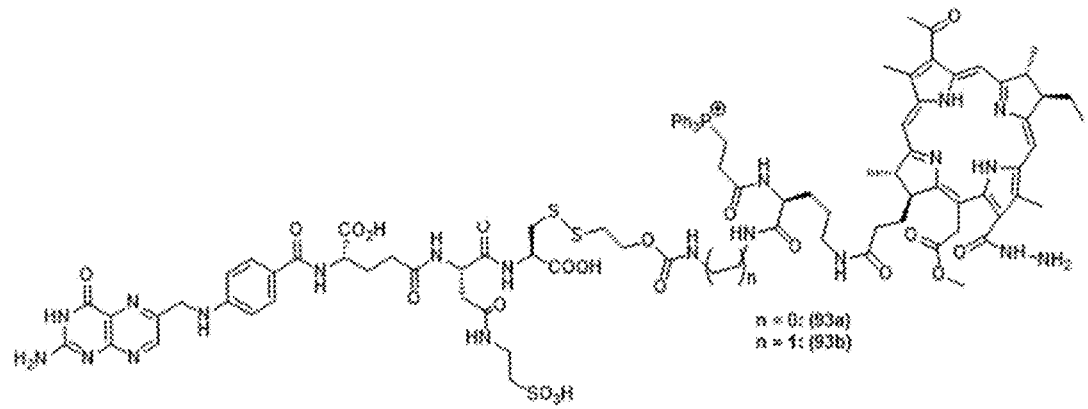
Figure 25H:
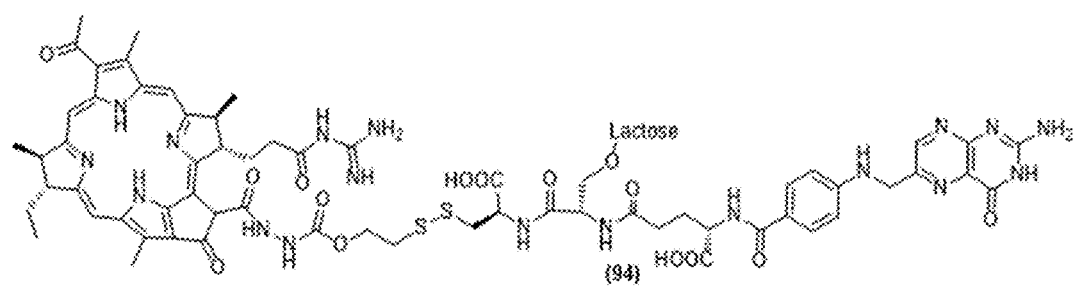
Figure 25I:
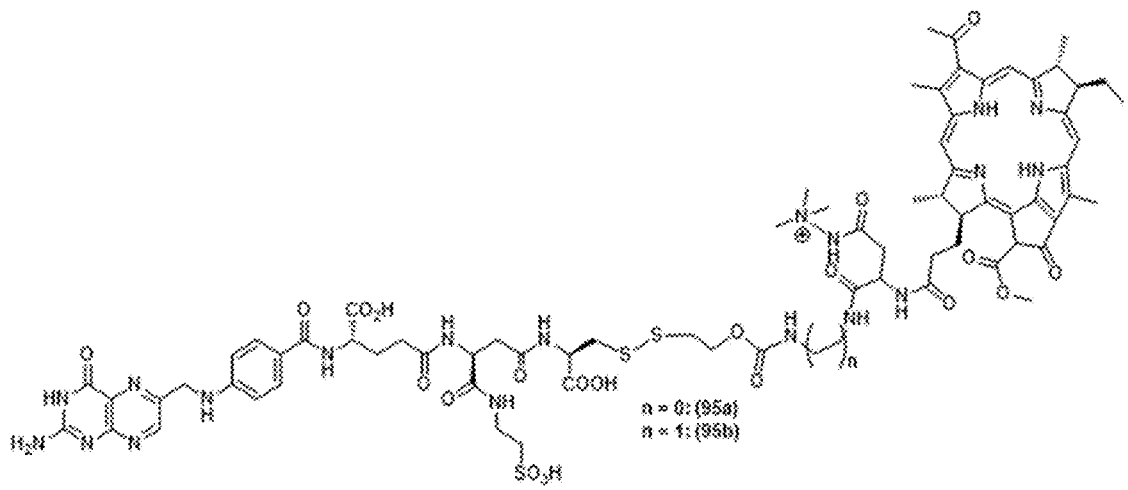
Figure 25J:
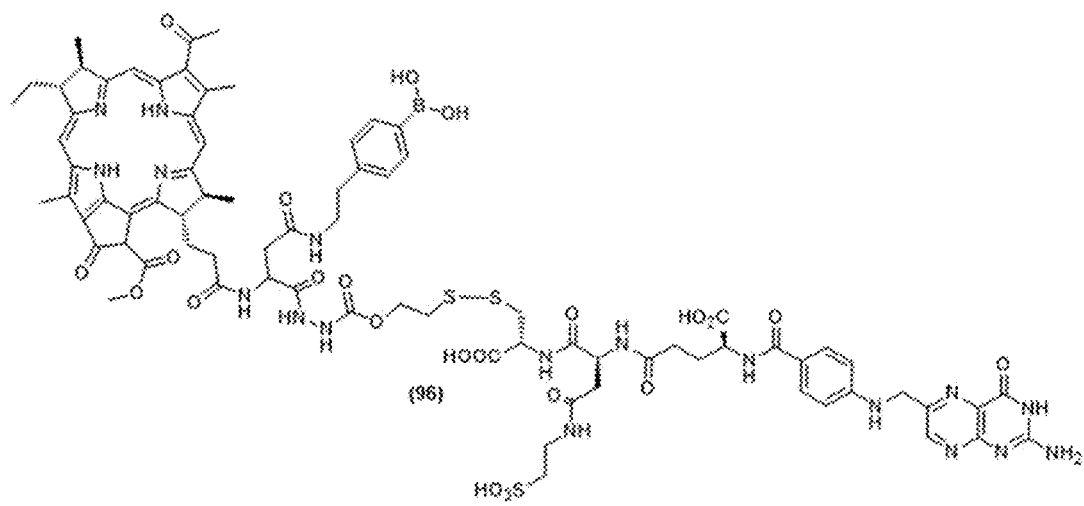
Figure 25K:
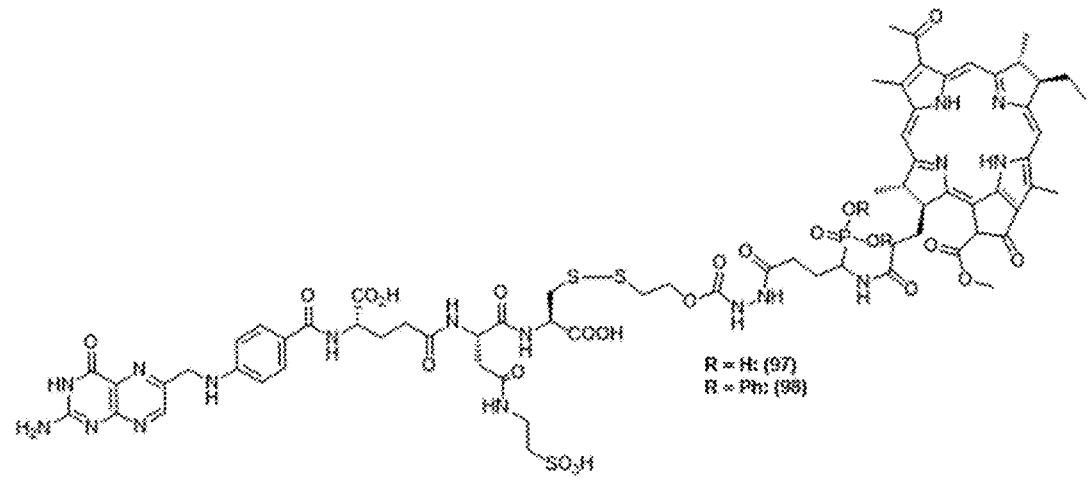
Figure 26:
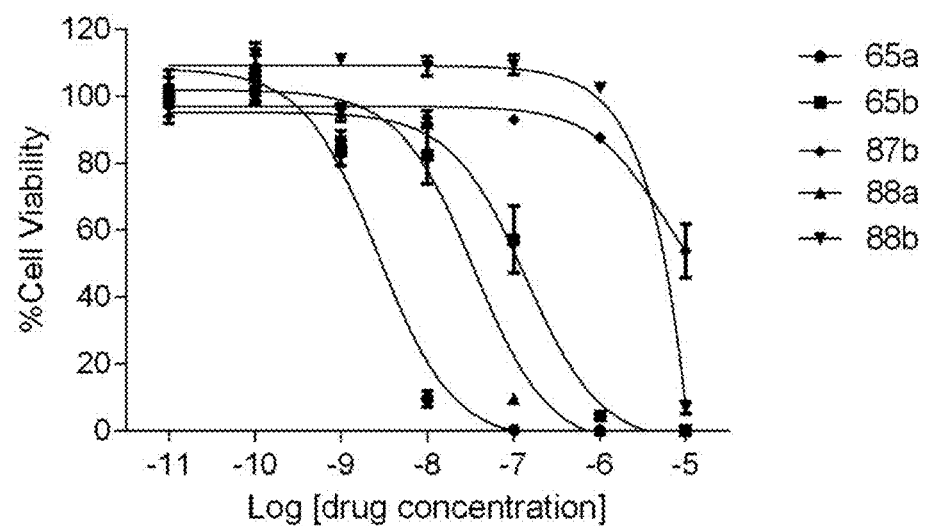
FIG. 26 depicts an effect of the drug concentration on the survival of KB cells (a derivative of HeLa cell line and HeLa cells are human cervical cancer cell line). Folate conjugate dissolved in folate free RPMI were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm2, 12 J/cm2 and exposure diameter=6 cm for 25 wells) for 32 min and incubated at 37° C. for an additional 24 h. Cell viability was measured using CellTiter Glo (Promega). Error bars represent s.d. (n=3).
Figure 27:
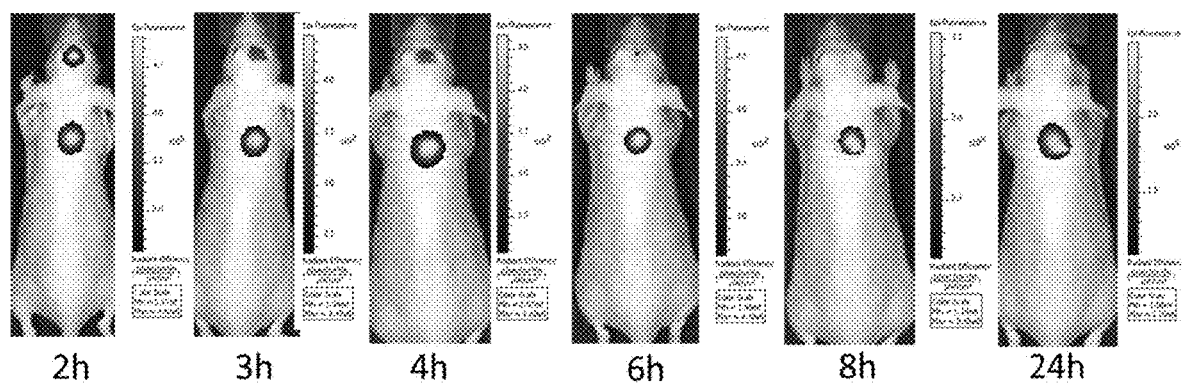
FIG. 27 depicts an overlay of time dependent whole body fluorescence image over white light images after adjusting the threshold. KB tumor bearing mice injected with 10 nmol of 89a and image 2 h after administering of 89a at different time intervals with IVIS imager (ex=745 nm, em=ICG, exposure time=1 s).
Figure 28:
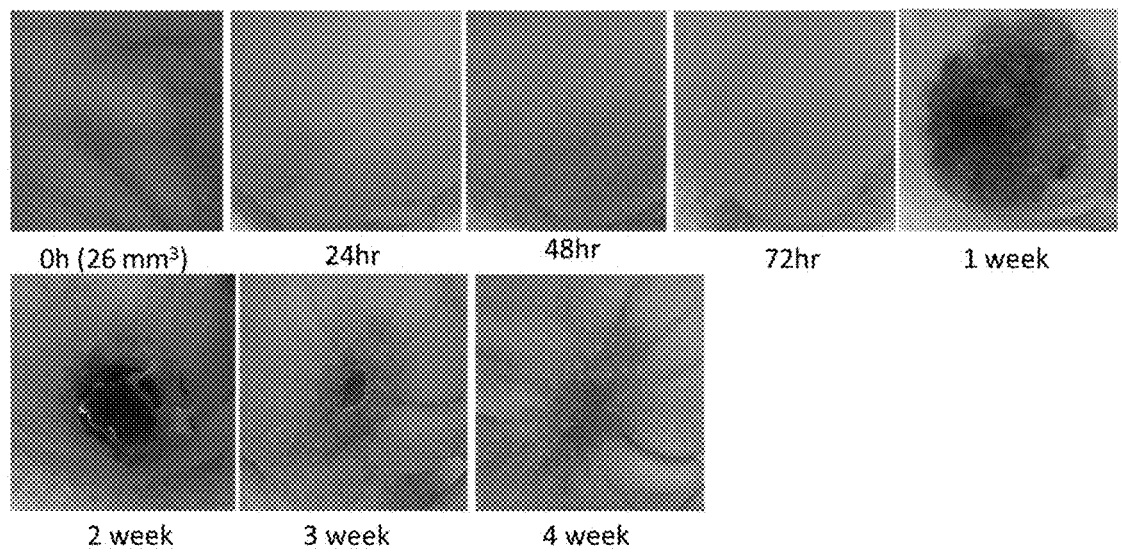
FIG. 28 depicts an effect of 50 nmol dose of 89 on the growth of subcutaneous KB tumor. Three hours (3 h) after injecting with 89, mouse with 26 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (4 weeks).
Figure 29:
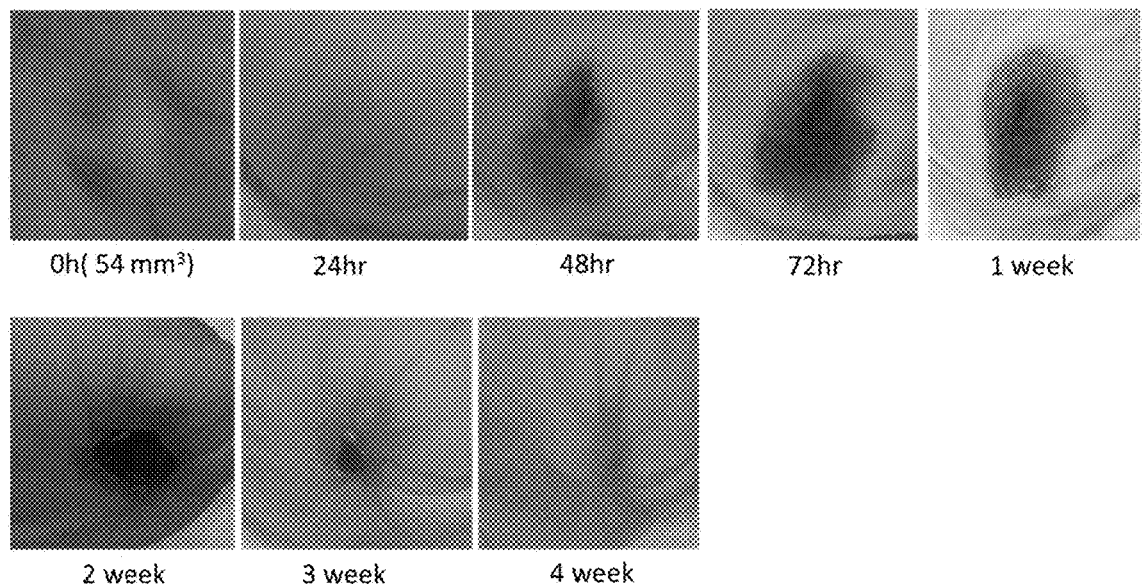
FIG. 29 depicts an effect of 50 nmol dose of 92 on the growth of subcutaneous KB tumor. Three hours (3 h) after injecting with 92, mouse with 26 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (4 weeks).
Figure 30A:
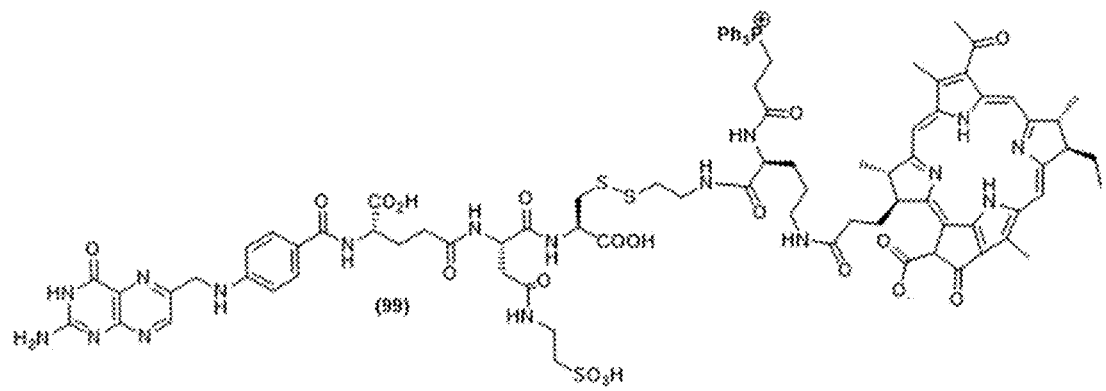
FIG. 30A-30E depicts structures of folate-targeted releasable disulfide linked BPhied-a conjugates to produce Zwitterionic PDT analogue inside the cancer cell.
Figure 30B:
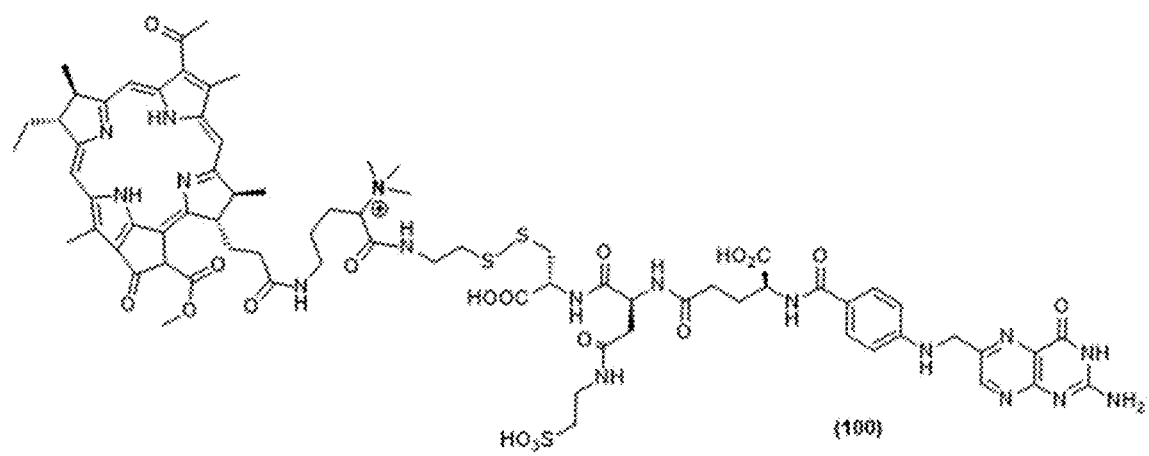
Figure 30C:
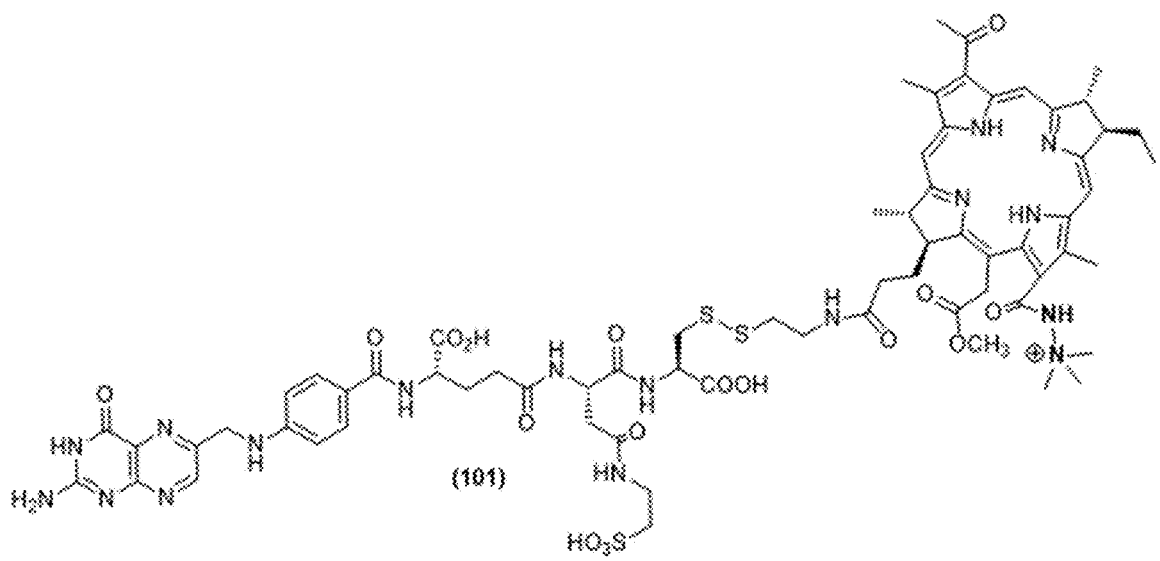
Figure 30D:
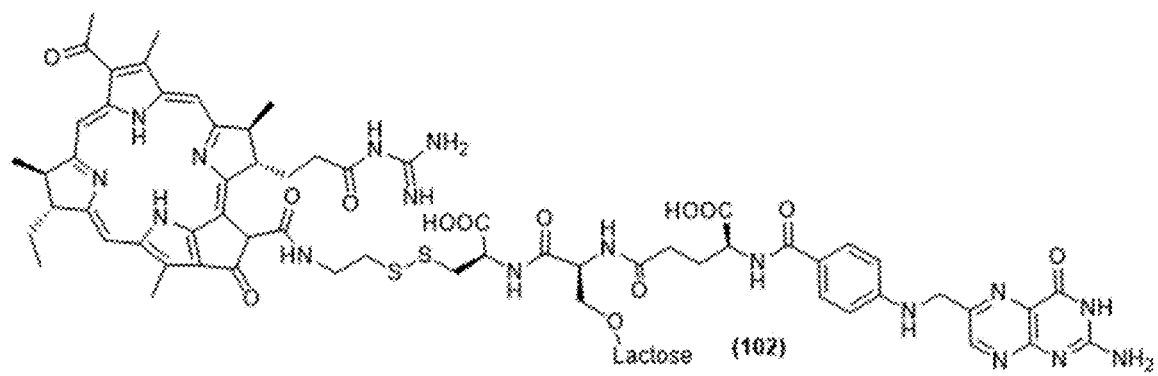
Figure 30E:
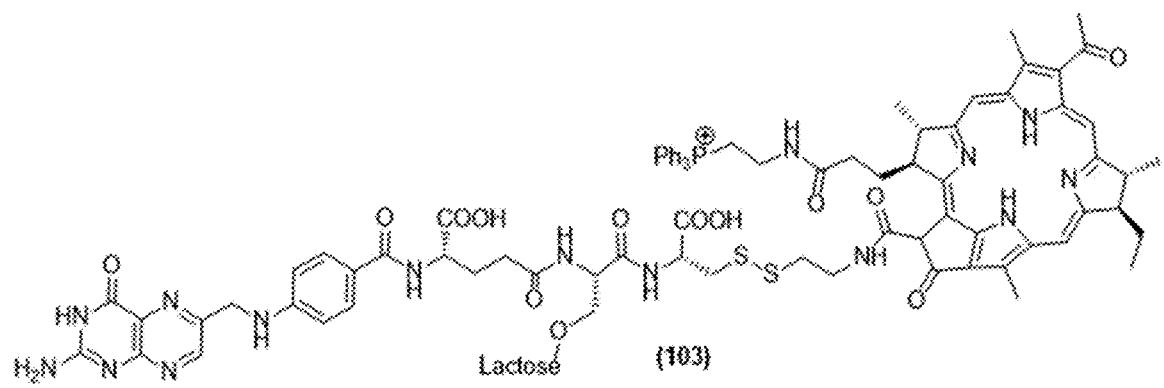
Figure 31:
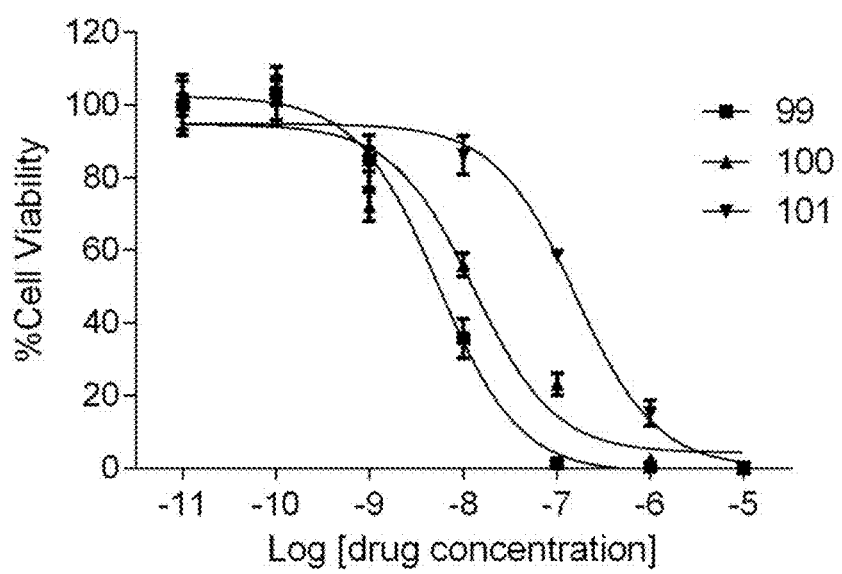
FIG. 31 depicts an effect of the drug concentration on the survival of KB cells (a derivative of HeLa cell line and HeLa cells are human cervical cancer cell line). Folate-drug conjugate dissolved in folate free RPMI were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell survival was then quantitated using viability was measured using CellTiter Glo (Promega). Error bars represent s.d. (n=3).
Figure 32:
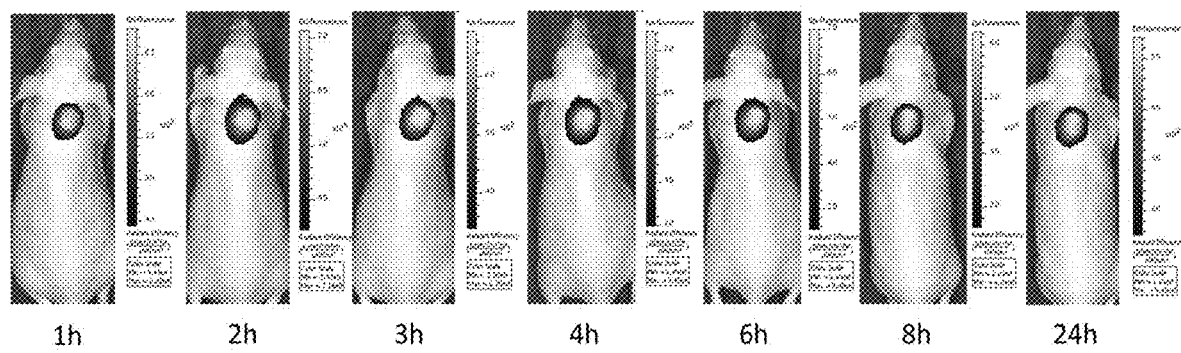
FIG. 32 depicts an overlay of whole body fluorescence image over white light images after adjusting the threshold. KB tumor bearing mice injected with 10 nmol of 100 and image with IVIS imager (ex=745 nm, em=ICG, exposure time=1 s) at different time intervals.
Figure 33:
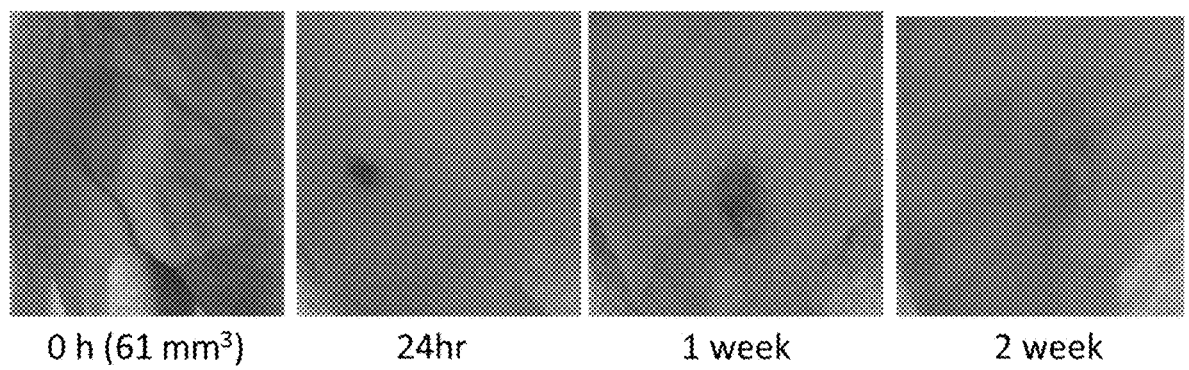
FIG. 33 depicts an effect of 50 nmol dose of 99 on the growth of subcutaneous KB tumor. Three hours (3 h) after injecting with 99, mouse with 61 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (2 weeks).
Figure 34:
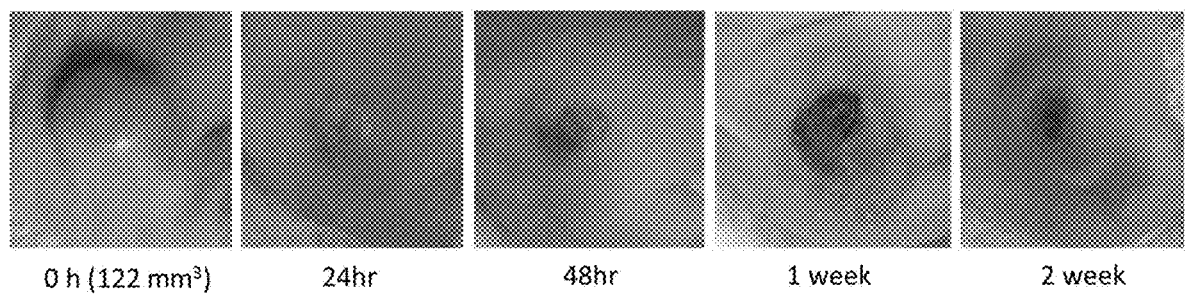
FIG. 34 depicts an effect of 50 nmol dose of 100 on the growth of subcutaneous KB tumor. Three hours (3 h) after injecting with 100, mouse with 122 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper. Tumor is completely cured with no recurrence during the monitored time (2 weeks).
Figure 35A:
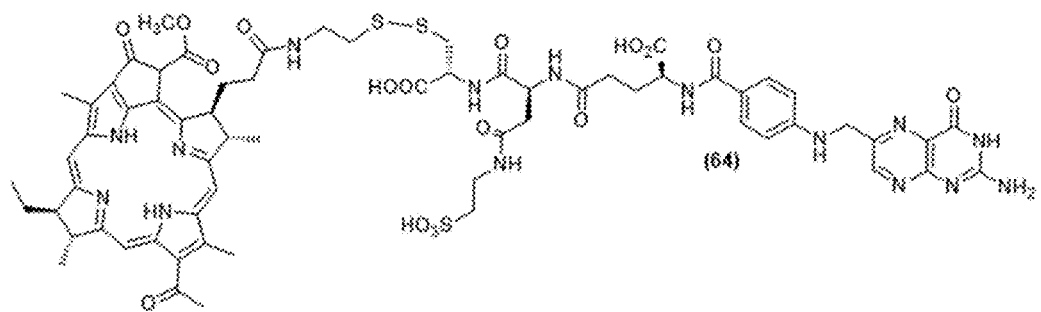
FIGS. 35A-35H depicts structures of folate-targeted releasable disulfide linked BPheid-a and visudyne conjugates to produce anionic PDT (negative charged) analogues inside the cancer cell.
Figure 35B:
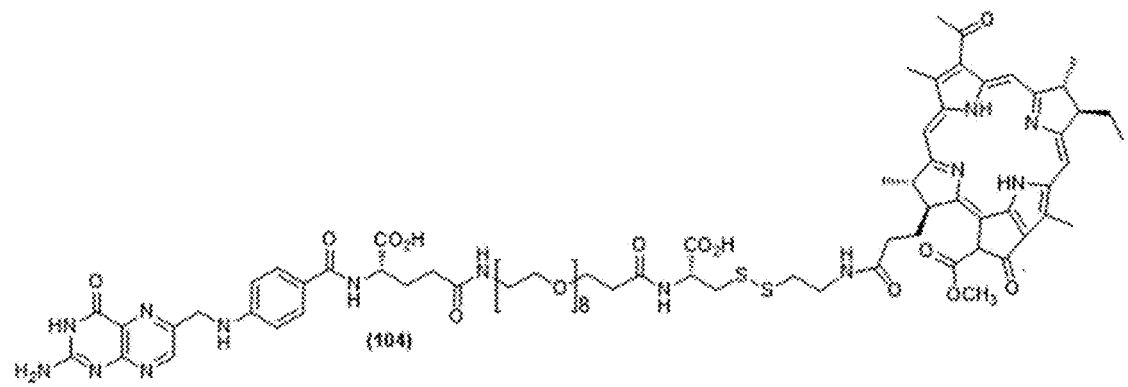
Figure 35C:
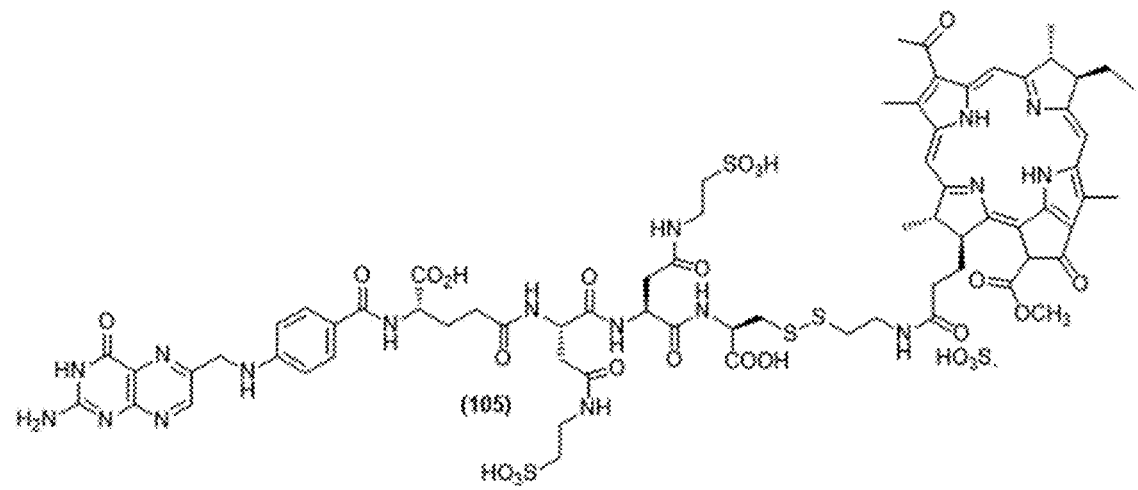
Figure 35D:
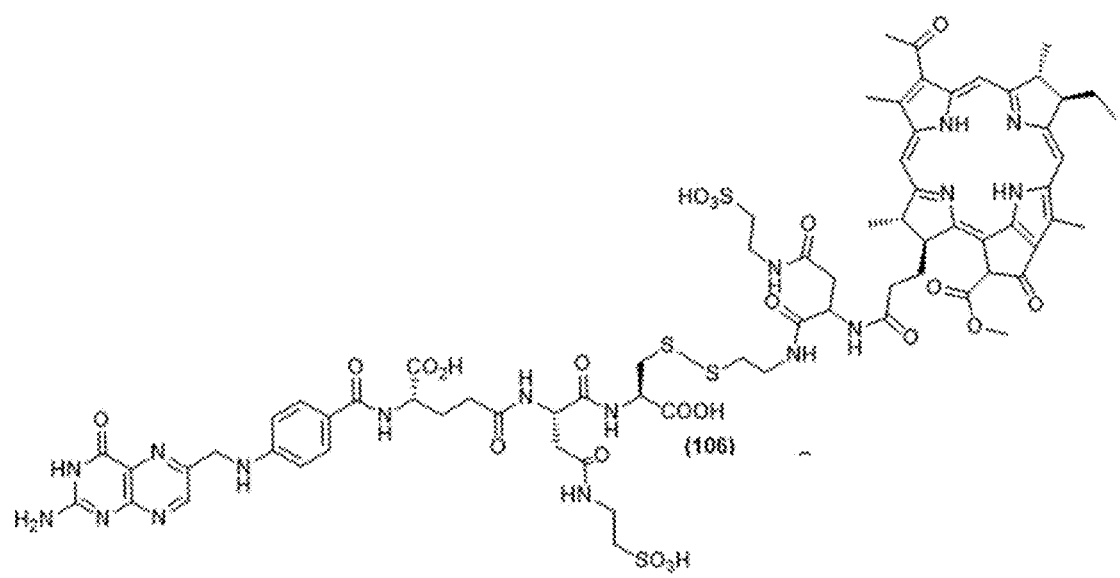
Figure 35E:
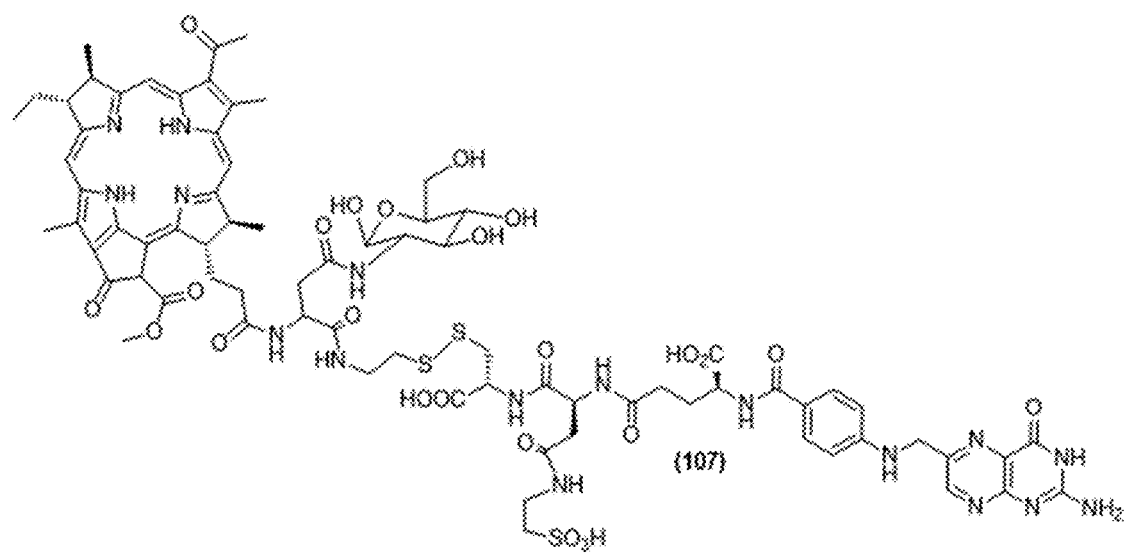
Figure 35F:
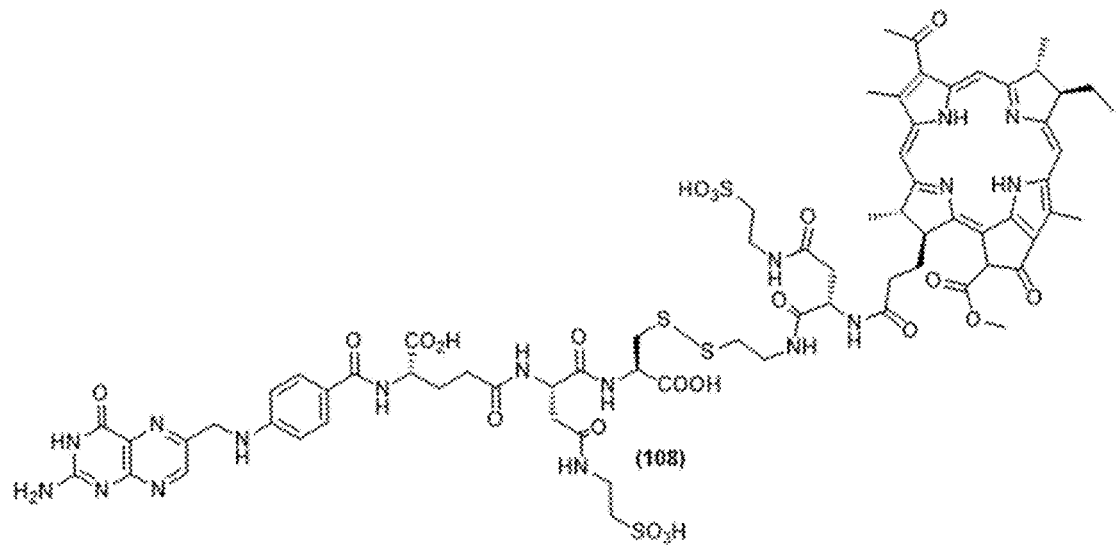
Figure 35G:
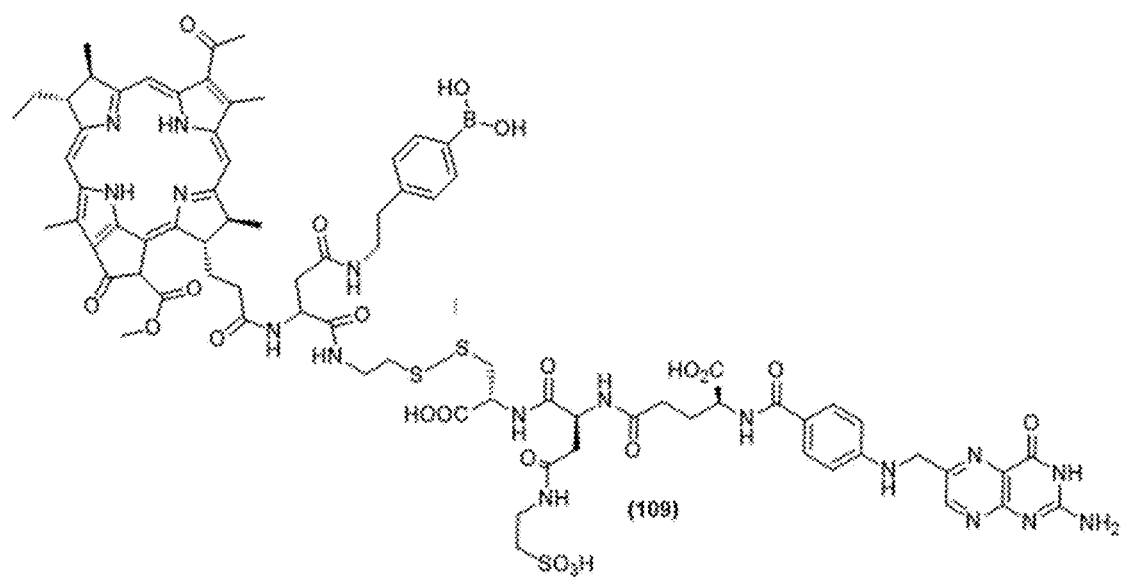
Figure 35H:
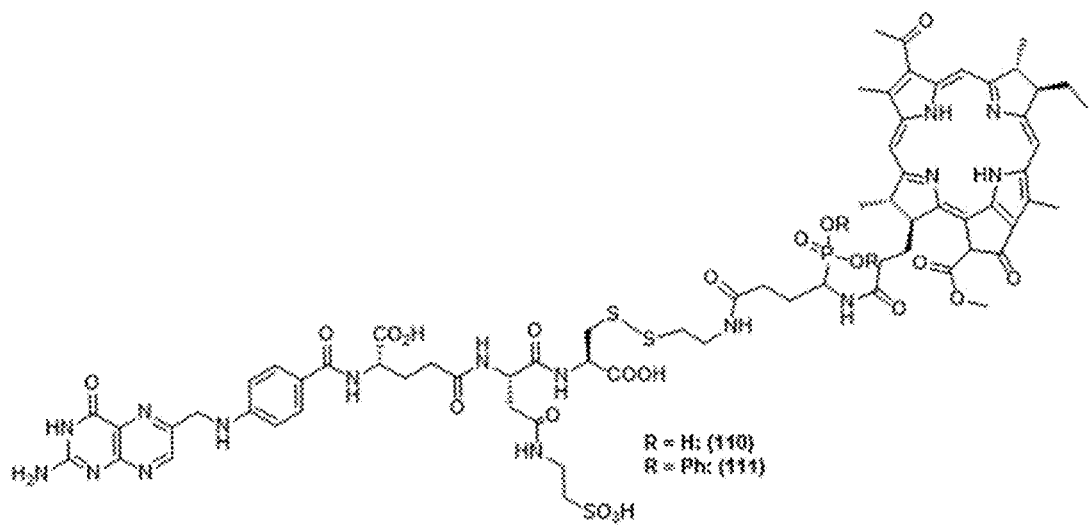
Figure 36:
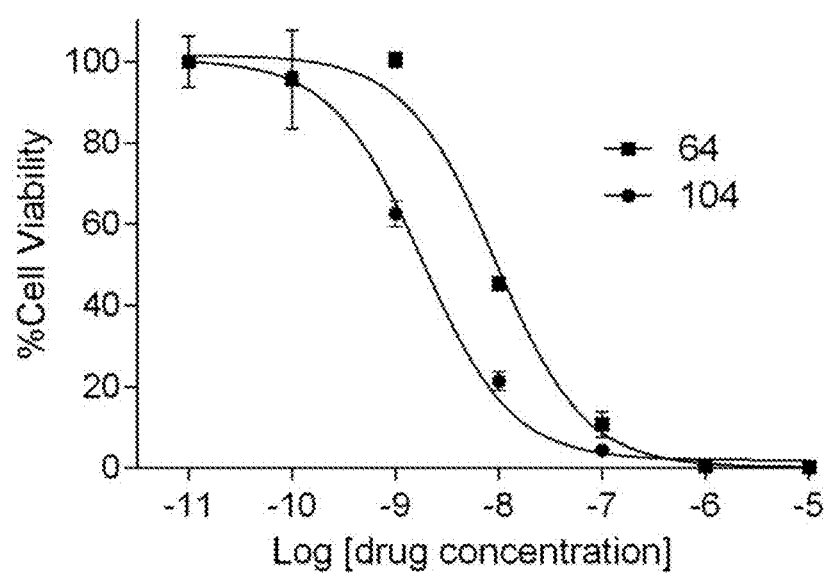
FIG. 36 depicts an effect of the drug concentration on the survival of KB cells (a derivative of HeLa cell line and HeLa cells are human cervical cancer cell line). Folate drug conjugates dissolved in folate free RPMI were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell viability was measured using CellTiter Glo (Promega). Error bars represent s.d. (n=3).
Figure 37:
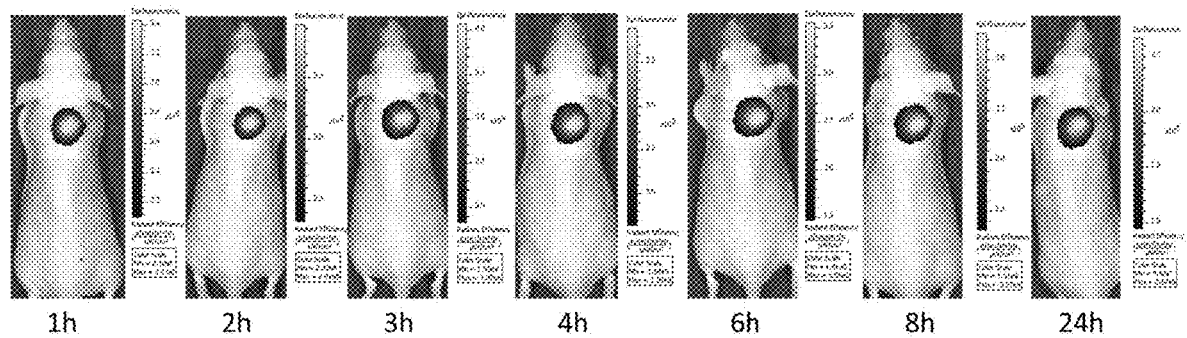
FIG. 37 depicts an overlay of whole body fluorescence image over white light images after adjusting the threshold. KB tumor bearing mice injected with 10 nmol of 104 and image with IVIS imager (ex=745 nm, em=ICG, exposure time=1 s) at different time intervals.
Figure 38:
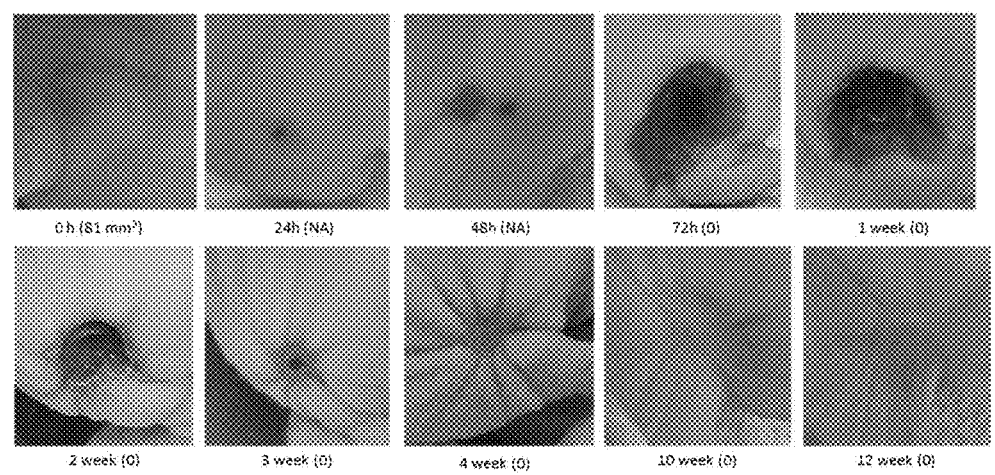
FIG. 38 depicts an effect of 104 on the growth of subcutaneous KB tumor. Three hours (3 h) after injecting with 50 nmol of 104, mouse with 81 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper.
Figure 39:
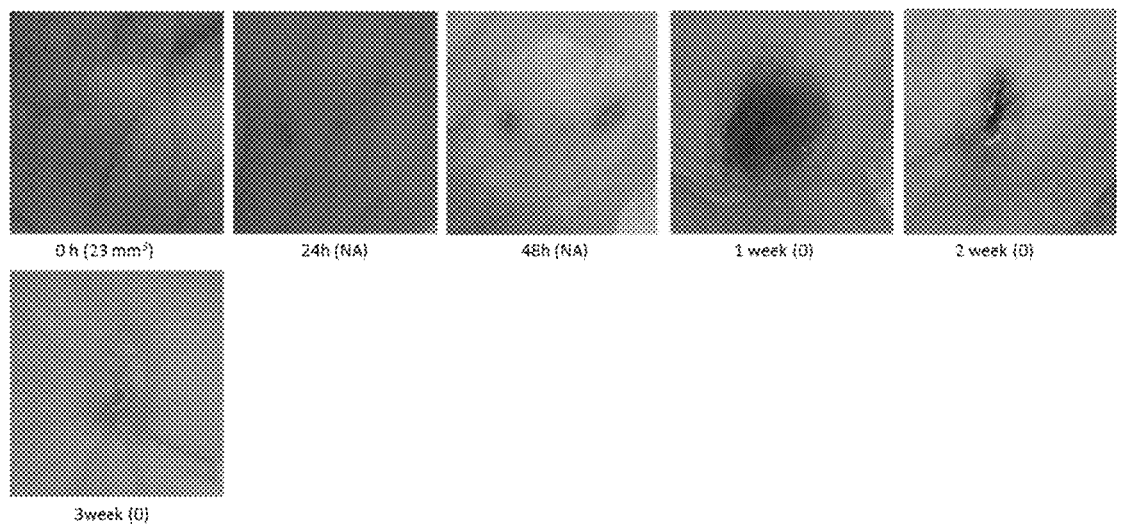
FIG. 39 depicts an effect of 104 on the growth of subcutaneous KB tumor. Three hours (3 h) after injecting with 25 nmol of 104, mouse with 23 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper.
Figure 40A:
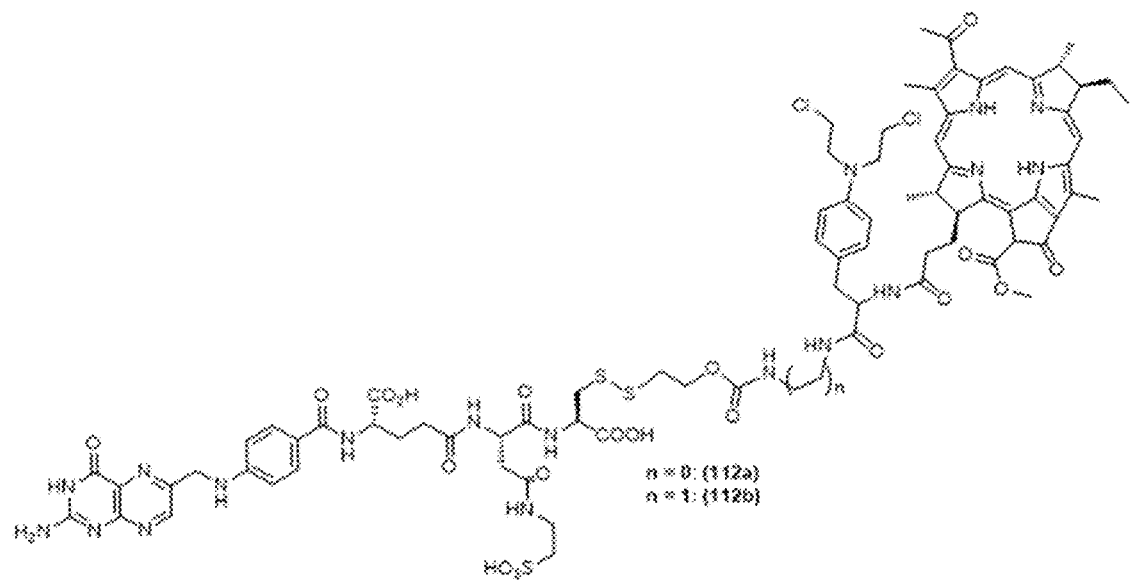
FIG. 40A-40G depict structures of folate-targeted releasable disulfide linked BPheid-a conjugates to produce anionic PDT (negatively charged) compound inside the cancer cell.
Figure 40B:
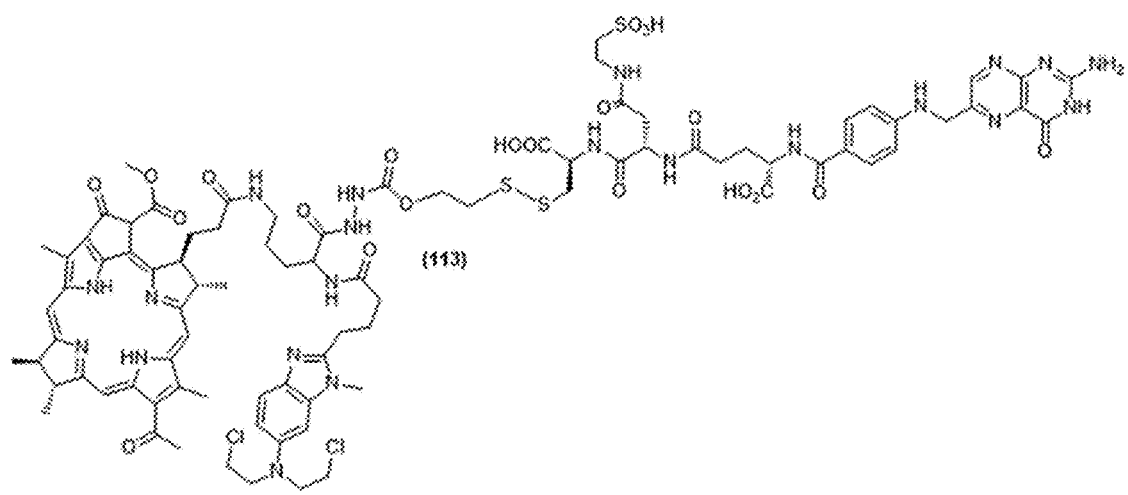
Figure 40C:
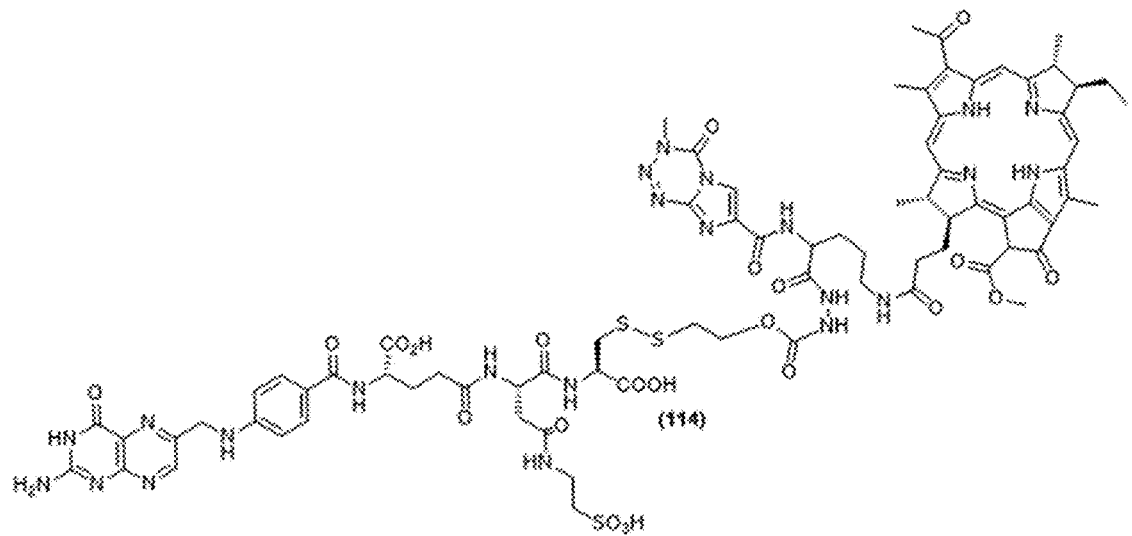
Figure 40D:
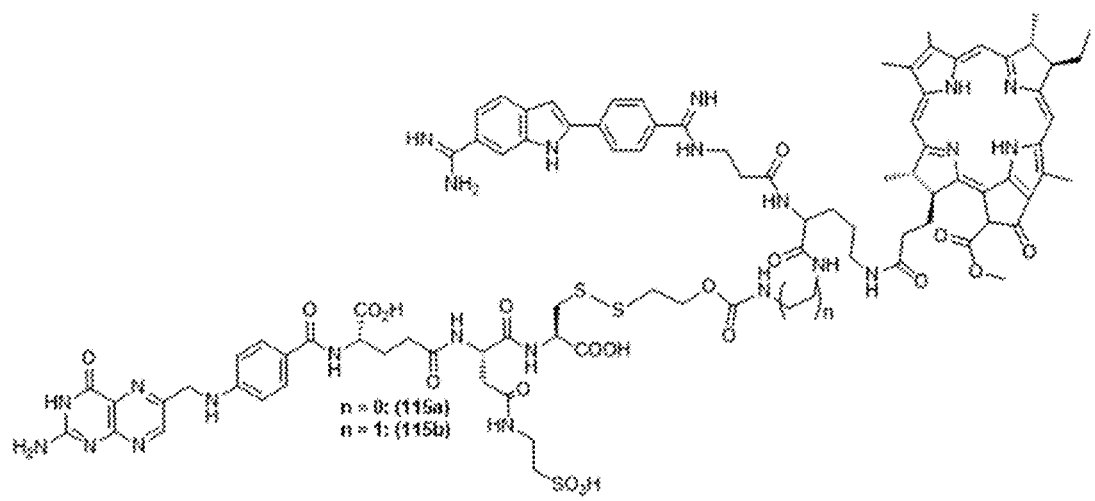
Figure 40E:
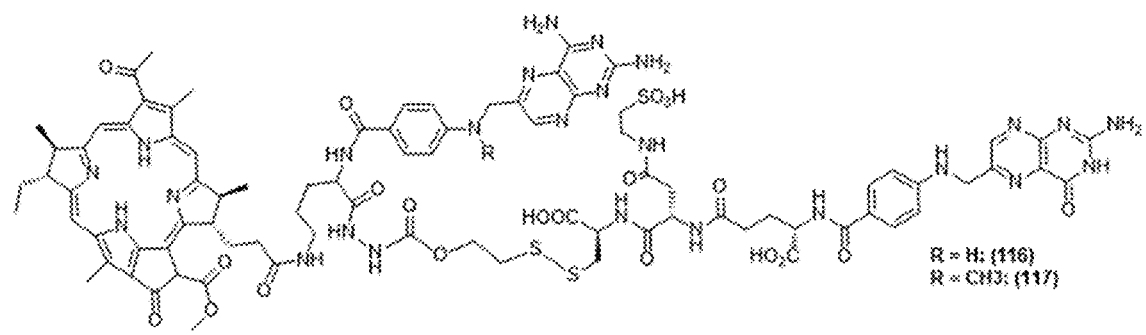
Figure 40F:
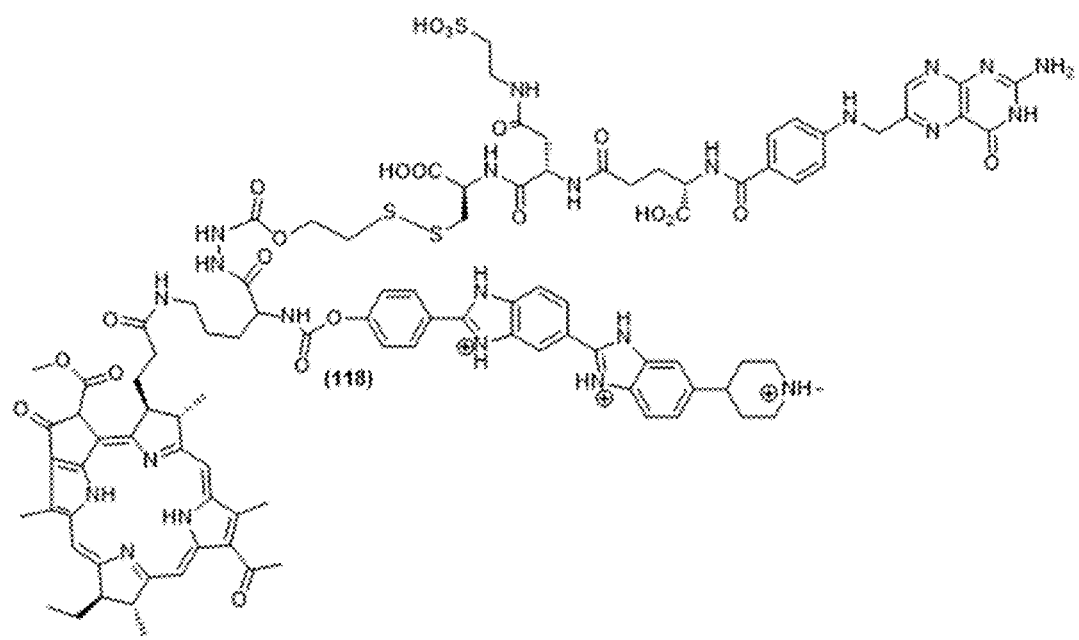
Figure 40G:
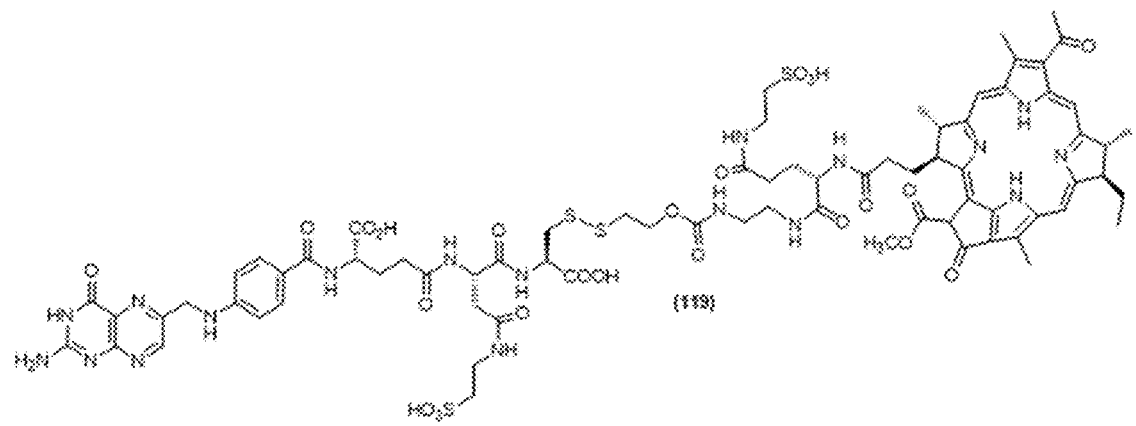
Figure 41:
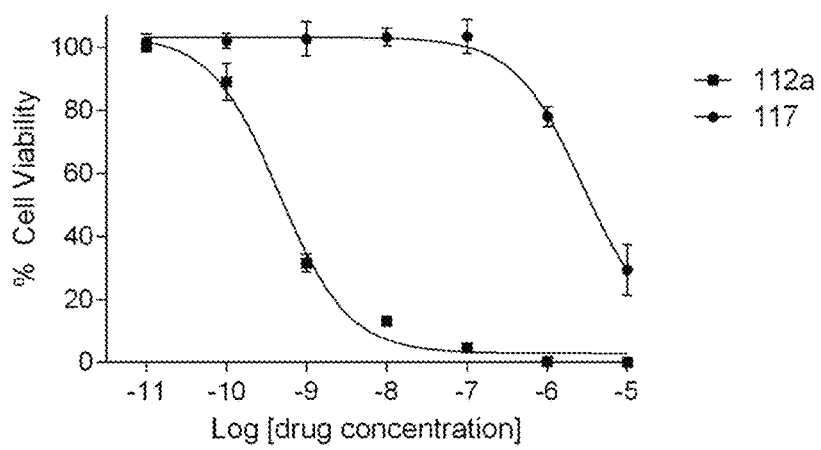
FIG. 41 depicts an effect of the drug concentration on the survival of KB cells (a derivative of HeLa cell line and HeLa cells are human cervical cancer cell line). Folate drug conjugates dissolved in folate free RPMI were added at the indicated concentrations to KB cells in folate free RPMI culture media and allowed to incubate for 2 h at 37° C. Media was then removed, washed with fresh media, and replaced with fresh media (drug-free). The cells were then exposed to laser beam (6 mW/cm$^2$, 12 J/cm$^2$ and exposure diameter=6 cm for 25 wells) for 32 min and incubated at 37° C. for an additional 24 h. Cell survival was then quantitated using viability was measured using CellTiter Glo (Promega). Error bars represent s.d. (n=3).
Figure 42:
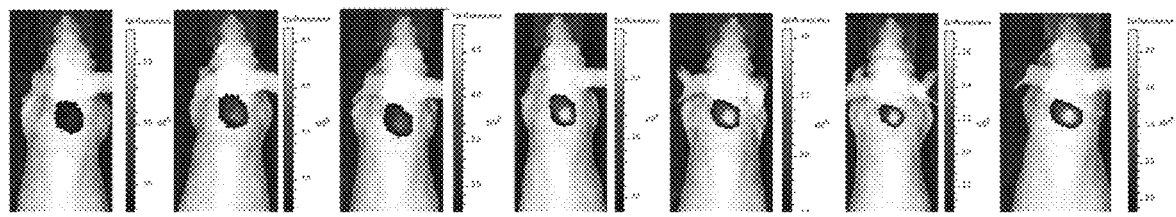
Figure 43:
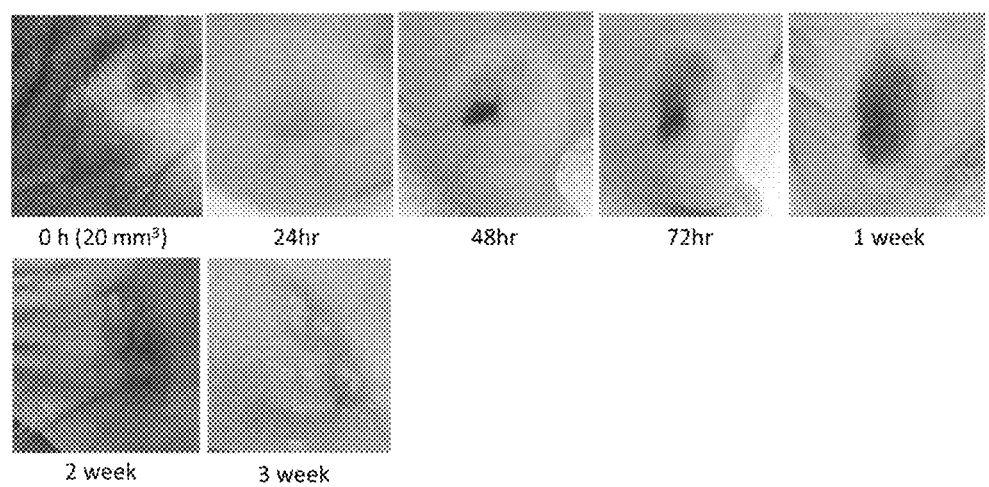
FIG. 43 depicts an effect of 117 on the growth of subcutaneous KB tumor. Three hours (3 h) after injecting with 25 nmol of 117, mouse with 20 mm$^3$ tumor was treated with laser beam 75 mW/cm$^2$, 137 J/cm$^2$, exposure diameter=7.5-8 mm) for 38 min. The growth of the tumor was monitored (images were taken) and tumor volume was measured using caliper.

Compounds 1 to 5 were tested on KB cells to determine their efficacy. FIG. 2 shows the effects of the concentration of these drugs on cell survival.

TABLE 1

Effect of various non-targeted PDT agents on the survival of KB cells in culture.

| Compound | EC50 (nM) | Activation Wavelength (nm) |
|---|---|---|
| BPheid - a (1) | 745 | 750 |
| Tookad (2) | 10,360 | 760 |
| 3 | 1750 | 740 |
| 4 | 7,763 | 750 |
| Visudyne (5) | 838.2 | 689 |
| Foscan (6) | Not active | 652 |
| Photofrin (7) | NA | 630 |

To determine the in vitro efficacy of non-targeted PSs, KB cells were used as described infra at the beginning of the Examples.

The EC50 values of all the non-targeted PSs that were tested show that these agents are not active in cancer cells and hence not suitable for PDT. There may be a number of reasons for this lack of activity, including for example, poor water solubility, poor cell penetration, and inefficient organelle localization within the cancer cells.

It was also noticed that the Pd chelated compounds (3 and 4) are less active when compared to non-chelated molecules (1 and 2). Moreover, compound 4 is less active when compared to compound 1. This loss of activity may be due to the opening of the five membered ring (that has a ketone group and a methyl ester) with nucleophile.

To establish the specificity of these non-targeted PSs for cancer cells, BPheid-a was injected into nude mice bearing KB tumors on their shoulders. The mice were monitored for accumulation of the PS in the tumor using fluorescence imaging using IVIS imager. Time dependent whole body images showed nonspecific uptake of BPheid-a in the skin of the mouse. Moreover, there was a prolonged time to clear from the skin. BPheid-a took ~24 hours to accumulate in the tumor and fluorescence in the tumor was very low indicating that very few BPheid-a molecules actually reached the tumor tissue. The lack of availability of the BPheid-a molecule may be attributable to various reasons, including, for example, poor water solubility, poor cell penetration, low bioavailability of the drug, the drug not providing a sufficient number of molecules to the to the tumor, and inefficient organelle localization within the cancer cells.

KB cells that overexpressed folate receptor were implanted subcutaneously into female nude mice and allowed to grow to ~50 mm$^3$ prior to initiation of treatment with 50 nmol of BPheid-a (1). Three hours (3 h) after injecting with 50 nmol of BPheid-a, tumor was treated with laser beam (75 mW/cm$^2$, 137 J/cm$^2$, exposure diameter=7.5-8 mm) for 38 min. In vivo efficacy of BPheid-a was evaluated by monitoring reduction of tumor volume. KB tumors treated with BPheid-a grew with a doubling time of <1 week and reached >600 mm$^3$ by the end of the two week treatment period and mouse has to euthanized in 3 weeks due to large tumor volume. On the other hand, PBS (phosphate buffered saline) treated mouse tumor grew to over 600 mm3 in three weeks before euthanizing due to tumor ulceration. This indicate that there were some effect from BPheid-a to tumor when compared to untreated control mouse.

From these studies we have concluded that non-targeted conventional PDT agents are at best inefficient PDT molecules. They are highly insoluble in water and appear to have low efficacy in cell culture. Moreover, they are highly non-specific at the same time as having both a high uptake in skin, and a low tumor-to-background ratio. These conventional and approved PDT molecules take 24 h or more to localize in the tumor, and when localized only present low concentrations of the drug molecule in the tumor and appear to have a very low efficacy in animal models. Moreover, the use of these molecules is hampered by the low concentration of PDT agents in the tumor, which means that there is very low level fluorescence which cannot produce sufficient fluorescence for tumor imaging or for use in image-guided surgery.

Example 2: Pre-Clinical Evaluation of Mitochondrial-Targeted Modified PDT Agents In this example the objective was to modify BPheid-a to target mitochondria by conjugating to lipophilic cationic molecule or cationic peptides or molecule binds selectively to a target within mitochondria; to evaluate photodynamic therapeutic efficacy of mitochondrial targeting modified BPheid-a analogues in cancer cells; and to evaluate in vivo whole body imaging ability and PDT efficacy in mice bearing tumor xenografts for most active molecules in cell culture.

(a) Synthesis of Selected Modified Bpheid-a Analogues

Hydrazine (10.2 uL, 0.33 mmol, 10 equiv) was added to the solution of BPheid-a (1) (20 mg, 0.033 mmol, 1 equiv) or tookad (2) in dimethylformamide (3.3 mL). The reaction mixture is degassed with argon for 5 minutes and stirred at 23° C. for 3 h under argon. The reaction was purified by preparative HPLC using C18 column to obtain compound (24) or (25) as a dark brown solid.

Diisopropylethylamine (13.5 uL, 0.078 mmol) and CH$_3$I (50 uL) were added to the solution of Compound (24) (5 mg, 0.0078 mmol) or (25) dissolved in degassed CHCl$_3$ (3 mL). The mixture was stirred at 23° C. for 4 days. The reaction mixture was purified by preparative HPLC using C18 column to obtain compound (26) as a dark brown solid.

Dimethyl sulfate (0.52 mL, 5.57 mmol) was added to the mixture of Compound (32) (400 mg, 1.11 mmol), K$_2$CO$_3$ (1.5 g, 11.1 mmol) in MeOH (8 mL) and water (5 mL). Stirred the suspension at 23° C. for 1 h. Upon completion the reaction mixture was diluted with water and extracted using EtOAc (3×70 mL). The organics were washed with water, brine, dried over anhyd. Na$_2$SO$_4$, filtered and concentrated to obtain compound (33) as a pale yellow oil.

Palladium on charcoal (80 mg) was added to the solution of Compound (33) (250 mg, 0.57 mmol) in DCM (10 mL). The reaction content was stirred under hydrogen balloon atmosphere for 4 h. Upon completion, the reaction mixture was filtered through celite and concentrated to obtain compound (34) as clear oil.

DIPEA (21 uL, 0.123 mmol, 3 equiv) was added to a solution of BPheid-a (25 mg, 0.041 mmol, 1 equiv) and HATU (15.5 mg, 0.041 mmol, 1 equiv) in degassed DMF (2 mL) and stirred the content at 23° C. for 15 minutes under argon. After this time, a solution of 5-amino-1-(tert-butoxy)-N,N,N-trimethyl-1-oxopentan-2-aminium methyl sulfate (35 mg, 0.054 mmol, 1 equiv) in degassed DMF (0.5 mL) was introduced in the reaction vessel. The reaction mixture was stirred at 23° C. for another 1 h. The coupling reagent was destroyed by addition of 0.5 mL of water and the reaction was purified by preparative HPLC using C18 column to obtain compound (16) as a dark brown solid.

Diisopropylethylamine (146 uL, 0.842 mmol) was added to a solution of Compound (32) (140 mg, 0.337 mmol), HATU (128 mg, 0.337 mmol) and (2-carboxyethyl)triphenylphosphonium bromide (121 mg, 0.337 mmol) in DMF (3.5 mL). The reaction content was stirred at 23° C. for 1 h. Upon completion, the reaction mixture was diluted with water and extracted using EtOAc (3×100 mL). The organics were washed with water, brine, dried over anhyd. Na$_2$SO$_4$, filtered and concentrated to obtain compound (35) as clear thick oil.

Palladium on charcoal (50 mg) was added to the solution of Compound (33) (100 mg, 0.148 mmol) in DCM (10 mL). The reaction content was stirred under hydrogen balloon atmosphere for 24 h. Upon completion, the reaction mixture was filtered through celite and concentrated and purified using HPLC to obtain compound (36).

DIPEA (21 uL, 0.123 mmol, 3 equiv) was added to a solution of BPheid-a (25 mg, 0.041 mmol, 1 equiv) and HATU (15.5 mg, 0.041 mmol, 1 equiv) in degassed DMF (2 mL) and stirred the content at 23° C. for 15 minutes under argon. After this time, a solution of (S)-(3-((5-amino-1-(tert-butoxy)-1-oxopentan-2-yl)amino)-3-oxopropyl)triphenylphosphonium bromide (30 mg, 0.054 mmol, 1 equiv) in degassed DMF (0.5 mL) was introduced in the reaction vessel. The reaction mixture was stirred at 23° C. for another 1 h. The coupling reagent was destroyed by addition of 0.5 mL of water and the reaction was purified by preparative HPLC using C18 column to obtain compound 13a as a dark brown solid.

Hydrazine (3.1 uL, 0.10 mmol, 5 equiv) was added to the solution of compound 13 (20 mg, 0.02 mmol, 1 equiv) in dimethylformamide (2 mL). The reaction mixture is degassed with argon for 5 minutes and stirred at 23° C. for 1 h under argon. The reaction was purified by preparative HPLC using C18 column to obtain compound 14a as a dark brown solid.

Diisopropylethylamine (120 uL, 0.697 mmol) was added to a solution of Bpheid-a (85 mg, 0.139 mmol), HATU (63.5 mg, 0.167 mmol) in DMF (13.9 mL). Argon was bubbled thorough the mixture for 5 minutes and stirred in dark for 20 minutes (solution A). In another flask (S)-3-amino-4-(tert-butoxy)-4-oxobutanoic acid (34 mg, 0.167 mmol) was dissolved in DMSO (5 mL) to form clear solution (Solution B). Solution B was added to solution A via cannula and stirred the content for 1 h. Upon completion the reaction mixture was purified by preparative HPLC using C18 column to obtain compound (37).

Diisopropylethylamine (38 uL, 0.214 mmol) was added to a solution of Compound (37) (57 mg, 0.072 mmol), HATU (27.2 mg, 0.072 mmol) in DMF (7.1 mL). Argon was bubbled thorough the mixture for 5 minutes and stirred in dark for 15 minutes (solution A). In another flask D-($\alpha$)-glucosamine.HCl (15.4 mg, 0.72 mmol) was dissolved in DMSO (2.5 mL) and added Diisopropylethylamine (25 uL, 0.143 mmol) (Solution B). Solution B was added to solution A via cannula and stirred the content for 1 h. Upon completion the reaction mixture was purified by preparative HPLC using C18 column.

Purified product (50 mg, 0.055 mmol) was dissolved in degassed TFA (3 mL) and stirred under argon at 23° C. for 1 h. The solvent was evaporated under vacuum and the crude residue was purified by preparative HPLC using C18 column to obtain compound (19a) as a dark brown solid.

In Vitro Studies

TABLE 2

Effect of mitochondrial-targeted modified PDT agents on the survival of KB cells in culture

| Compound | EC50 (nM) |
|---|---|
| 9 | 27 |
| 10 | 167.9 |
| 11a | 51.4 |
| 11b | 23.1 |
| 12a | 1346 |
| 12b | 15.4 |
| 13 | 20.5 |
| 14 | 3.7 |
| 15 | 47.6 |
| 16 | 26.6 |
| 19 | 550 |
| 24 | 316 |
| 25 | 361.7 |
| 26 | 8.4 |
| 27 | 64.8 |
| 28 | 1770 |
| 29 | 7917 |
| 30 | 97.4 |
| 31 | 477.7 |
| BPheid-a (1) | 745 |

To determine the in vitro efficacy of mitochondrial-targeted BPheid-a molecules, KB cells were used as described infra at the beginning of the Examples. The data are reported as EC50 values.

Modification of BPheid-a with mitochondrial targeting agents by conjugating to a lipophilic cationic molecule or cationic peptides or a molecule that binds selectively to a target within mitochondria such as sugars, etc., led to the discovery of very active compounds as compared to BPheid-a. Especially, both 14 and 26 had activity in the low nanomolar range (3.7 nM and 8.4 nM respectively) and were highly active in killing cancer cells. In addition, compounds 9, 11b, 12b, 13, and 16 were also effective at diminishing cancer cells effectively. Most of these active compounds have a cationic charge as quaternary ammonium [—N$^{(+)}$(CH$_3$)$_3$] or hydrazide [—NH—N$^{(+)}$(CH$_3$)$_3$] or triphenylphosphene [—P$^{(+)}$Ph$_3$].

We also noticed that hydrophobic molecules were more active than hydrophilic molecules, e.g. compounds 9,12b, and 13 are more hydrophobic when compared to 11a and 12a. While compounds 11a and 12a do have free carboxylic acid groups, those acid groups are protected with tert-butyl group, a hydrophobic protecting group, in compounds 9,12b, and 13. Therefore, 11a and 12a are more hydrophilic than 9,12b, and 13. Without being bound to a particular theory or mechanism of action, it is possible that the hydrophobic cation is more active due to the movement of lipophilic cations through the plasma and mitochondrial inner membranes. This is a result of the large hydrophobic surface area and the large ionic radius of the cation that effectively lowers the activation energy for membrane passage. The Nernst equation adequately describes the membrane potential-dependent uptake of lipophilic cations, which increases 10-fold for every ~60 mV of membrane potential, leading to their several hundred-fold uptakes within mitochondria.

We observed that Pd chelated compounds were less active than their non-chelated counterparts (e.g. 9 Vs 10 and 26 Vs 27 and 30 vs 31). This may be due to quenching of free radical formation by Pd metal.

Finally, except for compound 26, opening of the five membered ring (that has a ketone group and a methyl ester) with a nucleophile leads to loss of activity or reduce the efficacy of PDT agent.

(b) In Vivo Studies

To establish the specificity of our mitochondrial-targeted PSs for cancer cells, compound 14 (most active compound in cancer cells) was injected into nude mice bearing KB tumors on their shoulders and monitored the tumor accumulation by fluorescence imaging using IVIS imager. Time dependent whole body images shows nonspecific uptake of compound 14 in the skin and in the kidneys of the mouse. Fluorescence in kidneys may also due to clearance of the drug through the kidneys. From these data is seems that although modification of BPheid-a to target mitochondria gave highly active data in cell culture, in vivo data were not promising as cell culture data.

KB cells that overexpressed folate receptor were implanted subcutaneously into female nude mice and allowed to grow to ~50 mm$^3$ prior to initiation of treatment with 50 nmol of compound (14). Three hours (3 h) after injecting with 50 nmol of compound (14), tumor was treated with laser beam (75 mW/cm$^2$, 137 J/cm$^2$, exposure diameter=7.5-8 mm) for 38 min. In vivo efficacy of 14 was evaluated by monitoring reduction of tumor volume. KB tumors treated with 14 grew with a doubling time of <1 week and reached ~500 mm$^3$ by the end of the two week treatment period. This lack of in vivo efficacy may be due to poor solubility, poor PK properties, and absence of tumor targeting of the molecule.

Example 3. Pre-Clinical Evaluation of Nucleus-Targeted PDT Agents

The objective of this example was to modify BPheid-a to target the nucleus by conjugating to DNA binding agents, DNA alkylating agents, and the like to evaluate photodynamic therapeutic efficacy of nucleus-targeted modified BPheid-a analogues in cancer cells and to evaluate in vivo whole body imaging ability and PDT efficacy in mice bearing tumor xenografts for most active molecules in cell culture Diisopropylethylamine (120 uL, 0.691 mmol) was added to a solution of N[10]-Methyl-4-amino-4-deoxypteroic acid (75 mg, 0.23 mmol), HATU (88 mg, 0.23 mmol) in DMF (5 mL) and stirred at 23° C. for 15 minutes (solution A). In another flask Compound (32-a) (47 mg, 0.23 mmol) was dissolved in DMSO (5 mL) and added Diisopropylethylamine (120 uL, 0.691 mmol) (Solution B). Solution B was added to solution A via cannula and stirred the content for 1 h. Upon completion the reaction mixture was purified by preparative HPLC using C18 column. (2-carboxyethyl)triphenylphosphonium bromide (121 mg, 0.337 mmol) in DMF (3.5 mL). The reaction content was stirred at 23° C. for 1 h. Upon completion, the reaction mixture was added to ether (500 mL) and precipitated solid was filtered and dried under high vacuum to obtain compound (53) as thick oil.

Compound (53) (100 mg mg, 0.195 mmol) was dissolved in TFA (6 mL) and stirred under argon at 23° C. for 2 h. The solvent was evaporated under vacuum and the crude residue was purified by preparative HPLC using C18 column to obtain compound (55) as yellow solid.

Diisopropylethylamine (30 uL, 0.175 mmol) was added to a solution of Bpheid-a (35.6 mg, 0.058 mmol), HATU (22.1 mg, 0.058 mmol) in DMF (5.8 mL) and stirred at 23° C. for 15 minutes (solution A). In another flask Compound (55) (24 mg, 0.058 mmol) was dissolved in DMSO (5 mL) and added Diisopropylethylamine (30 uL, 0.175 mmol) (Solution B). Solution B was added to solution A via cannula and stirred the content for 1 h. Upon completion the reaction mixture was purified by preparative HPLC using C18 column to obtain compound (44).

TABLE 3

Effect of nucleus-targeted modified PDT agents on the survival of KB cells in culture

| Compound | IC50 (nM) |
|---|---|
| 39 | Not active* |
| 40 | 4078 |
| 41 | 68 |
| 43 | 342 |
| 44 | 425 |
| BPheid-a | 745 |

To determine the in vitro efficacy of nucleus-targeted, KB cells were as shown infra at the beginning of the Examples section and the data reported according to EC50 values.

Modification of BPheid-a with nucleus-targeting agents led to the discovery of active PSs compared to BPheid-a. Among the compounds that we synthesized, compound 41 is the most active. This BPheid-a molecule is modified with a chemotherapy drug belonging to the class of nitrogen mustard alkylating agents. This DNA alkylating agent (melphalan) has two alkyl chlorine groups that can react with the number 7 nitrogen atom of the imidazole ring thereby inhibiting the DNA synthesis and cell proliferation.

5. Pre-Clinical Evaluation of Folate-Targeted Releasable BPheid-a Conjugates. Group A: Variation of Releasable Linker Portion (Release of the Free Drug Through Different Release Mechanisms)

The objective of this example was to target-BPheid-a to folate receptor positive tumor cells by conjugating to folic acid (folate, vitamin B9) via various-releasable linkers with different releasable mechanisms under different conditions and to evaluate photodynamic therapeutic efficacy in cancer cells and to evaluate in vivo whole body imaging ability and PDT efficacy in mice bearing tumor xenografts for most active molecules in cell culture.

Synthesis

Scheme 11b: Synthesis of folate-Asp(SO₃H)-Cys-SH linker.

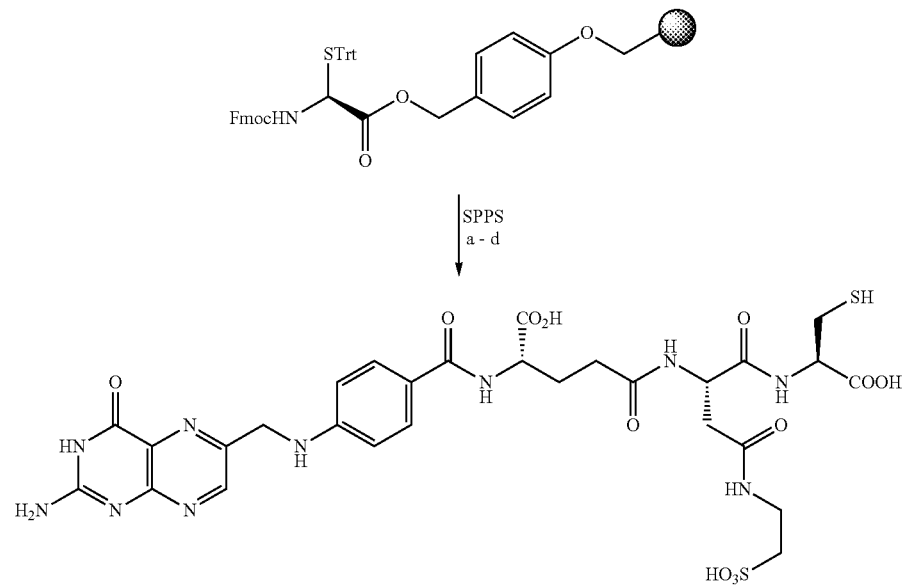

(70)

Reagents and conditions: (a) (i) 20% piperidine/DMF, r.t., 10 min; (ii) Fmoc-Asp(SO₃H)—OH, HATU, DMF/DIPEA, 2 h; b) (i) 20% piperidine/DMF, r.t., 10 min; (ii) Fmoc-Glu(O$^t$Bu)—OH, HATU, DMF/DIPEA, 2 h; c) (i) 20% piperidine/DMF, r.t., 10 min; (ii) N$^{10}$—TFA-Pteroic acid, HATU, DMF/DIPEA, 2 h; d) TFA:H₂O:TIPS:EDTA (92.5:2.5:2.5:2.5), 1 h.

The following synthesis scheme was used:

1. L-Cys(Trt)-2-chlorotrityl resin (700 mg, 0.49 mmol) was swollen with dichloromethane (DCM) (10 mL) followed by dimethylformamide (DMF, 10 mL).
2. A solution of 20% piperidine in DMF (3×10 mL) was added to the resin, and argon was bubbled for 10 minutes each time.
3. The resin was washed with DMF (3×10 mL) and DCM (1×10 mL) for 5 minutes each time.
4. Kaiser test was performed to determine the formation of free amine.
5. A solution Fmoc-Asp(SO$_3$H)—OH (500 mg, 1.29 mmol), HATU (490 mg, 1.29 mmol) and DIPEA (448 uL, 2.58 mmol) in DMF (8 mL) was added. Argon was bubbled for 2 h.
6. The resin was washed with DMF (3×10 mL) and DCM (1×10 mL) for 5 minutes each time.
7. Kaiser test was performed to determine the coupling efficiency.
8. A solution of 20% piperidine in DMF (3×10 mL) was added to the resin, and argon was bubbled for 10 minutes each time.
9. The resin was washed with DMF (3×10 mL) and DCM (1×10 mL) for 5 minutes each time.
10. Kaiser test was performed to determine the formation of free amine.
11. A solution of Fmoc-Glu-(α-OtBu)-OH (625 mg, 1.47 mmol), HATU (559 mg, 1.47 mmol) and DIPEA (6.0 equiv) in DMF (8 mL) was added. Argon was bubbled for 2 h.
12. The resin was washed with DMF (3×10 mL) and DCM (1×10 mL) for 5 minutes each time.
13. Kaiser test was performed to determine the coupling efficiency.
14. A solution of 20% piperidine in DMF (3×10 mL) was added to the resin, and argon was bubbled for 10 minutes each time.
15. The resin was washed with DMF (3×10 mL) and DCM (1×10 mL) for 5 minutes each time.
16. Kaiser test was performed to determine the formation of free amine.
17. A solution of Pte_$^{10}$N-TFA-OH (600 g, 1.47 mmol) HATU (559 mg, 1.47 mmol) and DIPEA (6.0 equiv) in DMF (8 mL) was added. Argon was bubbled for 2 h.
18. The resin was washed with DMF (3×10 mL) and isopropanol (3×10 mL) for 5 minutes each time.
19. Kaiser test was performed to determine the coupling efficiency.
20. The resin was swollen with DCM (10 mL).
21. Final compound was cleaved from the resin using a trifluoroacetic acid TFA: H$_2$O:triisopropylsilane (TIPS): EDT cocktail (92.5:2.5:2.5:2.5) (3×10 mL×30 min) and the cocktail wash was added dropwise to ether (300 mL) under stirring to obtain the light yellow precipitate.
22. Filtered the precipitated solid, washed with ether (5×50 mL) and dried under high vacuum to obtain desired compound (70) as an off white solid.

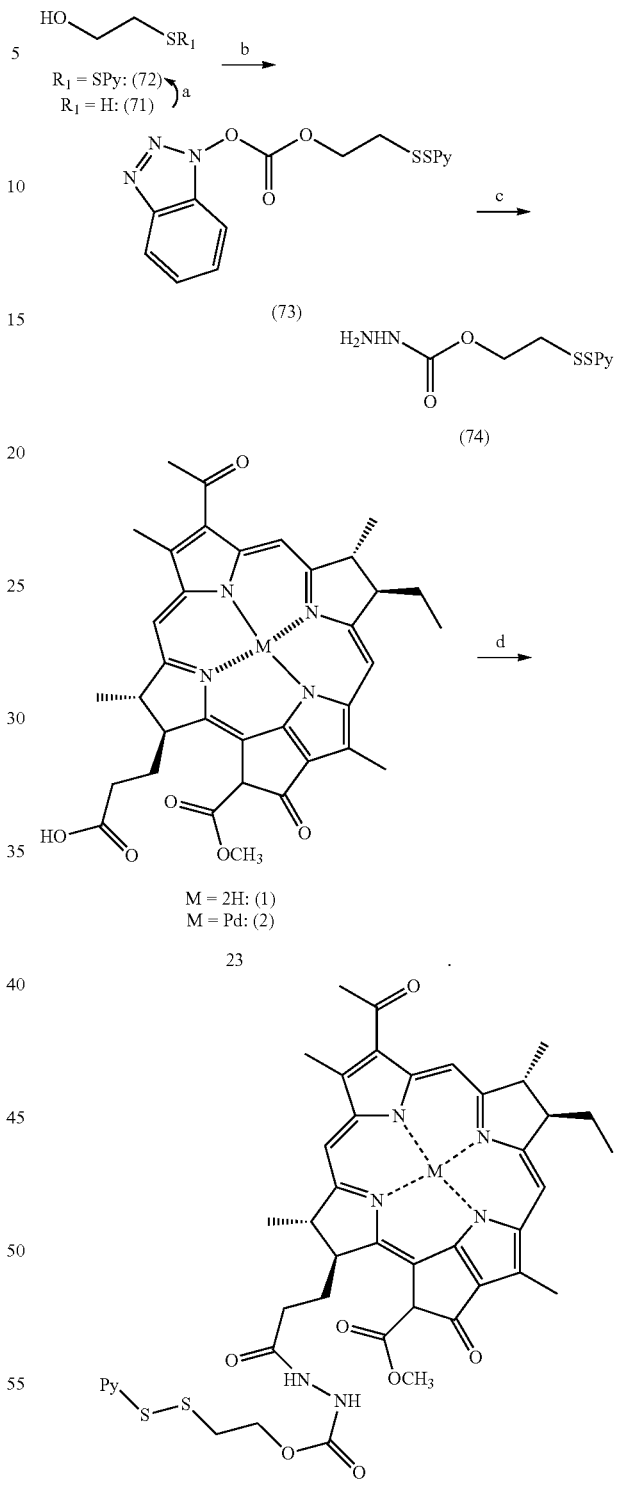

Scheme 11c: Synthesis of disulfide activated Bpheid-a.

Reagents and conditions: (a) i) MeOC(O)SCl/CH$_3$CN, 0° C., 0.5 h; ii) 2,2'-dipyridyl-disulfide/CH$_3$CN, 0° C., 2 h; (b) i) diphosgene, HOBt, TEA/ CH$_3$CN, 0° C.; ii) A/50° C., 24 h; (c) NH$_2$NH$_2$, DIPEA/CH$_2$Cl$_2$, 0° C. to r.t., 45 min; (d) i) HATU, DIPEA/DMF: -15° C., 45 min; ii) 74, DMF, -15° C. to r.t., 45 min. Py = Pyridyl.

To a solution of methoxycarbonylsulfenyl chloride (3.1 mL, 34.25 mmol) in CH$_3$CN (30.0 mL) at 0° C., 2-mercaptoethanol (2.4 mL, 34.25 mmol) in CH$_3$CN (1.0 mL) was added drop wise, and the reaction mixture was allowed to stir at −10° C. for 30 min. A solution of 2-thiopyridine (3.46 g, 31.13 mmol) in CH$_3$CN (18.0 mL) was added the reaction mixture and refluxed for 2 h. The reaction mixture was then stirred at 10° C. for 1 h and filtered. The solid was washed with CH$_3$CN and dried under vacuum at r. t. to yield the pure product (72) as a colorless solid (4.0 g, 57.5%).

To a solution of 2-(pyridine-2-yl-disulfanyl) ethanol (2.0, 8.94 mmol), HOBT (1.58 g, 11.71 mmol), and TEA (1.25 mL, 8.94 mmol) in CH$_3$CN (35 mL) at 0° C., diphosgene (0.72 mL, 5.98 mmol) was added. The reaction mixture was heated to 50° C. and stirred for 24 h. The solid was filtered, washed with CH$_3$CN, and dried under vacuum at r. t. to yield the pure product (73) as a pale white solid (3.48 g, 95.7%).

To a solution of 2-[benzotriazole-1-yl-(oxycarbonyloxy)-ethyldisulfanyl]-pyridine hydrochloride (685 mg, 1.62 mmol) and DIPEA (600 uL, 3.4 mmol) in CH$_2$Cl$_2$ (5.0 mL) at 0° C., hydrazine was added. The reaction mixture was allowed to stir at 0° C. for 15 min and 30 min at r. t. After filtering the precipitate, the crude compound was purified using flash column chromatography (silica gel, 2% MeOH in CH$_2$Cl$_2$) to yield the product (74) as colorless oil (371 mg, 93.4%).

Diisopropylethylamine (29 uL, 0.163 mmol, 2.4 equiv) was added to a solution of BPheid-a (compound 2) (40 mg, 0.065 mmol, 1 equiv) and HATU (30 mg, 0.079 mmol, 1.2 equiv) in DMF (3 mL). Argon was bubbled thorough the reaction mixture for 5 minutes and stirred in dark for 20 minutes (solution A). In another flask the compound 74 was dissolved in DMF to form clear solution (Solution B). Solution B was added to solution A via cannula and stirred the content for 1 h. Upon completion the reaction mixture was purified by preparative HPLC using C18 column to obtain compound (75a).

Scheme 12:

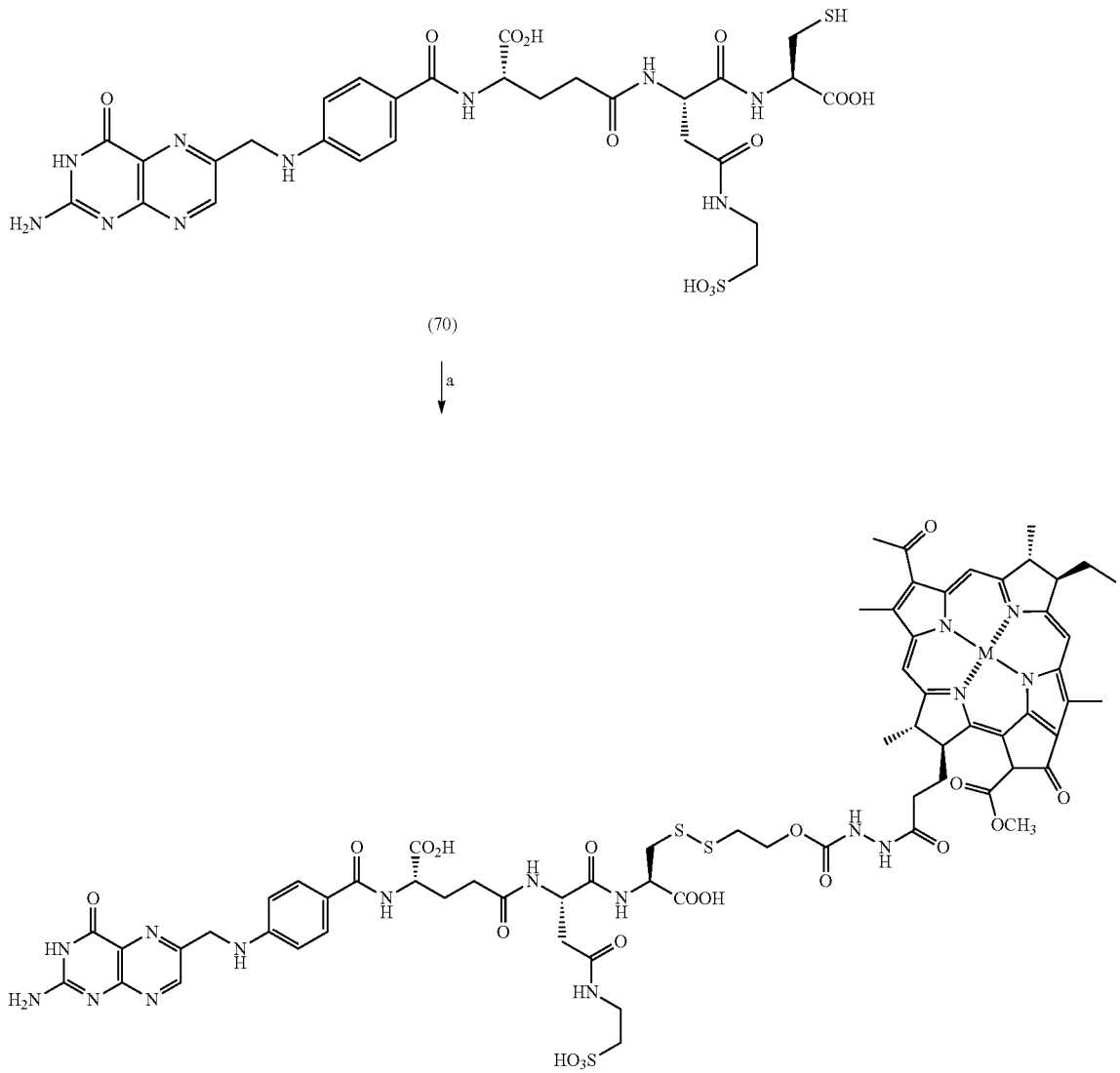

(a) Reagents and conditions: (a) i) H$_2$O/NaHCO$_3$ (pH = 7 ± 0.2), argon, r.t.; ii) 75a or 75b/DMSO, argon, r.t., 15 min.

To a solution of compound (75a) (8.5 mg, 0.0104 mmol, 1 equiv) and compound (70) (18.3 mg, 0.02048 mmol, 2 equiv) in DMSO (0.5 mL) was degassed with argon and stirred at 23° C. under argon for 7 h. The reaction mixture was purified by preparative HPLC using C18 column to obtain compound (65a) as a dark brown solid.

In Vitro Studies

TABLE 6

Effect of folate-targeted drug concentration on the survival of KB cells in culture

| Compound | EC50 (nM) |
|---|---|
| 64 | 8.4 |
| 65a | 2.5 |
| 65b | 138.1 |
| 65c | 11.6 |

To determine the in vitro efficacy of folate- and mitochondrial-targeted-BPheid-a conjugates, KB cells were used as described infra in at the beginning of the Examples section and the data are reported as EC50 values.

EC50 is half maximal effective concentration represents the concentration of a compound where 50% of its maximal effect is observed. Lower the EC50 value higher the activity. We consider that a compound with EC50<50 nM as active and EC50<10 nM as highly active.

Folate—targeted releasable modified BPheid-a conjugates were highly active on cancer cells in culture, especially 64, 65a and 65c. This may be due to higher solubility of the drug conjugate make more drugs to enter into the cell. Moreover, drug conjugate is now internalized through the folate receptor mediated endocytosis, and release the drug inside the endosomes. Released drug molecules may have carried to requisite organelle.

(a) In Vivo Studies
(i) Time Dependent Whole Body Imaging

To establish the specificity of folate- and mitochondrial-targeted releasable BPheid-a for cancer cells, compound 65a was injected into nude mice bearing KB tumors on their shoulders and monitored the tumor accumulation by fluorescence imaging using IVIS imager. Time dependent whole body images suggest that folate- and mitochondrial-targeted releasable BPheid-a localized to tumor within 1 h of administration of the drug and remained in the tumor over 24 hours without losing its fluorescence properties. Compound 65a was highly specific for FR-positive tumor and no fluorescence was observed in other tissues leading high tumor to background ratio. Moreover, the tumor with Compound 65a was more highly fluorescent than that folate-targeted non-releasable BPheid-a conjugate (59a) indicating higher number of molecules of 65a had reached the tumor than 59a. These increased pharmacokinetic properties may be due to higher solubility of 65a as compared to 59a. Moreover, release of folate conjugate inside the cancer cell may have increased free receptor recycling rate. More specifically, it is possible that the release of the mitochondrial-targeted BPheid-a inside the cancer cell may have increased the mitochondrial localization of the BPheid-a.

(ii) Effect of Folate-Targeted Non-Releasable-BPhied-a on Mice Bearing FR-Positive KB Tumors KB cells that overexpressed folate receptor were implanted subcutaneously into female nude mice and allowed to grow to ~50 mm$^3$ prior to initiation of treatment with 50 nmol or 25 nmol of Compound 65a or 65c. Three hours (3 h) after injecting of drug, tumor was treated with laser beam (75 mW/cm$^2$, 137 J/cm$^2$, exposure diameter=7.5-8 mm) for 38 min. In vivo efficacy of conjugates was evaluated by monitoring reduction of tumor volume. Both compounds inhibited growth of KB tumors. Mice treated with 65a or 65c showed tumor regression at both doses (50 and 25 nmol) that was sustained until end of the study period. The data presented for compounds 65a and 65c shows that they are a promising clinical candidate as an antitumor therapeutic.

Example 6. Pre-Clinical Evaluation of Folate-Targeted Releasable BPheid-a Conjugates. Group B: Variation of Water Soluble Linker Portion to Improve Bioavailability of the Drug The objective of this example was to target-BPheid-a to folate receptor positive tumor cells by conjugating to folic acid (folate, vitamin B9) via releasable linker with water soluble linkers and to evaluate photodynamic therapeutic efficacy in cancer cells and to evaluate in vivo whole body imaging ability and PDT efficacy in mice bearing tumor xenografts for most active molecules in cell culture.

(a) Synthesis
All the compounds were synthesized using similar methods and procedures described for 65a in example v.

(b) In Vitro Studies

TABLE 7

Effect of folate-targeted drug concentration on the survival modified PDT agents on the survival of KB cells in culture

| Compound | EC50 (nM) |
|---|---|
| 65a | 2.7 |
| 65b | 137.3 |
| 65c | 11.6 |
| 76a | 0.001 |
| 76b | 320 |
| 76c | 0.007 |
| 76d | 339 |
| BPheid-a | 745 |

To determine the in vitro efficacy of folate- and mitochondrial-targeted BPheid-a conjugates, KB cells were used as described infra at the beginning of the Examples section and the data are reported using EC50 values.

All the compounds are highly active when compared to BPheid-a (1). The compounds 65a, 65c, 76a and 76c were extremely potent for cancer cells. These unusual activities may be attributable to enhanced water solubility, release of the drug inside the cell, folate mediated endocytosis, and mitochondrial localization.

(c) In Vivo Studies

To establish the specificity of folate- and mitochondrial-targeted releasable BPheid-a for cancer cells, compound 76a & 76c were injected into nude mice bearing KB tumors on their shoulders and monitored the tumor accumulation by fluorescence imaging using IVIS imager (data for similar studies from 65a-c were included in example v). Time dependent whole body images suggest that folate- and mitochondrial-targeted releasable BPheid-a localized mainly in the tumor within 1 h of administration of the drug and remained in the tumor over 24 hours without losing its fluorescence properties. The compounds 76a & 76c were highly specific for FR-positive tumor and no fluorescence was observed in other tissues. Thus these compounds produce a useful and high tumor to background ratio of fluorescence. Moreover, the tumor was more highly fluorescent than folate-targeted non-releasable BPheid-a conjugate (59a) indicating that higher numbers of molecules of 76a & 76c were present inside tumor than 59a. Since both molecules have similar number of hydrophilic functional groups and similar solubility properties, difference in activity may attributable to the release of the mitochondrial-targeted BPheid-a inside the cancer tissue.

KB cells that overexpressed folate receptor were implanted subcutaneously into female nude mice and allowed to grow to ~50 mm³ prior to initiation of treatment with 50 nmol of 76a-c (data for similar studies from 65a-c were included in example v). Three hours (3 h) after injecting of drug, tumor was treated with laser beam (75 mW/cm², 137 J/cm², exposure diameter=7.5-8 mm) for 38 min. In vivo efficacy of conjugates was evaluated by monitoring reduction of tumor volume. All three compounds inhibited growth of KB tumors. However, it is notable that mice treated with 76c showed tumor regression for longer time showing promise for a good clinical candidate. Moreover, while still effective, the Pd-chelated conjugate 76b is less active in mice as compared to 76a and 76c.

Example 7: Pre-Clinical Evaluation of Folate-Targeted Releasable Visudyne Conjugates. Group C: Variation of Water Soluble Linker Portion to Improve Bioavailability of the Drug The objective of this example was to target-visudyne to folate receptor positive tumor cells by conjugating to folic acid (folate, vitamin B9) via releasable linker with water soluble linkers and to evaluate photodynamic therapeutic efficacy in cancer cells and to evaluate in vivo whole body imaging ability and PDT efficacy in mice bearing tumor xenografts for most active molecules in cell culture.

a) Synthesis

All the compounds were synthesized using similar methods and procedures as described for 65a in example V.

b) In Vitro Studies

TABLE 8

Effect of folate-targeted drug concentration on the survival modified PDT agents on the survival of KB cells in culture

| Compound | EC50 (nM) |
|---|---|
| 81 | Not active* |
| 85 | Not active* |
| 87 | Not active* |

To determine the in vitro efficacy of folate- and mitochondrial-targeted visudyne conjugates, KB cells were used as described infra at the beginning of the Examples section and the data are reported according to EC50 values. These data showed that the three conjugates 81, 85, and 87 were not active in cancer cells.

(c) In Vivo Studies

Time Dependent Whole Body Imaging of FR Positive KB Tumor Xenografts with (80) and (86)

To establish the specificity of folate- and mitochondrial-targeted releasable visudyne for cancer cells, compound 80 & 86 were injected into nude mice bearing KB tumors on their shoulders and monitored for tumor accumulation of the compounds by fluorescence imaging using IVIS imager. Time dependent whole body images suggest that both conjugates localized mainly in the tumor within 1 h of administration of the drug. However, fluorescence in the tumor was less than folate-BPheid-a conjugates (59a, 65a, 76a & 76c). This may due to difference in optical properties between BPheid-a and visudyne. We also noticed that both 80 and 86 accumulated in the eyes of mice. It is well documented in the literature that visudyne tend to accumulated in the eyes.

Example 8: Pre-Clinical Evaluation of Folate-Targeted Releasable BPheid-a Conjugates. Group D: Release of Cationic BPheid-a Analogues (Positively Charged PDT Agent) Inside the Cancer Cell The objective of this example was to target-BPheid-a to folate receptor positive tumor cells by conjugating to folic acid (folate, vitamin B9) via releasable linker with water soluble linkers which eventually release cationic BPheid-a analogue inside the cells. Second objective was to evaluate photodynamic therapeutic efficacy in cancer cells and to evaluate in vivo whole body imaging ability and PDT efficacy in mice bearing tumor xenografts for most active molecules in cell culture.

Scheme 13:
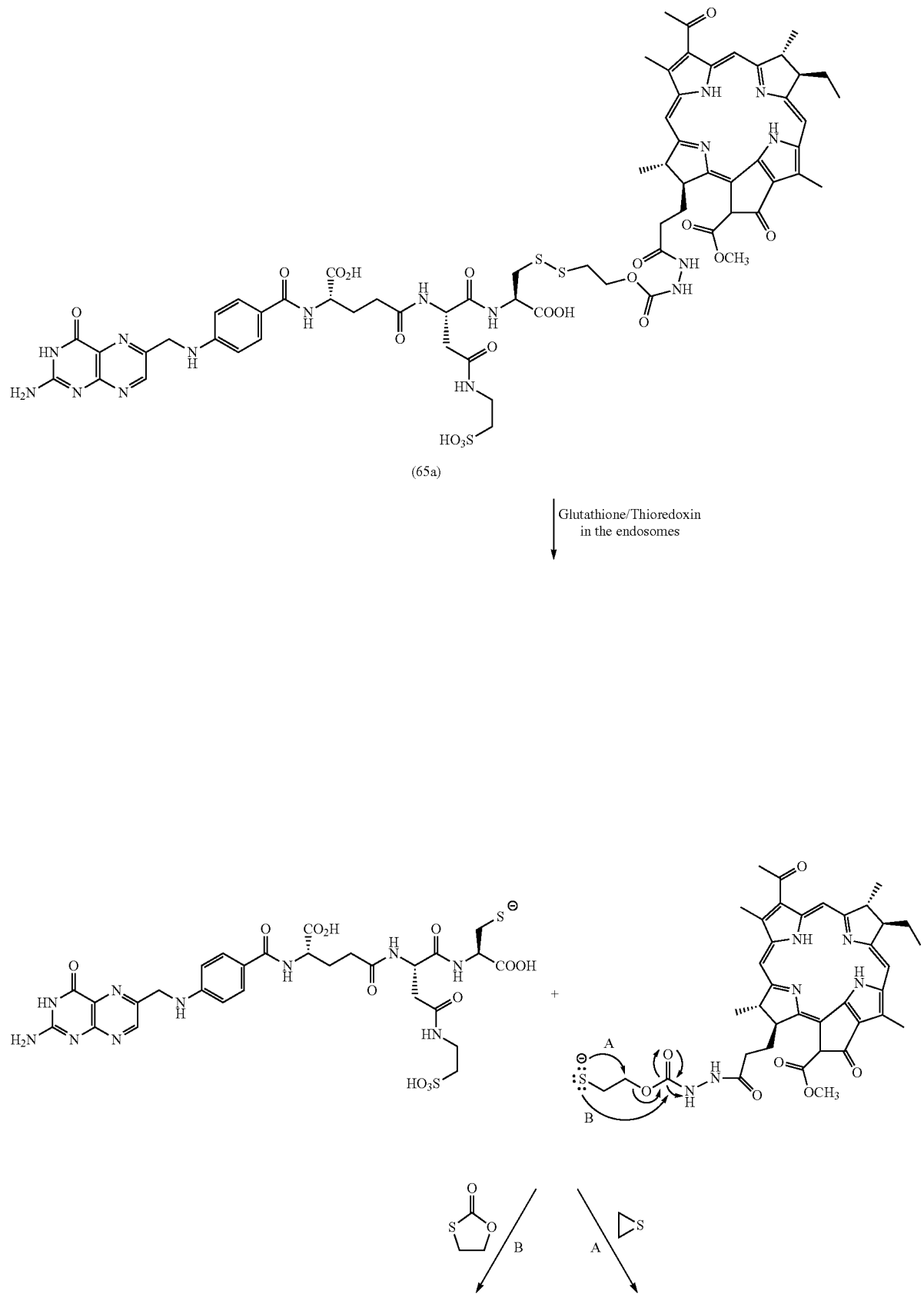

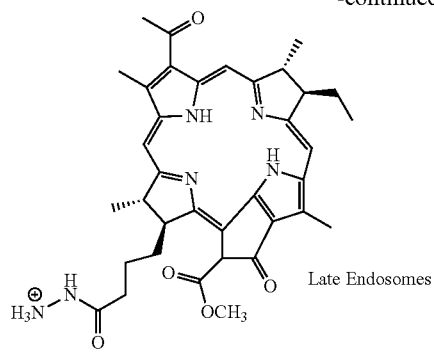
Late Endosomes

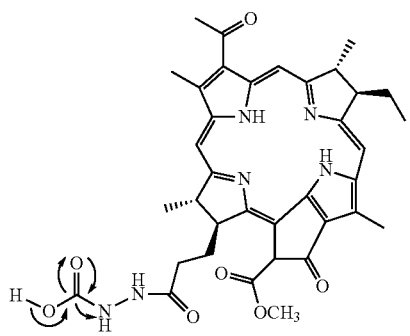
Cationic PDT agent

Possible mechanisms for disulfide mediated release of positively charged modified PDT agents from folate-targeted self-immolative prodrugs, such as 65a, in the presence of disulfide reducing agents such as glutathione, thioredoxin, etc. in the endosomes.

Synthesis: All the compounds were synthesized using similar methods and procedures as described for 65a in example 5.

(b) In Vitro Studies

TABLE 9

Effect of folate-targeted drug concentration on the survival modified PDT agents on the survival of KB cells in culture

| Compound | EC50 (nM) |
|---|---|
| 65a | 2.7 |
| 65b | 137.3 |
| 65c | 11.6 |
| 87b | 6040 |
| 88a | 34.5 |
| 88b | Not Active* |
| 89a | 3.7 |
| 92a | 32.8 |
| 95a | 166 |
| BPheid-a (1) | 745 |

To determine the in vitro efficacy folate- and mitochondrial-targeted BPheid-a, KB cells were used as described infra at the beginning of the Examples section and the data were reported using EC50 values.

Most of the compounds are active when compared to non-targeted BPheid-a (1). The compound 65a and 89a are extremely potent among this group and 88a and 92a can also be considered as active molecules.

(c) In Vivo Studies

To establish the specificity of folate- and mitochondrial-targeted releasable BPheid-a for cancer cells, compound 89a was injected into nude mice bearing KB tumors on their shoulders and monitored the tumor accumulation by fluorescence imaging using IVIS imager. Whole body images at 2 h time point suggest that folate- and mitochondrial-targeted releasable BPheid-a (89a) localized mainly in the tumor. The compound 89a was highly specific for FR-positive tumor and no fluorescence was observed in other tissues leading high tumor to background ratio. Moreover, tumor is highly fluorescence than folate-targeted non-releasable BPheid-a conjugate (59a) (and non-targeted BPheid-a and mitochondrial-targeted BPheid-a). High solubility and release of the molecule may have done the difference here.

KB cells that overexpressed folate receptor were implanted subcutaneously into female nude mice and allowed to grow to ~50 mm$^3$ prior to initiation of treatment with 50 nmol of 89a or 92a. Three hours (3 h) after injecting of drug, tumor was treated with laser beam (75 mW/cm$^2$, 137 J/cm$^2$, exposure diameter=7.5-8 mm) for 38 min. In vivo efficacy of conjugates was evaluated by monitoring reduction of tumor volume. Both compounds completely reduced the tumor and showed tumor regression for longer time showing promise as good clinical candidates.

Example 9: Pre-Clinical Evaluation of Folate-Targeted Releasable BPheid-a Group E: Release of Zwitterionic BPheid-a Analogues (Neutral Charged PDT Agent) Inside the Cancer Cell The objective of this example was to target-BPheid-a to folate receptor positive tumor cells by conjugating to folic acid (folate, vitamin B9) via releasable linker with water soluble linkers which eventually release neutral charged BPheid-a analogue inside the cells. Second objective was to evaluate photodynamic therapeutic efficacy in cancer cells and to evaluate in vivo whole body imaging ability and PDT efficacy in mice bearing tumor xenografts for most active molecules in cell culture.

Scheme 14:

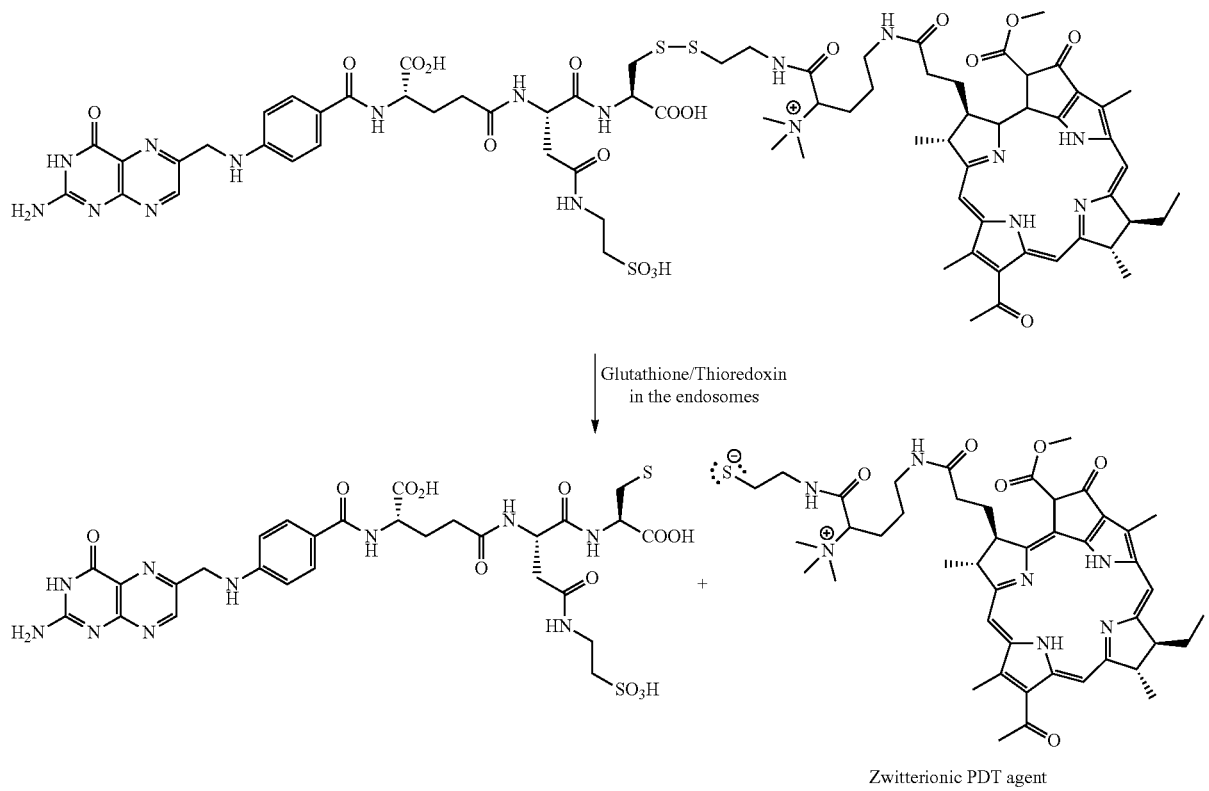

Zwitterionic PDT agent

Possible mechanisms for disulfide mediated release of zwitterionic PDT agents from folate-targeted self-immolative prodrugs, such as 99, in the presence of disulfide reducing agents such as glutathione, thioredoxin, etc. in the endosomes.

(a) Synthesis

DIPEA (21 uL, 0.123 mmol, 3 equiv) was added to a solution of BPheid-a (25 mg, 0.041 mmol, 1 equiv) and HATU (15.5 mg, 0.041 mmol, 1 equiv) in degassed DMF (2 mL) and stirred the content at 23° C. for 15 minutes under argon. After this time, a solution of 5-amino-1-(tert-butoxy)-N,N,N-trimethyl-1-oxopentan-2-aminium methyl sulfate (35 mg, 0.054 mmol, 1 equiv) in degassed DMF (0.5 mL) was introduced in the reaction vessel. The reaction mixture was stirred at 23° C. for another 1 h. The coupling reagent was destroyed by addition of 0.5 mL of water and the reaction was purified by preparative HPLC using C18 column to obtain compound (16) as a dark brown solid.

Compound (16) (10 mg, 0.011 mmol) was dissolved in degassed 80% TFA in water (6 mL) and stirred under argon at 23° C. for 6 h. The solvent was evaporated under vacuum and the crude residue was purified by preparative HPLC using C18 column to obtain compound (18) as a dark brown solid.

Diisopropylethylamine (29 uL, 0.163 mmol, 2.4 equiv) was added to a solution of BPheid-a (compound 2) (40 mg, 0.065 mmol, 1 equiv) and HATU (30 mg, 0.079 mmol, 1.2 equiv) in DMF (3 mL). Argon was bubbled thorough the reaction mixture for 5 minutes and stirred in dark for 20 minutes (solution A). In another flask 2-(phenyldisulfanyl) ethyl hydrazinecarboxylate was dissolved in DMF to form clear solution (Solution B). Solution B was added to solution A via cannula and stirred the content for 1 h. Upon completion the reaction mixture was purified by preparative HPLC using C18 column to obtain compound (4).

(a) In Vitro Studies

TABLE 10

Effect of folate-targeted drug concentration on the survival modified PDT agents on the survival of KB cells in culture

| Compound | EC50 (nM) |
|---|---|
| 99 | 5.3 |
| 100 | 12.8 |
| 101 | 158.9 |

To determine the in vitro efficacy of folate- and mitochondrial-targeted BPheid-a, KB cells were used according to method shown infra at the beginning of the Examples section and the data are reported according to EC50 values.

Three compounds that we tested are active when compared to non-targeted BPheid-a (1). The compounds 99 and 100 are extremely potent among the group.

In Vivo Studies:

(i) Time Dependent Whole Body Imaging of FR Positive KB Tumor Xenografts with (100)

To establish the specificity of folate- and mitochondrial-targeted releasable BPheid-a for cancer cells, compound 100 was injected into nude mice bearing KB tumors on their shoulders and monitored the tumor accumulation by fluorescence imaging using IVIS imager. Time dependent whole body images suggest that folate- and mitochondrial-targeted releasable BPheid-a (100) localized mainly in the tumor within 1 h. The compound 100 was highly specific for FR-positive tumor and no fluorescence was observed in other tissues leading high tumor to background ratio. Moreover, tumor is highly fluorescence than folate-targeted non-releasable BPheid-a conjugate (59a) (and non-targeted BPheid-a and mitochondrial-targeted BPheid-a). Higher solubility and release of the molecule may have accounted for the difference here.

KB cells that overexpressed folate receptor were implanted subcutaneously into female nude mice and allowed to grow to ~100 mm$^3$ prior to initiation of treatment with 50 nmol of 99 or 100. Three hours (3 h) after injecting of drugs, tumor was treated with laser beam (75 mW/cm$^2$, 137 J/cm$^2$, exposure diameter=7.5-8 mm) for 38 min. In vivo efficacy of conjugates was evaluated by monitoring reduction of tumor volume. Both compounds completely cure the tumor and showed tumor regression for 2 weeks.

Example 10: Pre-Clinical Evaluation of Folate-Targeted Releasable BPheid-a Conjugates. Group F: Release of Anionic Modified BPheid-a Analogues (Negative Charged) Inside the Cancer Cell The objective of this example was to target-BPheid-a to folate receptor positive tumor cells by conjugating to folic acid (folate, vitamin B9) via releasable linker with water soluble linkers which eventually release negative charge BPheid-a analogue inside the cells. Second objective was to evaluate photodynamic therapeutic efficacy in cancer cells and to evaluate in vivo whole body imaging ability and PDT efficacy in mice bearing tumor xenografts for most active molecules in cell culture.

Scheme 15:

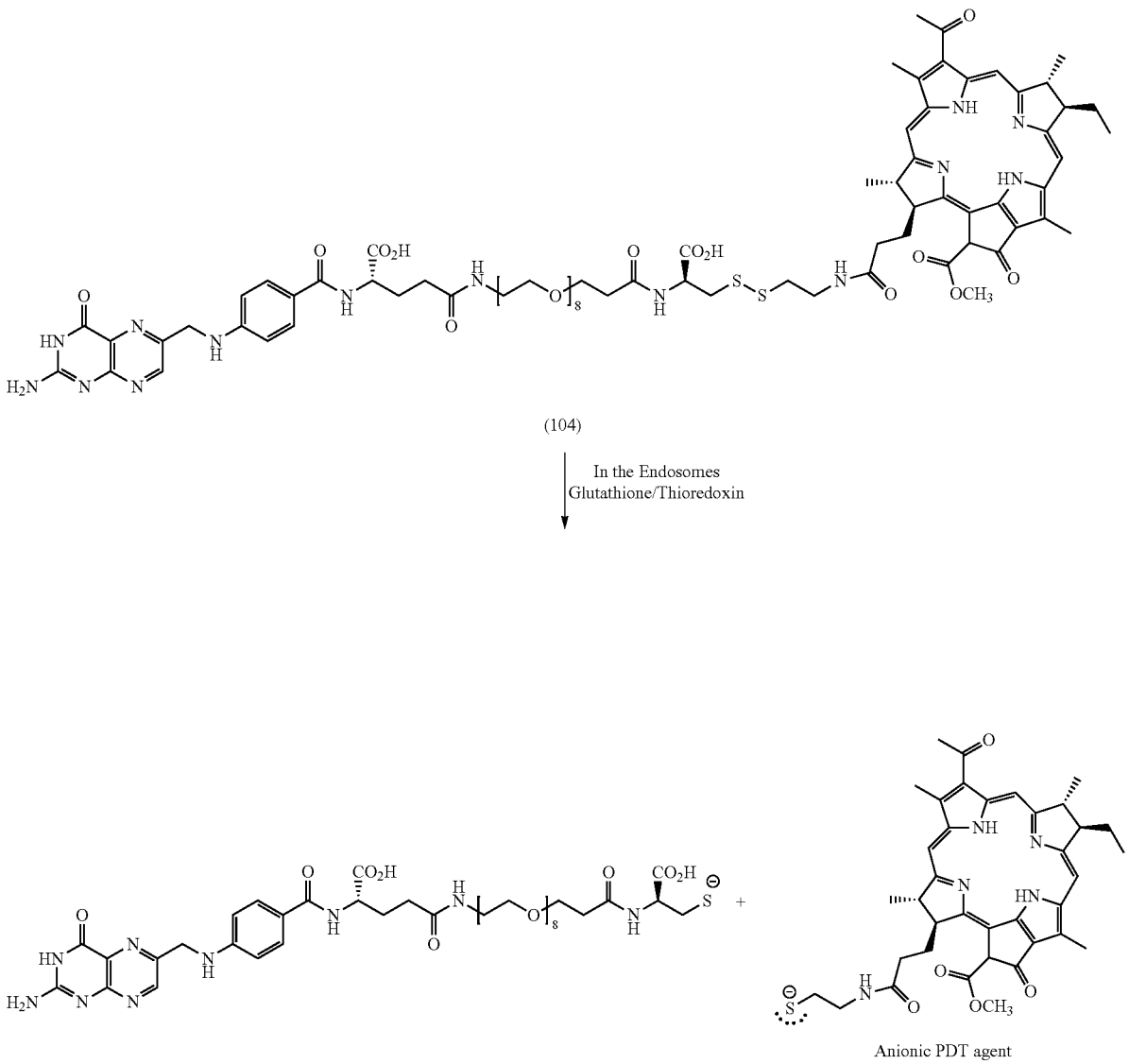

Possible mechanisms for disulfide mediated release of zwitterionic PDT agents from folate-targeted self-immolative prodrugs, such as 104, in the presence of disulfide reducing agents such as glutathione, thioredoxin, etc. in the endosomes.

83

(a) In Vitro Studies

TABLE 11

Effect of folate-targeted drug concentration on the survival modified PDT agents on the survival of KB cells in culture

| Compound | EC50 (nM) |
|---|---|
| 64 | 4.8 |
| 104 | 1.8 |
| 105 | 45.3 |
| BPheid-a | 745 |

To determine the in vitro efficacy of folate- and mitochondrial-targeted BPheid-a, KB cells as shown infra at the beginning of the Examples section and the data are reported according to EC50 values.

Both compound 64 and 104 actively killed the cancer cells.

(b) In Vivo Studies (i) Whole Body Imaging

To establish the specificity of folate- and mitochondrial-targeted releasable BPheid-a for cancer cells, compound 104 was injected into nude mice bearing KB tumors on their shoulders and monitored the tumor accumulation by fluorescence imaging using IVIS imager. Time dependent whole body images suggest that folate- and mitochondrial-targeted releasable BPheid-a (104) localized mainly in the tumor within 1 h. The compound 104 was highly specific for FR-positive tumor and no fluorescence was observed in other tissues. Thus, compound 104 is useful for producing a high high tumor to background ratio. Moreover, the tumor is more highly fluorescent than folate-targeted non-releasable BPheid-a conjugate (59a) (and non-targeted BPheid-a and mitochondrial-targeted BPheid-a). Higher solubility and release of the molecule may have accounted for this difference.

KB cells that overexpressed folate receptor were implanted subcutaneously into female nude mice and allowed to grow to ~20 mm$^3$ prior to initiation of treatment with 50 nmol of 104 (similar data for the compound 64 is reported in the previous example). Three hours (3 h) after injecting of drugs, tumor was treated with laser beam (75 mW/cm$^2$, 137 J/cm$^2$, exposure diameter=7.5-8 mm) for 38 min. In vivo efficacy of conjugates was evaluated by monitoring reduction of tumor volume. Compounds 64 and 104 were able to completely cure the tumor and showed tumor regression for 2 weeks. Both compounds can be considered as clinical candidates.

Example 11. Pre-Clinical Evaluation of Folate-Targeted Releasable BPhied-a Group G: Miscellaneous (a) In Vitro Studies

TABLE 12

Effect of folate-targeted drug concentration on the survival modified PDT agents on the survival of KB cells in culture

| Compound | EC50 (nM) |
|---|---|
| 112a | 0.5 |
| 117 | 2846 |
| 119 | 538 |

To determine the in vitro efficacy of folate- and nucleus-targeted BPheid-a, KB cells as described infra at the beginning of the Examples section and the data are reported above according to EC50 values.

(b) In Vivo Studies (i) Whole Body Imaging

To establish the specificity of folate- and nucleus-targeted releasable BPheid-a for cancer cells, compound 112a was injected into nude mice bearing KB tumors on their shoulders and monitored the tumor accumulation by fluorescence imaging using IVIS imager. Whole body images suggest that folate- and nucleus-targeted releasable BPheid-a (112a) localized mainly in the tumor. The compound 112a was highly specific for FR-positive tumors and there was no fluorescence in other tissues. Thus this compound produces a high tumor to background ratio. Moreover, tumor is more highly fluorescent than folate-targeted non-releasable BPheid-a conjugate (59a) (and non-targeted BPheid-a and mitochondrial-targeted BPheid-a). Higher solubility and release of the molecule may have done the difference here.

KB cells that overexpressed folate receptor were implanted subcutaneously into female nude mice and allowed to grow to ~20 mm$^3$ prior to initiation of treatment with 50 nmol of 117. Three hours (3 h) after injecting of drugs, tumor was treated with laser beam (75 mW/cm$^2$, 137 J/cm$^2$, exposure diameter=7.5-8 mm) for 38 min. In vivo efficacy of conjugates was evaluated by monitoring reduction of tumor volume. Compound 117 was able to completely cure the tumor and showed tumor regression for 3 weeks.

The invention claimed is:

1. A compound having the formula:

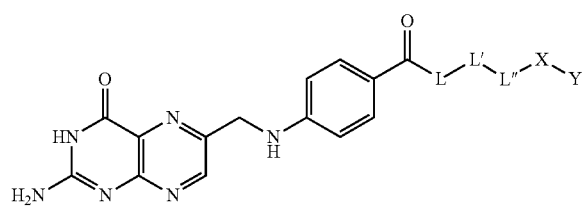

or a pharmaceutically acceptable salt thereof, or isotopes thereof, wherein

L is an amino acid,

L$'$ is a linker to improve pharmacokinetic properties,

L$''$ is a linker which may be configured to release an organelle-targeted photodynamic therapeutic (PDT) agent, X is an organelle-targeting agent, and Y is a photodynamic therapeutic agent selected from the group consisting of:

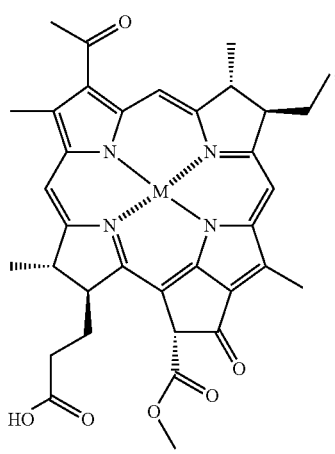
BPheid-a
M = 2H: (1)
M = Pd (2)
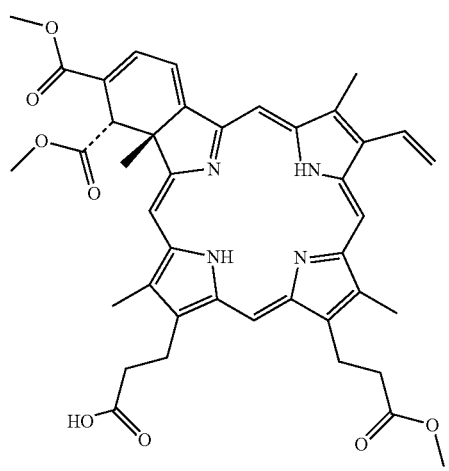
Visudyne (1:1 mixture)
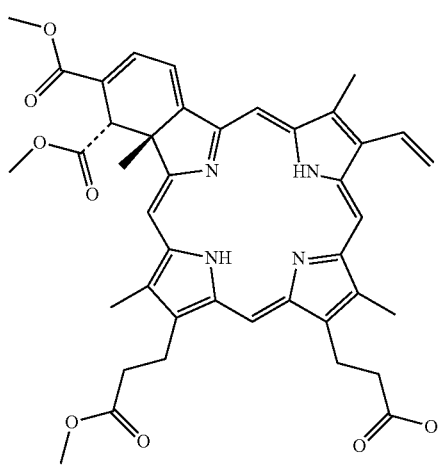
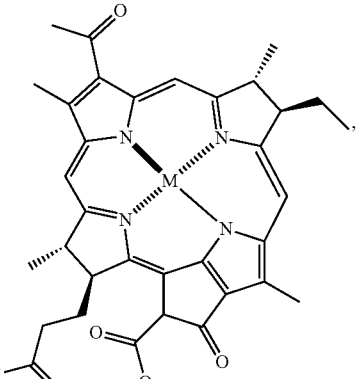
M = 2H: (9)
M = Pd: (10)
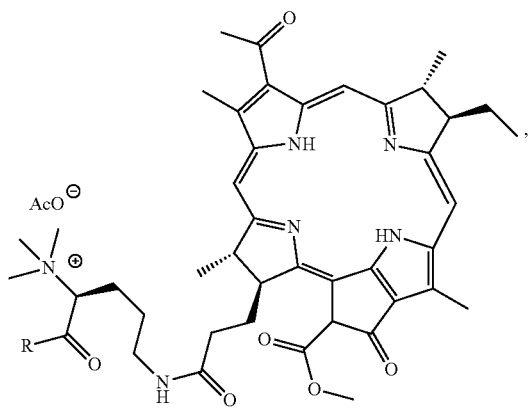
R = OH: (11a)
R = NHNH$_2$: (11b)
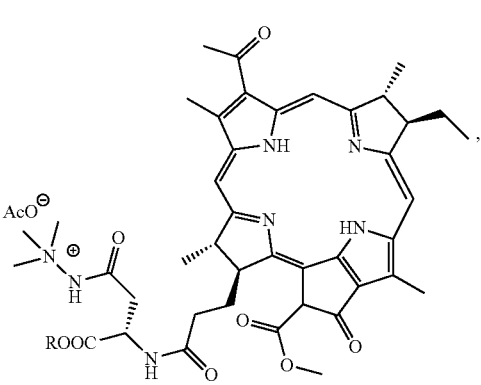
R = H: (12a)
R = $^t$Bu: (12b)

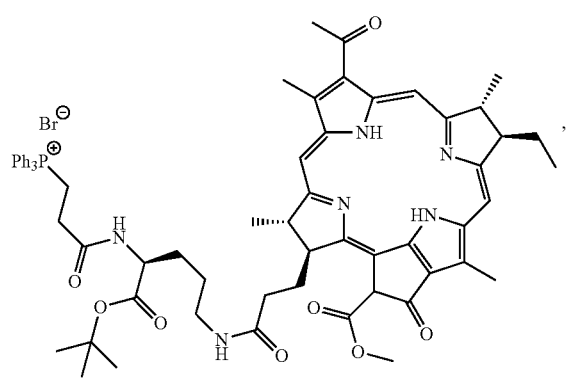
(13)
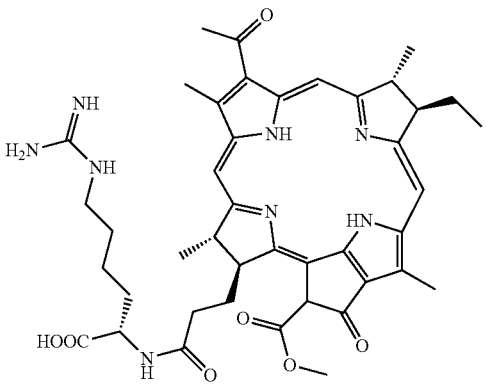
(17)
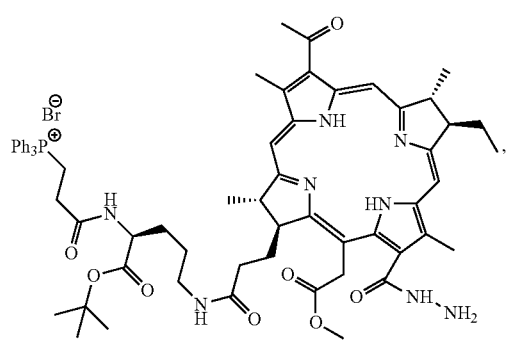
(14)
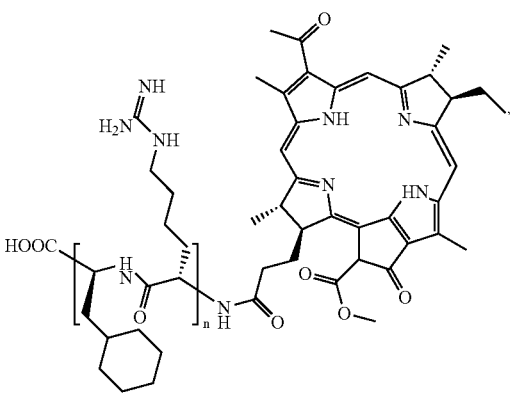
(18)
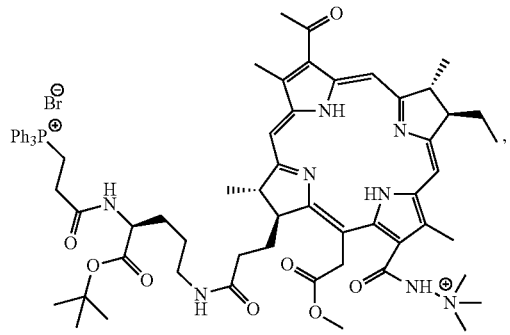
(15)
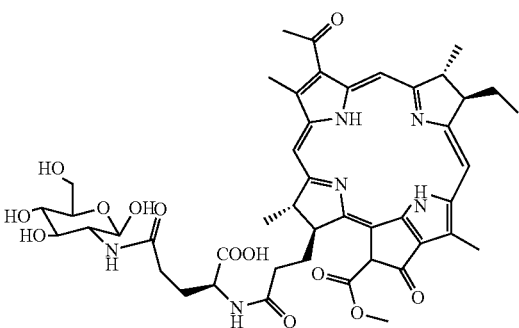
(19)
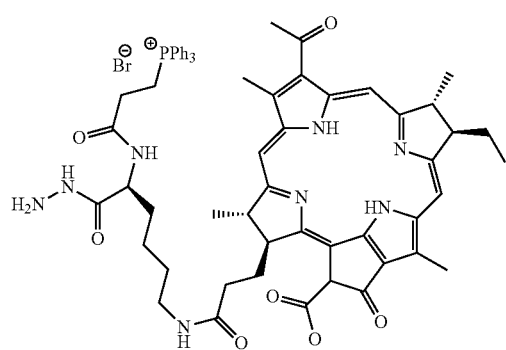
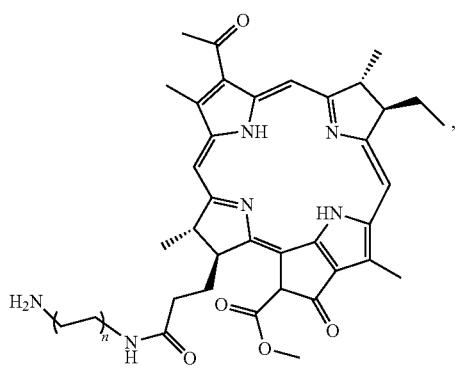
n = 0: (20a)
n = 1: (20b)

89
-continued
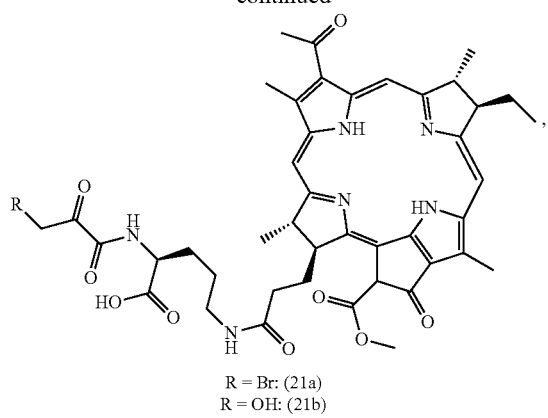
R = Br: (21a)
R = OH: (21b)
(22)
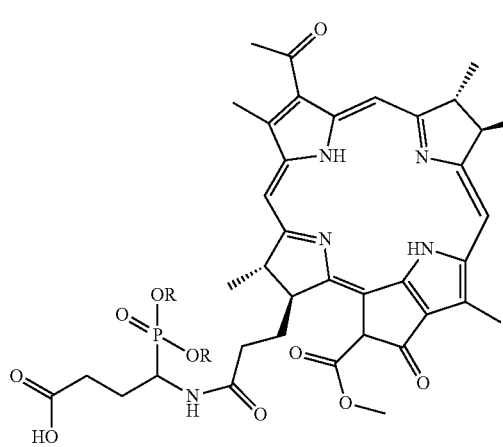
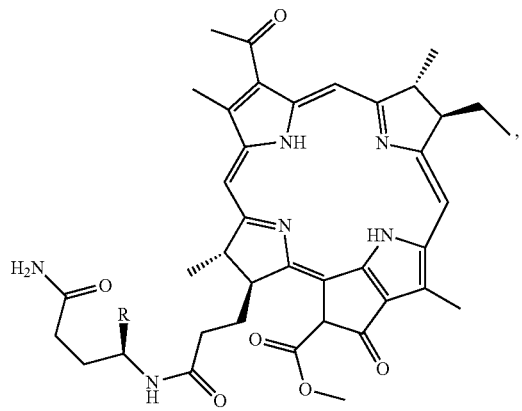
R = COOH: (23a)
R = NH2: (23b)
90
-continued
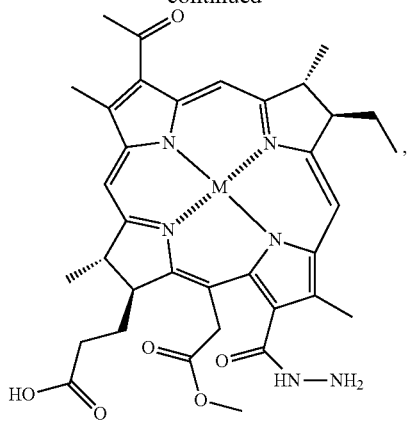
M = 2H: (24)
M = Pd: (25)
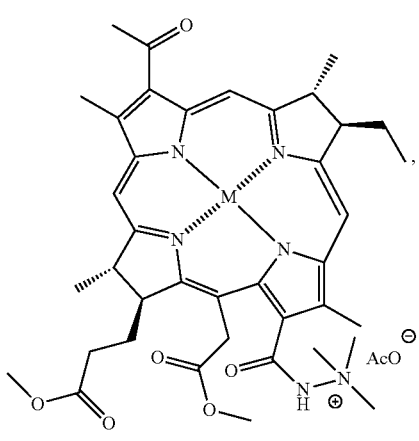
M = 2H: (26)
M = Pd: (27)
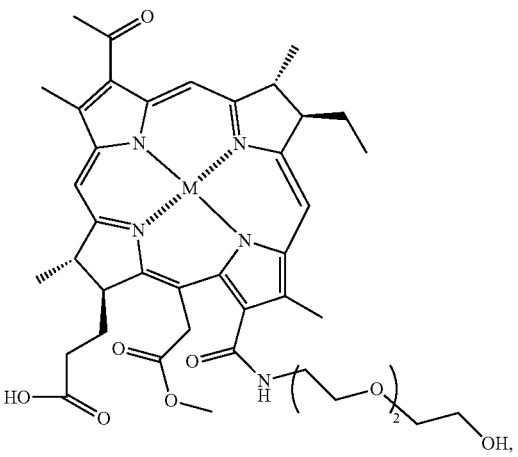
M = 2H: (28)
M = Pd: (29)

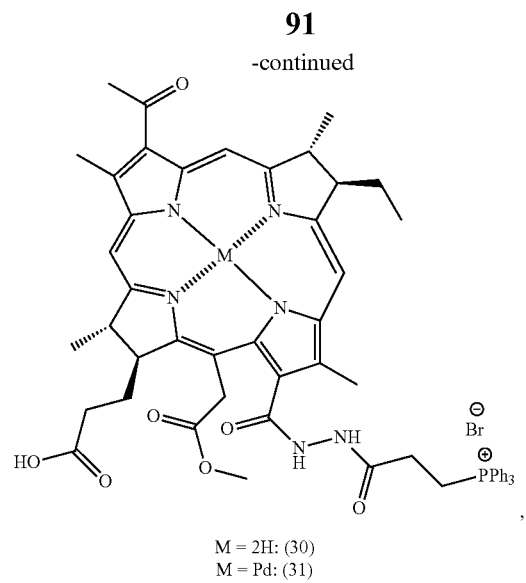
M = 2H: (30)
M = Pd: (31)
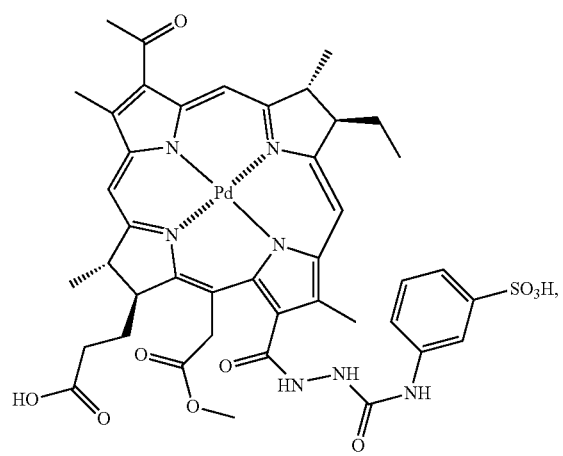
(39)
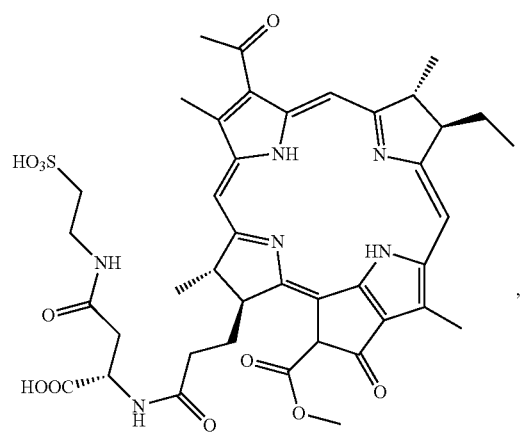
(40)
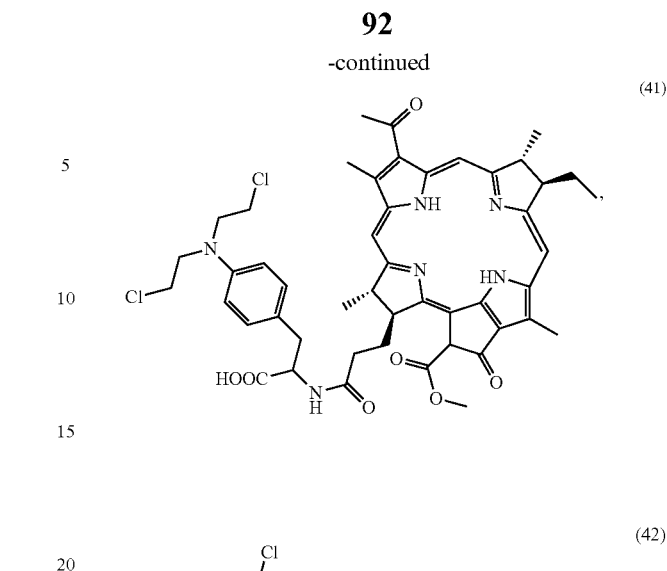
(41)
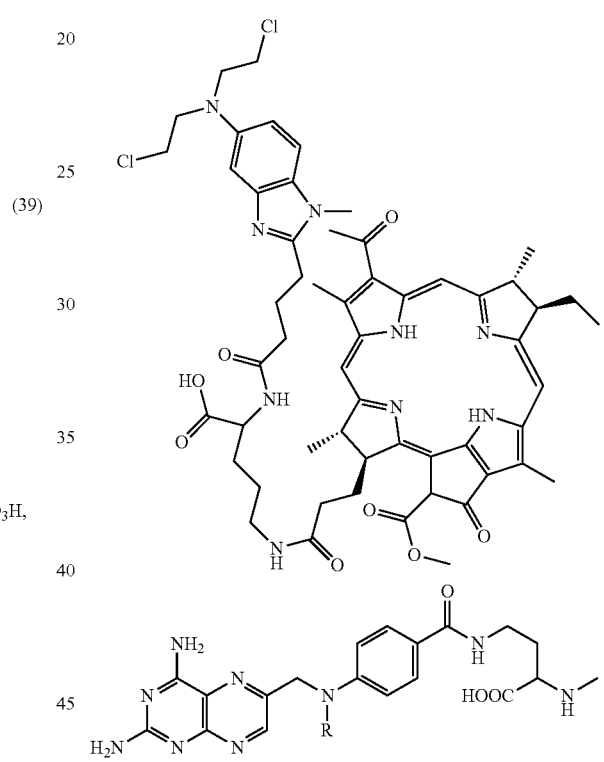
(42)
R = H: (43)
R = Me (44)
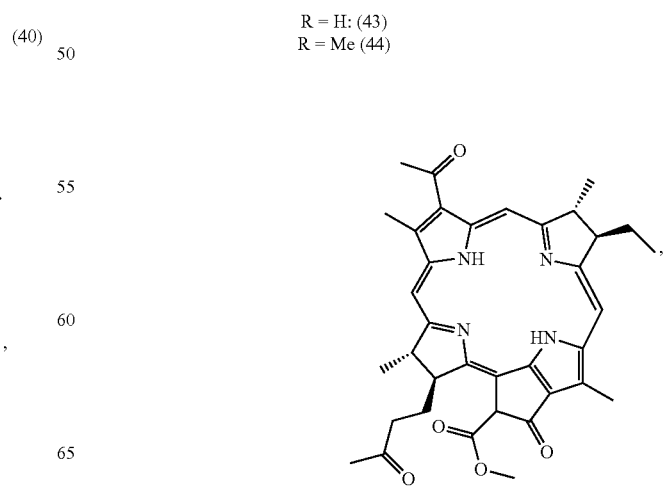

(45)
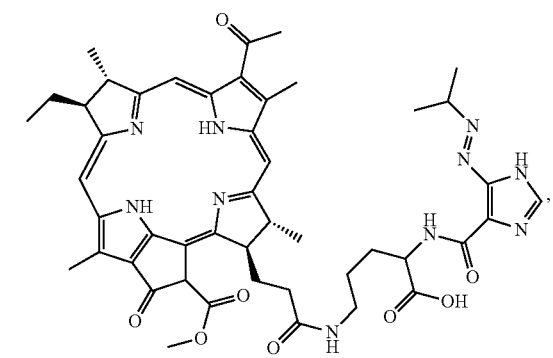

(46)
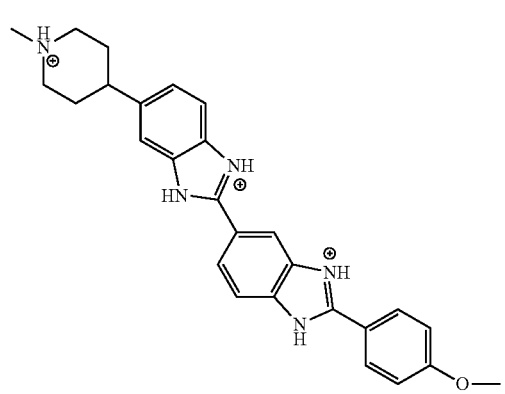

(47)
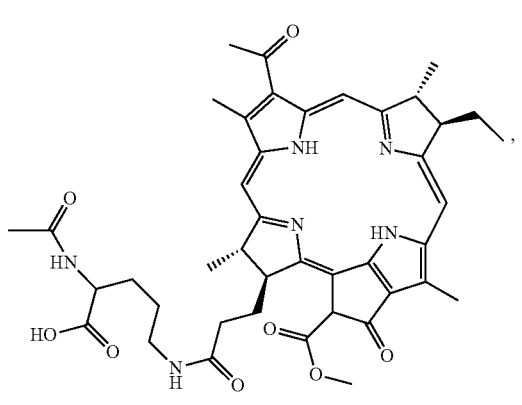

(48)
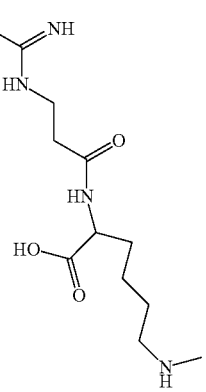

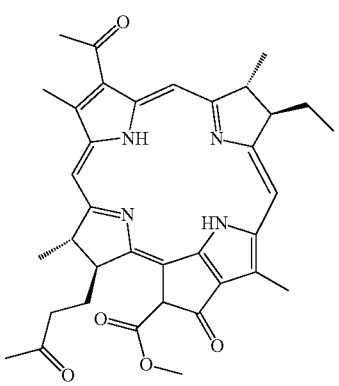 and

(49)
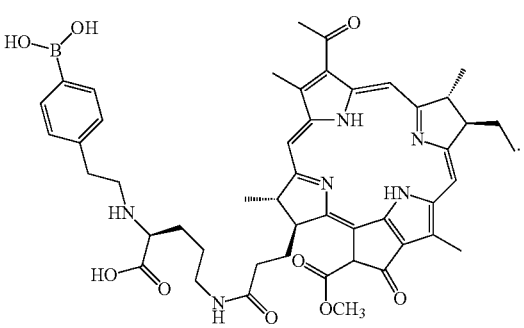

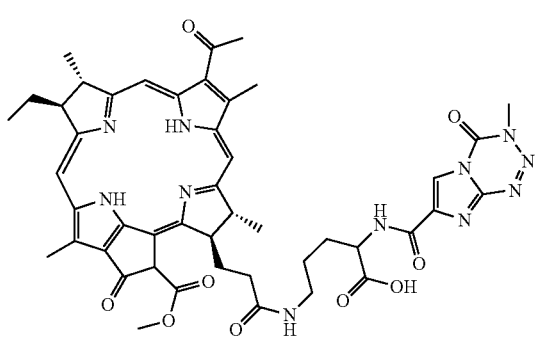

2. The compound of claim 1, wherein Y has an absorption and emission maxima in the visible spectrum.

3. The compound of claim 2, wherein Y has an absorption and emission maxima of about 680 nm to about 800 nm.

4. The compound of claim 1, wherein Y has an $\epsilon_{max}$ of about 50,000 to about 100,000 $M^{-1}$ $cm^{-1}$.

5. The compound of claim 1, wherein the compound has a formula selected from the group consisting of:

(64)
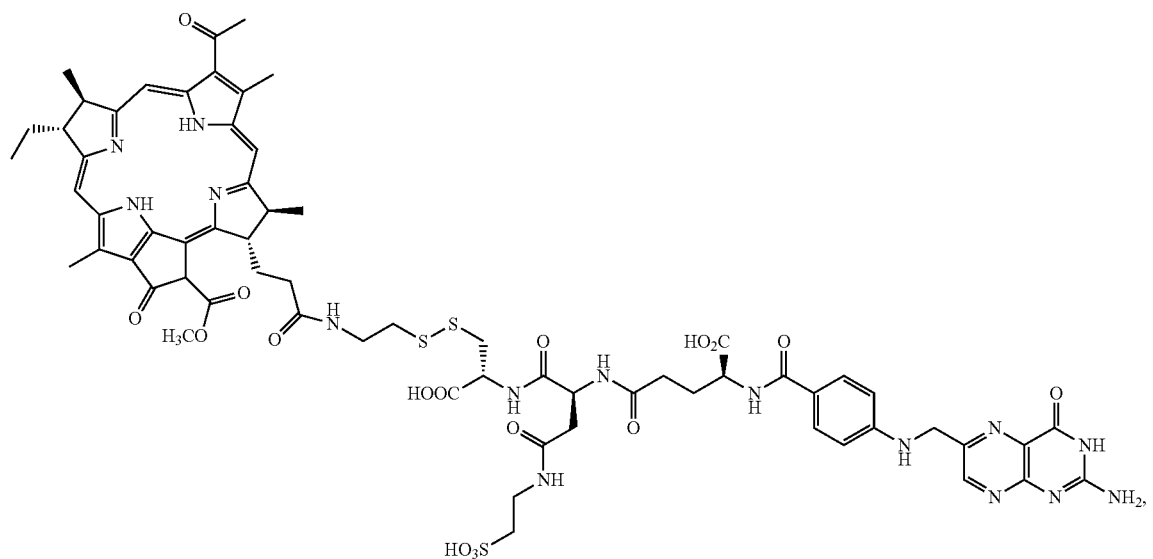
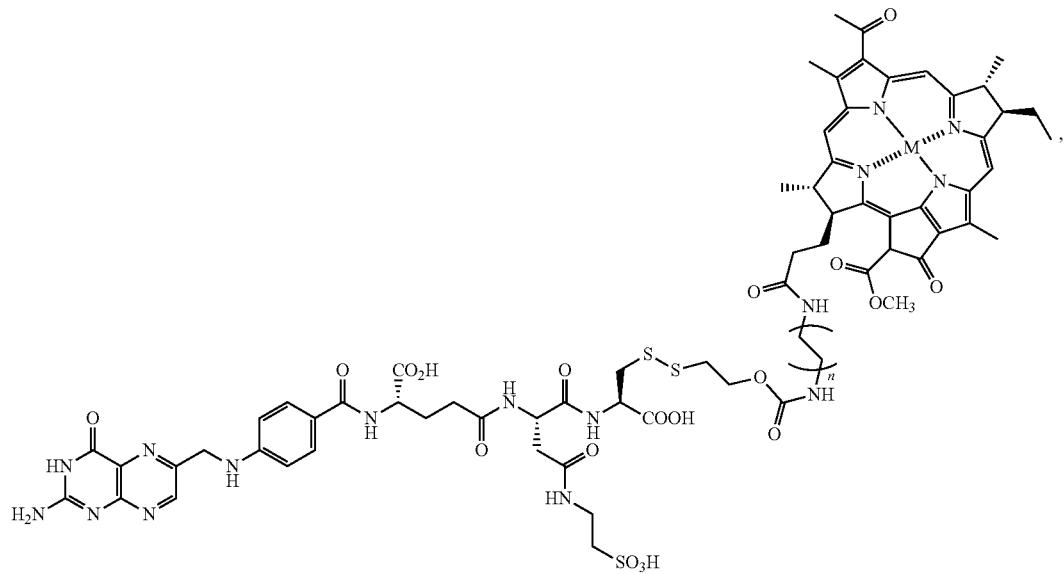
n = 0; M = 2H: (65a)  n = 0; M = Pd: (65b)
n = 1; M = 2H: (65c)
(66)
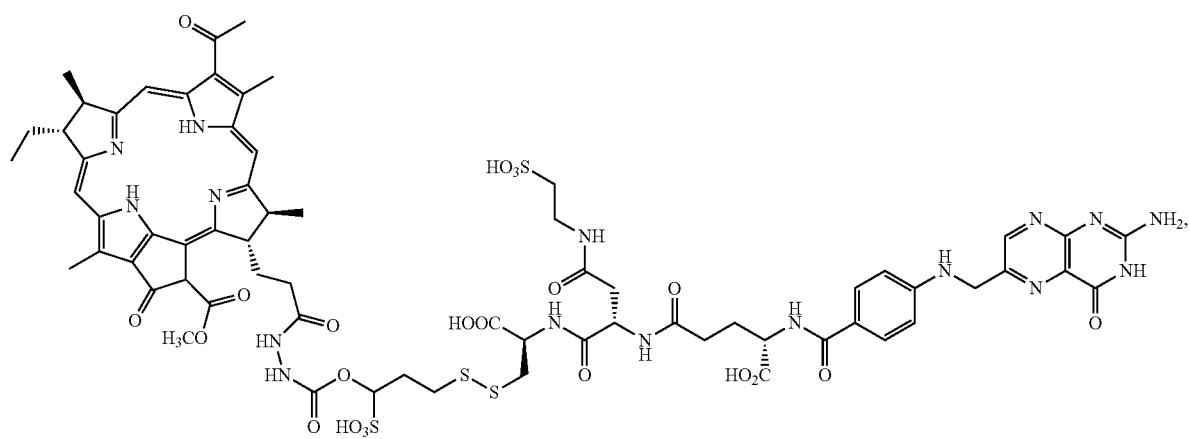

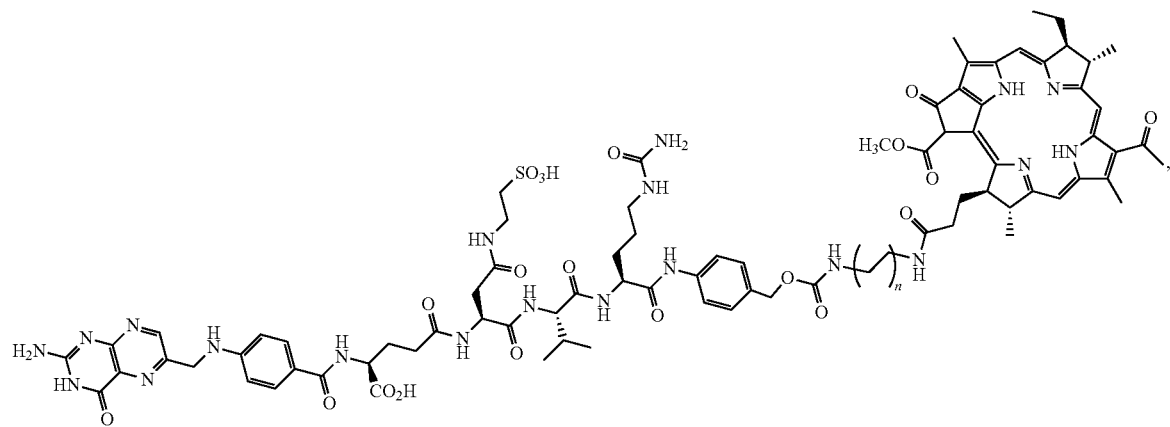
n = 0: (67a)
n = 1: (67b)
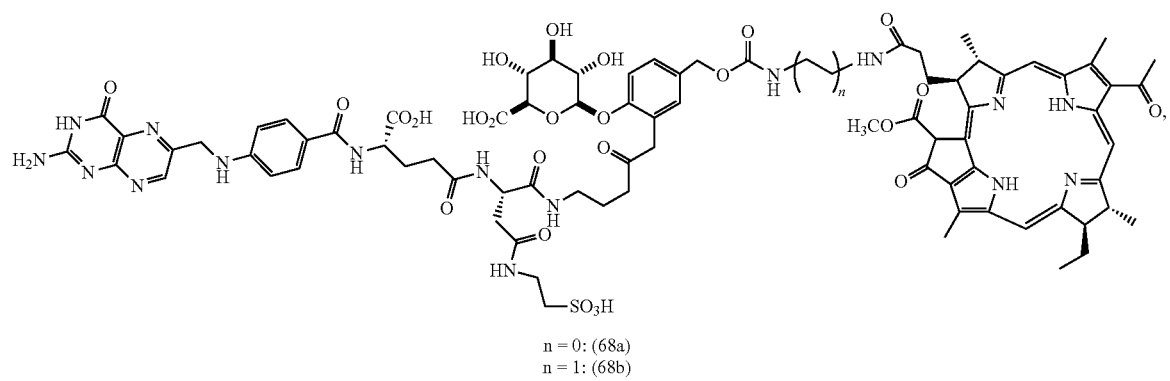
n = 0: (68a)
n = 1: (68b)
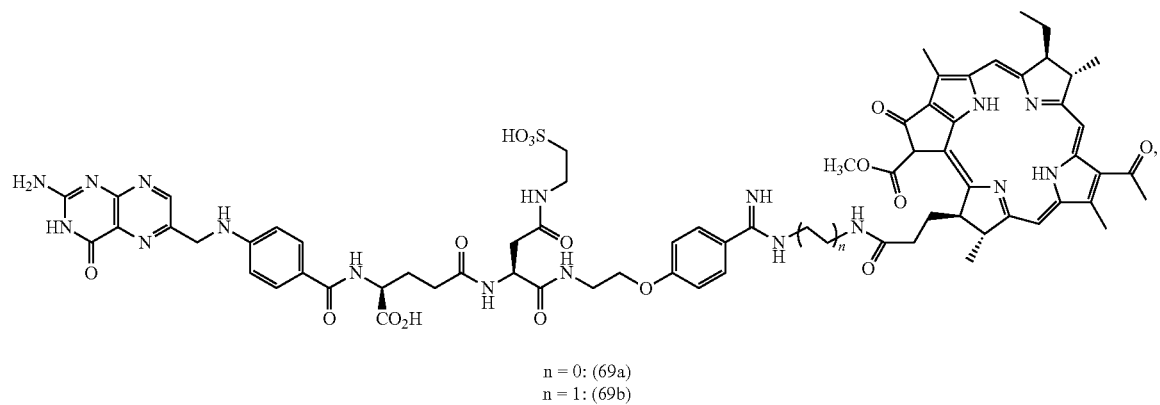
n = 0: (69a)
n = 1: (69b)

-continued
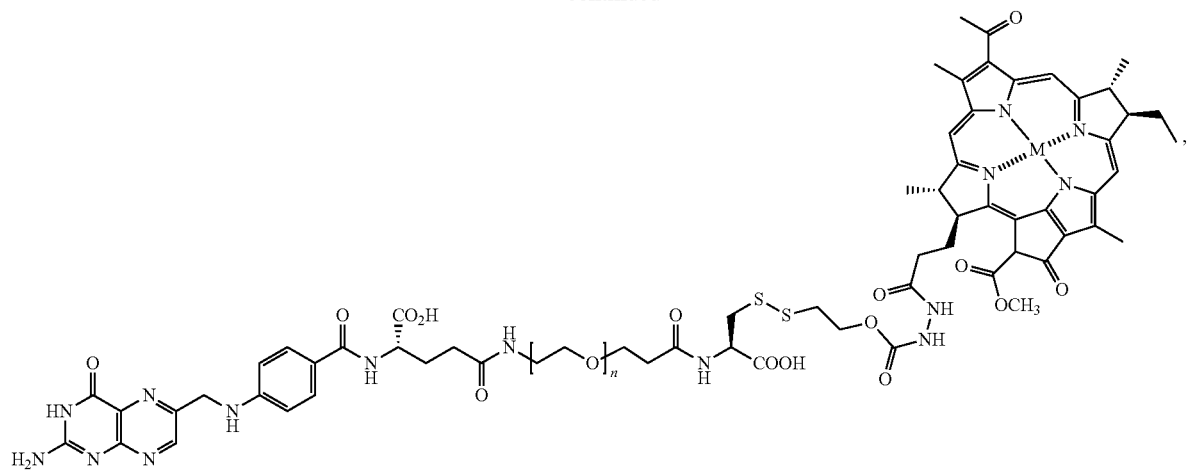
n = 6, M = 2H: (76a)
n = 6, M = Pd: (76b)
n = 8: M = 2H: (76c)
n = 8: M = Pd: (76d)
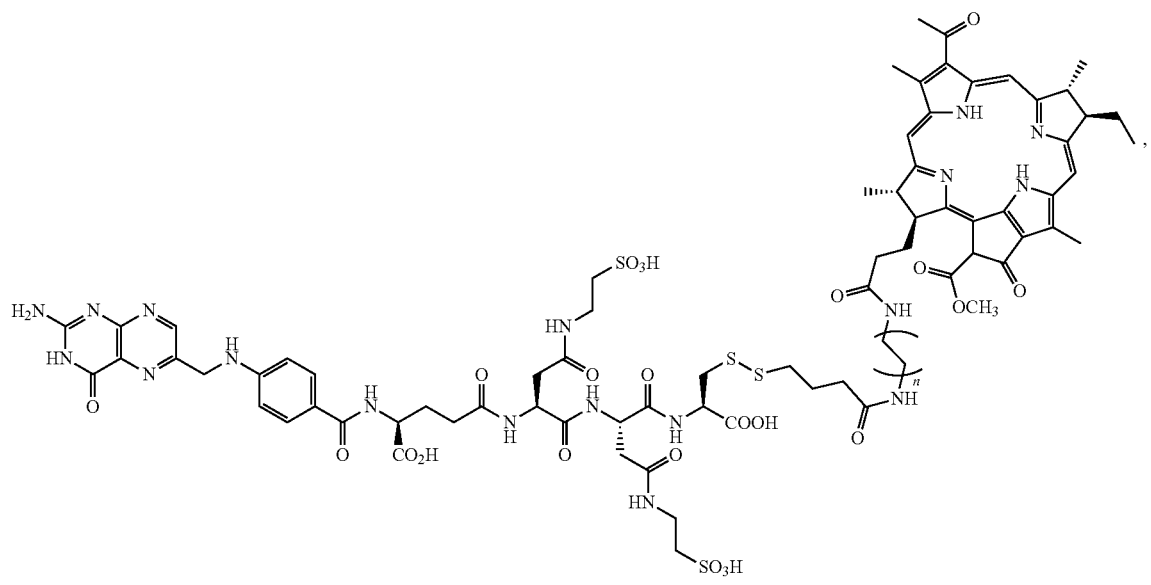
n = 0: (77a)
n = 1: (77b)

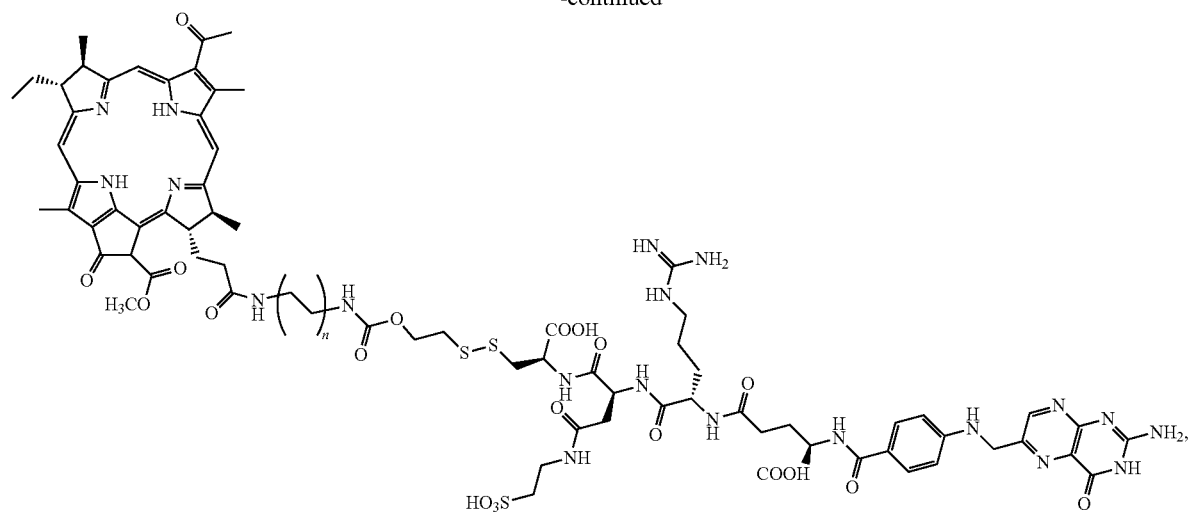
n = 0: (78a)
n = 1: (78b)
(80)
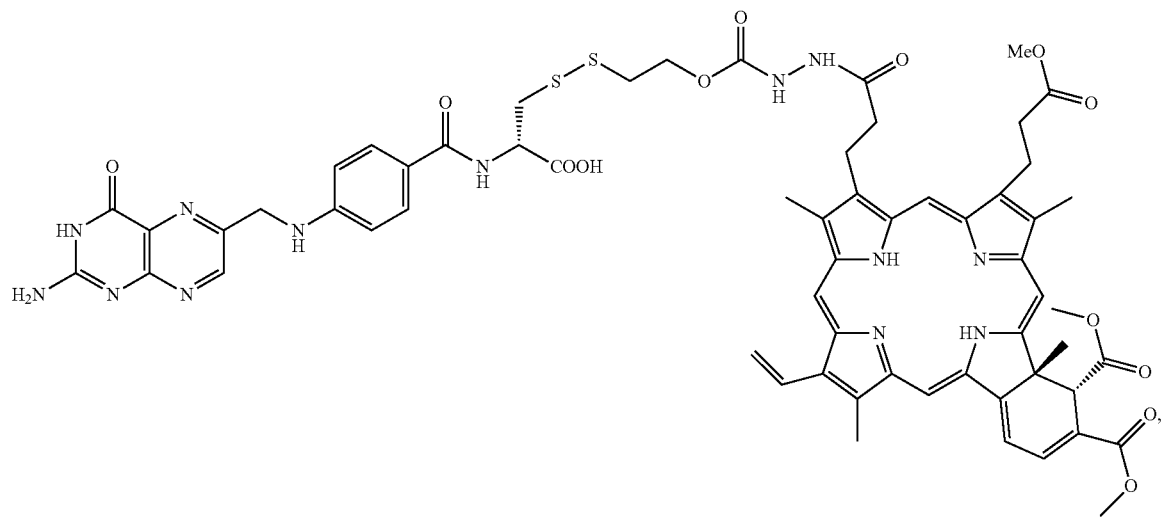
(81)
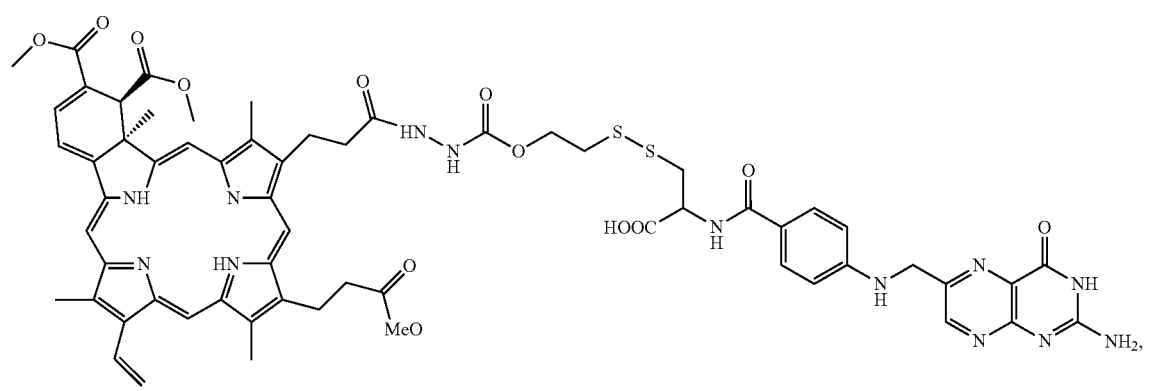

103
104
-continued
(82)
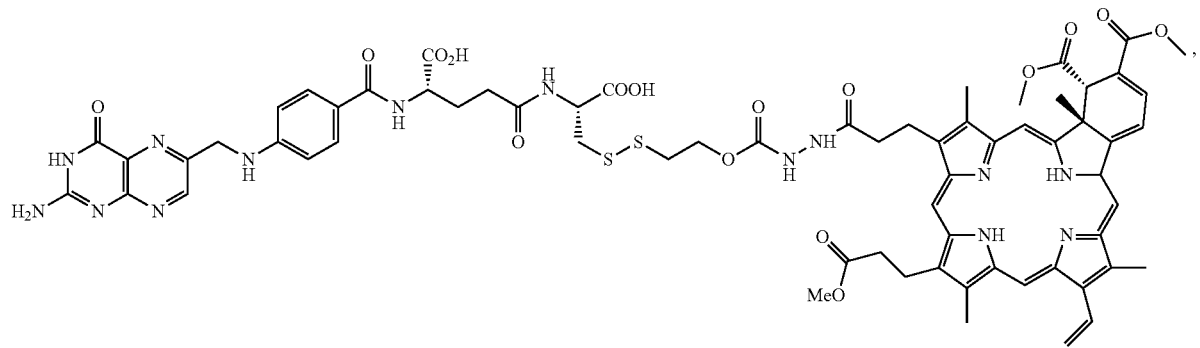
(83)
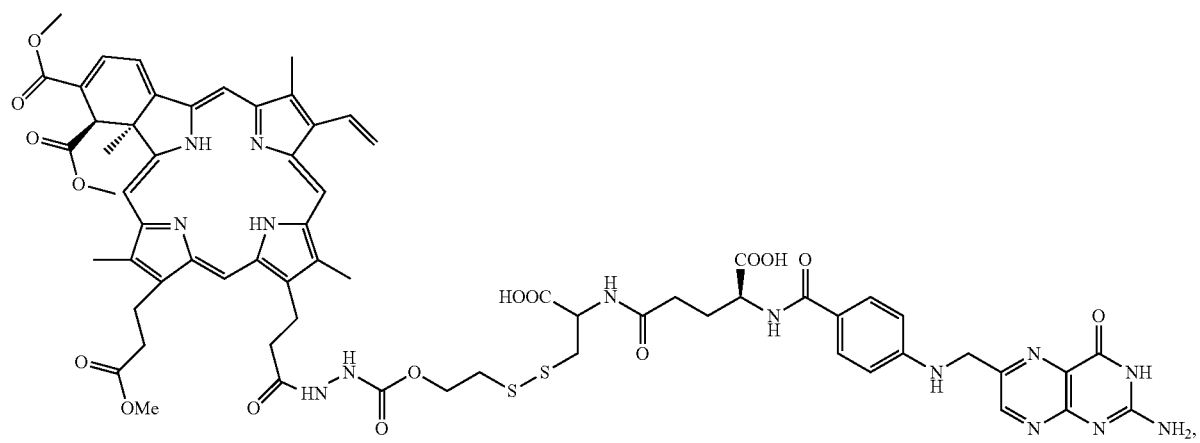
(84)
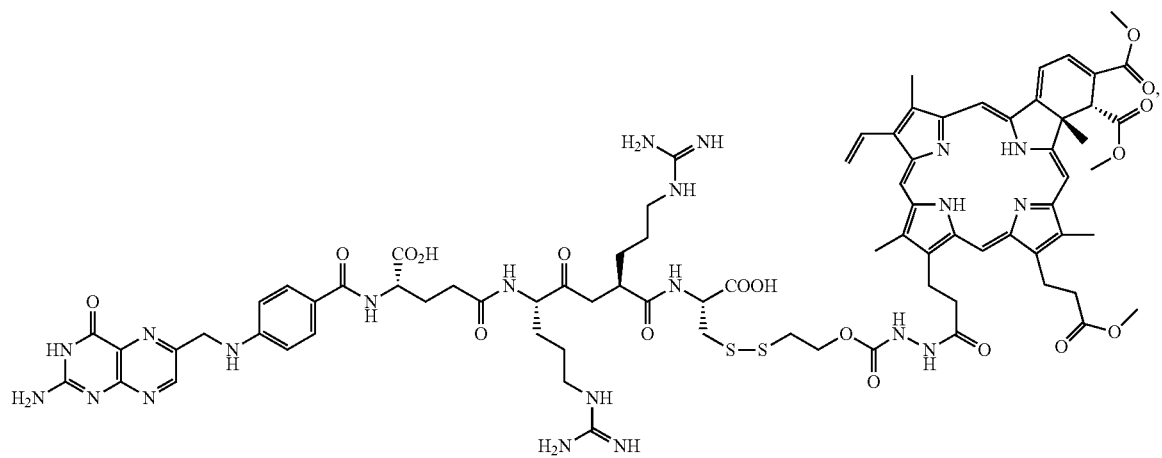

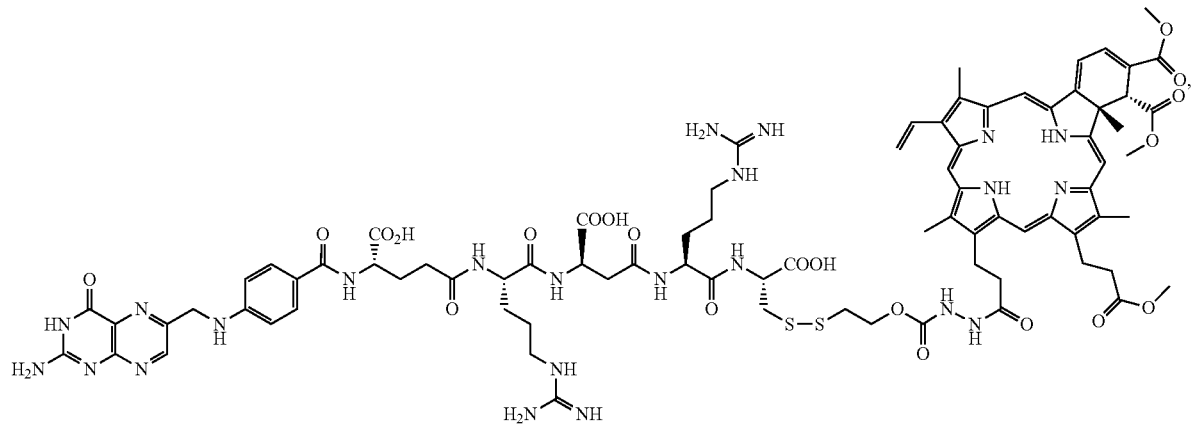
(85)
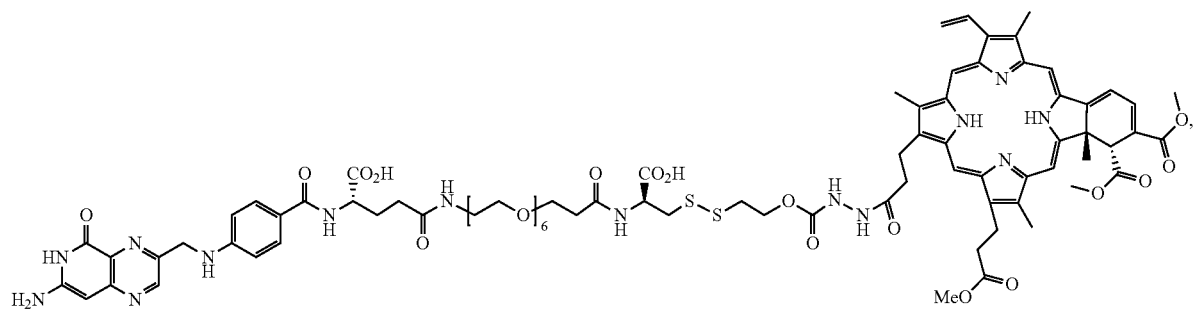
(86)
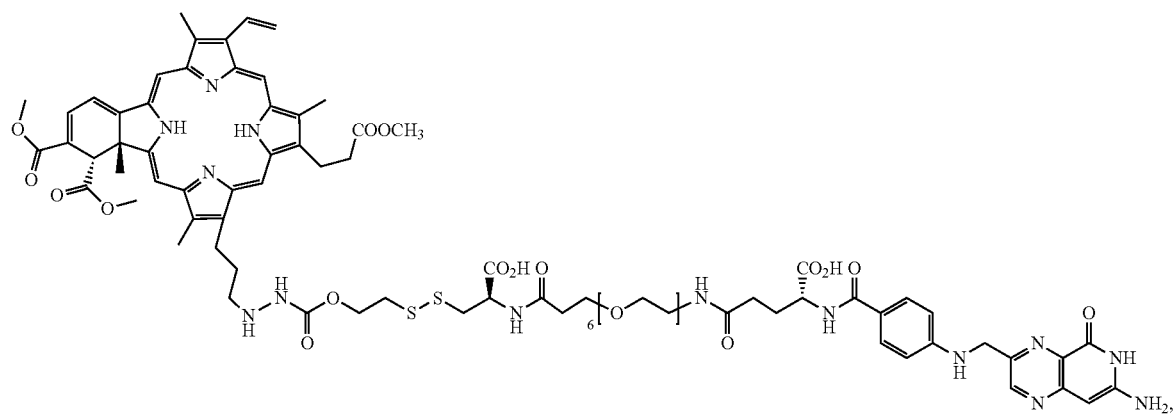
(87)

-continued
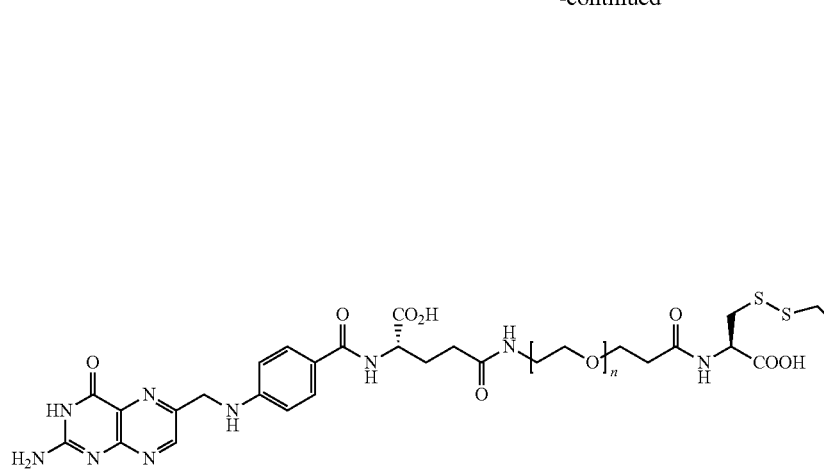
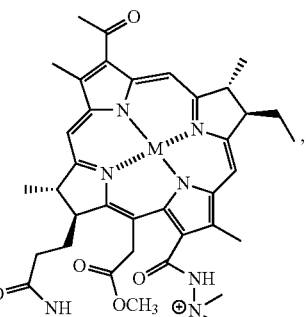
n = 6, M = 2H: (87a)
n = 6, M = Pd: (87b)
n = 8: M = 2H: (87c)
n = 8: M = Pd: (87d)
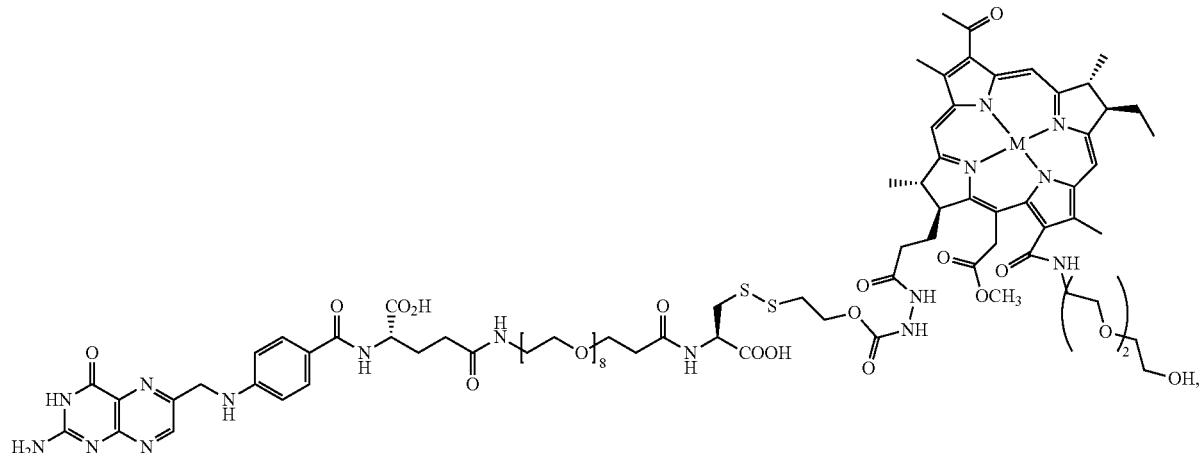
M = 2H: (88a)
M = Pd: (88b)
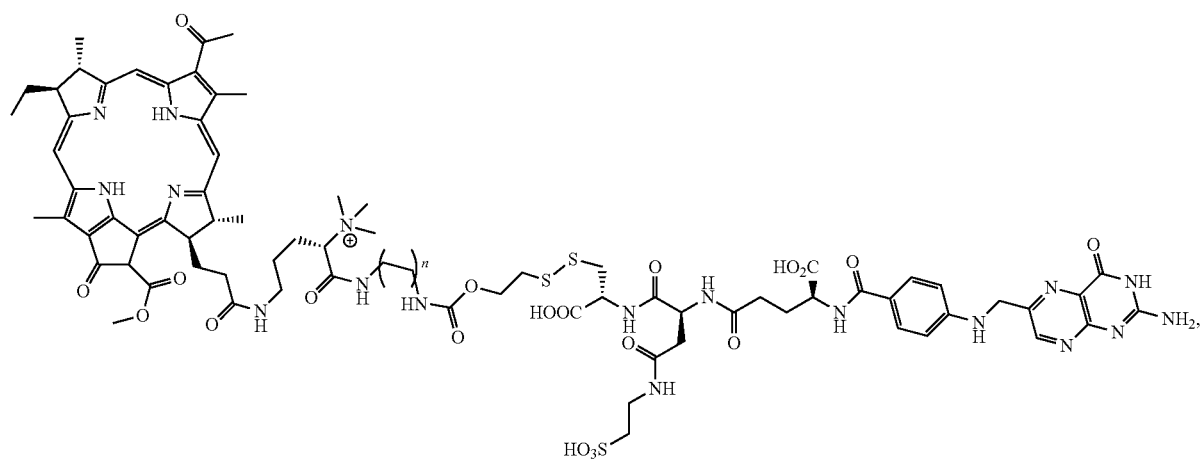
n = 0: (89a)
n = 1: (89b)

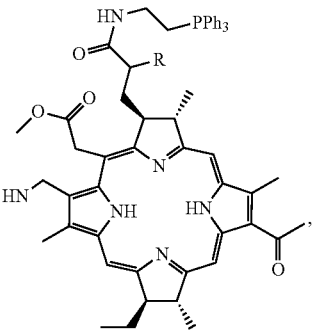
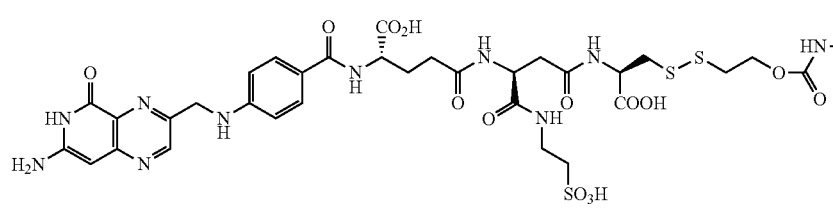
n = 0; R = H: (90a)
n = 1; R = H: (90b)
n = 0; R = COO'Bu: (91a)
n = 1; R = COO'Bu: (91b)
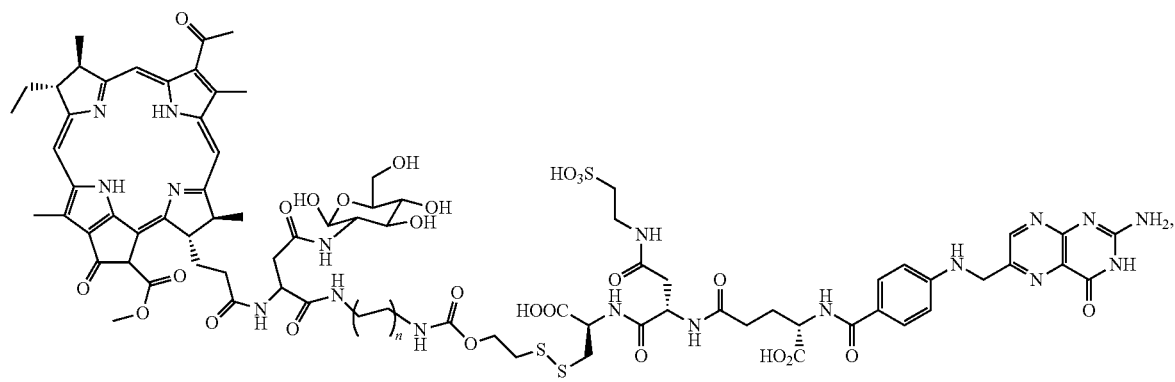
n = 0: (92a)
n = 1: (92b)
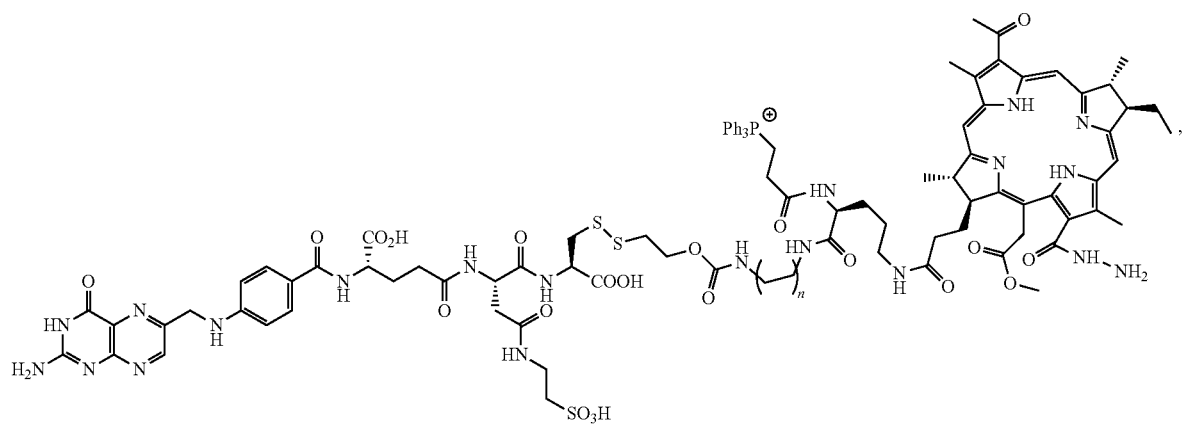
n = 0: (93a)
n = 1: (93b)

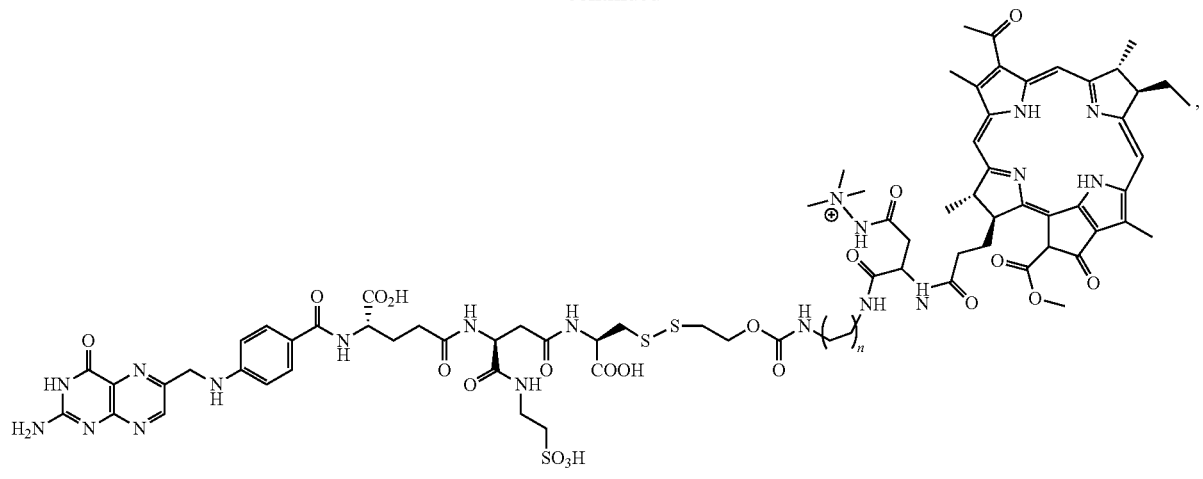
n = 0: (95a)
n = 1: (95b)
(96)
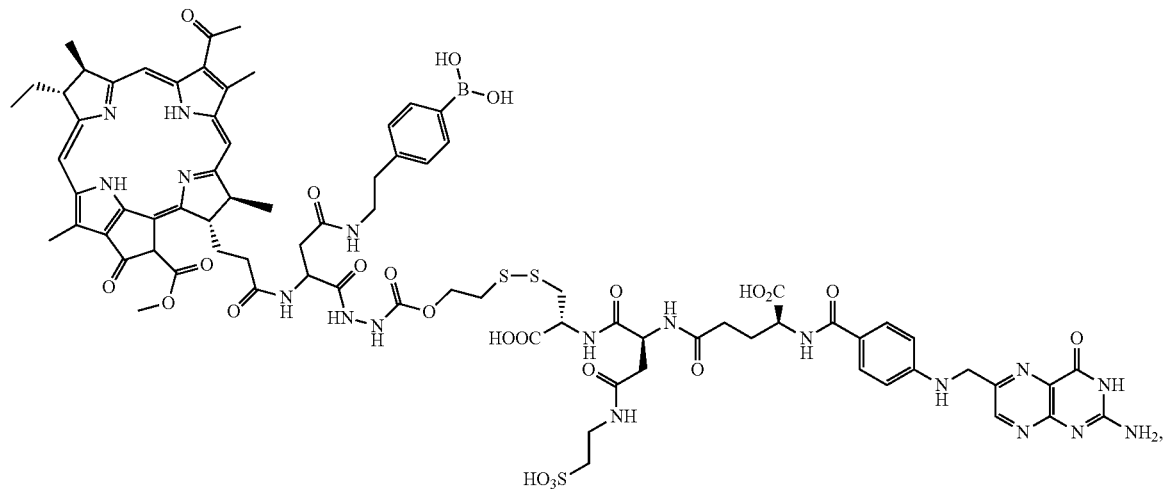
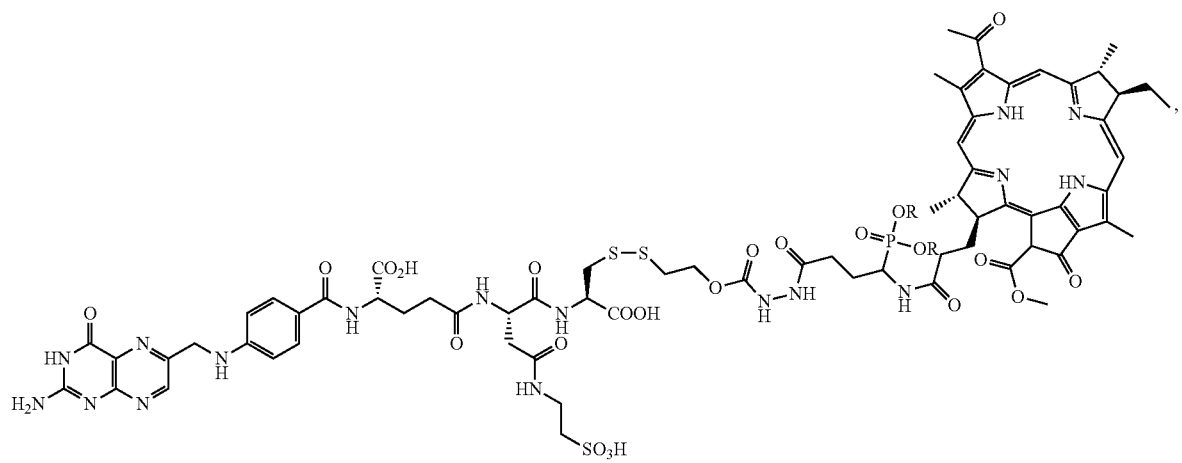
R = H: (97)
R = Ph: (98)

(99)
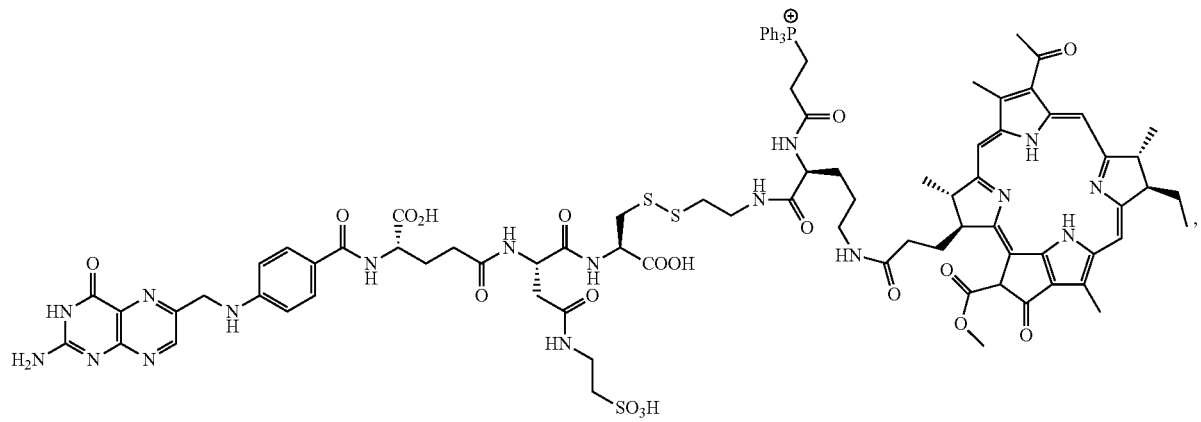
(100)
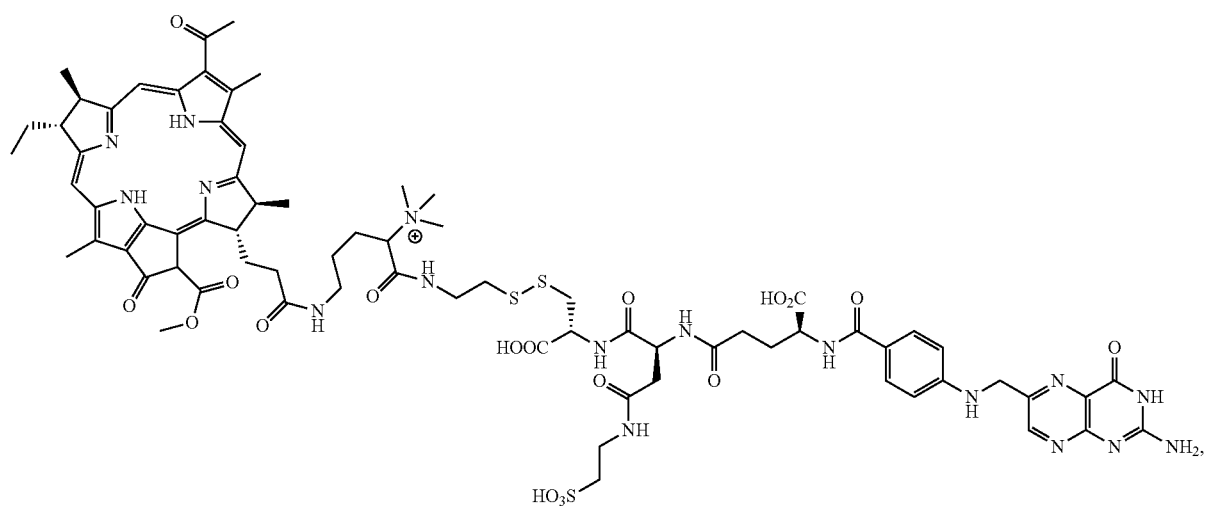
(101)
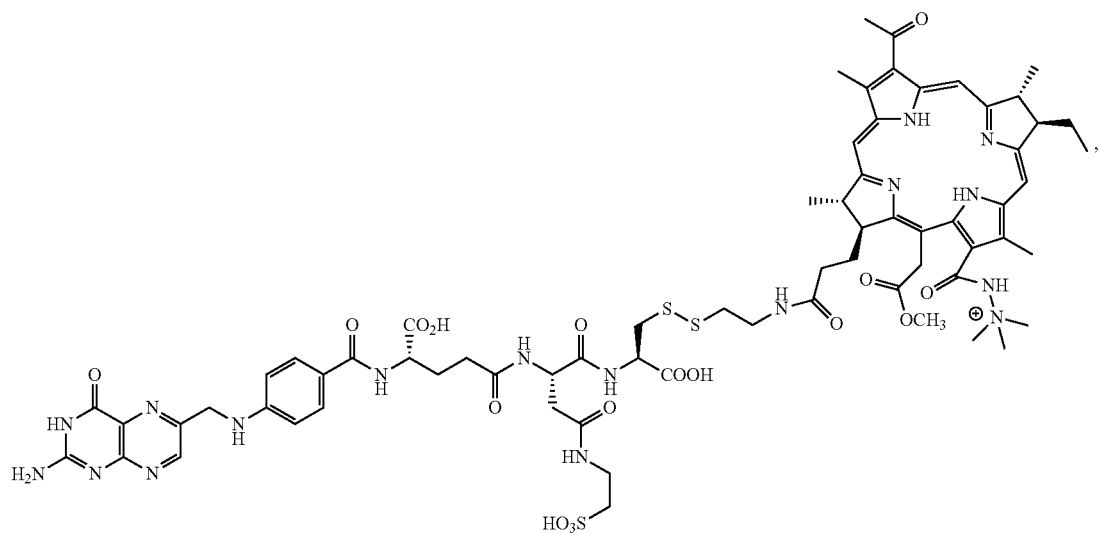

(104)
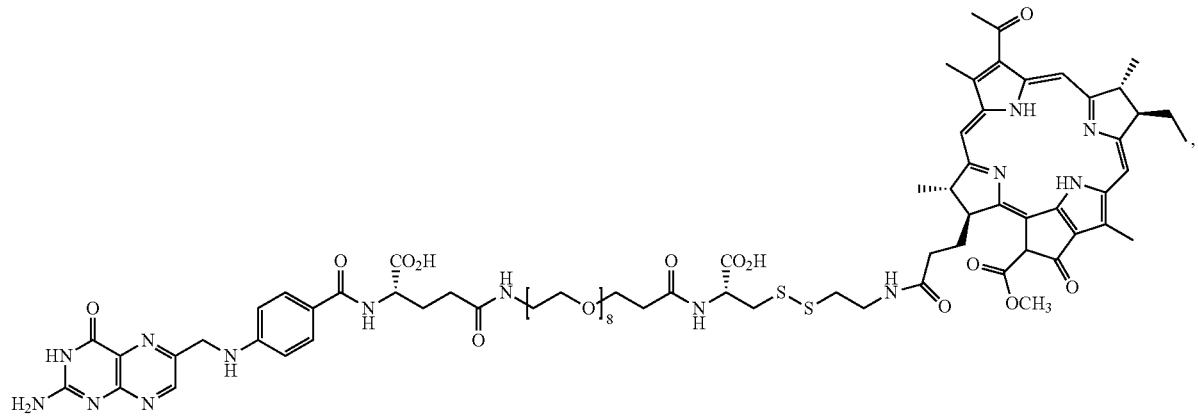
(105)
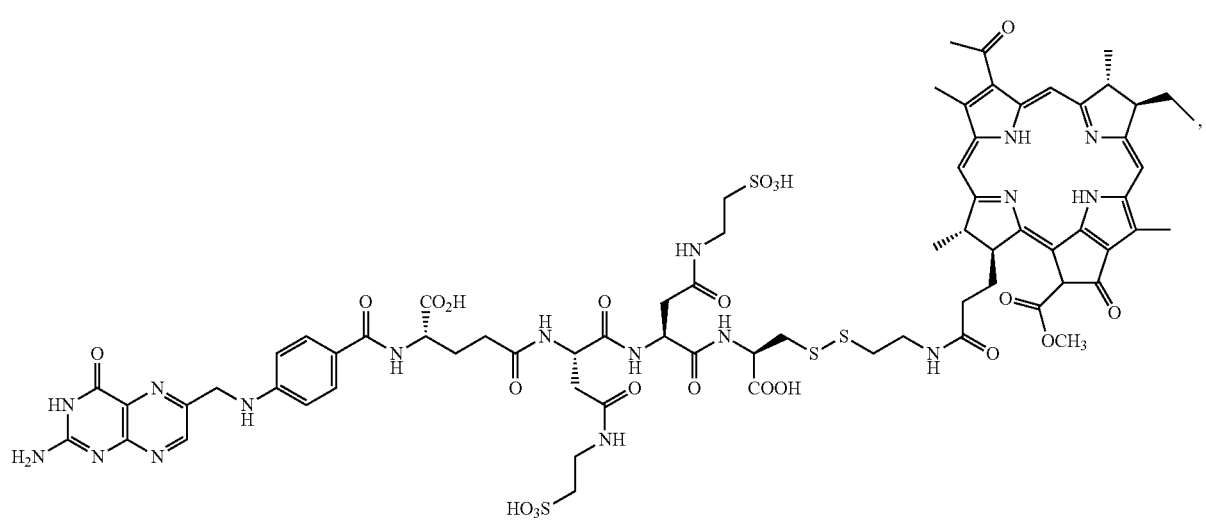
(106)
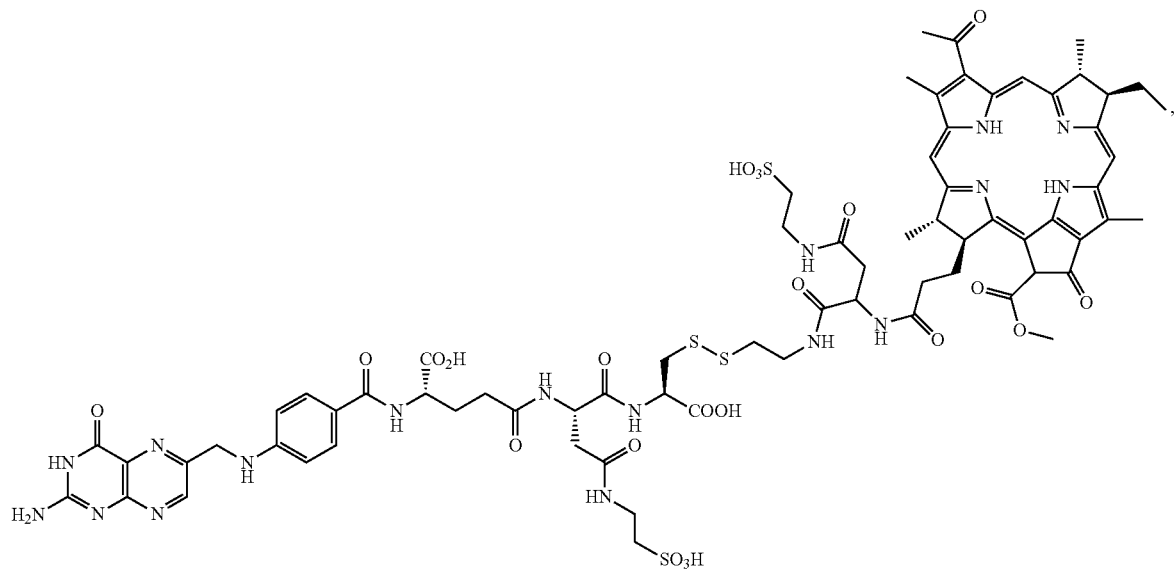

(107)
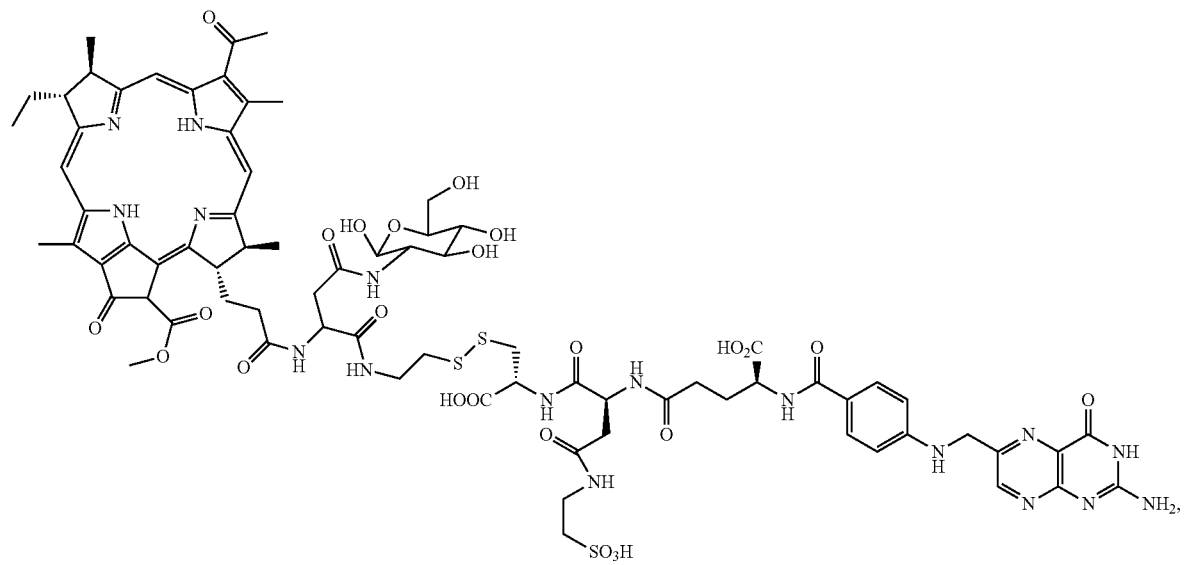
(108)
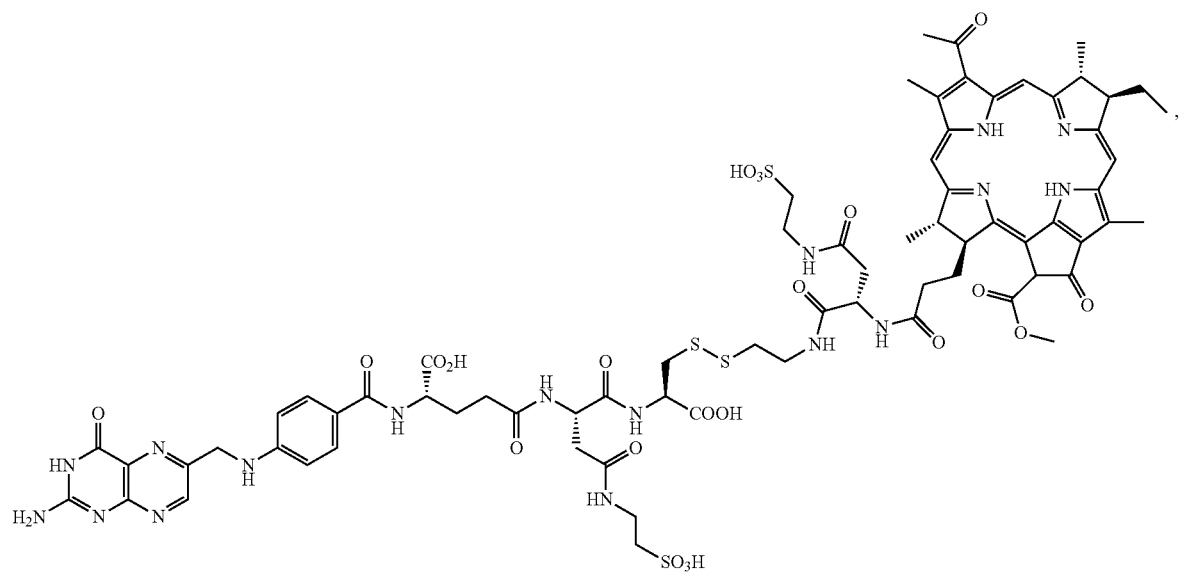

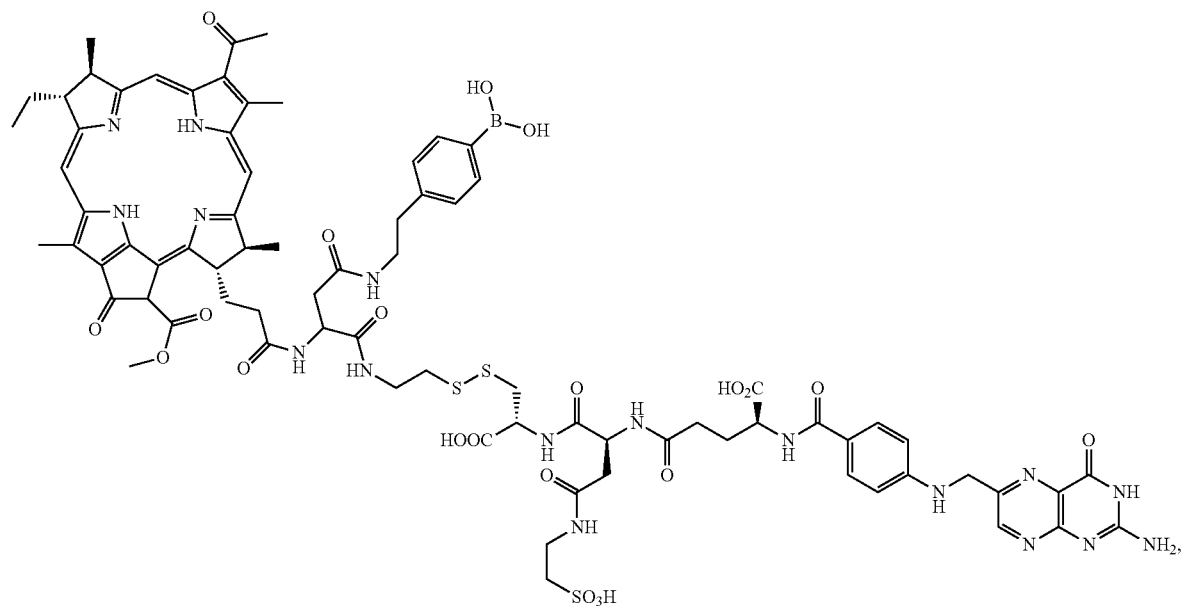
(109)
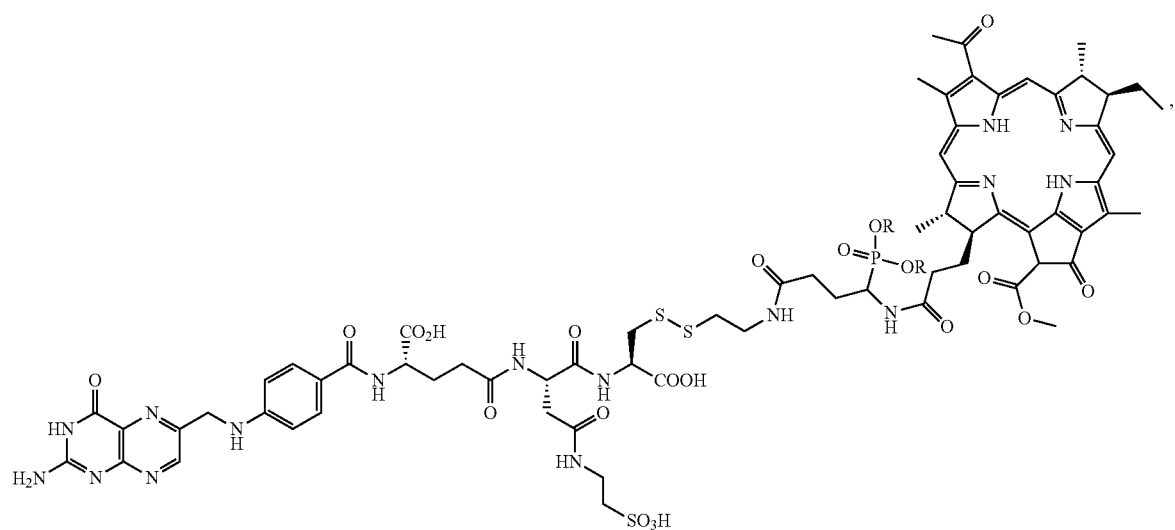
R = H: (110)
R = Ph: (111)

-continued
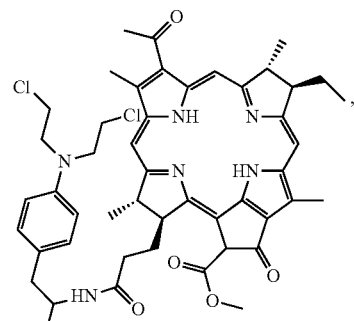
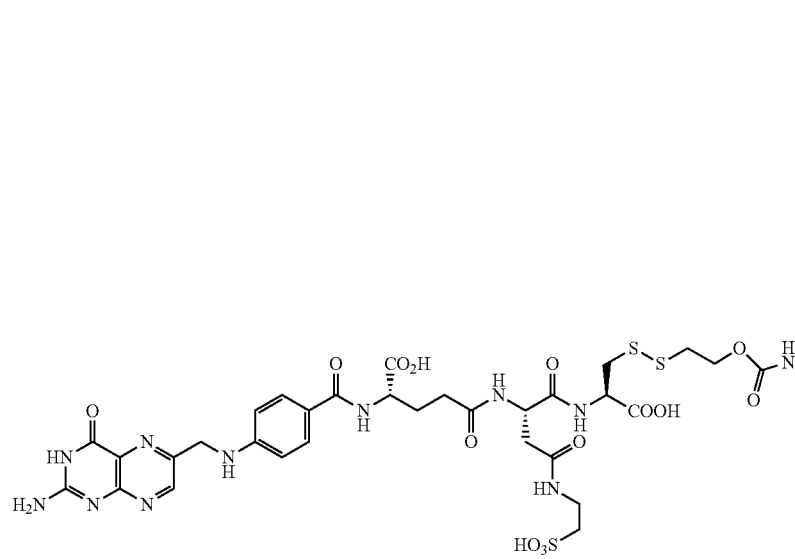
n = 0: (112a)
n = 1: (112b)
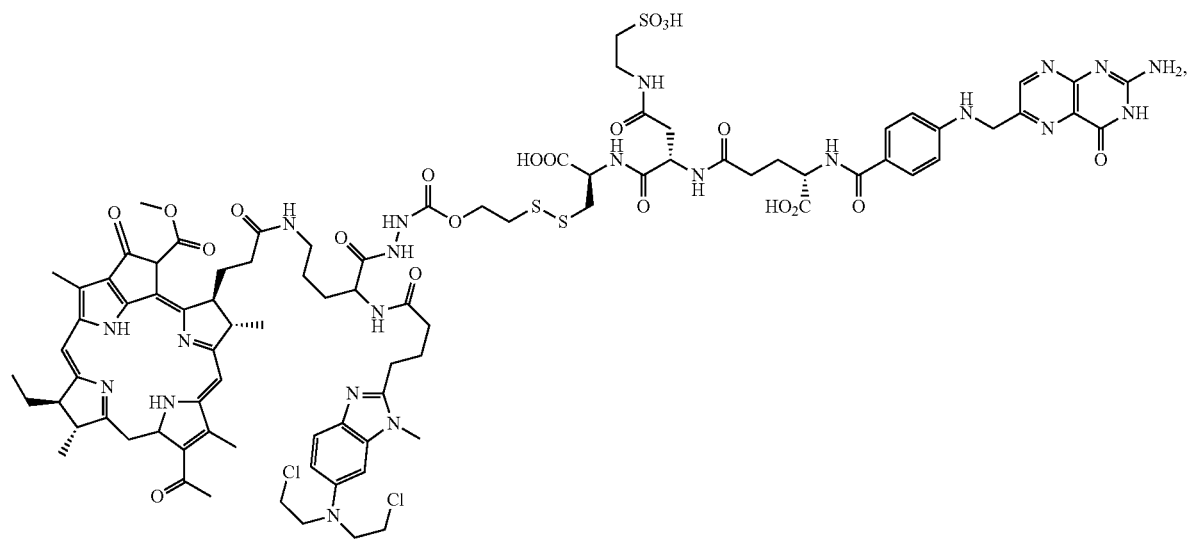
(113)

-continued
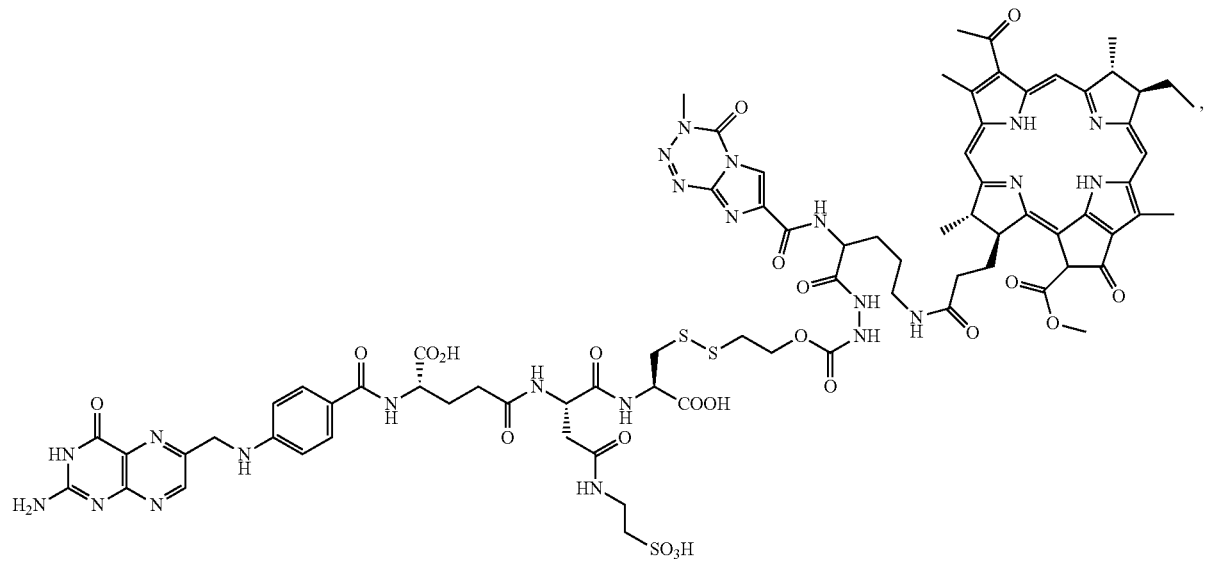
(114)
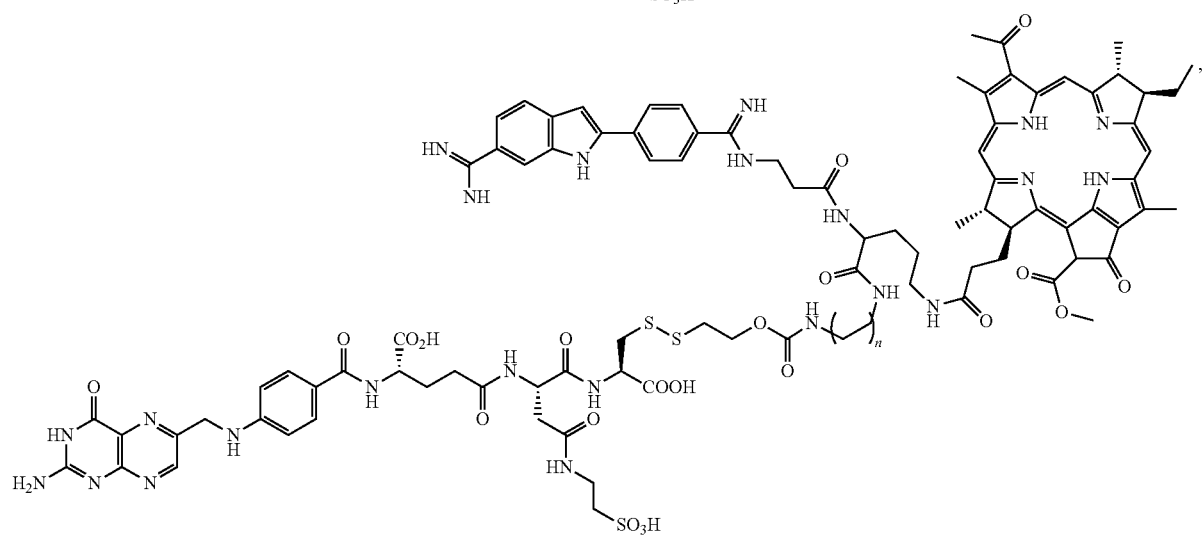
n = 0: (115a)
n = 1: (115b)
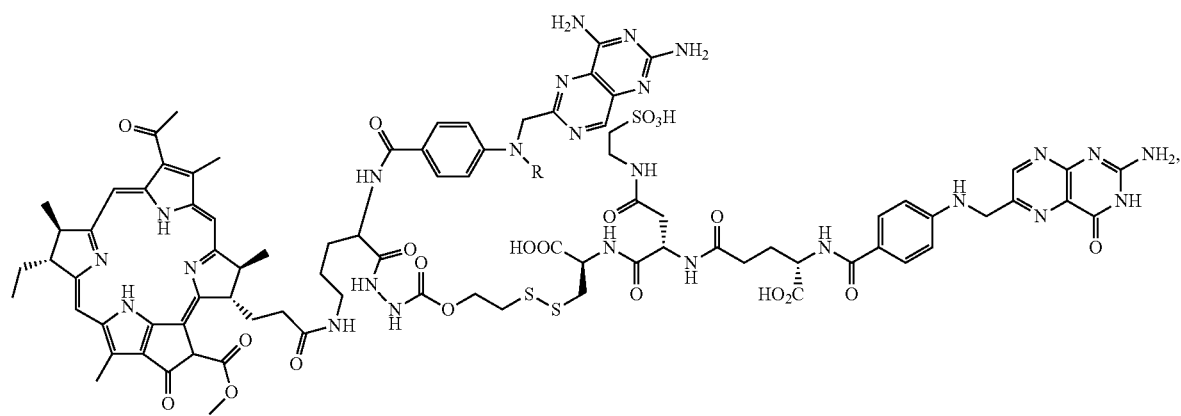
R = H: (116)
R = CH3: (117)

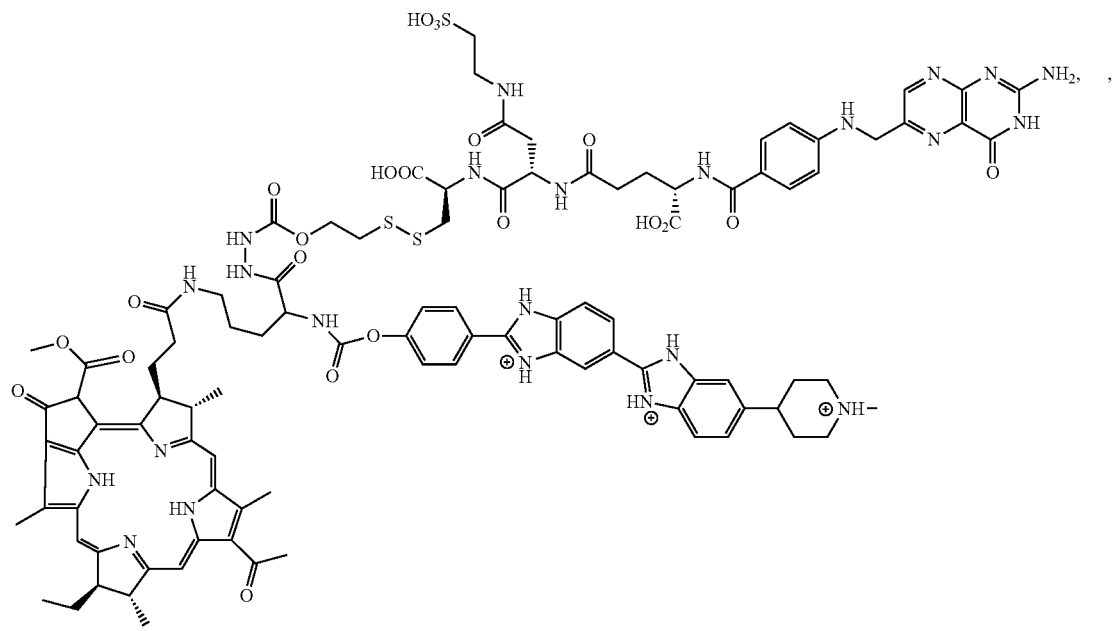

(118)

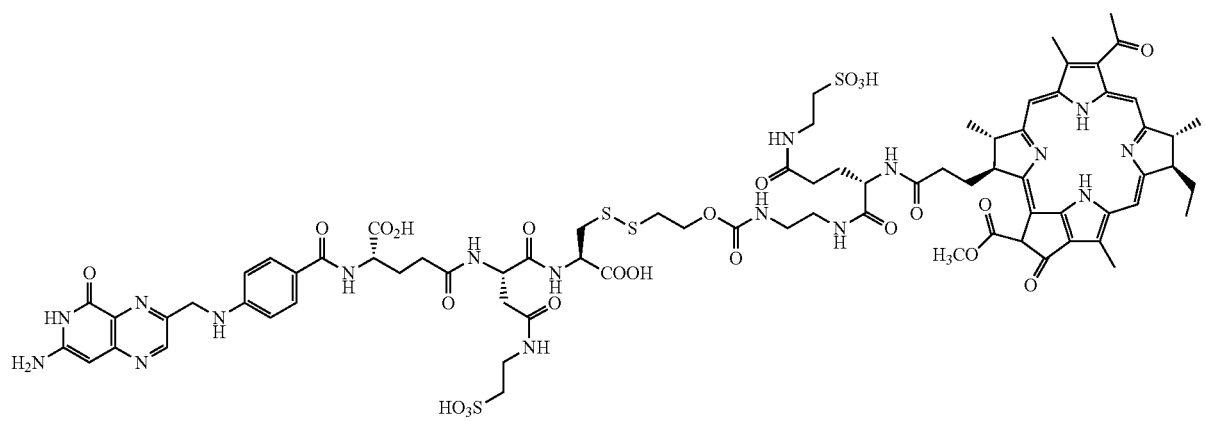

(119)

and a salt thereof.

6. The compound of claim 1, wherein the compound is capable of or adapted to fluoresce after distribution thereof in tissue.

7. The compound of claim 6, wherein the compound is made to fluoresce by subjecting the compound to excitation light of near infrared wavelength.

8. The compound of claim 1, wherein the amino acid or amino acid derivative is selected from the group consisting of glutamic acid, aspartic acid, lysine, ornithine, cysteine, serine, arginine, an alpha amino acid, a homo amino acid, a beta amino acid and isomers thereof.

9. The compound of claim 1, wherein L' is selected from the group consisting of polyether, a sulfonic acid, glycans, and amino acid.

10. The compound of claim 9, wherein the polyether is selected from the group consisting of polyethylene glycol, polyethylene oxide, and polyoxyethylene.

11. The compound of claim 9, wherein the sulfonic acid is selected from the group consisting of:

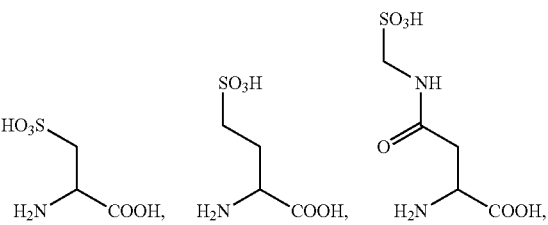

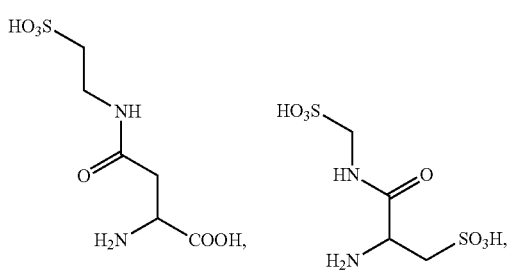

-continued

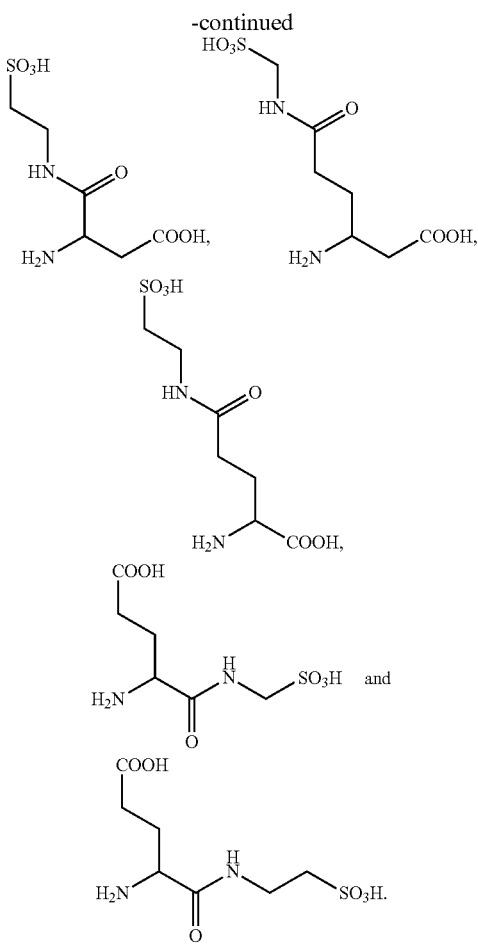

12. The compound of claim 9, wherein the glycans are selected from the group consisting of:

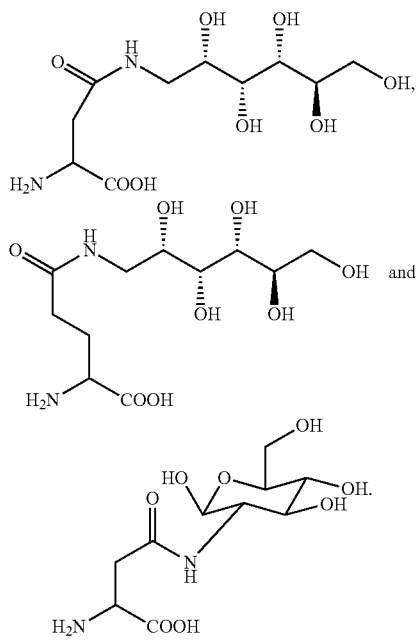

13. The compound of claim 9, wherein the amino acid or an amino acid derivative is selected from the group consisting of a naturally occurring amino acid or an amino acid derivative.

14. The compound of claim 13, wherein the amino acid or an amino acid derivative is selected from the group consisting of an alpha amino acid, a homo amino acid, a beta amino acid, positively charged amino acid, negatively charged amino acid, and derivatives thereof.

15. The compound of claim 14, wherein the positively charged amino acid or an amino acid derivative is selected from the group consisting of arginine, lysine, ornithine, histidine and derivatives thereof.

16. The compound of claim 14, wherein the negatively charged amino acid or an amino acid derivative is selected from the group consisting of aspartic acid, glutamic acid, isomers and derivatives thereof.

17. The compound of claim 13, wherein the amino acid or amino acid derivative includes a sulfur-containing side chain group.

18. The compound of claim 17, wherein the amino acid including a sulfur-containing side chain group is cysteine.

19. The compound of claim 13, wherein the amino acid or amino acid derivative includes a chalcogen-containing side chain group.

20. The compound of claim 19, wherein the amino acid including a chalcogen-containing side chain group is selenocysteine.

21. The compound of claim 1, wherein $L''$ is a releasable linker or a non-releasable linker.

22. The compound of claim 21, wherein the releasable linker is selected from the group consisting of:

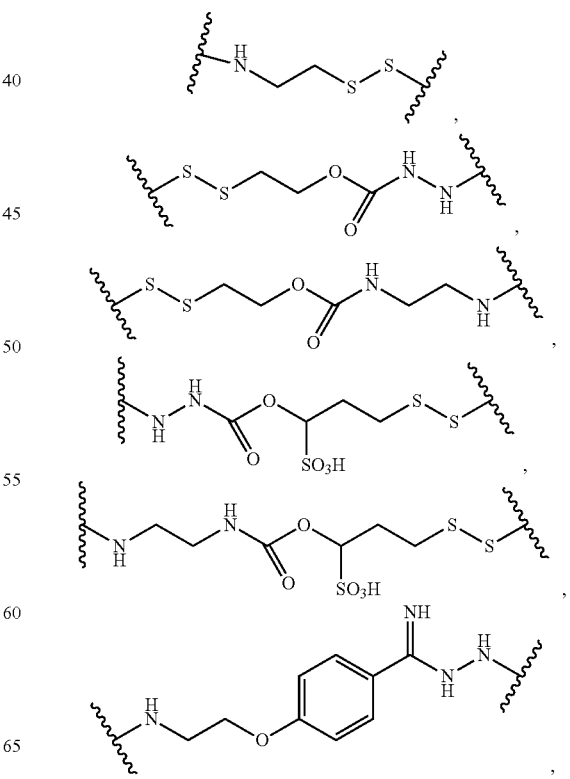

-continued
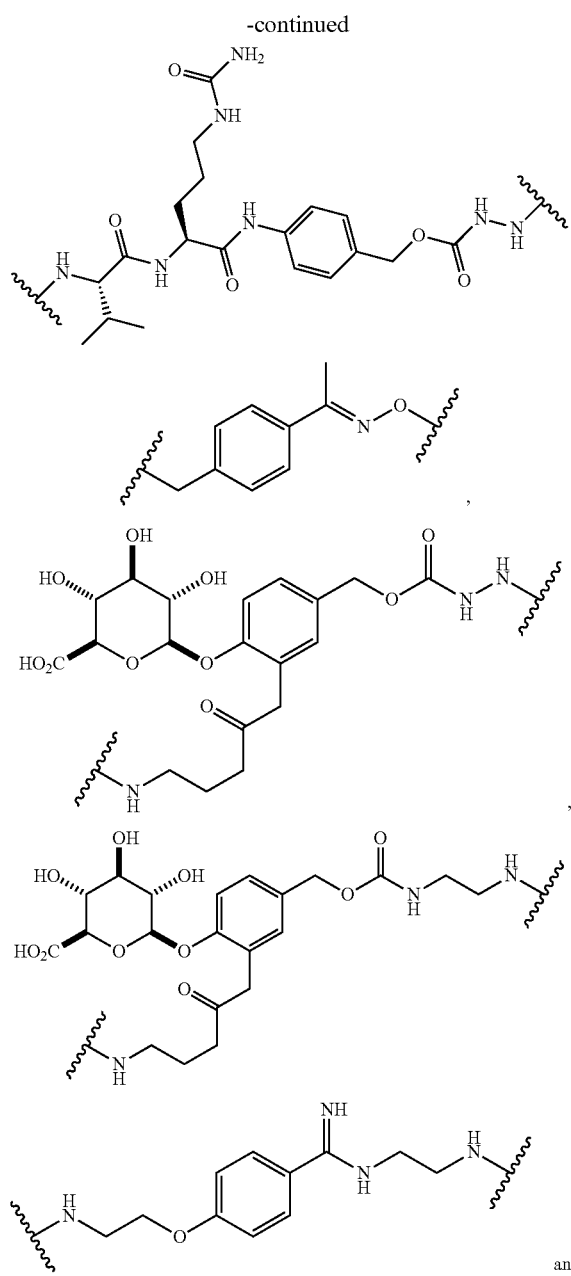
23. The compound of claim 1, wherein X is an organelle targeting agent that targets an organelle within a diseased cell.
24. The compound of claim 23, wherein the organelle targeting agent targets said PDT agent to the mitochondria of the diseased cell.
25. The compound of claim 24, wherein the organelle targeting agent is selected from the group consisting of:
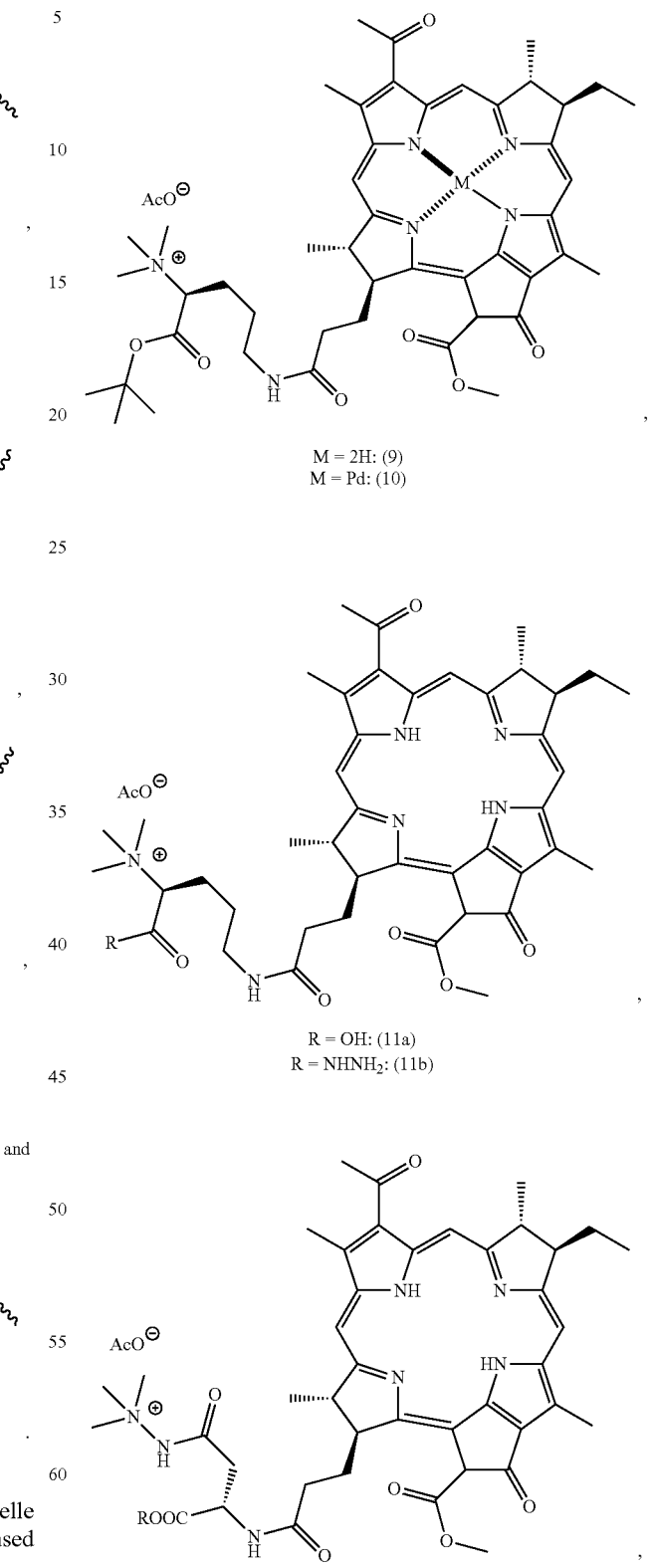

-continued
(13)
(14)
(15)
(16)
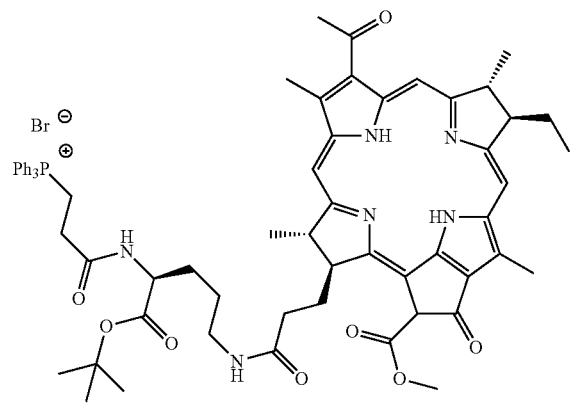
-continued
(17)
(18)
(19)
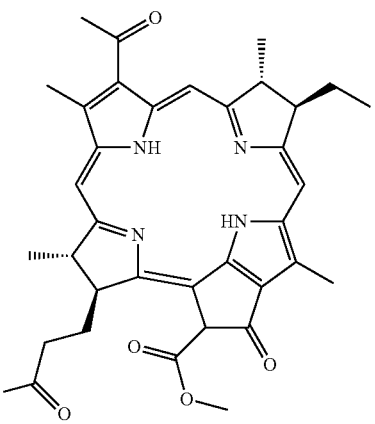
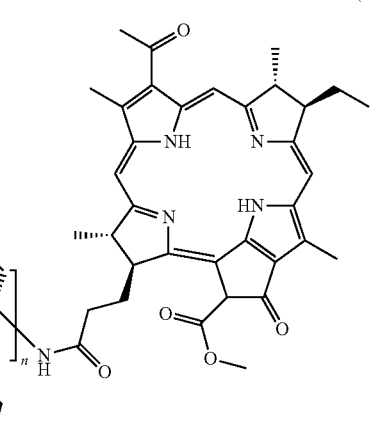
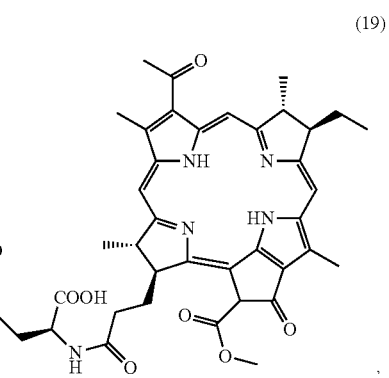

-continued
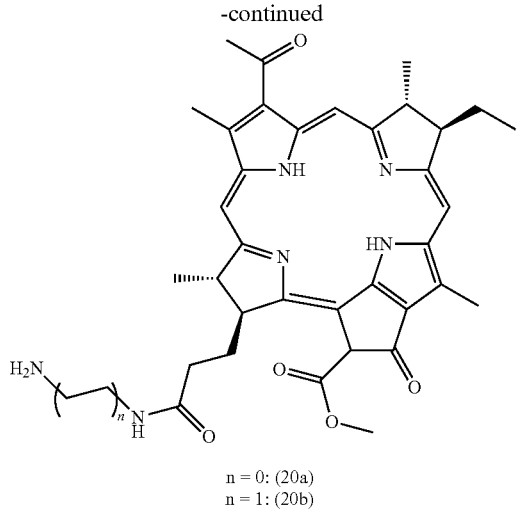
n = 0: (20a)
n = 1: (20b)
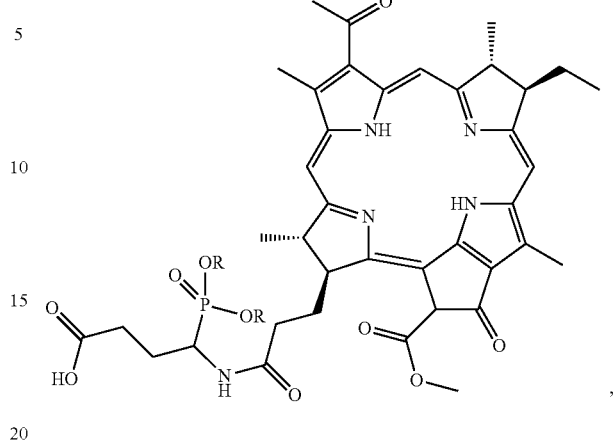
(22)
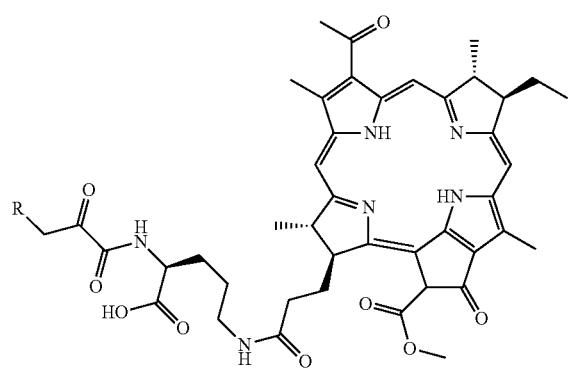
n = Br: (21a)
n = OH: (21b)
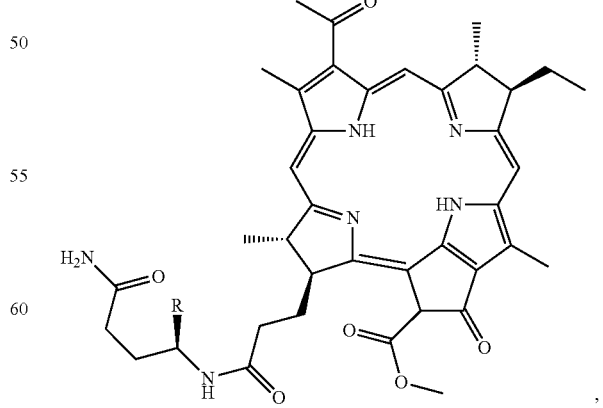
R = COOH: (23a)
R = NH2: (23b)

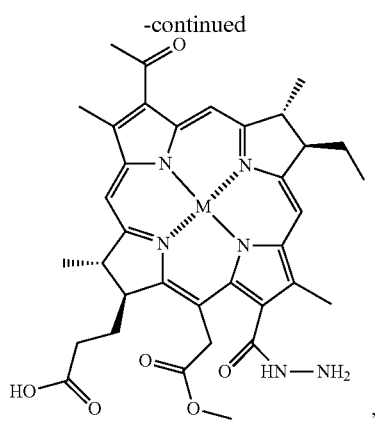
M = 2H: (24)
M = Pd: (25)
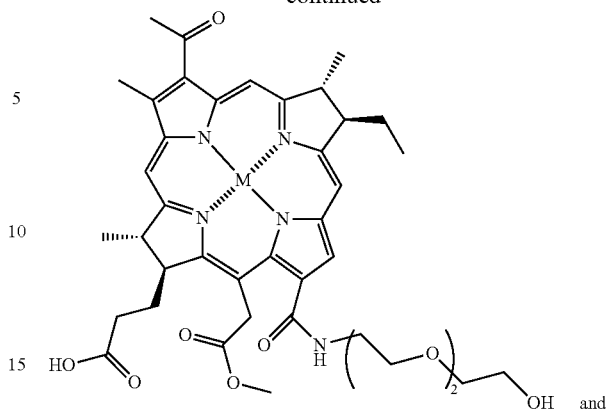
M = 2H: (28)
M = Pd: (29)
and
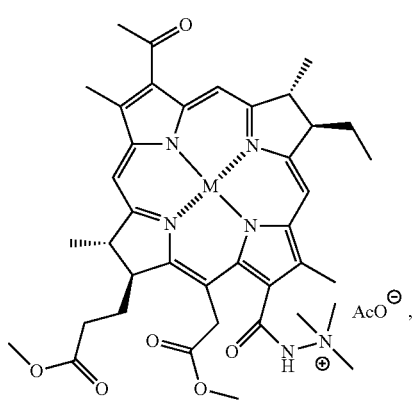
M = 2H: (26)
M = Pd: (27)
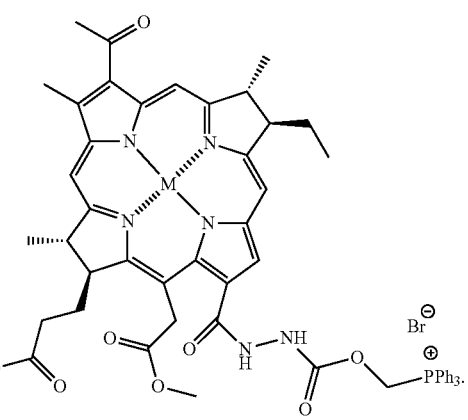
M = 2H: (30)
M = Pd: (31)
26. The compound of claim 23, wherein the organelle targeting agent targets said PDT agent to the nucleus of a diseased cell.
27. The compound of claim 26, the organelle targeting agent is selected from the group consisting of:

137
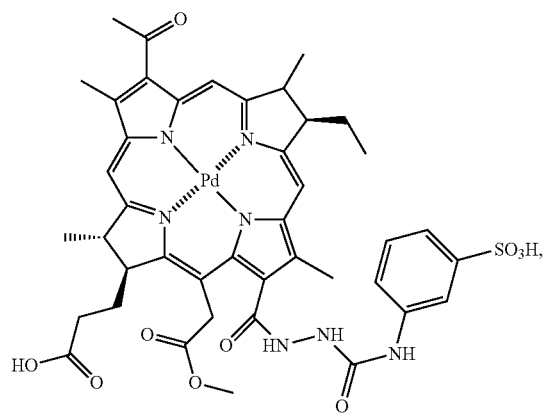
(39)
138
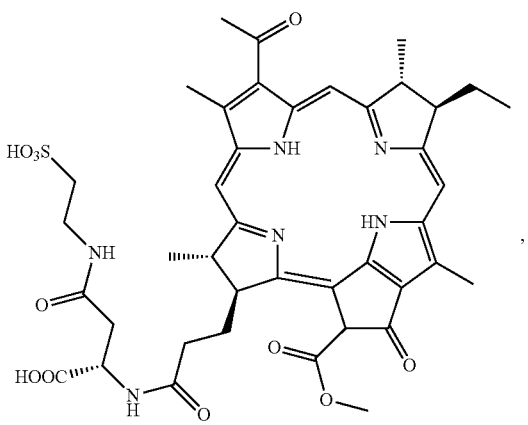
(40)
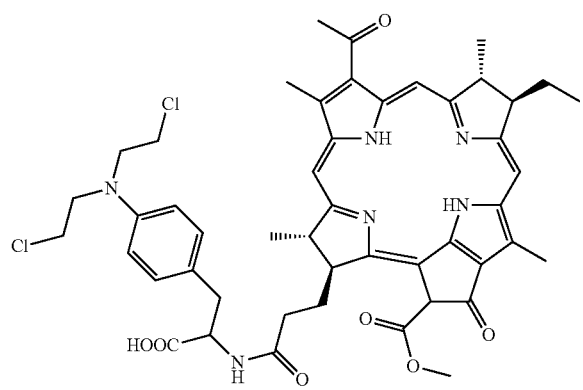
(41)
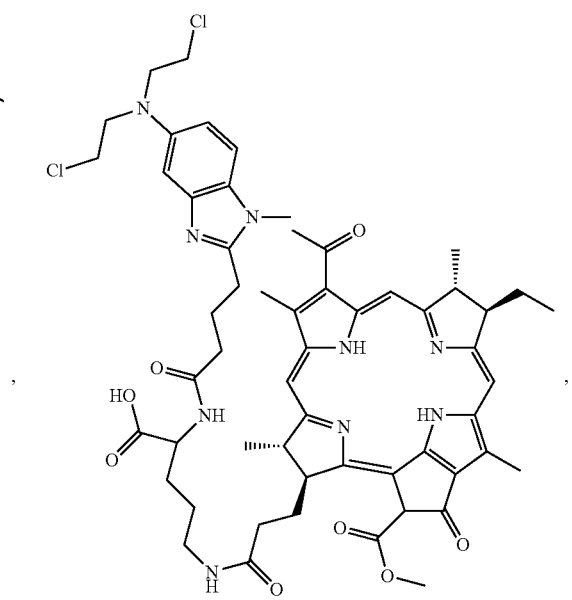
(42)
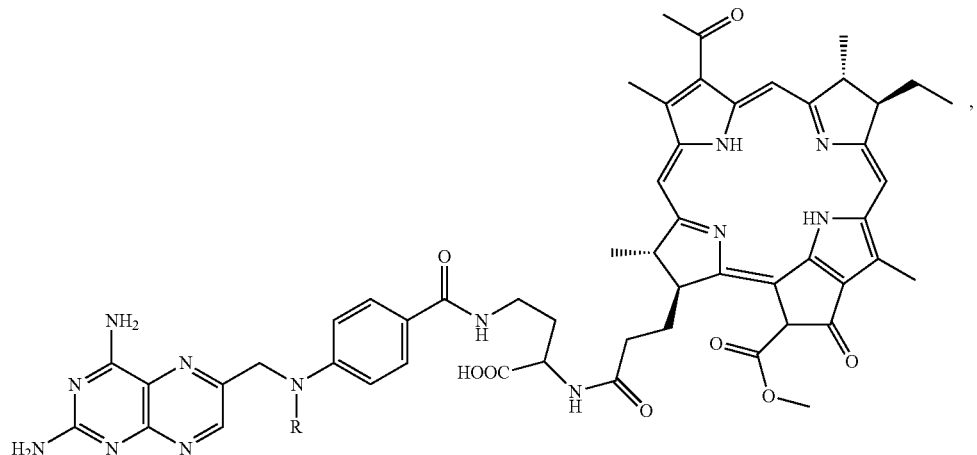
R = H: (43)
R = Me: (44)

(45)
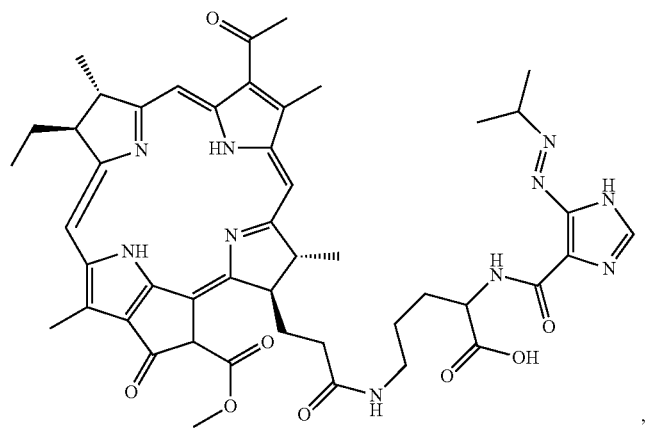
,
(46)
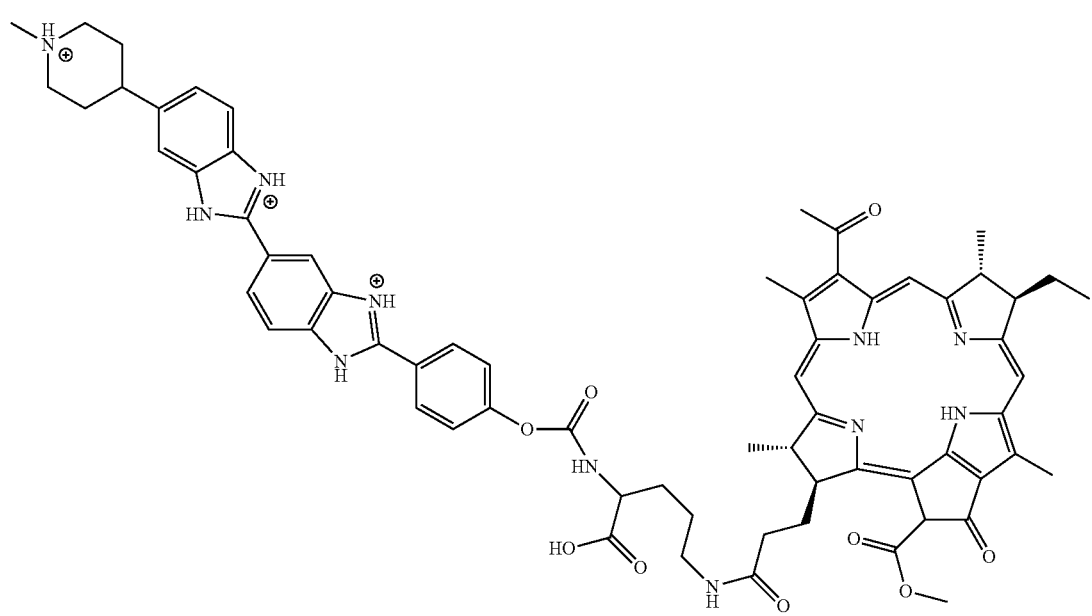
,
(47)
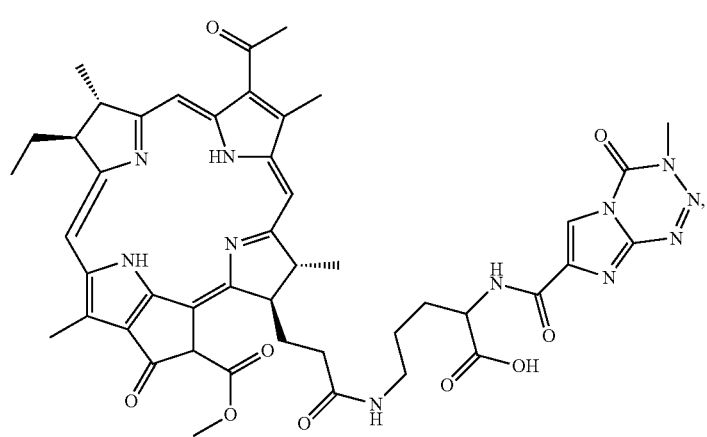
;

(48)

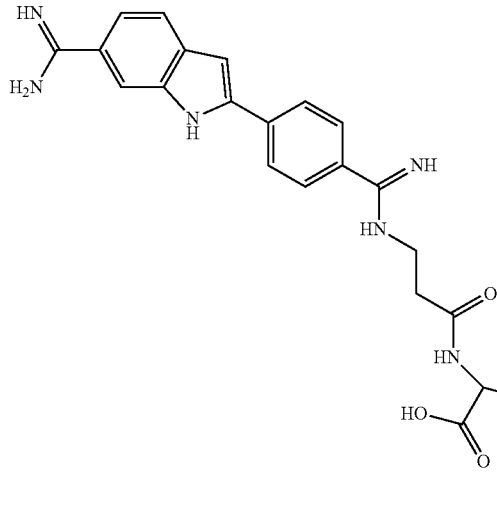

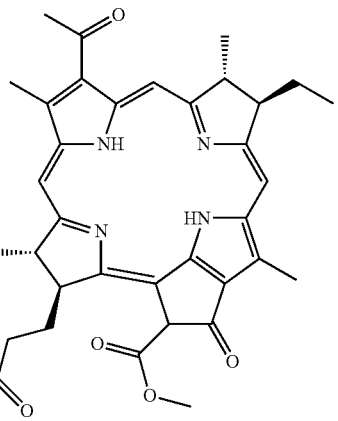

and (49)

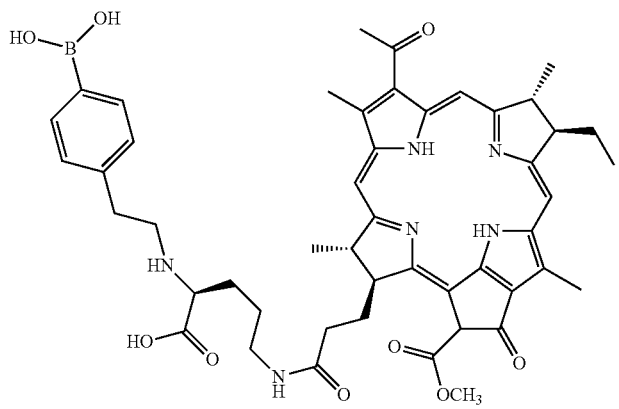

28. A composition comprising a compound of claim 1 and a pharmaceutically acceptable carrier, excipient or diluent.

29. A method of performing photodynamic therapy on a biological tissue that expresses a folate receptor, the method comprising:
 (a) contacting the biological tissue with a composition of claim 1,
 (b) allowing time for the compound in the composition to distribute within the targeted biological tissue and clear from non-targeted tissues; and
 (c) illuminating the biological tissue with an excitation light of a wavelength absorbable by the compound;
 wherein the composition produces reactive oxygen species (ROSs) thereby inducing cell death and necrosis of diseased cells and destroying the biological tissue.

30. The method of claim 29, wherein the biological tissue is in a subject and the subject is an animal or human.

31. The method of claim 29, wherein the biological tissue comprises a diseased cell that overexpresses the folate receptor.

32. The method of claim 31, wherein the diseased cell is selected from the group consisting of a malignant cell, tumor-associated macrophages, and myeloid-derived suppressor cells.

33. The method of claim 31, the disease is selected from the group consisting of cancer, a neurodegenerative disease, a respiratory disease, a metabolic disease, an inherited disease, a bone disease, an environmental disease, and skin disease.

34. The method of claim 33, wherein the biological tissue is a cancer or a lymph node that expresses the folate receptor.

35. The method of claim 34, wherein the cancer is selected from the group consisting of ovarian cancer, lung cancer, endometrial cancer, uterus cancer, breast cancer, kidney cancer, liver cancer, bladder cancer, gastric cancer, colorectal cancer, pancreatic cancer, pituitary cancer, thyroid cancer, cervical cancer, mesothelioma cancer, brain cancer, head and neck cancer, prostate cancer, testicular cancer, skin cancer, and esophageal cancer.

36. The method of claim 34, wherein the cancer is ovarian cancer.

37. The method of claim 34, wherein the cancer is lung cancer.

38. The method of claim 34, wherein the cancer is endometrial cancer.

39. The method of claim 34, wherein the cancer is uterus cancer.

40. The method of claim 34, wherein the cancer is breast cancer.

41. The method of claim 34, wherein the cancer is kidney cancer.

42. The method of claim 34, wherein the cancer is cervical cancer.

43. The method of claim 29, wherein the biological tissue or a lymph node is tumor tissue that has tumor associated macrophages that express the folate receptor.

44. The method of claim 29, wherein the excitation light is near-infrared wavelength light.

45. The method of claim 44, wherein the excitation light wavelength is within a range from about 600 to about 1000 nanometers.

46. The method of claim 44, wherein the excitation light wavelength is within a range from about 670 to about 850 nanometers.

47. A kit comprising a compound of claim 1 and a pharmaceutically acceptable carrier, excipient or diluent.

48. The kit of claim 47, wherein the kit is for treatment of a disease selected from the group consisting of cancer, neurodegenerative diseases, respiratory diseases, metabolic diseases, and skin disease.

49. A compound selected from the group consisting of Compound 9, Compound 11a, Compound 11b, Compound 12b, Compound 13, Compound 14, Compound 15, Compound 26, Compound 27, Compound 41, Compound 58a, Compound 59a, Compound 60a, Compound 64, Compound 65a, Compound 65c, Compound 76a, Compound 76c, Compound 88a, Compound 89, Compound 92a, Compound 99, Compound 100, Compound 104, Compound 112a, Compound 112b, Compound 116, and Compound 117.

50. The compound of claim 1, wherein the compound is selected from the group consisting of

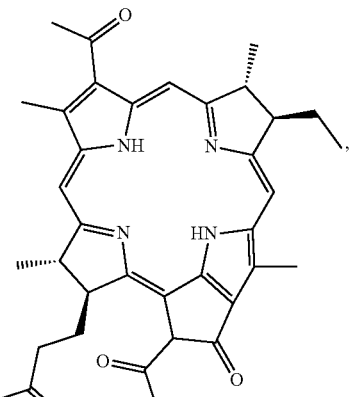

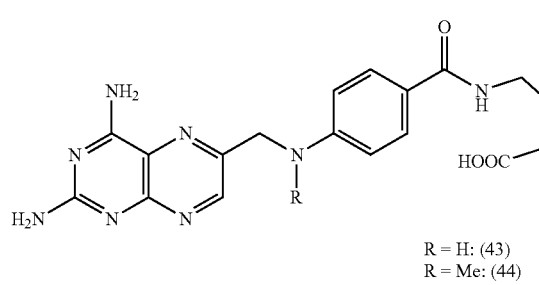

R = H: (43)
R = Me: (44)

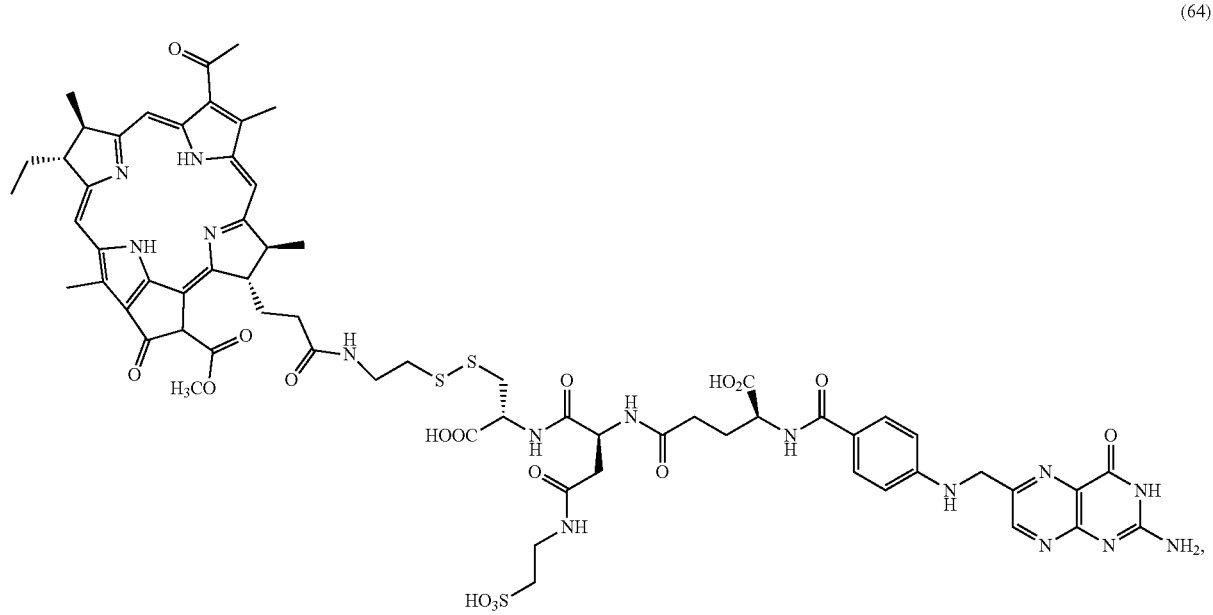

(64)

-continued
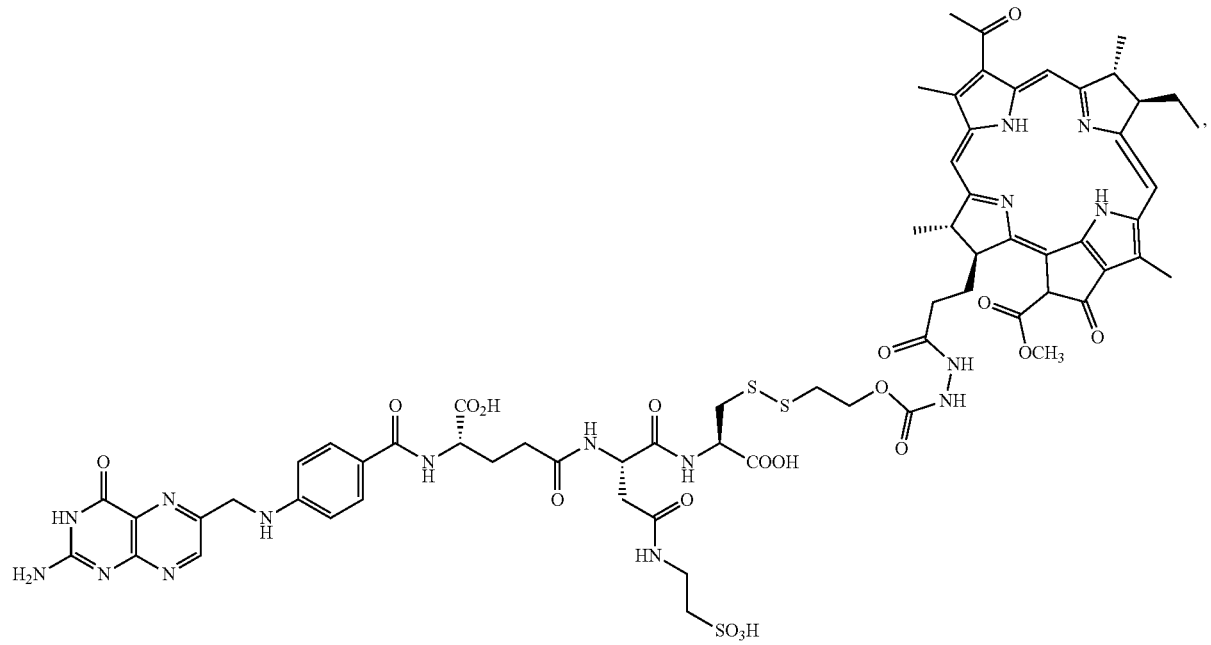
(65a)
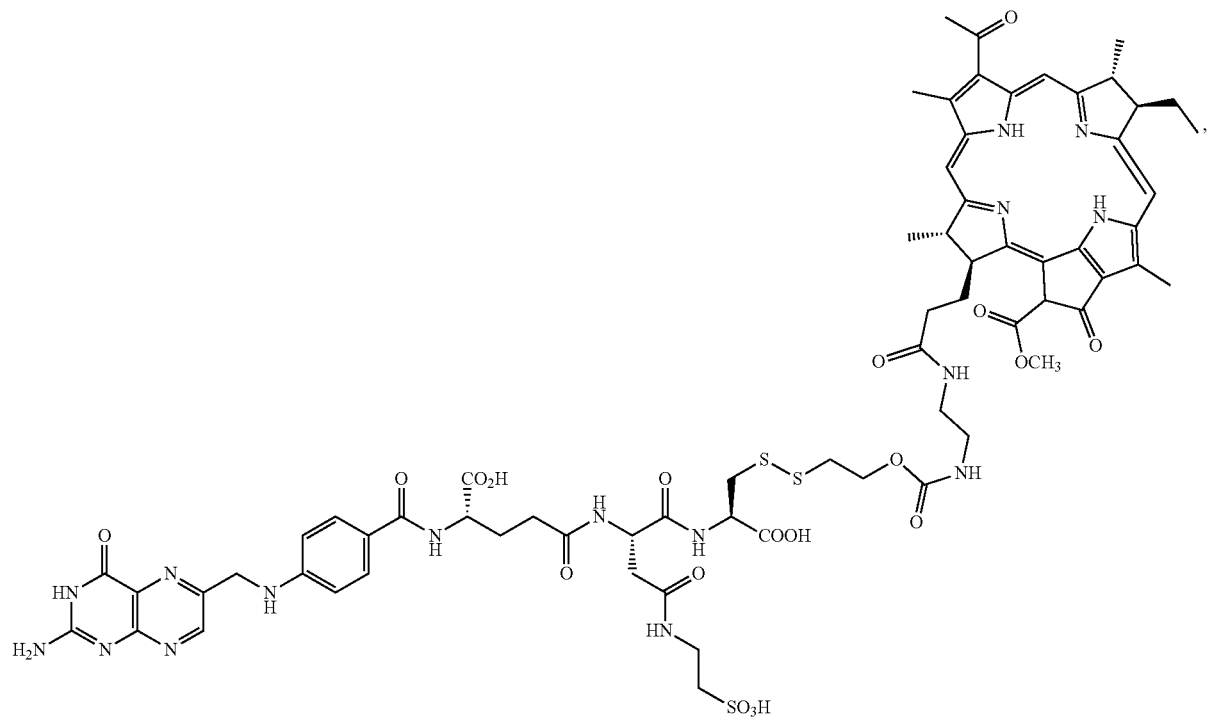
(65c)

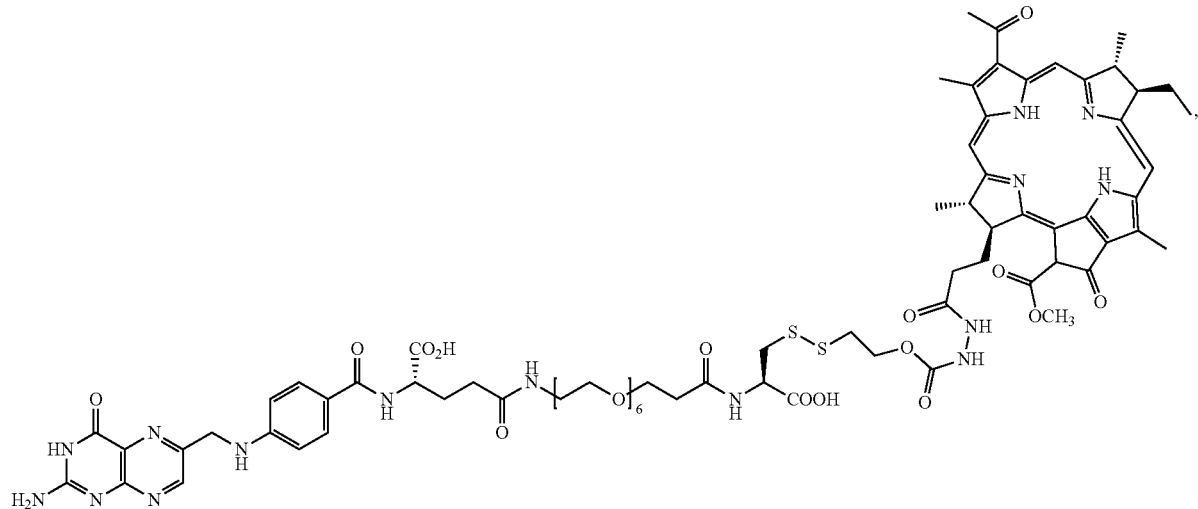
(76a)
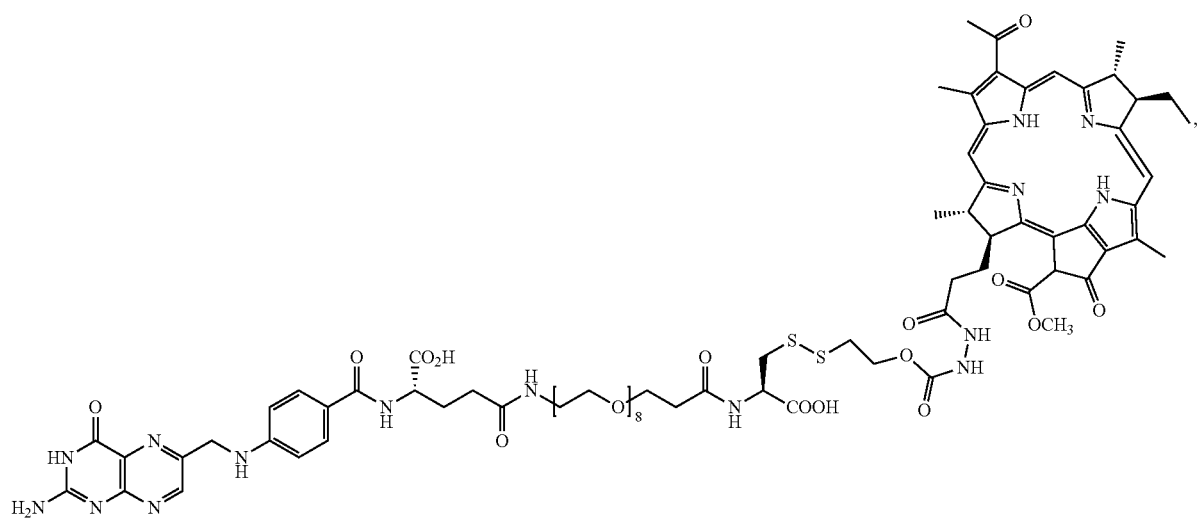
(76c)
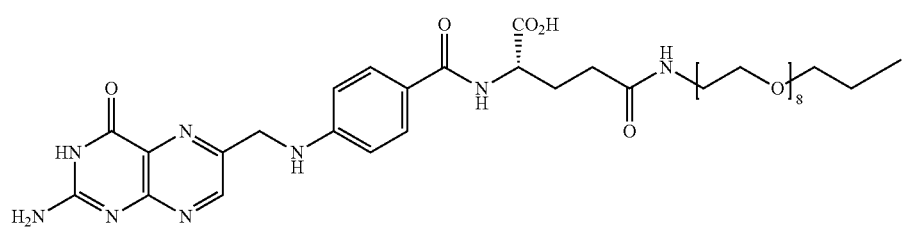
(88a)

-continued
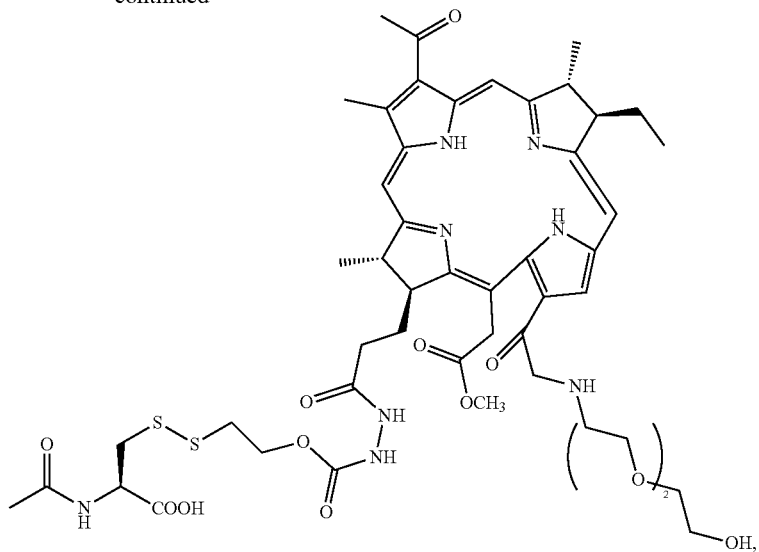
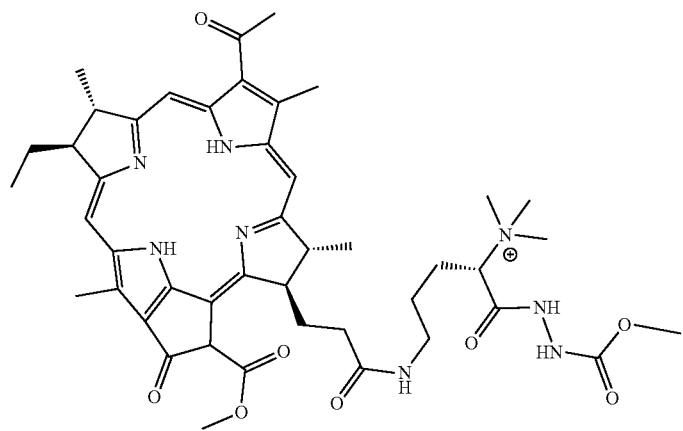
(89a)
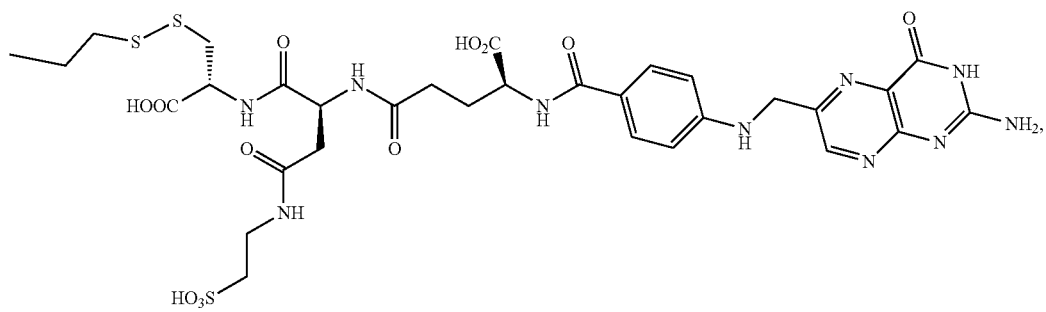

-continued
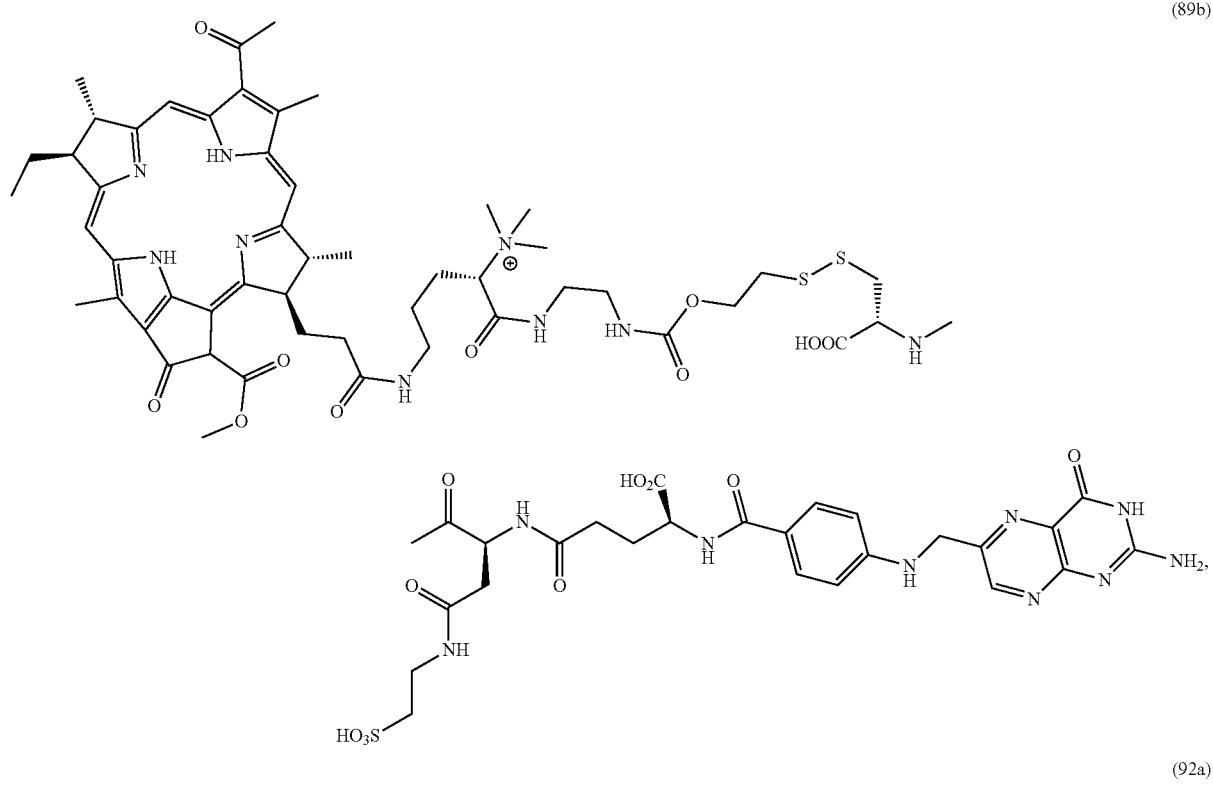
(89b)
(92a)
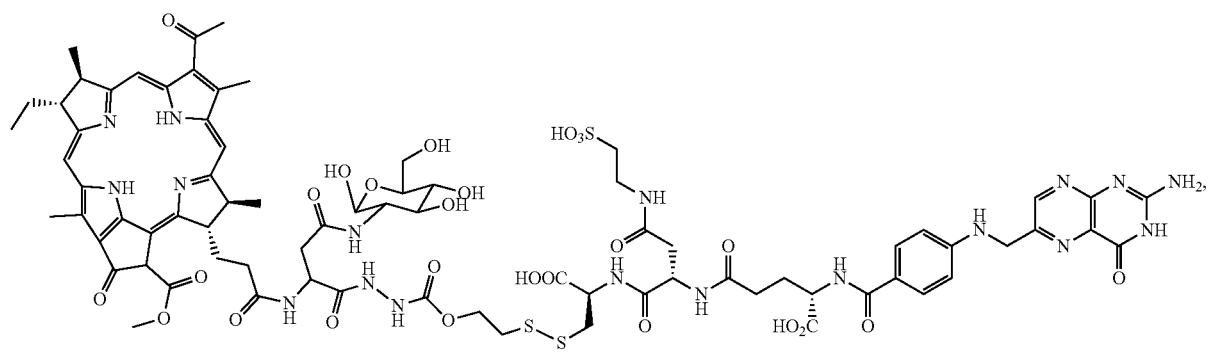
(99)
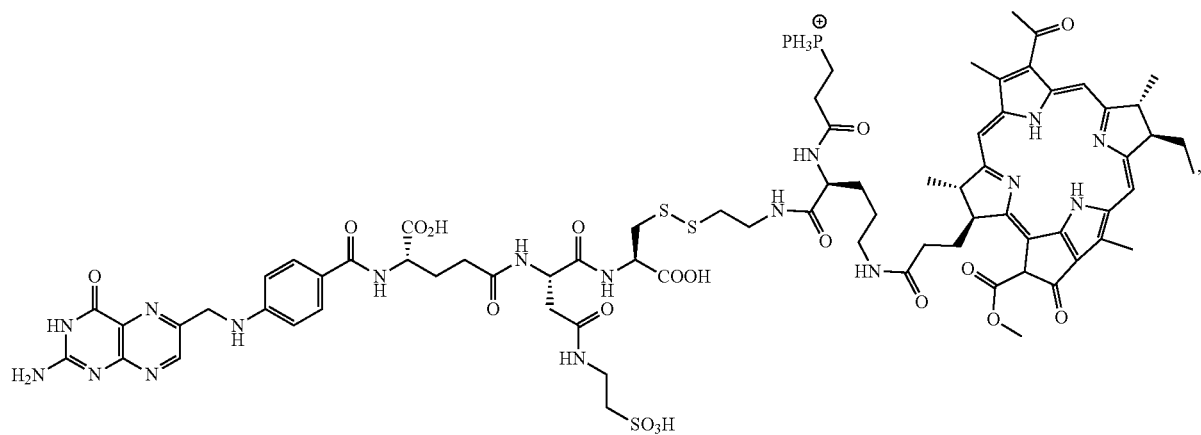

(100)
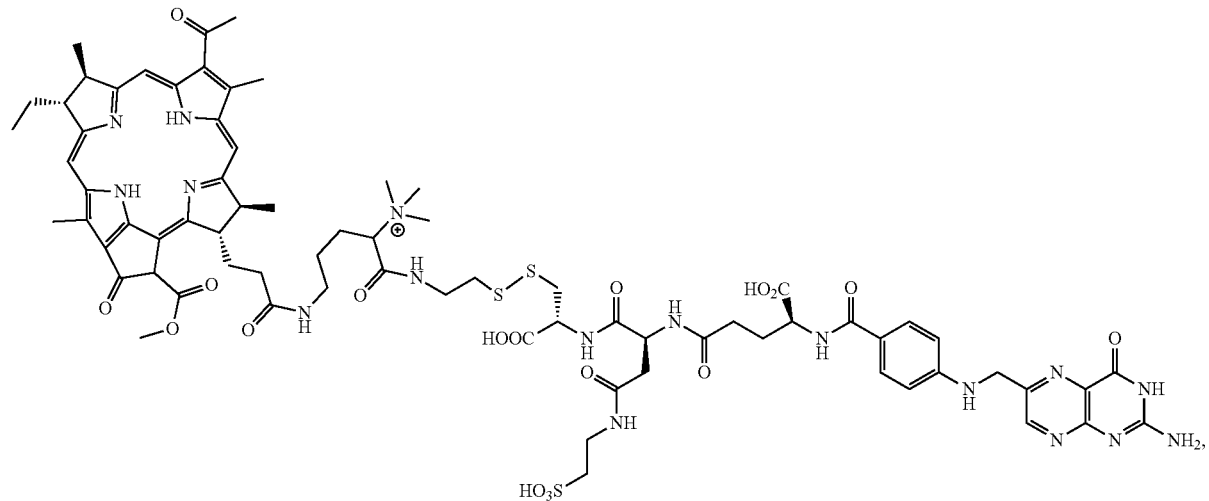
(104)
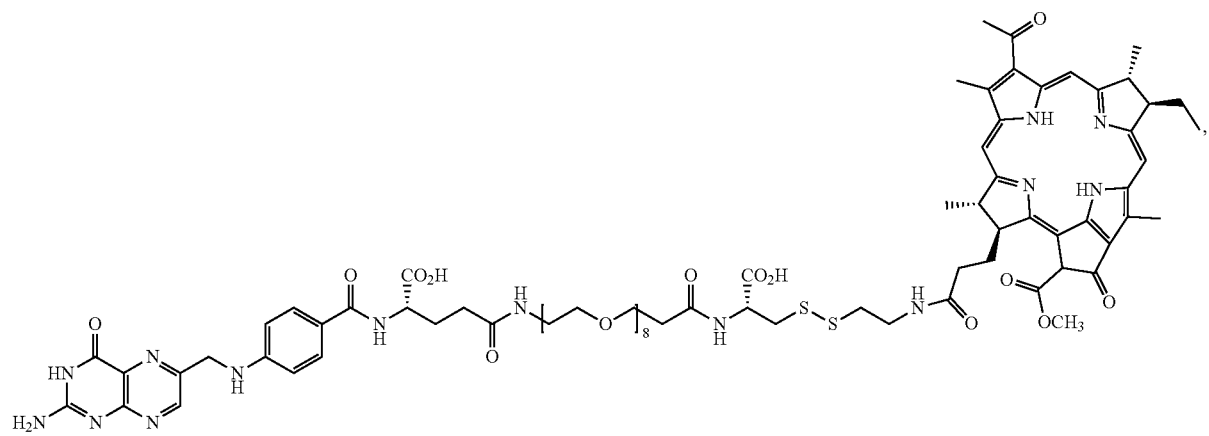
(112a)
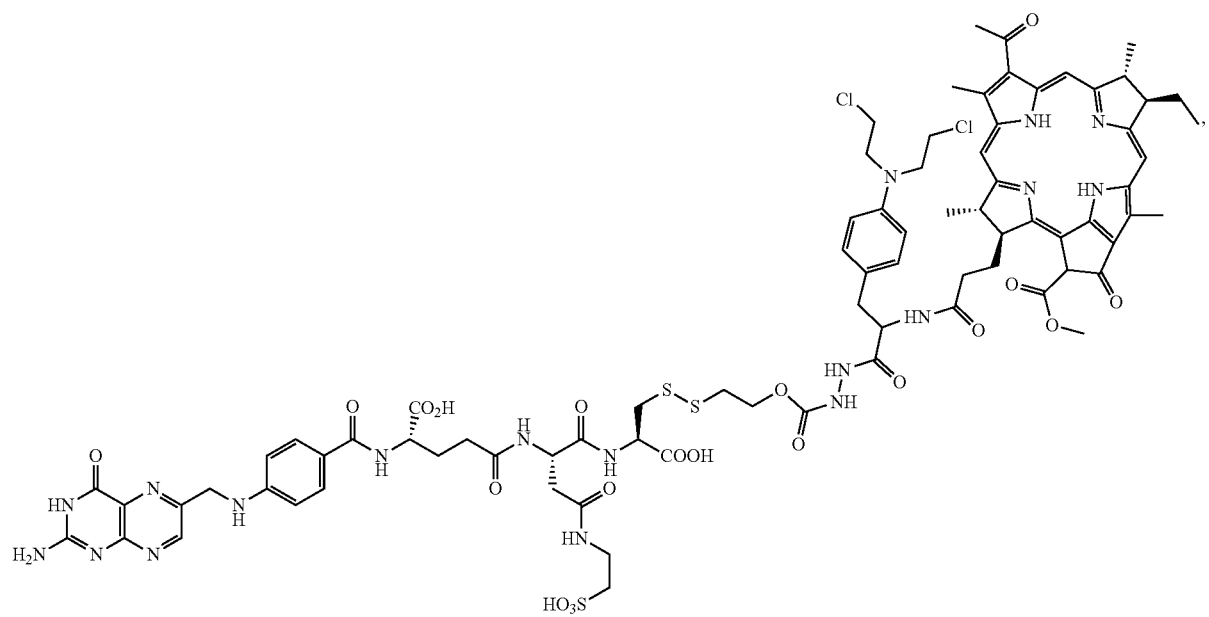

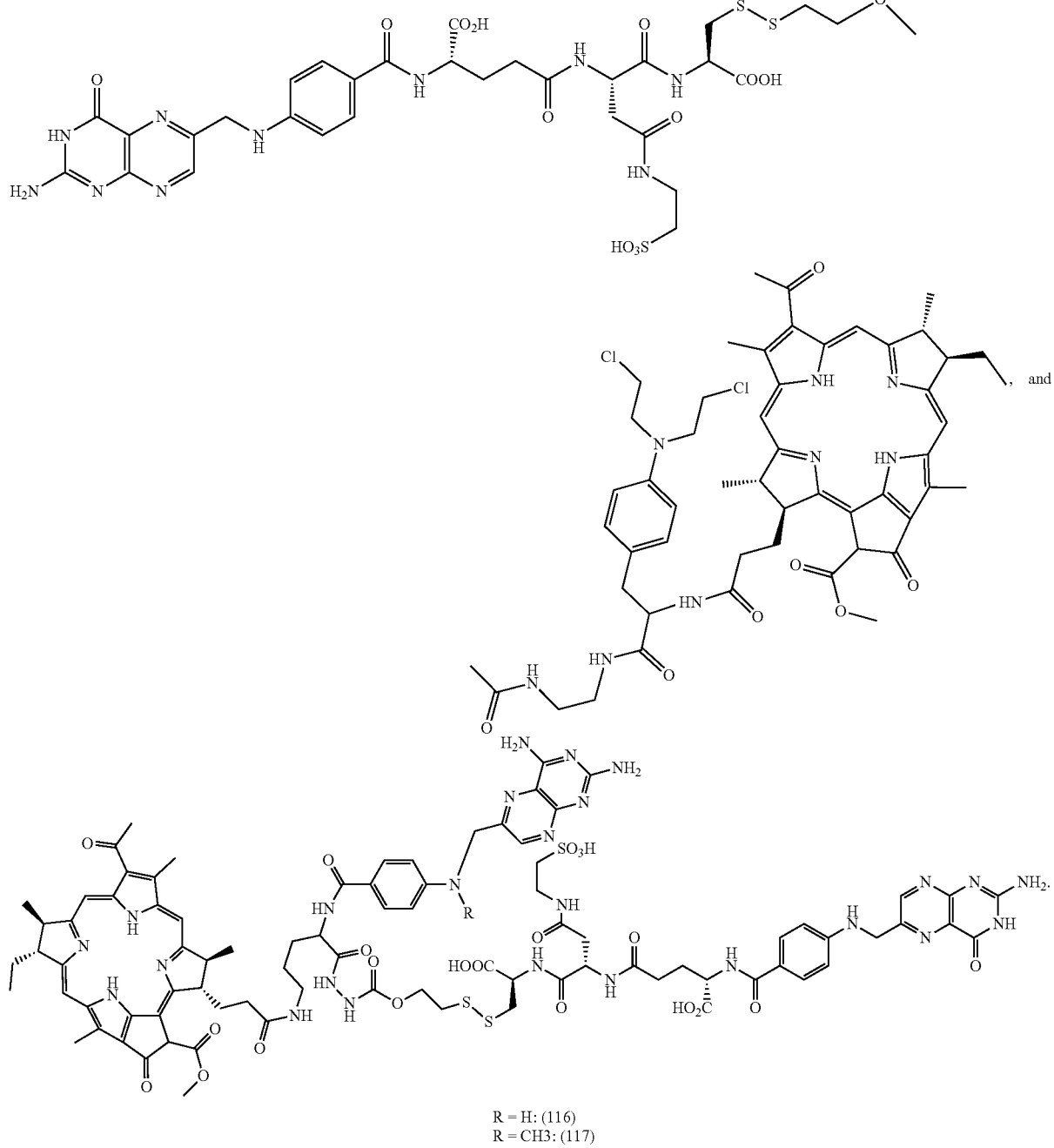

R = H: (116)
R = CH3: (117)

51. A method of performing photodynamic therapy on a biological tissue that expresses a folate receptor, the method comprising:
(a) contacting the biological tissue with a compound of claim 50;
(b) allowing time for the compound to distribute within the targeted biological tissue; and
(c) illuminating the biological tissue with an excitation light of a wavelength absorbable by the compound;
wherein the compound produces reactive oxygen species (ROSs) thereby inducing cell death and necrosis of diseased cells and destroying the biological tissue.

52. A method of treating a cancer characterized by a solid tumor that expresses a folate receptor, the method comprising:
(a) administering to the solid tumor a composition comprising a compound of claim 50;
(b) allowing time for the compound in the composition to distribute within the solid tumor; and
(c) illuminating the solid tumor with an excitation light of a wavelength absorbable by the compound to produce cell death, cell reduction or otherwise effect treatment of the solid tumor.

53. The method of claim 52, wherein the solid tumor is resected prior to, subsequent to, or simultaneously with the administration of said composition.

54. The method of claim 51, wherein the biological tissue is in a subject and the subject is an animal or human.

55. The method of claim 54, wherein the biological tissue comprises a diseased cell that overexpresses the folate receptor.

56. The method of claim 55, wherein the diseased cell is selected from the group consisting of a malignant cell, an inflammatory cell, and a microbial cell.

57. The method of claim 56, wherein the disease is selected from the group consisting of cancer, inflammatory disease, immunologic disease, autoimmune disease, cardiovascular disease, neurodegenerative disease, respiratory disease, metabolic disease, inherited disease, infectious disease, bone disease, environmental disease, and skin disease.

58. The method of claim 57, wherein the biological tissue is a cancer or a lymph node that expresses the folate receptor.

59. The method of claim 58, wherein the cancer is selected from the group consisting of ovarian cancer, lung cancer, endometrial cancer, uterus cancer, breast cancer, kidney cancer, liver cancer, bladder cancer, gastric cancer, colorectal cancer, pancreatic cancer, pituitary cancer, thyroid cancer, cervical cancer, mesothelioma cancer, brain cancer, head and neck cancer, prostate cancer, testicular cancer, skin cancer, and esophageal cancer.

60. The method of claim 58, wherein the cancer is ovarian cancer.

61. The method of claim 58, wherein the cancer is lung cancer.

62. The method of claim 58, wherein the cancer is endometrial cancer.

63. The method of claim 58, wherein the cancer is uterus cancer.

64. The method of claim 58, wherein the cancer is breast cancer.

65. The method of claim 58, wherein the cancer is kidney cancer.

66. The method of claim 58, wherein the cancer is cervical cancer.

67. The method of claim 58, wherein the cancer or the lymph node is tumor tissue that has tumor associated macrophages that express the folate receptor.

* * * * *